US008372612B2

(12) United States Patent
Larossa et al.

(10) Patent No.: US 8,372,612 B2
(45) **Date of Patent: *Feb. 12, 2013**

(54) PRODUCTION OF FOUR CARBON ALCOHOLS USING IMPROVED STRAIN

(75) Inventors: Robert A. Larossa, Chadds Ford, PA (US); Dana R. Smulski, Wilmington, DE (US); Vasantha Nagarajan, Wilmington, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 725 days.

This patent is subject to a terminal disclaimer.

(21) Appl. No.: 12/330,530

(22) Filed: Dec. 9, 2008

(65) Prior Publication Data

US 2009/0203139 A1 Aug. 13, 2009

Related U.S. Application Data

(60) Provisional application No. 61/015,689, filed on Dec. 21, 2007, provisional application No. 61/015,694, filed on Dec. 21, 2007.

(51) Int. Cl.
*C12N 1/21* (2006.01)
*C12P 7/26* (2006.01)
*C12P 7/16* (2006.01)

(52) U.S. Cl. ..................... 435/148; 435/160; 435/252.3; 435/252.31; 435/252.33; 435/252.34

(58) Field of Classification Search ........................ None
See application file for complete search history.

(56) References Cited

U.S. PATENT DOCUMENTS

| | | | |
|---|---|---|---|
| 5,192,673 | A | 3/1993 | Jain et al. |
| 6,358,717 | B1 | 3/2002 | Blaschek et al. |
| 6,960,465 | B1 | 11/2005 | Papoutsakis et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2009/0155870 | A1 | 6/2009 | Donaldson et al. |
| 2009/0162911 | A1 | 6/2009 | LaRossa et al. |
| 2009/0203097 | A1 | 8/2009 | Flint et al. |

FOREIGN PATENT DOCUMENTS

| | | |
|---|---|---|
| JP | 11-221080 | 8/1999 |

OTHER PUBLICATIONS

Butanols, Ullmann's Encyclopedia of Industrial Chemistry, Sixth Edition, 2003, vol. 5:716-719.

Carlini et al., Guerbet Condensation of Methanol With N-Propanol to Isobutyl Alcohol Over Heterogeneous Copper Chromite/MG-A1 Mixed Oxides Catalysts, J. Molec. Catal. A: Chem., 2004, vol. 220:215-220.

Girbal et al., Regulation of Solvent Production in *Clostridium acetobutylicum*, Trends in Biotechnology, 1998, vol. 16:11-16.

Tomas et al., Overexpression of Groesl in *Clostridium acetobutylicum* Results in Increased Solvent Production and Tolerance, Prolonged Metabolism, and Changes in the Cell's Transcriptional Program, Appl. Environ. Microbiol., 2003, vol. 69:4951-4965.

Quratulain et al., Development and Characterization of Butanol-Resistant Strain of *acetobutylicum* in Molasses Medium, Folia Microbiologica, 1995, vol. 40:467-471.

Soucaille et al., Butanol Tolerance and Autobacteriocin Production by *Clostridium acetobutylicum*, Current Microbiology, 1987, vol. 14:295-299.

Desmond et al., Improved Stress Tolerance of Groesl-Overproducing *Lactococcus lactis* and Probiotic *Lactobacillus paracasei* NFBC 338, Appl. Environ. Microbiol., 2004, vol. 70:5929-5936.

Sardessai et al., Organic Solvent-Tolerant Bacteria in Mangrove Ecosystem, Current Science, 2002, vol. 82, 622-623.

Bieszkiewicz et al., Studies on the Resistance of Activated Sludge Bacteria to High Concentrations of Methanol. Butanol. Glycol. Cyclohexanone and Cyclohexylamine, Acta Microbiologica Polonica, 1987, vol. 36, 259-265.

Couto et al., Enhancement of Apparent Resistance to Ethanol in *Lactobacillus hilgardii*, Biotechnology Letter, vol. 19, No. 5, 487-490, 1997.

Ingram et al., Effects of Alcohols on Micro-Organisms, Adv. Micribial. Physiol., 1984, vol. 25, 253-300.

Kristien Braeken et al., New Horizons for (P) PPGPP in Bacterial and Plant Physiology, Trends in Microbiology, 2006, vol. 14, No. 1, 45-54.

Katarzyna Potrykus et al., (p) PPGPP: Still Magical?, Annu. Rev. Microbiol., 2008, vol. 62:35-51.

John J. Mitchell et al., The Effect of Alcohols on Guanosine 5'-Diphosphate-3'-Diphosphate Metabolism in Stringent and Relaxed *Escherichia coli*, The Journal of Biological Chemistry, Jul. 10, 1980, vol. 255, No. 13, 6307-6313.

Anjana Srivatsan et al., Control of Bacterial Transcription, Translation and Replication by (p)ppGpp, Current Opinion in Microbiology, 2008, vol. 11, No. 2, 100-105.

Brian J. Paul et al., DksA Potentiates Direct Activation of Amino Acid Promoters by ppGpp, Proceedings of the National Academy of Sciences of the USA, May 31, 2005, vol. 102, No. 22, 7823-7828.

Gerhard Mittenhuber, Comparative Genomics and Evolution of Genese Encoding Bacterial (p)ppGpp Synthetases/Hydrolases (The Rel, RelA and SpoT Proteins), J. Mol. Micobiol. Biotechnol, 2001, vol. 3, No. 4, 585-600.

Daniel R. Gentry et al., Mutational Analysis of the *Escerichia coli* spoT Gene Identifies Distinct but Overlapping Regions Involved in ppGpp Synthesis and Degradation, Molecular Microbiology, 1996, vol. 19, No. 6, 1373-1384.

Baba et al., "Construction of *Escherichia coli* K-12 in-frame, single gene knockout mutants: the Keio collection," Mol. Syst. Biol. 2:2006. 0008 (2006).

Battesti and Bouveret, "Acyl carrier protein/SpoT interaction, the switch linking SpoT-dependent stress response to fatty acid metabolism," Molecular Microbiology 62:1048-1063 (2006).

(Continued)

*Primary Examiner* — Rebecca Prouty

(57) ABSTRACT

Using screening of transposon random insertion mutants, genes involved in accumulation of (p)ppGpp were found to be involved in bacterial cell response to butanol. Reduced production of proteins with enzymatic activity for (p)ppGpp biosynthesis confers increased butanol tolerance. Bacterial strains with reduced (p)ppGpp accumulation and having a butanol or 2-butanone biosynthetic pathway are useful for production of butanol or 2-butanone.

13 Claims, 12 Drawing Sheets

OTHER PUBLICATIONS

Cashel et al., "The stringent response," Chapter 92, In F. C. Neidhardt (ed.), *Escherichia coli* and *Salmonella*: Cellular and Molecular Biology, 2nd Ed. ASM Press, Washington, DC (1996).

Chaloner-Larsson and Yamazaki, "Effects of the spoT and relA mutation on the synthesis and accumulation of ppGpp and RNA during glucose starvation," Can. J. Biochem. 56:264-72 (1978).

Datsenko and Wanner, "One-step inactivation of chromosomal genes in *Escherichia coli* K-12 using PCR products," Proc. Natl. Acad. Sci. USA 97:6640-6645 (2000).

Fujita et al., "Guanosine 5'-diphosphate 3'-diphosphate (ppGpp) synthetic activities on *Escherichia coli* SpoT domains," Biosci. Biotechnol. Biochem. (2002) 66:1515-1523.

Hernandez and Bremer, "*Escherichia coli* ppGpp synthetase II activity requires spoT," J. Biol. Chem. 266:5991-9 (1991).

Mechold et al., "Intramolecular regualtion of the opposing (p)ppGpp catalytic activities of Rel(seq), the Rel/Spo enzyme from *Streptococcus equisimilis*," J. Bacteriol. 184:2878-88 (2002).

Seyfzadeh and Keener, "spoT-dependent accumulation of guanosine tetraphosphate in response to fatty acid starvation in *Escherichia coli*," Proc. Natl. Acad.Sci. U S A 90:11004-8 (1993).

Yakunin et al., "The HD Domain of the *Escherichia coli* tRNA nucleotidyltransferase has 2',3'-cyclic phosphodiesterase, 2'-nucleotidase, and phsophate ," J . Biol. Chem. 279:36819-36827 (2004).

Atsumi et al., "Metabolic engineering of *Escherichia coli* for 1-butanol production," Metabolic Engineering 10 (6):305-311 (2008) Elsevier, Inc.

Chang et al., "Membrane cyclopropane fatty acid content is a major factor in acid resistance of *Escherichia coli*," Mol. Microbiol. 33(2):249-59 (1999).

Chica et al., "Semi-rational approaches to engineering enzyme activity: combining the benefits of directed evolution and rational design," Curr. Opin. Biotechnol. 16(4):378-84 (2005).

Drew et al., "The structure of the efflux pump AcrB in complex with bile acid," Mol. Membrane Biol. 25(8):677-82 (2008).

Eichel et al., "effect of ppGpp on *Escherichia coli* cyclopropane fatty acid synthesis is mediated through the Rpos sigma factor," J. Bacteriol. 181:572-6 (1999).

Elkins et al., "Chimeric analysis of ArcA function reveals the importance of its C-terminal domain in its interaction with the AcrB multidrug efflux pump," J. Bacteriol. 185918):5349-56 (2003).

Grandvale et al., "Changes in membrane lipid composition in ethanol and acid-adapted *Oenococcus oeni* cells: characterization of the CFA gene by heterologous complementation," Microbiol. 154:2611-9 (2008).

Grogan et al., Cyclopropane ring formation in membrane lipids of bacteria, Microbiol. and Mol. Biol. Rev. 61(4): D429-41 (1997).

Higgins et al., "Structure of the periplasmic component of a bacterial drug efflux pump," PNAS 101(27):9994-9 (2004).

International Search Report and Written Opinion of corresponding PCT/US2008/087646 mailed Mar. 11, 2009.

International Search Report and Written Opinion of corresponding PCT/US2008/087635 mailed Jun. 22, 2009.

LePage et al., "Changes in membrane lipid composition of *Clostridium acetobutylicum* during acetone-butanol fermentation: effects of solvents, growth temperature and Ph," J. Gen. Microbiol. 133:103-10 (1987).

Martin et al., "Structural requirements for marbox function in transcriptional activation of mar/sox/rob regulon promoters in *Escherichia coli*: sequence, orientation, and spatial relationship to the core promoter," Mol. Microbiol. 34(3):431-41 (1999).

Mikolosko et al., "Conformational flexibility in the multidrug efflux system protein AcrA," Structure 14:577-87 (2006).

Mikolosko et al., "Conformational flexibility in the multidrug efflux system protein AcrA," NIH-Public Access Author Manuscript, available PMC, Oct. 1, 2007:1-21, published in final edited forma as: Structure 14(3):577-87 (2006).

Moken et al., "Selection of multiple-antibiotic-resistant (Mar) mutants of *Escherichia coli* by using disinfectant pine oil: roles of the mar and acr/AB loci," Antimicrobial Agents and Chemother. 41(12):2270-2 (1997).

Murakami et al., "Crystal structure of bacterial multidrug efflux transporter AcrB," Nature 419:587-93 (2002).

Murakami et al., "Crystal structure of a multidrug transporter reveal a functionally rotating mechanism," Nature 443:173-9 (2006).

Office Action in related U.S. Appl. No. 12/330,531 issued on Mar. 11, 2011.

Office Action in related U.S. Appl. No. 12/330,531 issued on Nov. 3, 2011.

Office Action in related U.S. Appl. No. 12/330,534 issued on Mar. 14, 2011.

Office Action in related U.S. Appl. No. 12/330,534 issued on Nov. 4, 2011.

Seeger et al., "Structural asymmetry of AcrB trimer suggests a peristalic pump mechanism," Science 313:1295-8 (2006).

Sen et al., "Developments in directed evolution for improving enzyme functions," Appl. Biochem. Biotechnol. 143 (3):212-23 (2007).

Takatsuka et al., "Covalently linked trimer of the ArcB multidrug efflux pump provides support for the functional rotating mechanism," J. Bacteriol. 191(6):1729-37 (2009).

Vollherbst-Schneck et al., "Effect of butanol on lipid composition and fluidity of *Clostridium acetobutylicom* ATCC 824," Applied and Environmental Microbiology 47:193-4 (1984).

Yu et al., "AcrB multidrug efflux pump of *Escheria coli*: composite substrate-binding cavity of exceptional flexibility generates its extremely wide substrate specificity," J. Bacteriol. 185(19):5657-64 (2003).

Zhao et al., "Expression of a cloned cyclopropane fatty acid synthase gene reduces solvent formation in *Clostridium acetobutylicum* ATCC 824," Applied and Enivron. Microbiol. 69(5):2831-41 (2003).

| Number | Identity | Gene |
|---|---|---|
| 1 | DPD1854 | gmk |
| 2 | DPD1865 | rpoZ |
| 3 | DPD1848 | spoT |
| 4 | DPD1850 | spoT |
| 5 | DPD1868 | spoT |
| 6 | DPD1859 | spoT |

1 *Escherichia coli* RelA
2 *Pseudomonas putida* RelA
3 *Clostridium acetobutylicum* SpoT
4 *Lactobacillus plantarum* SpoT
5 *Enterococcus faecium* SpoT
6 *Enterococcus faecalis* SpoT
7 *Bacillus subtilis* SpoT
8 *Bacillus licheniformis* SpoT
9 *Rhodococcus erythropolis* SpoT
10 *Escherichia coli* SpoT
11 *Pseudomonas putida* SpoT

SEQUENCE LISTING

```
<160> NUMBER OF SEQ ID NOS: 70

<210> SEQ ID NO 1
<211> LENGTH: 1179
<212> TYPE: DNA
<213> ORGANISM: Clostridium acetobutylicum

<400> SEQUENCE: 1

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300

attataaaag caggagatgc tgacgtaata atagcaggtg gtatggaaaa tatgtctaga     360

gctccttact tagcgaataa cgctagatgg ggatatagaa tgggaaacgc taaatttgtt     420

gatgaaatga tcactgacgg attgtgggat gcatttaatg attaccacat gggaataaca     480
```

-continued

```
gcagaaaaca tagctgagag atggaacatt tcaagagaag aacaagatga gtttgctctt    540

gcatcacaaa aaaaagctga agaagctata aaatcaggtc aatttaaaga tgaaatagtt    600

cctgtagtaa ttaaaggcag aaagggagaa actgtagttg atacagatga gcaccctaga    660

tttggatcaa ctatagaagg acttgcaaaa ttaaaacctg ccttcaaaaa agatggaaca    720

gttacagctg gtaatgcatc aggattaaat gactgtgcag cagtacttgt aatcatgagt    780

gcagaaaaag ctaaagagct tggagtaaaa ccacttgcta agatagtttc ttatggttca    840

gcaggagttg acccagcaat aatgggatat ggacctttct atgcaacaaa agcagctatt    900

gaaaaagcag gttggacagt tgatgaatta gatttaatag aatcaaatga agcttttgca    960

gctcaaagtt tagcagtagc aaaagattta aaatttgata tgaataaagt aaatgtaaat   1020

ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179


<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255
```

```
Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390
```

<210> SEQ ID NO 3
<211> LENGTH: 1179
<212> TYPE: DNA
<213> ORGANISM: Clostridium acetobutylicum

<400> SEQUENCE: 3

```
atgagagatg tagtaatagt aagtgctgta agaactgcaa taggagcata tggaaaaaca     60

ttaaaggatg tacctgcaac agagttagga gctatagtaa taaaggaagc tgtaagaaga    120

gctaatataa atccaaatga gattaatgaa gttatttttg gaaatgtact tcaagctgga    180

ttaggccaaa acccagcaag acaagcagca gtaaaagcag gattaccttt agaaacacct    240

gcgtttacaa tcaataaggt ttgtggttca ggtttaagat ctataagttt agcagctcaa    300

attataaaag ctggagatgc tgataccatt gtagtaggtg gtatggaaaa tatgtctaga    360

tcaccatatt tgattaacaa tcagagatgg ggtcaaagaa tgggagatag tgaattagtt    420

gatgaaatga taaaggatgg tttgtgggat gcatttaatg gatatcatat gggagtaact    480

gcagaaaata ttgcagaaca atggaatata acaagagaag agcaagatga attttcactt    540

atgtcacaac aaaaagctga aaaagccatt aaaaatggag aatttaagga tgaaatagtt    600

cctgtattaa taaagactaa aaaaggtgaa atagtctttg atcaagatga atttcctaga    660

ttcggaaaca ctattgaagc attaagaaaa cttaaaccta ttttcaagga aaatggtact    720

gttacagcag gtaatgcatc cggattaaat gatggagctg cagcactagt aataatgagc    780

gctgataaag ctaacgctct cggaataaaa ccacttgcta agattacttc ttacggatca    840

tatggggtag atccatcaat aatgggatat ggagcttttt atgcaactaa agctgcctta    900

gataaaatta atttaaaacc tgaagactta gatttaattg aagctaacga ggcatatgct    960

tctcaaagta tagcagtaac tagagattta aatttagata tgagtaaagt taatgttaat   1020

ggtggagcta tagcacttgg acatccaata ggtgcatctg gtgcacgtat tttagtaaca   1080

ttactatacg ctatgcaaaa aagagattca aaaaaaggtc ttgctactct atgtattggt   1140

ggaggtcagg gaacagctct cgtagttgaa agagactaa                          1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390
```

<210> SEQ ID NO 5

-continued

<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt      60

gcagctaaag gatttgaagt agtattaaga gatattaaag atgaatttgt tgatagagga     120

ttagatttta tcaataaaaa tctttctaaa ttagttaaaa aaggaaagat agaagaagct     180

actaaagttg aaatcttaac tagaatttcc ggaacagttg accttaatat ggcagctgat     240

tgcgatttag ttatagaagc agctgttgaa agaatggata ttaaaaagca gatttttgct     300

gacttagaca atatatgcaa gccagaaaca attcttgcat caaatacatc atcactttca     360

ataacagaag tggcatcagc aactaaaaga cctgataagg ttataggtat gcatttcttt     420

aatccagctc ctgttatgaa gcttgtagag gtaataagag gaatagctac atcacaagaa     480

acttttgatg cagttaaaga gacatctata gcaataggaa aagatcctgt agaagtagca     540

gaagcaccag gatttgttgt aaatagaata ttaataccaa tgattaatga agcagttggt     600

atattagcag aaggaatagc ttcagtagaa gacatagata aagctatgaa acttggagct     660

aatcacccaa tgggaccatt agaattaggt gattttatag gtcttgatat atgtcttgct     720

ataatggatg ttttatactc agaaactgga gattctaagt atagaccaca tacattactt     780

aagaagtatg taagagcagg atggcttgga agaaaatcag gaaaaggttt ctacgattat     840

tcaaaataa                                                             849
```

<210> SEQ ID NO 6
<211> LENGTH: 282
<212> TYPE: PRT
<213> ORGANISM: Clostridium acetobutylicum

<400> SEQUENCE: 6

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190
```

-continued

```
Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280


<210> SEQ ID NO 7
<211> LENGTH: 786
<212> TYPE: DNA
<213> ORGANISM: Clostridium acetobutylicum

<400> SEQUENCE: 7

atggaactaa acaatgtcat ccttgaaaag gaaggtaaag ttgctgtagt taccattaac      60

agacctaaag cattaaatgc gttaaatagt gatacactaa aagaaatgga ttatgttata     120

ggtgaaattg aaaatgatag cgaagtactt gcagtaattt taactggagc aggagaaaaa     180

tcatttgtag caggagcaga tatttctgag atgaaggaaa tgaataccat tgaaggtaga     240

aaattcggga tacttggaaa taaagtgttt agaagattag aacttcttga aaagcctgta     300

atagcagctg ttaatggttt tgctttagga ggcggatgcg aaatagctat gtcttgtgat     360

ataagaatag cttcaagcaa cgcaagattt ggtcaaccag aagtaggtct cggaataaca     420

cctggttttg gtggtacaca aagactttca agattagttg gaatgggcat ggcaaagcag     480

cttatattta ctgcacaaaa tataaaggca gatgaagcat taagaatcgg acttgtaaat     540

aaggtagtag aacctagtga attaatgaat acagcaaaag aaattgcaaa caaaattgtg     600

agcaatgctc cagtagctgt taagttaagc aaacaggcta ttaatagagg aatgcagtgt     660

gatattgata ctgctttagc atttgaatca gaagcatttg gagaatgctt ttcaacagag     720

gatcaaaagg atgcaatgac agctttcata gagaaaagaa aaattgaagg cttcaaaaat     780

agatag                                                                786


<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95
```

```
Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260


<210> SEQ ID NO 9
<211> LENGTH: 1197
<212> TYPE: DNA
<213> ORGANISM: Clostridium acetobutylicum

<400> SEQUENCE: 9

atgatagtaa aagcaaagtt tgtaaaagga tttatcagag atgtacatcc ttatggttgc      60

agaagggaag tactaaatca aatagattat tgtaagaagg ctattgggtt taggggacca     120

aagaaggttt taattgttgg agcctcatct gggtttggtc ttgctactag aatttcagtt     180

gcatttggag gtccagaagc tcacacaatt ggagtatcct atgaaacagg agctacagat     240

agaagaatag gaacagcggg atggtataat aacatatttt ttaaagaatt tgctaaaaaa     300

aaaggattag ttgcaaaaaa cttcattgag gatgcctttt ctaatgaaac caaagataaa     360

gttattaagt atataaagga tgaatttggt aaaatagatt tatttgttta tagtttagct     420

gcgcctagga gaaaggacta taaaactgga aatgtttata cttcaagaat aaaaacaatt     480

ttaggagatt ttgagggacc gactattgat gttgaaagag acgagattac tttaaaaaag     540

gttagtagtg ctagcattga agaaattgaa gaaactagaa aggtaatggg tggagaggat     600

tggcaagagt ggtgtgaaga gctgctttat gaagattgtt tttcggataa agcaactacc     660

atagcatact cgtatatagg atccccaaga acctacaaga tatatagaga aggtactata     720

ggaatagcta aaaaggatct tgaagataag gctaagctta taaatgaaaa acttaacaga     780

gttataggtg gtagagcctt tgtgtctgtg aataaagcat tagttacaaa agcaagtgca     840

tatattccaa cttttcctct ttatgcagct attttatata aggtcatgaa agaaaaaaat     900

attcatgaaa attgtattat gcaaattgag agaatgtttt ctgaaaaaat atattcaaat     960

gaaaaaatac aatttgatga caagggaaga ttaaggatgg acgatttaga gcttagaaaa    1020

gacgttcaag acgaagttga tagaatatgg agtaatatta ctcctgaaaa ttttaaggaa    1080

ttatctgatt ataagggata caaaaaagaa ttcatgaact taaacggttt tgatctagat    1140

ggggttgatt atagtaaaga cctggatata gaattattaa gaaaattaga accttaa       1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380
```

-continued

Ser Lys Asp Leu Asp Ile Glu Leu Leu Arg Lys Leu Glu Pro
385 390 395

<210> SEQ ID NO 11
<211> LENGTH: 1407
<212> TYPE: DNA
<213> ORGANISM: Clostridium beijerinckii

<400> SEQUENCE: 11
atgaataaag acacactaat acctacaact aaagatttaa aagtaaaaac aaatggtgaa 60
aacattaatt taaagaacta caaggataat tcttcatgtt tcggagtatt cgaaaatgtt 120
gaaaatgcta taagcagcgc tgtacacgca caaaagatat tatcccttca ttatacaaaa 180
gagcaaagag aaaaaatcat aactgagata agaaaggccg cattacaaaa taaagaggtc 240
ttggctacaa tgattctaga agaaacacat atgggaagat atgaggataa aatattaaaa 300
catgaattgg tagctaaata tactcctggt acagaagatt taactactac tgcttggtca 360
ggtgataatg gtcttacagt tgtagaaatg tctccatatg gtgttatagg tgcaataact 420
ccttctacga atccaactga aactgtaata tgtaatagca taggcatgat agctgctgga 480
aatgctgtag tatttaacgg acacccatgc gctaaaaaat gtgttgcctt tgctgttgaa 540
atgataaata aggcaattat ttcatgtggc ggtcctgaaa atctagtaac aactataaaa 600
aatccaacta tggagtctct agatgcaatt attaagcatc cttcaataaa acttctttgc 660
ggaactgggg gtccaggaat ggtaaaaacc ctcttaaatt ctggtaagaa agctataggt 720
gctggtgctg gaaatccacc agttattgta gatgatactg ctgatataga aaaggctggt 780
aggagcatca ttgaaggctg ttcttttgat aataatttac cttgtattgc agaaaaagaa 840
gtatttgttt ttgagaatgt tgcagatgat ttaatatcta acatgctaaa aaataatgct 900
gtaattataa atgaagatca agtatcaaaa ttaatagatt tagtattaca aaaaaataat 960
gaaactcaag aatactttat aaacaaaaaa tgggtaggaa aagatgcaaa attattctta 1020
gatgaaatag atgttgagtc tccttcaaat gttaaatgca taatctgcga agtaaatgca 1080
aatcatccat ttgttatgac agaactcatg atgccaatat tgccaattgt aagagttaaa 1140
gatatagatg aagctattaa atatgcaaag atagcagaac aaaatagaaa acatagtgcc 1200
tatatttatt ctaaaaatat agacaaccta aatagatttg aaagagaaat agatactact 1260
atttttgtaa agaatgctaa atcttttgct ggtgttggtt atgaagcaga aggatttaca 1320
actttcacta ttgctggatc tactggtgag ggaataacct ctgcaaggaa ttttacaaga 1380
caaagaagat gtgtacttgc cggctaa 1407

<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1 5 10 15

Thr Asn Gly Glu Asn Ile Asn Leu Lys Asn Tyr Lys Asp Asn Ser Ser
20 25 30

Cys Phe Gly Val Phe Glu Asn Val Glu Asn Ala Ile Ser Ser Ala Val
35 40 45

His Ala Gln Lys Ile Leu Ser Leu His Tyr Thr Lys Glu Gln Arg Glu
50 55 60

```
Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465
```

<210> SEQ ID NO 13

<211> LENGTH: 1215
<212> TYPE: DNA
<213> ORGANISM: Clostridium acetobutylicum

<400> SEQUENCE: 13

```
atggttgatt tcgaatattc aataccaact agaatttttt tcggtaaaga taagataaat     60

gtacttggaa gagagcttaa aaaatatggt tctaaagtgc ttatagttta tggtggagga    120

agtataaaga gaaatggaat atatgataaa gctgtaagta tacttgaaaa aaacagtatt    180

aaattttatg aacttgcagg agtagagcca aatccaagag taactacagt tgaaaaagga    240

gttaaaatat gtagagaaaa tggagttgaa gtagtactag ctataggtgg aggaagtgca    300

atagattgcg caaaggttat agcagcagca tgtgaatatg atggaaatcc atgggatatt    360

gtgttagatg gctcaaaaat aaaaagggtg cttcctatag ctagtatatt aaccattgct    420

gcaacaggat cagaaatgga tacgtgggca gtaataaata atatggatac aaacgaaaaa    480

ctaattgcgg cacatccaga tatggctcct aagttttcta tattagatcc aacgtatacg    540

tataccgtac ctaccaatca aacagcagca ggaacagctg atattatgag tcatatattt    600

gaggtgtatt ttagtaatac aaaaaacagca tatttgcagg atagaatggc agaagcgtta    660

ttaagaactt gtattaaata tggaggaata gctcttgaga agccggatga ttatgaggca    720

agagccaatc taatgtgggc ttcaagtctt gcgataaatg gacttttaac atatggtaaa    780

gacactaatt ggagtgtaca cttaatggaa catgaattaa gtgcttatta cgacataaca    840

cacggcgtag ggcttgcaat tttaacacct aattggatgg agtatatttt aaataatgat    900

acagtgtaca agtttgttga atatggtgta aatgtttggg gaatagacaa agaaaaaaat    960

cactatgaca tagcacatca agcaatacaa aaaacaagag attactttgt aaatgtacta   1020

ggtttaccat ctagactgag agatgttgga attgaagaag aaaaattgga cataatggca   1080

aaggaatcag taaagcttac aggaggaacc ataggaaacc taagaccagt aaacgcctcc   1140

gaagtcctac aaatattcaa aaaatctgtg taaaacgcct ccgaagtcct acaaatattc   1200

aaaaaatctg tgtaa                                                    1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125
```

-continued

```
Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390
```

<210> SEQ ID NO 15
<211> LENGTH: 1170
<212> TYPE: DNA
<213> ORGANISM: Clostridium acetobutylicum

<400> SEQUENCE: 15

```
atgctaagtt ttgattattc aataccaact aaagtttttt ttggaaaagg aaaaatagac      60

gtaattggag aagaaattaa gaaatatggc tcaagagtgc ttatagttta tggcggagga     120

agtataaaaa ggaacggtat atatgataga gcaacagcta tattaaaaga aaacaatata     180

gctttctatg aactttcagg agtagagcca aatcctagga taacaacagt aaaaaaaggc     240

atagaaatat gtagagaaaa taatgtggat ttagtattag caatagggggg aggaagtgca     300

atagactgtt ctaaggtaat tgcagctgga gtttattatg atggcgatac atgggacatg     360

gttaaagatc catctaaaat aactaaagtt cttccaattg caagtatact tactctttca     420

gcaacagggt ctgaaatgga tcaaattgca gtaatttcaa atatggagac taatgaaaag     480

cttggagtag gacatgatga tatgagacct aaattttcag tgttagatcc tacatatact     540

tttacagtac ctaaaaatca aacagcagcg ggaacagctg acattatgag tcacaccttt     600

gaatcttact ttagtggtgt tgaaggtgct tatgtgcagg acggtatagc agaagcaatc     660
```

-continued

```
ttaagaacat gtataaagta tggaaaaata gcaatggaga agactgatga ttacgaggct     720

agagctaatt tgatgtgggc ttcaagttta gctataaatg gtctattatc acttggtaag     780

gatagaaaat ggagttgtca tcctatggaa cacgagttaa gtgcatatta tgatataaca     840

catggtgtag gacttgcaat tttaacacct aattggatgg aatatattct aaatgacgat     900

acacttcata aatttgtttc ttatggaata aatgtttggg gaatagacaa gaacaaagat     960

aactatgaaa tagcacgaga ggctattaaa aatacgagag aatactttaa ttcattgggt    1020

attccttcaa agcttagaga agttggaata ggaaaagata aactagaact aatggcaaag    1080

caagctgtta gaaattctgg aggaacaata ggaagtttaa gaccaataaa tgcagaggat    1140

gttcttgaga tatttaaaaa atcttattaa                                     1170


<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285
```

Thr Pro Asn Trp Met Glu Tyr Ile Leu Asn Asp Asp Thr Leu His Lys
290 295 300

Phe Val Ser Tyr Gly Ile Asn Val Trp Gly Ile Asp Lys Asn Lys Asp
305 310 315 320

Asn Tyr Glu Ile Ala Arg Glu Ala Ile Lys Asn Thr Arg Glu Tyr Phe
325 330 335

Asn Ser Leu Gly Ile Pro Ser Lys Leu Arg Glu Val Gly Ile Gly Lys
340 345 350

Asp Lys Leu Glu Leu Met Ala Lys Gln Ala Val Arg Asn Ser Gly Gly
355 360 365

Thr Ile Gly Ser Leu Arg Pro Ile Asn Ala Glu Asp Val Leu Glu Ile
370 375 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt 60
tccgcgcagc atcccgagag cgtgctctat cagacatcgc tcatgagcgc cctgctgagc 120
ggggtttacg aaggcagcac caccatcgcg gacctgctga aacacggcga tttcggcctc 180
ggcaccttta atgagctgga cggggagctg atcgccttca gcagtcaggt ctatcagctg 240
cgcgccgacg gcagcgcgcg caaagcccag ccggagcaga aaacgccgtt cgcggtgatg 300
acctggttcc agccgcagta ccggaaaacc tttgaccatc cggtgagccg ccagcagctg 360
cacgaggtga tcgaccagca aatcccctct gacaacctgt tctgcgccct gcgcatcgac 420
ggccatttcc gccatgccca tacccgcacc gtgccgcgcc agacgccgcc gtaccgggcg 480
atgaccgacg tcctcgacga tcagccggtg ttccgcttta accagcgcga aggggtgctg 540
gtcggcttcc ggaccccgca gcatatgcag gggatcaacg tcgccgggta tcacgagcac 600
tttattaccg atgaccgcaa aggcggcggt cacctgctgg attaccagct cgaccatggg 660
gtgctgacct tcggcgaaat tcacaagctg atgatcgacc tgcccgccga cagcgcgttc 720
ctgcaggcta atctgcatcc cgataatctc gatgccgcca tccgttccgt agaaagttaa 780

<210> SEQ ID NO 18
<211> LENGTH: 259
<212> TYPE: PRT
<213> ORGANISM: Klebsiella pneumoniae

<400> SEQUENCE: 18

Met Asn His Ser Ala Glu Cys Thr Cys Glu Glu Ser Leu Cys Glu Thr
1 5 10 15

Leu Arg Ala Phe Ser Ala Gln His Pro Glu Ser Val Leu Tyr Gln Thr
20 25 30

Ser Leu Met Ser Ala Leu Leu Ser Gly Val Tyr Glu Gly Ser Thr Thr
35 40 45

Ile Ala Asp Leu Leu Lys His Gly Asp Phe Gly Leu Gly Thr Phe Asn
50 55 60

Glu Leu Asp Gly Glu Leu Ile Ala Phe Ser Ser Gln Val Tyr Gln Leu
65 70 75 80

Arg Ala Asp Gly Ser Ala Arg Lys Ala Gln Pro Glu Gln Lys Thr Pro

-continued

```
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag     60

ctggaagctc agggagtacg ccaggtgttc ggcatccccg gcgccaaaat tgacaaggtc    120

ttcgactcac tgctggattc ctcgattcgc attattccgg tacgccacga agccaacgcc    180

gcgtttatgg ccgccgccgt cggacgcatt accggcaaag cgggcgtggc gctggtcacc    240

tccggtccgg gctgttccaa cctgatcacc ggcatggcca ccgcgaacag cgaaggcgac    300

ccggtggtgg ccctgggcgg cgcggtaaaa cgcgccgata aagcgaagca ggtccaccag    360

agtatggata cggtggcgat gttcagcccg gtcaccaaat acgccgtcga ggtgacggcg    420

ccggatgcgc tggcggaagt ggtctccaac gccttccgcg ccgccgagca gggccggccg    480

ggcagcgcgt tcgttagcct gccgcaggat gtggtcgatg gcccggtcag cggcaaagtg    540

ctgccggcca gcggggcccc gcagatgggc gccgcgccgg atgatgccat cgaccaggtg    600

gcgaagctta tcgcccaggc gaagaacccg atcttcctgc tcggcctgat ggccagccag    660

ccggaaaaca gcaaggcgct gcgccgtttg ctggagacca gccatattcc agtcaccagc    720

acctatcagg ccgccggagc ggtgaatcag gataacttct ctcgcttcgc cggccgggtt    780

gggctgttta acaaccaggc cggggaccgt ctgctgcagc tcgccgacct ggtgatctgc    840

atcggctaca gcccggtgga atacgaaccg gcgatgtgga acagcggcaa cgcgacgctg    900

gtgcacatcg acgtgctgcc cgcctatgaa gagcgcaact acaccccgga tgtcgagctg    960

gtgggcgata tcgccggcac tctcaacaag ctggcgcaaa atatcgatca tcggctggtg   1020

ctctccccgc aggcggcgga gatcctccgc gaccgccagc accagcgcga gctgctggac   1080

cgccgcggcg cgcagctgaa ccagtttgcc ctgcatccgc tgcgcatcgt tcgcgccatg   1140
```

-continued

```
caggacatcg tcaacagcga cgtcacgttg accgtggaca tgggcagctt ccatatctgg   1200

attgcccgct acctgtacag cttccgcgcc cgtcaggtga tgatctccaa cggccagcag   1260

accatgggcg tcgccctgcc ctgggctatc ggcgcctggc tggtcaatcc tgagcgaaaa   1320

gtggtctccg tctccggcga cggcggcttc ctgcagtcga gcatggagct ggagaccgcc   1380

gtccgcctga aagccaacgt actgcacctg atctgggtcg ataacggcta caacatggtg   1440

gccattcagg aagagaaaaa ataccagcgc ctgtccggcg tcgagttcgg gccgatggat   1500

tttaaagcct atgccgaatc cttcggcgcg aaagggtttg ccgtggaaag cgccgaggcg   1560

ctggagccga ccctgcacgc ggcgatggac gtcgacggcc cggcggtggt ggccattccg   1620

gtggattatc gcgataaccc gctgctgatg ggccagctgc atctgagtca gattctgtaa   1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285
```

-continued

```
Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555
```

<210> SEQ ID NO 21
<211> LENGTH: 771
<212> TYPE: DNA
<213> ORGANISM: Klebsiella pneumoniae

<400> SEQUENCE: 21

```
atgaaaaaag tcgcacttgt taccggcgcc ggccagggga ttggtaaagc tatcgccctt      60

cgtctggtga aggatggatt tgccgtggcc attgccgatt ataacgacgc caccgccaaa     120

gcggtcgcct cggaaatcaa ccaggccggc ggacacgccg tggcggtgaa agtggatgtc     180

tccgaccgcg atcaggtatt tgccgccgtt gaacaggcgc gcaaaacgct gggcggcttc     240

gacgtcatcg tcaataacgc cggtgtggca ccgtctacgc cgatcgagtc cattaccccg     300

gagattgtcg acaaagtcta caacatcaac gtcaaagggg tgatctgggg tattcaggcg     360

gcggtcgagg cctttaagaa agaggggcac ggcgggaaaa tcatcaacgc ctgttcccag     420

gccggccacg tcggcaaccc ggagctggcg gtgtatagct ccagtaaatt cgcggtacgc     480

ggcttaaccc agaccgccgc tcgcgacctc gcgccgctgg gcatcacggt caacggctac     540

tgcccgggga ttgtcaaaac gccaatgtgg gccgaaattg accgccaggt gtccgaagcc     600

gccggtaaac cgctgggcta cggtaccgcc gagttcgcca aacgcatcac tctcggtcgt     660
```

ctgtccgagc cggaagatgt cgccgcctgc gtctcctatc ttgccagccc ggattctgat 720
tacatgaccg gtcagtcgtt gctgatcgac ggcgggatgg tatttaacta a 771

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1 5 10 15

Ala Ile Ala Leu Arg Leu Val Lys Asp Gly Phe Ala Val Ala Ile Ala
20 25 30

Asp Tyr Asn Asp Ala Thr Ala Lys Ala Val Ala Ser Glu Ile Asn Gln
35 40 45

Ala Gly Gly His Ala Val Ala Val Lys Val Asp Val Ser Asp Arg Asp
50 55 60

Gln Val Phe Ala Ala Val Glu Gln Ala Arg Lys Thr Leu Gly Gly Phe
65 70 75 80

Asp Val Ile Val Asn Asn Ala Gly Val Ala Pro Ser Thr Pro Ile Glu
85 90 95

Ser Ile Thr Pro Glu Ile Val Asp Lys Val Tyr Asn Ile Asn Val Lys
100 105 110

Gly Val Ile Trp Gly Ile Gln Ala Ala Val Glu Ala Phe Lys Lys Glu
115 120 125

Gly His Gly Gly Lys Ile Ile Asn Ala Cys Ser Gln Ala Gly His Val
130 135 140

Gly Asn Pro Glu Leu Ala Val Tyr Ser Ser Ser Lys Phe Ala Val Arg
145 150 155 160

Gly Leu Thr Gln Thr Ala Ala Arg Asp Leu Ala Pro Leu Gly Ile Thr
165 170 175

Val Asn Gly Tyr Cys Pro Gly Ile Val Lys Thr Pro Met Trp Ala Glu
180 185 190

Ile Asp Arg Gln Val Ser Glu Ala Ala Gly Lys Pro Leu Gly Tyr Gly
195 200 205

Thr Ala Glu Phe Ala Lys Arg Ile Thr Leu Gly Arg Leu Ser Glu Pro
210 215 220

Glu Asp Val Ala Ala Cys Val Ser Tyr Leu Ala Ser Pro Asp Ser Asp
225 230 235 240

Tyr Met Thr Gly Gln Ser Leu Leu Ile Asp Gly Gly Met Val Phe Asn
245 250 255

<210> SEQ ID NO 23
<211> LENGTH: 1665
<212> TYPE: DNA
<213> ORGANISM: Klebsiella oxytoca

<400> SEQUENCE: 23
atgagatcga aaagatttga agcactggcg aaacgccctg tgaatcagga cggcttcgtt 60
aaggagtgga tcgaagaagg ctttatcgcg atggaaagcc cgaacgaccc aaaaccgtcg 120
attaaaatcg ttaacggcgc ggtgaccgag ctggacggga aaccggtaag cgattttgac 180
ctgatcgacc actttatcgc ccgctacggt atcaacctga accgcgccga agaagtgatg 240
gcgatggatt cggtcaagct ggccaacatg ctgtgcgatc cgaacgttaa acgcagcgaa 300
atcgtcccgc tgaccaccgc gatgacgccg gcgaaaattg tcgaagtggt ttcgcatatg 360

```
aacgtcgtcg agatgatgat ggcgatgcag aaaatgcgcg cccgccgcac cccgtcccag    420

caggcgcacg tcaccaacgt caaagataac ccggtacaga ttgccgccga cgccgccgaa    480

ggggcatggc gcggatttga cgaacaggaa accaccgttg cggtagcgcg ctatgcgccg    540

ttcaacgcca tcgcgctgct ggtgggctcg caggtaggcc gtccgggcgt gctgacgcag    600

tgctcgctgg aagaagccac cgagctgaag ctcggcatgc tgggccacac ctgctacgcc    660

gaaaccatct ccgtctacgg caccgagccg gtctttaccg acggcgacga cacgccgtgg    720

tcgaagggct tcctcgcctc gtcctacgcc tctcgcgggc tgaaaatgcg ctttacctcc    780

ggctccggct cggaagtgca gatgggctac gccgaaggca aatccatgct ttatctggaa    840

gcgcgctgca tctacatcac caaagccgcg ggcgtacagg gtctgcaaaa cggttccgta    900

agctgcatcg gcgtgccgtc tgcggtgcct tccggcattc gcgcggtgct ggcggaaaac    960

ctgatctgtt cgtcgctgga tctggagtgc gcctccagca acgaccagac cttcacccac   1020

tccgatatgc gtcgtaccgc gcgcctgctg atgcagttcc tgccgggcac cgactttatc   1080

tcctccggtt attccgcggt gccgaactac gacaacatgt tcgccggctc caacgaagat   1140

gccgaagact ttgacgacta caacgtcatc cagcgcgacc tgaaggtgga cggcggtttg   1200

cgtccggttc gcgaagagga cgtcatcgcc atccgtaaca aagccgcccg cgcgctgcag   1260

gccgtgtttg ccggaatggg gctgccgccg attaccgatg aagaagttga agccgcgacc   1320

tacgcccacg gttcgaaaga tatgccggag cgcaacatcg tcgaagacat caagttcgcc   1380

caggaaatca tcaataaaaa ccgcaacggt ctggaagtgg tgaaagcgct ggcgcagggc   1440

ggattcaccg acgtggccca ggacatgctc aacatccaga aagctaagct gaccggggac   1500

tacctgcata cctccgcgat tatcgtcggc gacgggcagg tgctgtcagc cgtcaacgac   1560

gtcaacgact atgccggtcc ggcaacgggc tatcgcctgc agggcgaacg ctgggaagag   1620

attaaaaaca tccctggcgc tcttgatccc aacgagattg attaa                   1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140
```

-continued

Thr Asn Val Lys Asp Asn Pro Val Gln Ile Ala Ala Asp Ala Ala Glu
145 150 155 160

Gly Ala Trp Arg Gly Phe Asp Glu Gln Glu Thr Thr Val Ala Val Ala
165 170 175

Arg Tyr Ala Pro Phe Asn Ala Ile Ala Leu Leu Val Gly Ser Gln Val
180 185 190

Gly Arg Pro Gly Val Leu Thr Gln Cys Ser Leu Glu Glu Ala Thr Glu
195 200 205

Leu Lys Leu Gly Met Leu Gly His Thr Cys Tyr Ala Glu Thr Ile Ser
210 215 220

Val Tyr Gly Thr Glu Pro Val Phe Thr Asp Gly Asp Asp Thr Pro Trp
225 230 235 240

Ser Lys Gly Phe Leu Ala Ser Ser Tyr Ala Ser Arg Gly Leu Lys Met
245 250 255

Arg Phe Thr Ser Gly Ser Gly Ser Glu Val Gln Met Gly Tyr Ala Glu
260 265 270

Gly Lys Ser Met Leu Tyr Leu Glu Ala Arg Cys Ile Tyr Ile Thr Lys
275 280 285

Ala Ala Gly Val Gln Gly Leu Gln Asn Gly Ser Val Ser Cys Ile Gly
290 295 300

Val Pro Ser Ala Val Pro Ser Gly Ile Arg Ala Val Leu Ala Glu Asn
305 310 315 320

Leu Ile Cys Ser Ser Leu Asp Leu Glu Cys Ala Ser Ser Asn Asp Gln
325 330 335

Thr Phe Thr His Ser Asp Met Arg Arg Thr Ala Arg Leu Leu Met Gln
340 345 350

Phe Leu Pro Gly Thr Asp Phe Ile Ser Ser Gly Tyr Ser Ala Val Pro
355 360 365

Asn Tyr Asp Asn Met Phe Ala Gly Ser Asn Glu Asp Ala Glu Asp Phe
370 375 380

Asp Asp Tyr Asn Val Ile Gln Arg Asp Leu Lys Val Asp Gly Gly Leu
385 390 395 400

Arg Pro Val Arg Glu Glu Asp Val Ile Ala Ile Arg Asn Lys Ala Ala
405 410 415

Arg Ala Leu Gln Ala Val Phe Ala Gly Met Gly Leu Pro Pro Ile Thr
420 425 430

Asp Glu Glu Val Glu Ala Ala Thr Tyr Ala His Gly Ser Lys Asp Met
435 440 445

Pro Glu Arg Asn Ile Val Glu Asp Ile Lys Phe Ala Gln Glu Ile Ile
450 455 460

Asn Lys Asn Arg Asn Gly Leu Glu Val Val Lys Ala Leu Ala Gln Gly
465 470 475 480

Gly Phe Thr Asp Val Ala Gln Asp Met Leu Asn Ile Gln Lys Ala Lys
485 490 495

Leu Thr Gly Asp Tyr Leu His Thr Ser Ala Ile Ile Val Gly Asp Gly
500 505 510

Gln Val Leu Ser Ala Val Asn Asp Val Asn Asp Tyr Ala Gly Pro Ala
515 520 525

Thr Gly Tyr Arg Leu Gln Gly Glu Arg Trp Glu Glu Ile Lys Asn Ile
530 535 540

Pro Gly Ala Leu Asp Pro Asn Glu Ile Asp
545 550

<210> SEQ ID NO 25

<211> LENGTH: 675
<212> TYPE: DNA
<213> ORGANISM: Klebsiella oxytoca

<400> SEQUENCE: 25

```
atggaaatta atgaaaaatt gctgcgccag ataattgaag acgtgctcag cgagatgaag      60

ggcagcgata aaccggtctc gtttaatgcg ccggcggcct ccgcggcgcc ccaggccacg     120

ccgcccgccg gcgacggctt cctgacggaa gtgggcgaag cgcgtcaggg aacccagcag     180

gacgaagtga ttatcgccgt cggcccggct ttcggcctgg cgcagaccgt caatatcgtc     240

ggcatcccgc ataagagcat tttgcgcgaa gtcattgccg gtattgaaga agaaggcatt     300

aaggcgcgcg tgattcgctg ctttaaatcc tccgacgtgg ccttcgtcgc cgttgaaggt     360

aatcgcctga gcggctccgg catctctatc ggcatccagt cgaaaggcac cacggtgatc     420

caccagcagg ggctgccgcc gctctctaac ctggagctgt tcccgcaggc gccgctgctg     480

accctggaaa cctatcgcca gatcggcaaa aacgccgccc gctatgcgaa acgcgaatcg     540

ccgcagccgg tcccgacgct gaatgaccag atggcgcggc cgaagtacca ggcgaaatcg     600

gccattttgc acattaaaga gaccaagtac gtggtgacgg gcaaaaaccc gcaggaactg     660

cgcgtggcgc tttga                                                      675
```

<210> SEQ ID NO 26
<211> LENGTH: 224
<212> TYPE: PRT
<213> ORGANISM: Klebsiella oxytoca

<400> SEQUENCE: 26

```
Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg 60
cagggcgagg cgcctgcggc ggctccggcg gctggcggcg cgtcccgtag cgccagggtc 120
agcgactacc cgctggcgaa caagcacccg gaatgggtga aaaccgccac caataaaacg 180
ctggacgact ttacgctgga aaacgtgctg agcaataaag tcaccgccca ggatatgcgt 240
attaccccgg aaaccctgcg cttacaggct tctattgcca aagacgcggg ccgcgaccgg 300
ctggcgatga acttcgagcg cgccgccgag ctgaccgcgg taccggacga tcgcattctt 360
gaaatctaca acgccctccg cccctatcgc tcgacgaaag aggagctgct ggcgatcgcc 420
gacgatctcg aaagccgcta tcaggcgaag atttgcgccg ctttcgttcg cgaagcggcc 480
acgctgtacg tcgagcgtaa aaaactcaaa ggcgacgatt aa 522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1 5 10 15

Met Asn Ser Leu Gln Gly Glu Ala Pro Ala Ala Ala Pro Ala Ala Gly
20 25 30

Gly Ala Ser Arg Ser Ala Arg Val Ser Asp Tyr Pro Leu Ala Asn Lys
35 40 45

His Pro Glu Trp Val Lys Thr Ala Thr Asn Lys Thr Leu Asp Asp Phe
50 55 60

Thr Leu Glu Asn Val Leu Ser Asn Lys Val Thr Ala Gln Asp Met Arg
65 70 75 80

Ile Thr Pro Glu Thr Leu Arg Leu Gln Ala Ser Ile Ala Lys Asp Ala
85 90 95

Gly Arg Asp Arg Leu Ala Met Asn Phe Glu Arg Ala Ala Glu Leu Thr
100 105 110

Ala Val Pro Asp Asp Arg Ile Leu Glu Ile Tyr Asn Ala Leu Arg Pro
115 120 125

Tyr Arg Ser Thr Lys Glu Glu Leu Leu Ala Ile Ala Asp Asp Leu Glu
130 135 140

Ser Arg Tyr Gln Ala Lys Ile Cys Ala Ala Phe Val Arg Glu Ala Ala
145 150 155 160

Thr Leu Tyr Val Glu Arg Lys Lys Leu Lys Gly Asp Asp
165 170

<210> SEQ ID NO 29
<211> LENGTH: 1041
<212> TYPE: DNA
<213> ORGANISM: Rhodococcus ruber

<400> SEQUENCE: 29
atgaaagccc tccagtacac cgagatcggc tccgagccgg tcgtcgtcga cgtccccacc 60
ccggcgcccg ggccgggtga gatcctgctg aaggtcaccg cggccggctt gtgccactcg 120
gacatcttcg tgatggacat gccggcagag cagtacatct acggtcttcc cctcaccctc 180

```
ggccacgagg gcgtcggcac cgtcgccgaa ctcggcgccg gcgtcaccgg attcgagacg     240

ggggacgccg tcgccgtgta cgggccgtgg gggtgcggtg cgtgccacgc gtgcgcgcgc     300

ggccgggaga actactgcac ccgcgccgcc gagctgggca tcaccccgcc cggtctcggc     360

tcgcccgggt cgatggccga gtacatgatc gtcgactcgg cgcgccacct cgtcccgatc     420

ggggacctcg accccgtcgc ggcggttccg ctcaccgacg cgggcctgac gccgtaccac     480

gcgatctcgc gggtcctgcc cctgctggga cccggctcga ccgcggtcgt catcggggtc     540

ggcggactcg ggcacgtcgg catccagatc ctgcgcgccg tcagcgcggc ccgcgtgatc     600

gccgtcgatc tcgacgacga ccgactcgcg ctcgcccgcg aggtcggcgc cgacgcggcg     660

gtgaagtcgg gcgccggggc ggcggacgcg atccgggagc tgaccggcgg tgagggcgcg     720

acggcggtgt tcgacttcgt cggcgcccag tcgacgatcg acacggcgca gcaggtggtc     780

gcgatcgacg ggcacatctc ggtggtcggc atccatgccg gcgcccacgc caaggtcggc     840

ttcttcatga tcccgttcgg cgcgtccgtc gtgacgccgt actggggcac gcggtccgag     900

ctgatggacg tcgtggacct ggcccgtgcc ggccggctcg acatccacac cgagacgttc     960

accctcgacg agggacccac ggcctaccgg cggctacgcg agggcagcat ccgcggccgc    1020

ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220
```

```
Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345


<210> SEQ ID NO 31
<211> LENGTH: 1476
<212> TYPE: DNA
<213> ORGANISM: Escherichia coli

<400> SEQUENCE: 31

atggctaact acttcaatac actgaatctg cgccagcagc tggcacagct gggcaaatgt      60

cgctttatgg gccgcgatga attcgccgat ggcgcgagct accttcaggg taaaaaagta     120

gtcatcgtcg gctgtggcgc acagggtctg aaccagggcc tgaacatgcg tgattctggt     180

ctcgatatct cctacgctct gcgtaaagaa gcgattgccg agaagcgcgc gtcctggcgt     240

aaagcgaccg aaaatggttt taaagtgggt acttacgaag aactgatccc acaggcggat     300

ctggtgatta acctgacgcc ggacaagcag cactctgatg tagtgcgcac cgtacagcca     360

ctgatgaaag acggcgcggc gctgggctac tcgcacggtt tcaacatcgt cgaagtgggc     420

gagcagatcc gtaaagatat caccgtagtg atggttgcgc cgaaatgccc aggcaccgaa     480

gtgcgtgaag agtacaaacg tgggttcggc gtaccgacgc tgattgccgt tcacccggaa     540

aacgatccga aaggcgaagg catggcgatt gccaaagcct gggcggctgc aaccggtggt     600

caccgtgcgg gtgtgctgga atcgtccttc gttgcggaag tgaaatctga cctgatgggc     660

gagcaaacca tcctgtgcgg tatgttgcag gctggctctc tgctgtgctt cgacaagctg     720

gtggaagaag gtaccgatcc agcatacgca gaaaaactga ttcagttcgg ttgggaaacc     780

atcaccgaag cactgaaaca gggcggcatc accctgatga tggaccgtct ctctaacccg     840

gcgaaactgc gtgcttatgc gctttctgaa cagctgaaag agatcatggc accccctgttc     900

cagaaacata tggacgacat catctccggc gaattctctt ccggtatgat ggcggactgg     960

gccaacgatg ataagaaact gctgacctgg cgtgaagaga ccggcaaaac cgcgtttgaa    1020

accgcgccgc agtatgaagg caaaatcggc gagcaggagt acttcgataa aggcgtactg    1080

atgattgcga tggtgaaagc gggcgttgaa ctggcgttcg aaaccatggt cgattccggc    1140

atcattgaag agtctgcata ttatgaatca ctgcacgagc tgccgctgat tgccaacacc    1200

atcgcccgta agcgtctgta cgaaatgaac gtggttatct ctgataccgc tgagtacggt    1260

aactatctgt tctcttacgc ttgtgtgccg ttgctgaaac cgtttatggc agagctgcaa    1320

ccgggcgacc tgggtaaagc tattccggaa ggcgcggtag ataacgggca actgcgtgat    1380

gtgaacgaag cgattcgcag ccatgcgatt gagcaggtag gtaagaaact gcgcggctat    1440
```

atgacagata tgaaacgtat tgctgttgcg ggttaa 1476

<210> SEQ ID NO 32
<211> LENGTH: 491
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1 5 10 15

Leu Gly Lys Cys Arg Phe Met Gly Arg Asp Glu Phe Ala Asp Gly Ala
20 25 30

Ser Tyr Leu Gln Gly Lys Lys Val Val Ile Val Gly Cys Gly Ala Gln
35 40 45

Gly Leu Asn Gln Gly Leu Asn Met Arg Asp Ser Gly Leu Asp Ile Ser
50 55 60

Tyr Ala Leu Arg Lys Glu Ala Ile Ala Glu Lys Arg Ala Ser Trp Arg
65 70 75 80

Lys Ala Thr Glu Asn Gly Phe Lys Val Gly Thr Tyr Glu Glu Leu Ile
85 90 95

Pro Gln Ala Asp Leu Val Ile Asn Leu Thr Pro Asp Lys Gln His Ser
100 105 110

Asp Val Val Arg Thr Val Gln Pro Leu Met Lys Asp Gly Ala Ala Leu
115 120 125

Gly Tyr Ser His Gly Phe Asn Ile Val Glu Val Gly Glu Gln Ile Arg
130 135 140

Lys Asp Ile Thr Val Val Met Val Ala Pro Lys Cys Pro Gly Thr Glu
145 150 155 160

Val Arg Glu Glu Tyr Lys Arg Gly Phe Gly Val Pro Thr Leu Ile Ala
165 170 175

Val His Pro Glu Asn Asp Pro Lys Gly Glu Gly Met Ala Ile Ala Lys
180 185 190

Ala Trp Ala Ala Ala Thr Gly Gly His Arg Ala Gly Val Leu Glu Ser
195 200 205

Ser Phe Val Ala Glu Val Lys Ser Asp Leu Met Gly Glu Gln Thr Ile
210 215 220

Leu Cys Gly Met Leu Gln Ala Gly Ser Leu Leu Cys Phe Asp Lys Leu
225 230 235 240

Val Glu Glu Gly Thr Asp Pro Ala Tyr Ala Glu Lys Leu Ile Gln Phe
245 250 255

Gly Trp Glu Thr Ile Thr Glu Ala Leu Lys Gln Gly Gly Ile Thr Leu
260 265 270

Met Met Asp Arg Leu Ser Asn Pro Ala Lys Leu Arg Ala Tyr Ala Leu
275 280 285

Ser Glu Gln Leu Lys Glu Ile Met Ala Pro Leu Phe Gln Lys His Met
290 295 300

Asp Asp Ile Ile Ser Gly Glu Phe Ser Ser Gly Met Met Ala Asp Trp
305 310 315 320

Ala Asn Asp Asp Lys Lys Leu Leu Thr Trp Arg Glu Glu Thr Gly Lys
325 330 335

Thr Ala Phe Glu Thr Ala Pro Gln Tyr Glu Gly Lys Ile Gly Glu Gln
340 345 350

Glu Tyr Phe Asp Lys Gly Val Leu Met Ile Ala Met Val Lys Ala Gly
355 360 365

-continued

```
Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490


<210> SEQ ID NO 33
<211> LENGTH: 1851
<212> TYPE: DNA
<213> ORGANISM: Escherichia coli

<400> SEQUENCE: 33

atgcctaagt accgttccgc caccaccact catggtcgta atatggcggg tgctcgtgcg      60

ctgtggcgcg ccaccggaat gaccgacgcc gatttcggta agccgattat cgcggttgtg     120

aactcgttca cccaatttgt accgggtcac gtccatctgc gcgatctcgg taaactggtc     180

gccgaacaaa ttgaagcggc tggcggcgtt gccaaagagt tcaacaccat tgcggtggat     240

gatgggattg ccatgggcca cggggggatg ctttattcac tgccatctcg cgaactgatc     300

gctgattccg ttgagtatat ggtcaacgcc cactgcgccg acgccatggt ctgcatctct     360

aactgcgaca aaatcacccc ggggatgctg atggcttccc tgcgcctgaa tattccggtg     420

atctttgttt ccggcggccc gatggaggcc gggaaaacca aactttccga tcagatcatc     480

aagctcgatc tggttgatgc gatgatccag ggcgcagacc cgaaagtatc tgactcccag     540

agcgatcagg ttgaacgttc cgcgtgtccg acctgcggtt cctgctccgg gatgtttacc     600

gctaactcaa tgaactgcct gaccgaagcg ctgggcctgt cgcagccggg caacggctcg     660

ctgctggcaa cccacgccga ccgtaagcag ctgttcctta atgctggtaa acgcattgtt     720

gaattgacca aacgttatta cgagcaaaac gacgaaagtg cactgccgcg taatatcgcc     780

agtaaggcgg cgtttgaaaa cgccatgacg ctggatatcg cgatgggtgg atcgactaac     840

accgtacttc acctgctggc ggcggcgcag gaagcggaaa tcgacttcac catgagtgat     900

atcgataagc tttcccgcaa ggttccacag ctgtgtaaag ttgcgccgag cacccagaaa     960

taccatatgg aagatgttca ccgtgctggt ggtgttatcg gtattctcgg cgaactggat    1020

cgcgcggggt tactgaaccg tgatgtgaaa aacgtacttg gcctgacgtt gccgcaaacg    1080

ctggaacaat acgacgttat gctgacccag gatgacgcgg taaaaaatat gttccgcgca    1140

ggtcctgcag gcattcgtac cacacaggca ttctcgcaag attgccgttg ggatacgctg    1200

gacgacgatc gcgccaatgg ctgtatccgc tcgctggaac acgcctacag caaagacggc    1260

ggcctggcgg tgctctacgg taactttgcg gaaaacggct gcatcgtgaa aacggcaggc    1320

gtcgatgaca gcatcctcaa attcaccggc ccggcgaaag tgtacgaaag ccaggacgat    1380

gcggtagaag cgattctcgg cggtaaagtt gtcgccggag atgtggtagt aattcgctat    1440
```

-continued gaaggcccga aaggcggtcc ggggatgcag gaaatgctct acccaaccag cttcctgaaa 1500
tcaatgggtc tcggcaaagc ctgtgcgctg atcaccgacg gtcgtttctc tggtggcacc 1560
tctggtcttt ccatcggcca cgtctcaccg gaagcggcaa gcggcggcag cattggcctg 1620
attgaagatg gtgacctgat cgctatcgac atcccgaacc gtggcattca gttacaggta 1680
agcgatgccg aactggcggc gcgtcgtgaa gcgcaggacg ctcgaggtga caaagcctgg 1740
acgccgaaaa atcgtgaacg tcaggtctcc tttgccctgc gtgcttatgc cagcctggca 1800
accagcgccg acaaaggcgc ggtgcgcgat aaatcgaaac tgggggggtta a 1851

<210> SEQ ID NO 34
<211> LENGTH: 616
<212> TYPE: PRT
<213> ORGANISM: Escherichia coli

<400> SEQUENCE: 34

Met Pro Lys Tyr Arg Ser Ala Thr Thr Thr His Gly Arg Asn Met Ala
1 5 10 15

Gly Ala Arg Ala Leu Trp Arg Ala Thr Gly Met Thr Asp Ala Asp Phe
20 25 30

Gly Lys Pro Ile Ile Ala Val Val Asn Ser Phe Thr Gln Phe Val Pro
35 40 45

Gly His Val His Leu Arg Asp Leu Gly Lys Leu Val Ala Glu Gln Ile
50 55 60

Glu Ala Ala Gly Gly Val Ala Lys Glu Phe Asn Thr Ile Ala Val Asp
65 70 75 80

Asp Gly Ile Ala Met Gly His Gly Gly Met Leu Tyr Ser Leu Pro Ser
85 90 95

Arg Glu Leu Ile Ala Asp Ser Val Glu Tyr Met Val Asn Ala His Cys
100 105 110

Ala Asp Ala Met Val Cys Ile Ser Asn Cys Asp Lys Ile Thr Pro Gly
115 120 125

Met Leu Met Ala Ser Leu Arg Leu Asn Ile Pro Val Ile Phe Val Ser
130 135 140

Gly Gly Pro Met Glu Ala Gly Lys Thr Lys Leu Ser Asp Gln Ile Ile
145 150 155 160

Lys Leu Asp Leu Val Asp Ala Met Ile Gln Gly Ala Asp Pro Lys Val
165 170 175

Ser Asp Ser Gln Ser Asp Gln Val Glu Arg Ser Ala Cys Pro Thr Cys
180 185 190

Gly Ser Cys Ser Gly Met Phe Thr Ala Asn Ser Met Asn Cys Leu Thr
195 200 205

Glu Ala Leu Gly Leu Ser Gln Pro Gly Asn Gly Ser Leu Leu Ala Thr
210 215 220

His Ala Asp Arg Lys Gln Leu Phe Leu Asn Ala Gly Lys Arg Ile Val
225 230 235 240

Glu Leu Thr Lys Arg Tyr Tyr Glu Gln Asn Asp Glu Ser Ala Leu Pro
245 250 255

Arg Asn Ile Ala Ser Lys Ala Ala Phe Glu Asn Ala Met Thr Leu Asp
260 265 270

Ile Ala Met Gly Gly Ser Thr Asn Thr Val Leu His Leu Leu Ala Ala
275 280 285

Ala Gln Glu Ala Glu Ile Asp Phe Thr Met Ser Asp Ile Asp Lys Leu
290 295 300

Ser Arg Lys Val Pro Gln Leu Cys Lys Val Ala Pro Ser Thr Gln Lys

-continued

```
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615
```

<210> SEQ ID NO 35
<211> LENGTH: 1662
<212> TYPE: DNA
<213> ORGANISM: Lactococcus lactis

<400> SEQUENCE: 35

```
tctagacata tgtatactgt gggggattac ctgctggatc gcctgcacga actggggatt      60

gaagaaattt tcggtgtgcc aggcgattat aacctgcagt tcctggacca gattatctcg     120

cacaaagata tgaagtgggt cggtaacgcc aacgaactga acgcgagcta tatggcagat     180

ggttatgccc gtaccaaaaa agctgctgcg tttctgacga cctttggcgt tggcgaactg     240

agcgccgtca acggactggc aggaagctac gccgagaacc tgccagttgt cgaaattgtt     300

gggtcgccta cttctaaggt tcagaatgaa ggcaaatttg tgcaccatac tctggctgat     360

ggggatttta aacattttat gaaaatgcat gaaccggtta ctgcggcccg cacgctgctg     420
```

```
acagcagaga atgctacggt tgagatcgac cgcgtcctgt ctgcgctgct gaaagagcgc    480

aagccggtat atatcaatct gcctgtcgat gttgccgcag cgaaagccga aaagccgtcg    540

ctgccactga aaaaagaaaa cagcacctcc aatacatcgg accaggaaat tctgaataaa    600

atccaggaat cactgaagaa tgcgaagaaa ccgatcgtca tcaccggaca tgagatcatc    660

tcttttggcc tggaaaaaac ggtcacgcag ttcatttcta agaccaaact gcctatcacc    720

accctgaact tcggcaaatc tagcgtcgat gaagcgctgc cgagttttct gggtatctat    780

aatggtaccc tgtccgaacc gaacctgaaa gaattcgtcg aaagcgcgga ctttatcctg    840

atgctgggcg tgaaactgac ggatagctcc acaggcgcat ttacccacca tctgaacgag    900

aataaaatga tttccctgaa tatcgacgaa ggcaaaatct ttaacgagcg catccagaac    960

ttcgattttg aatctctgat tagttcgctg ctggatctgt ccgaaattga gtataaaggt   1020

aaatatattg ataaaaaaca ggaggatttt gtgccgtcta atgcgctgct gagtcaggat   1080

cgtctgtggc aagccgtaga aaacctgaca cagtctaatg aaacgattgt tgcggaacag   1140

ggaacttcat ttttcggcgc ctcatccatt tttctgaaat ccaaaagcca tttcattggc   1200

caaccgctgt gggggagtat tggttatacc tttccggcgg cgctgggttc acagattgca   1260

gataaggaat cacgccatct gctgtttatt ggtgacggca gcctgcagct gactgtccag   1320

gaactggggc tggcgatccg tgaaaaaatc aatccgattt gctttatcat caataacgac   1380

ggctacaccg tcgaacgcga aattcatgga ccgaatcaaa gttacaatga catcccgatg   1440

tggaactata gcaaactgcc ggaatccttt ggcgcgacag aggatcgcgt ggtgagtaaa   1500

attgtgcgta cggaaaacga atttgtgtcg gttatgaaag aagcgcaggc tgacccgaat   1560

cgcatgtatt ggattgaact gatcctggca aaagaaggcg caccgaaagt tctgaaaaag   1620

atggggaaac tgtttgcgga gcaaaataaa agctaaggat cc                       1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160
```

```
Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 37
<211> LENGTH: 1164
<212> TYPE: DNA

<213> ORGANISM: Escherichia coli

<400> SEQUENCE: 37
atgaacaact ttaatctgca caccccaacc cgcattctgt ttggtaaagg cgcaatcgct 60
ggtttacgcg aacaaattcc tcacgatgct cgcgtattga ttacctacgg cggcggcagc 120
gtgaaaaaaa ccggcgttct cgatcaagtt ctggatgccc tgaaaggcat ggacgtgctg 180
gaatttggcg gtattgagcc aaacccggct tatgaaacgc tgatgaacgc cgtgaaactg 240
gttcgcgaac agaaagtgac tttcctgctg gcggttggcg gcggttctgt actggacggc 300
accaaattta tcgccgcagc ggctaactat ccggaaaata tcgatccgtg gcacattctg 360
caaacgggcg gtaaagagat taaaagcgcc atcccgatgg gctgtgtgct gacgctgcca 420
gcaaccggtt cagaatccaa cgcaggcgcg gtgatctccc gtaaaaccac aggcgacaag 480
caggcgttcc attctgccca tgttcagccg gtatttgccg tgctcgatcc ggtttatacc 540
tacaccctgc cgccgcgtca ggtggctaac ggcgtagtgg acgcctttgt acacaccgtg 600
gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080
gaagagcacg gcatgaccca actgggcgaa aatcatgaca ttacgttgga tgtcagccgc 1140
cgtatatacg aagccgcccg ctaa 1164

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1 5 10 15

Gly Ala Ile Ala Gly Leu Arg Glu Gln Ile Pro His Asp Ala Arg Val
20 25 30

Leu Ile Thr Tyr Gly Gly Gly Ser Val Lys Lys Thr Gly Val Leu Asp
35 40 45

Gln Val Leu Asp Ala Leu Lys Gly Met Asp Val Leu Glu Phe Gly Gly
50 55 60

Ile Glu Pro Asn Pro Ala Tyr Glu Thr Leu Met Asn Ala Val Lys Leu
65 70 75 80

Val Arg Glu Gln Lys Val Thr Phe Leu Leu Ala Val Gly Gly Gly Ser
85 90 95

Val Leu Asp Gly Thr Lys Phe Ile Ala Ala Ala Ala Asn Tyr Pro Glu
100 105 110

Asn Ile Asp Pro Trp His Ile Leu Gln Thr Gly Gly Lys Glu Ile Lys
115 120 125

Ser Ala Ile Pro Met Gly Cys Val Leu Thr Leu Pro Ala Thr Gly Ser
130 135 140

Glu Ser Asn Ala Gly Ala Val Ile Ser Arg Lys Thr Thr Gly Asp Lys

```
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 39
<211> LENGTH: 2109
<212> TYPE: DNA
<213> ORGANISM: Escherichia coli

<400> SEQUENCE: 39

ttgtatctgt ttgaaagcct gaatcaactg attcaaacct acctgccgga agaccaaatc      60

aagcgtctgc ggcaggcgta tctcgttgca cgtgatgctc acgaggggca aacacgttca     120

agcggtgaac cctatatcac gcacccggta gcggttgcct gcattctggc cgagatgaaa     180

ctcgactatg aaacgctgat ggcggcgctg ctgcatgacg tgattgaaga tactcccgcc     240

acctaccagg atatggaaca gctttttggt aaaagcgtcg ccgagctggt agagggggtg     300

tcgaaacttg ataaactcaa gttccgcgat aagaaagagg cgcaggccga aaactttcgc     360

aagatgatta tggcgatggt gcaggatatc cgcgtcatcc tcatcaaact tgccgaccgt     420

acccacaaca tgcgcacgct gggctcactt cgcccggaca aacgtcgccg catcgcccgt     480

gaaactctcg aaatttatag cccgctggcg caccgtttag gtatccacca cattaaaacc     540

gaactcgaag agctgggttt tgaggcgctg tatcccaacc gttatcgcgt aatcaaagaa     600

gtggtgaaag ccgcgcgcgg caaccgtaaa gagatgatcc agaagattct ttctgaaatc     660

gaagggcgtt tgcaggaagc gggaataccg tgccgcgtca gtggtcgcga gaagcatctt     720

tattcgattt actgcaaaat ggtgctcaaa gagcagcgtt ttcactcgat catggacatc     780
```

-continued

```
tacgctttcc gcgtgatcgt caatgattct gacacctgtt atcgcgtgct gggccagatg    840

cacagcctgt acaagccgcg tccgggccgc gtgaaagact atatcgccat tccaaaagcg    900

aacggctatc agtctttgca cacctcgatg atcggcccgc acggtgtgcc ggttgaggtc    960

cagatccgta ccgaagatat ggaccagatg gcggagatgg gtgttgccgc gcactgggct   1020

tataaagagc acggcgaaac cagtactacc gcacaaatcc gcgcccagcg ctggatgcaa   1080

agcctgctgg agctgcaaca gagcgccggt agttcgtttg aatttatcga gagcgttaaa   1140

tccgatctct tcccggatga gatttacgtt ttcacaccgg aagggcgcat tgtcgagctg   1200

cctgccggtg caacgcccgt cgacttcgct tatgcagtgc ataccgatat cggtcatgcc   1260

tgcgtgggcg cacgcgttga ccgccagcct tacccgctgt cgcagccgct taccagcggt   1320

caaaccgttg aaatcattac cgctccgggc gctcgcccga atgccgcttg gctgaacttt   1380

gtcgttagct cgaaagcgcg cgccaaaatt cgtcagttgc tgaaaaacct caagcgtgat   1440

gattctgtaa gcctgggccg tcgtctgctc aaccatgctt tgggtggtag ccgtaagctg   1500

aatgaaatcc cgcaggaaaa tattcagcgc gagctggatc gcatgaagct ggcaacgctt   1560

gacgatctgc tggcagaaat cggacttggt aacgcaatga gcgtggtggt cgcgaaaaat   1620

ctgcaacatg gggacgcctc cattccaccg gcaacccaaa gccacggaca tctgcccatt   1680

aaaggtgccg atggcgtgct gatcaccttt gcgaaatgct gccgccctat tcctggcgac   1740

ccgattatcg cccacgtcag ccccggtaaa ggtctggtga tccaccatga atcctgccgt   1800

aatatccgtg gctaccagaa agagccagag aagtttatgg ctgtggaatg ggataaagag   1860

acggcgcagg agttcatcac cgaaatcaag gtggagatgt tcaatcatca gggtgcgctg   1920

gcaaacctga cggcggcaat taacaccacg acttcgaata ttcaaagttt gaatacggaa   1980

gagaaagatg gtcgcgtcta cagcgccttt attcgtctga ccgctcgtga ccgtgtgcat   2040

ctggcgaata tcatgcgcaa aatccgcgtg atgccagacg tgattaaagt cacccgaaac   2100

cgaaattaa                                                           2109
```

```
<210> SEQ ID NO 40
<211> LENGTH: 702
<212> TYPE: PRT
<213> ORGANISM: Escherichia coli

<400> SEQUENCE: 40

Met Tyr Leu Phe Glu Ser Leu Asn Gln Leu Ile Gln Thr Tyr Leu Pro
1               5                   10                  15

Glu Asp Gln Ile Lys Arg Leu Arg Gln Ala Tyr Leu Val Ala Arg Asp
            20                  25                  30

Ala His Glu Gly Gln Thr Arg Ser Ser Gly Glu Pro Tyr Ile Thr His
        35                  40                  45

Pro Val Ala Val Ala Cys Ile Leu Ala Glu Met Lys Leu Asp Tyr Glu
    50                  55                  60

Thr Leu Met Ala Ala Leu Leu His Asp Val Ile Glu Asp Thr Pro Ala
65                  70                  75                  80

Thr Tyr Gln Asp Met Glu Gln Leu Phe Gly Lys Ser Val Ala Glu Leu
                85                  90                  95

Val Glu Gly Val Ser Lys Leu Asp Lys Leu Lys Phe Arg Asp Lys Lys
            100                 105                 110

Glu Ala Gln Ala Glu Asn Phe Arg Lys Met Ile Met Ala Met Val Gln
        115                 120                 125

Asp Ile Arg Val Ile Leu Ile Lys Leu Ala Asp Arg Thr His Asn Met
```

-continued

```
    130                 135                 140

Arg Thr Leu Gly Ser Leu Arg Pro Asp Lys Arg Arg Arg Ile Ala Arg
145                 150                 155                 160

Glu Thr Leu Glu Ile Tyr Ser Pro Leu Ala His Arg Leu Gly Ile His
                165                 170                 175

His Ile Lys Thr Glu Leu Glu Glu Leu Gly Phe Glu Ala Leu Tyr Pro
            180                 185                 190

Asn Arg Tyr Arg Val Ile Lys Glu Val Val Lys Ala Ala Arg Gly Asn
        195                 200                 205

Arg Lys Glu Met Ile Gln Lys Ile Leu Ser Glu Ile Glu Gly Arg Leu
    210                 215                 220

Gln Glu Ala Gly Ile Pro Cys Arg Val Ser Gly Arg Glu Lys His Leu
225                 230                 235                 240

Tyr Ser Ile Tyr Cys Lys Met Val Leu Lys Glu Gln Arg Phe His Ser
                245                 250                 255

Ile Met Asp Ile Tyr Ala Phe Arg Val Ile Val Asn Asp Ser Asp Thr
            260                 265                 270

Cys Tyr Arg Val Leu Gly Gln Met His Ser Leu Tyr Lys Pro Arg Pro
        275                 280                 285

Gly Arg Val Lys Asp Tyr Ile Ala Ile Pro Lys Ala Asn Gly Tyr Gln
    290                 295                 300

Ser Leu His Thr Ser Met Ile Gly Pro His Gly Val Pro Val Glu Val
305                 310                 315                 320

Gln Ile Arg Thr Glu Asp Met Asp Gln Met Ala Glu Met Gly Val Ala
                325                 330                 335

Ala His Trp Ala Tyr Lys Glu His Gly Glu Thr Ser Thr Thr Ala Gln
            340                 345                 350

Ile Arg Ala Gln Arg Trp Met Gln Ser Leu Leu Glu Leu Gln Gln Ser
        355                 360                 365

Ala Gly Ser Ser Phe Glu Phe Ile Glu Ser Val Lys Ser Asp Leu Phe
    370                 375                 380

Pro Asp Glu Ile Tyr Val Phe Thr Pro Glu Gly Arg Ile Val Glu Leu
385                 390                 395                 400

Pro Ala Gly Ala Thr Pro Val Asp Phe Ala Tyr Ala Val His Thr Asp
                405                 410                 415

Ile Gly His Ala Cys Val Gly Ala Arg Val Asp Arg Gln Pro Tyr Pro
            420                 425                 430

Leu Ser Gln Pro Leu Thr Ser Gly Gln Thr Val Glu Ile Ile Thr Ala
        435                 440                 445

Pro Gly Ala Arg Pro Asn Ala Ala Trp Leu Asn Phe Val Val Ser Ser
    450                 455                 460

Lys Ala Arg Ala Lys Ile Arg Gln Leu Leu Lys Asn Leu Lys Arg Asp
465                 470                 475                 480

Asp Ser Val Ser Leu Gly Arg Arg Leu Leu Asn His Ala Leu Gly Gly
                485                 490                 495

Ser Arg Lys Leu Asn Glu Ile Pro Gln Glu Asn Ile Gln Arg Glu Leu
            500                 505                 510

Asp Arg Met Lys Leu Ala Thr Leu Asp Asp Leu Leu Ala Glu Ile Gly
        515                 520                 525

Leu Gly Asn Ala Met Ser Val Val Val Ala Lys Asn Leu Gln His Gly
    530                 535                 540

Asp Ala Ser Ile Pro Pro Ala Thr Gln Ser His Gly His Leu Pro Ile
545                 550                 555                 560
```

-continued

```
Lys Gly Ala Asp Gly Val Leu Ile Thr Phe Ala Lys Cys Cys Arg Pro
                565                 570                 575

Ile Pro Gly Asp Pro Ile Ile Ala His Val Ser Pro Gly Lys Gly Leu
            580                 585                 590

Val Ile His His Glu Ser Cys Arg Asn Ile Arg Gly Tyr Gln Lys Glu
        595                 600                 605

Pro Glu Lys Phe Met Ala Val Glu Trp Asp Lys Glu Thr Ala Gln Glu
    610                 615                 620

Phe Ile Thr Glu Ile Lys Val Glu Met Phe Asn His Gln Gly Ala Leu
625                 630                 635                 640

Ala Asn Leu Thr Ala Ala Ile Asn Thr Thr Thr Ser Asn Ile Gln Ser
                645                 650                 655

Leu Asn Thr Glu Glu Lys Asp Gly Arg Val Tyr Ser Ala Phe Ile Arg
            660                 665                 670

Leu Thr Ala Arg Asp Arg Val His Leu Ala Asn Ile Met Arg Lys Ile
        675                 680                 685

Arg Val Met Pro Asp Val Ile Lys Val Thr Arg Asn Arg Asn
    690                 695                 700


<210> SEQ ID NO 41
<211> LENGTH: 2235
<212> TYPE: DNA
<213> ORGANISM: Escherichia coli

<400> SEQUENCE: 41

atggttgcgg taagaagtgc acatatcaat aaggctggtg aatttgatcc ggaaaaatgg      60

atcgcaagtc tgggtattac cagccagaag tcgtgtgagt gcttagccga aacctgggcg     120

tattgtctgc aacagacgca ggggcatccg gatgccagtc tgttattgtg gcgtggtgtt     180

gagatggtgg agatcctctc gacattaagt atggacattg acacgctgcg ggcggcgctg     240

cttttccctc tggcggatgc caacgtagtc agcgaagatg tgctgcgtga gagcgtcggt     300

aagtcggtcg ttaaccttat tcacggcgtg cgtgatatgg cggcgatccg ccagctgaaa     360

gcgacgcaca ctgattctgt ttcctccgaa caggtcgata acgttcgccg gatgttattg     420

gcgatggtcg atgattttcg ctgcgtagtc atcaaactgg cggagcgtat tgctcatctg     480

cgcgaagtaa aagatgcgcc ggaagatgaa cgtgtactgg cggcaaaaga gtgtaccaac     540

atctacgcac cgctggctaa ccgtctcgga atcggacaac tgaaatggga actggaagat     600

tactgcttcc gttacctcca tccaaccgaa tacaaacgaa ttgccaaact gctgcatgaa     660

cggcgtctcg accgcgaaca ctacatcgaa gagttcgttg gtcatctgcg cgctgagatg     720

aaagctgaag gcgttaaagc ggaagtgtat ggtcgtccga aacacatcta cagcatctgg     780

cgtaaaatgc agaaaaagaa cctcgccttt gatgagctgt ttgatgtgcg tgcggtacgt     840

attgtcgccg agcgtttaca ggattgctat gccgcactgg ggatagtgca cactcactat     900

cgccacctgc cggatgagtt tgacgattac gtcgctaacc cgaaaccaaa cggttatcag     960

tctattcata ccgtggttct ggggccgggt ggaaaaaccg ttgagatcca aatccgcacc    1020

aaacagatgc atgaagatgc agagttgggt gttgctgcgc actggaaata taaagagggc    1080

gcggctgctg gcggcgcacg ttcgggacat gaagaccgga ttgcctggct gcgtaaactg    1140

attgcgtggc aggaagagat ggctgattcc ggcgaaatgc tcgacgaagt acgtagtcag    1200

gtctttgacg accgggtgta cgtctttacg ccgaaaggtg atgtcgttga tttgcctgcg    1260

ggatcaacgc cgctggactt cgcttaccac atccacagtg atgtcggaca ccgctgcatc    1320

ggggcaaaaa ttggcgggcg cattgtgccg ttcacctacc agctgcagat gggcgaccag    1380
```

attgaaatta tcacccagaa acagccgaac cccagccgtg actggttaaa cccaaacctc 1440
ggttacgtca caaccagccg tgggcgttcg aaaattcacg cctggttccg taaacaggac 1500
cgtgacaaaa acattctggc tgggcggcaa atccttgacg acgagctgga acatctgggg 1560
atcagcctga aagaagcaga aaaacatctg ctgccgcgtt acaacttcaa tgatgtcgac 1620
gagttgctgg cggcgattgg tggcggggat atccgtctca atcagatggt gaacttcctg 1680
caatcgcaat ttaataagcc gagtgccgaa gagcaggacg ccgccgcgct gaagcaactt 1740
cagcaaaaaa gctacacgcc gcaaaaccgc agtaaagata acggtcgcgt ggtagtcgaa 1800
ggtgttggca acctgatgca ccacatcgcg cgctgctgcc agccgattcc tggagatgag 1860
attgtcggct tcattaccca ggggcgcggt atttcagtac accgcgccga ttgcgaacaa 1920
ctggcggaac tgcgctccca tgcgccagaa cgcattgttg acgcggtatg gggtgagagc 1980
tactccgccg gatattcgct ggtggtccgc gtggtagcta atgatcgtag tgggttgtta 2040
cgtgatatca cgaccattct cgccaacgag aaggtgaacg tgcttggcgt tgccagccgt 2100
agcgacacca aacagcaact ggcgaccatc gacatgacca ttgagattta caacctgcaa 2160
gtgctggggc gcgtgctggg taaactcaac caggtgccgg atgttatcga cgcgcgtcgg 2220
ttgcacggga gttag 2235

<210> SEQ ID NO 42
<211> LENGTH: 744
<212> TYPE: PRT
<213> ORGANISM: Echerichia coli

<400> SEQUENCE: 42

Met Val Ala Val Arg Ser Ala His Ile Asn Lys Ala Gly Glu Phe Asp
1 5 10 15

Pro Glu Lys Trp Ile Ala Ser Leu Gly Ile Thr Ser Gln Lys Ser Cys
20 25 30

Glu Cys Leu Ala Glu Thr Trp Ala Tyr Cys Leu Gln Gln Thr Gln Gly
35 40 45

His Pro Asp Ala Ser Leu Leu Leu Trp Arg Gly Val Glu Met Val Glu
50 55 60

Ile Leu Ser Thr Leu Ser Met Asp Ile Asp Thr Leu Arg Ala Ala Leu
65 70 75 80

Leu Phe Pro Leu Ala Asp Ala Asn Val Val Ser Glu Asp Val Leu Arg
85 90 95

Glu Ser Val Gly Lys Ser Val Val Asn Leu Ile His Gly Val Arg Asp
100 105 110

Met Ala Ala Ile Arg Gln Leu Lys Ala Thr His Thr Asp Ser Val Ser
115 120 125

Ser Glu Gln Val Asp Asn Val Arg Arg Met Leu Leu Ala Met Val Asp
130 135 140

Asp Phe Arg Cys Val Val Ile Lys Leu Ala Glu Arg Ile Ala His Leu
145 150 155 160

Arg Glu Val Lys Asp Ala Pro Glu Asp Glu Arg Val Leu Ala Ala Lys
165 170 175

Glu Cys Thr Asn Ile Tyr Ala Pro Leu Ala Asn Arg Leu Gly Ile Gly
180 185 190

Gln Leu Lys Trp Glu Leu Glu Asp Tyr Cys Phe Arg Tyr Leu His Pro
195 200 205

Thr Glu Tyr Lys Arg Ile Ala Lys Leu Leu His Glu Arg Arg Leu Asp
210 215 220

-continued

```
Arg Glu His Tyr Ile Glu Glu Phe Val Gly His Leu Arg Ala Glu Met
225                 230                 235                 240

Lys Ala Glu Gly Val Lys Ala Glu Val Tyr Gly Arg Pro Lys His Ile
                245                 250                 255

Tyr Ser Ile Trp Arg Lys Met Gln Lys Lys Asn Leu Ala Phe Asp Glu
            260                 265                 270

Leu Phe Asp Val Arg Ala Val Arg Ile Val Ala Glu Arg Leu Gln Asp
        275                 280                 285

Cys Tyr Ala Ala Leu Gly Ile Val His Thr His Tyr Arg His Leu Pro
    290                 295                 300

Asp Glu Phe Asp Asp Tyr Val Ala Asn Pro Lys Pro Asn Gly Tyr Gln
305                 310                 315                 320

Ser Ile His Thr Val Val Leu Gly Pro Gly Gly Lys Thr Val Glu Ile
                325                 330                 335

Gln Ile Arg Thr Lys Gln Met His Glu Asp Ala Glu Leu Gly Val Ala
            340                 345                 350

Ala His Trp Lys Tyr Lys Glu Gly Ala Ala Ala Gly Gly Ala Arg Ser
        355                 360                 365

Gly His Glu Asp Arg Ile Ala Trp Leu Arg Lys Leu Ile Ala Trp Gln
    370                 375                 380

Glu Glu Met Ala Asp Ser Gly Glu Met Leu Asp Glu Val Arg Ser Gln
385                 390                 395                 400

Val Phe Asp Asp Arg Val Tyr Val Phe Thr Pro Lys Gly Asp Val Val
                405                 410                 415

Asp Leu Pro Ala Gly Ser Thr Pro Leu Asp Phe Ala Tyr His Ile His
            420                 425                 430

Ser Asp Val Gly His Arg Cys Ile Gly Ala Lys Ile Gly Gly Arg Ile
        435                 440                 445

Val Pro Phe Thr Tyr Gln Leu Gln Met Gly Asp Gln Ile Glu Ile Ile
    450                 455                 460

Thr Gln Lys Gln Pro Asn Pro Ser Arg Asp Trp Leu Asn Pro Asn Leu
465                 470                 475                 480

Gly Tyr Val Thr Thr Ser Arg Gly Arg Ser Lys Ile His Ala Trp Phe
                485                 490                 495

Arg Lys Gln Asp Arg Asp Lys Asn Ile Leu Ala Gly Arg Gln Ile Leu
            500                 505                 510

Asp Asp Glu Leu Glu His Leu Gly Ile Ser Leu Lys Glu Ala Glu Lys
        515                 520                 525

His Leu Leu Pro Arg Tyr Asn Phe Asn Asp Val Asp Glu Leu Leu Ala
    530                 535                 540

Ala Ile Gly Gly Gly Asp Ile Arg Leu Asn Gln Met Val Asn Phe Leu
545                 550                 555                 560

Gln Ser Gln Phe Asn Lys Pro Ser Ala Glu Glu Gln Asp Ala Ala Ala
                565                 570                 575

Leu Lys Gln Leu Gln Gln Lys Ser Tyr Thr Pro Gln Asn Arg Ser Lys
            580                 585                 590

Asp Asn Gly Arg Val Val Val Glu Gly Val Gly Asn Leu Met His His
        595                 600                 605

Ile Ala Arg Cys Cys Gln Pro Ile Pro Gly Asp Glu Ile Val Gly Phe
    610                 615                 620

Ile Thr Gln Gly Arg Gly Ile Ser Val His Arg Ala Asp Cys Glu Gln
625                 630                 635                 640

Leu Ala Glu Leu Arg Ser His Ala Pro Glu Arg Ile Val Asp Ala Val
```

```
                645                 650                 655

Trp Gly Glu Ser Tyr Ser Ala Gly Tyr Ser Leu Val Val Arg Val Val
            660                 665                 670

Ala Asn Asp Arg Ser Gly Leu Leu Arg Asp Ile Thr Thr Ile Leu Ala
        675                 680                 685

Asn Glu Lys Val Asn Val Leu Gly Val Ala Ser Arg Ser Asp Thr Lys
    690                 695                 700

Gln Gln Leu Ala Thr Ile Asp Met Thr Ile Glu Ile Tyr Asn Leu Gln
705                 710                 715                 720

Val Leu Gly Arg Val Leu Gly Lys Leu Asn Gln Val Pro Asp Val Ile
                725                 730                 735

Asp Ala Arg Arg Leu His Gly Ser
            740


<210> SEQ ID NO 43
<211> LENGTH: 2268
<212> TYPE: DNA
<213> ORGANISM: Lactobacillus plantarum

<400> SEQUENCE: 43

atgcccaaac aacctacctg gactgcccag gatgtcctgg acatggttca aaagtatatg     60

aatagtgatc acgtcgcgtt agttaaacgg gcgtgtgatt ttgcaactta tgtgcataag    120

gatcagtatc gccaatctgg tgagccgtat attatgcatc cgattcaagt tgctggtatc    180

ttagctgaat tgaagatgga ccctgaaacc gtcgcttcgg gtttcttaca cgacgttgtg    240

gaagatactg gtgttacttt aggagacgtt gaagaactgt ttggtcatga cgtggccgtt    300

attgttgacg gggtcaccaa gctgggtaag attcggtaca agtccaacaa agaacagctt    360

gctgaaaatc accgtaaatt actgttggcg atgtctaaag atattcgagt catgattgtc    420

aaattagctg atcgcttgca taatatgcgg acattgcagc atctgcggcc cgataaacag    480

cggcgaattg caaatgaaac gttggaaatt tacgccccca ttgccgatcg attagggatc    540

agcacgatta aatgggaact agaagatatt tcactacgtt atttgaatcc tcaacagtat    600

tatcgcattg tccacttgat gaattcgcgg cgtgaggacc gtgaaaagta catcgagatt    660

gccattcaag acattcaaaa ggcgctccat gatctggaac taccagaagc tgaaatttat    720

ggtcgtccga agcatatcta ttcaatttat aagaagatgc gggacaaaca caaacagttt    780

agccaacttt acgatctgct ggcaattcgg gtggtcgtgg attcaatcaa ggactgttat    840

gcagttttag gtgcgattca cacacaatgg aagcccatgc cggggcgttt taaagattat    900

attgcgatgc ccaaggccaa tatgtatcaa tctttgcata ccacggtggt cggtcctgaa    960

ggtaagcccc tcgaaataca gatccggacg tttgaaatgc accgggtcgc tgaatacggg   1020

gtcgcagcac actgggcgta taaggaaggt aaacgcgacg aggtccaaga gactcagtcg   1080

ggcaacaagt tgaacttagt caaagaaatc attgagctac aggatgaaag taaggacgct   1140

gccgacttta tggagggcgt caagggcgac ctctttagtg accgggtcta tgcttttacg   1200

cccaagggtg acgtgacaga attaccaaag ggcgctggac cactggatat ggcatattcg   1260

atccatacgg aagtgggtaa ccatacgact ggtgcgaaag tcaatggcaa gatcgttcca   1320

ttggattacc aaatcaaaaa tggtgatatc gtggatattt taacgtccac tagttcaact   1380

ggtcctagcc gtgattggca gaaattagtc tatacgcggc gggcccgtaa taaaatcaaa   1440

cagttcttcc gcaatgctga ccgtgaggaa aacatcatta cgggtcgtga tttgcttgag   1500

aagcagctac gtgatttaga gtttaatcca aaagaaatca tgactaagga caaggtgacg   1560
```

-continued

```
gcggtcgctc aaaagatgca ctacggtagt gaggatgatt tgttcgcggc cttggggttt   1620

ggtgacgtcc aaccggtagg gattgctaac cggttaacga gtgatgttcg taaacagcgc   1680

gaggctaatc ggcagcgtga acgtgaggag gccattttgg cagactctac ggaagcgcca   1740

gcgaagaaga aatcgaaaga tcatcataat gaggatcagg agaagcagga tcggaagcgg   1800

caaaaggtct catcttctgg tggggtgatt attcaaggcg tcgacaactt actcgtacgt   1860

ctaagtcatt gctgttctcc aattccgggt gatgagattg ttggttatat tacgaagggg   1920

cgcggtgttt cggttcaccg tgttgattgt ccgaacgtta agagcgcaga agcaaatggt   1980

gaacggttga ttgatgttca gtgggagaat cccgagggtg accgaacgaa ctacaattct   2040

gatttggaaa ttcaaggtta taaccgtaat ggcatgctca acgatgtgtt gaaagttatc   2100

aataatcaca cgaaattttt gaccaatgtc aacggtaagg tcgatcacaa caagatggtc   2160

attattagtg tttcgttggg ggttcgcaac ttggaacatc tccaacgaat cattgacagt   2220

ctgaaaaatg ttcaggatct ttacgttgtc gaacggaaaa tgttttag                2268
```

```
<210> SEQ ID NO 44
<211> LENGTH: 755
<212> TYPE: PRT
<213> ORGANISM: Lactobacillus plantarum

<400> SEQUENCE: 44

Met Pro Lys Gln Pro Thr Trp Thr Ala Gln Asp Val Leu Asp Met Val
1               5                   10                  15

Gln Lys Tyr Met Asn Ser Asp His Val Ala Leu Val Lys Arg Ala Cys
            20                  25                  30

Asp Phe Ala Thr Tyr Val His Lys Asp Gln Tyr Arg Gln Ser Gly Glu
        35                  40                  45

Pro Tyr Ile Met His Pro Ile Gln Val Ala Gly Ile Leu Ala Glu Leu
    50                  55                  60

Lys Met Asp Pro Glu Thr Val Ala Ser Gly Phe Leu His Asp Val Val
65                  70                  75                  80

Glu Asp Thr Gly Val Thr Leu Gly Asp Val Glu Glu Leu Phe Gly His
                85                  90                  95

Asp Val Ala Val Ile Val Asp Gly Val Thr Lys Leu Gly Lys Ile Arg
            100                 105                 110

Tyr Lys Ser Asn Lys Glu Gln Leu Ala Glu Asn His Arg Lys Leu Leu
        115                 120                 125

Leu Ala Met Ser Lys Asp Ile Arg Val Met Ile Val Lys Leu Ala Asp
    130                 135                 140

Arg Leu His Asn Met Arg Thr Leu Gln His Leu Arg Pro Asp Lys Gln
145                 150                 155                 160

Arg Arg Ile Ala Asn Glu Thr Leu Glu Ile Tyr Ala Pro Ile Ala Asp
                165                 170                 175

Arg Leu Gly Ile Ser Thr Ile Lys Trp Glu Leu Glu Asp Ile Ser Leu
            180                 185                 190

Arg Tyr Leu Asn Pro Gln Gln Tyr Tyr Arg Ile Val His Leu Met Asn
        195                 200                 205

Ser Arg Arg Glu Asp Arg Glu Lys Tyr Ile Glu Ile Ala Ile Gln Asp
    210                 215                 220

Ile Gln Lys Ala Leu His Asp Leu Glu Leu Pro Glu Ala Glu Ile Tyr
225                 230                 235                 240

Gly Arg Pro Lys His Ile Tyr Ser Ile Tyr Lys Lys Met Arg Asp Lys
                245                 250                 255
```

-continued

```
His Lys Gln Phe Ser Gln Leu Tyr Asp Leu Leu Ala Ile Arg Val Val
            260                 265                 270

Val Asp Ser Ile Lys Asp Cys Tyr Ala Val Leu Gly Ala Ile His Thr
        275                 280                 285

Gln Trp Lys Pro Met Pro Gly Arg Phe Lys Asp Tyr Ile Ala Met Pro
    290                 295                 300

Lys Ala Asn Met Tyr Gln Ser Leu His Thr Thr Val Val Gly Pro Glu
305                 310                 315                 320

Gly Lys Pro Leu Glu Ile Gln Ile Arg Thr Phe Glu Met His Arg Val
                325                 330                 335

Ala Glu Tyr Gly Val Ala Ala His Trp Ala Tyr Lys Glu Gly Lys Arg
            340                 345                 350

Asp Glu Val Gln Glu Thr Gln Ser Gly Asn Lys Leu Asn Leu Val Lys
        355                 360                 365

Glu Ile Ile Glu Leu Gln Asp Glu Ser Lys Asp Ala Ala Asp Phe Met
    370                 375                 380

Glu Gly Val Lys Gly Asp Leu Phe Ser Asp Arg Val Tyr Ala Phe Thr
385                 390                 395                 400

Pro Lys Gly Asp Val Thr Glu Leu Pro Lys Gly Ala Gly Pro Leu Asp
                405                 410                 415

Met Ala Tyr Ser Ile His Thr Glu Val Gly Asn His Thr Thr Gly Ala
            420                 425                 430

Lys Val Asn Gly Lys Ile Val Pro Leu Asp Tyr Gln Ile Lys Asn Gly
        435                 440                 445

Asp Ile Val Asp Ile Leu Thr Ser Thr Ser Ser Thr Gly Pro Ser Arg
    450                 455                 460

Asp Trp Gln Lys Leu Val Tyr Thr Arg Arg Ala Arg Asn Lys Ile Lys
465                 470                 475                 480

Gln Phe Phe Arg Asn Ala Asp Arg Glu Glu Asn Ile Ile Thr Gly Arg
                485                 490                 495

Asp Leu Leu Glu Lys Gln Leu Arg Asp Leu Glu Phe Asn Pro Lys Glu
            500                 505                 510

Ile Met Thr Lys Asp Lys Val Thr Ala Val Ala Gln Lys Met His Tyr
        515                 520                 525

Gly Ser Glu Asp Asp Leu Phe Ala Ala Leu Gly Phe Gly Asp Val Gln
    530                 535                 540

Pro Val Gly Ile Ala Asn Arg Leu Thr Ser Asp Val Arg Lys Gln Arg
545                 550                 555                 560

Glu Ala Asn Arg Gln Arg Glu Arg Glu Glu Ala Ile Leu Ala Asp Ser
                565                 570                 575

Thr Glu Ala Pro Ala Lys Lys Lys Ser Lys Asp His His Asn Glu Asp
            580                 585                 590

Gln Glu Lys Gln Asp Arg Lys Arg Gln Lys Val Ser Ser Ser Gly Gly
        595                 600                 605

Val Ile Ile Gln Gly Val Asp Asn Leu Leu Val Arg Leu Ser His Cys
    610                 615                 620

Cys Ser Pro Ile Pro Gly Asp Glu Ile Val Gly Tyr Ile Thr Lys Gly
625                 630                 635                 640

Arg Gly Val Ser Val His Arg Val Asp Cys Pro Asn Val Lys Ser Ala
                645                 650                 655

Glu Ala Asn Gly Glu Arg Leu Ile Asp Val Gln Trp Glu Asn Pro Glu
            660                 665                 670

Gly Asp Arg Thr Asn Tyr Asn Ser Asp Leu Glu Ile Gln Gly Tyr Asn
        675                 680                 685
```

-continued

```
Arg Asn Gly Met Leu Asn Asp Val Leu Lys Val Ile Asn Asn His Thr
    690                 695                 700

Lys Phe Leu Thr Asn Val Asn Gly Lys Val Asp His Asn Lys Met Val
705                 710                 715                 720

Ile Ile Ser Val Ser Leu Gly Val Arg Asn Leu Glu His Leu Gln Arg
                725                 730                 735

Ile Ile Asp Ser Leu Lys Asn Val Gln Asp Leu Tyr Val Val Glu Arg
            740                 745                 750

Lys Met Phe
        755


<210> SEQ ID NO 45
<211> LENGTH: 2202
<212> TYPE: DNA
<213> ORGANISM: Bacillus licheniformis

<400> SEQUENCE: 45

atggcgaacg aacaagtatt aaccgctgag caagtcattg agaaggcgaa aagttacctt     60

tccgatgaac atgttgcttt tataaaaaag gcttatcagt acgcggaaga cgcacatcgc    120

gaacaatacc gcaaatcggg cgagccgtat attatccatc cgatccaggt cgcgggaatc    180

ctcgtcgatt tagaaatgga ccccgccaca atagcgggag gatttctcca tgatgtggtg    240

gaagatacga gcgtaacgct tgaagattta aaggaagcat tcaacgaaga agttgcgatg    300

cttgtcgacg gcgtcacgaa gcttgggaaa attaaatata aatcacagga agaacagcag    360

gcagaaaatc atcggaaaat gtttgtggct atggctcagg acatccgcgt cattttgatc    420

aagctggcgg accgccttca caacatgaga accctgaagc atctgccgca ggaaaagcag    480

cgcagaattt caaatgagac gcttgaaata tttgctccgc tggctcatcg ccttgggatt    540

tcaaaaataa agtgggagct tgaggatacc gctttacggt atttaaatcc gcagcaatat    600

taccggatcg tcaatttgat gaagaaaaag cgggccgaaa gggaattgta cgtcgaagag    660

gtcgtaaacg aagtgaaaag ccgcgtcgaa gaggtcaata ttaaagcgga cttttccggc    720

cggccgaagc atatttacag catctacaga aaaatggcga tgcaaaacaa gcaattcaac    780

gaaatttacg acttgctcgc agtccggatc ctcgtcaaca gcatcaagga ctgctacgcg    840

gttttaggca tcattcatac gtgctggaag ccgatgccgg gcagatttaa agactatatc    900

gcaatgccga agccgaacat gtaccaatcg ctccacacca cggtcatcgg tccgaagggc    960

gatccgctgg aagtccagat caggacgttt gaaatgcatg aaattgcgga gtacggaatc   1020

gctgcccact gggcttacaa agaaggcaaa aatgccaatg aagattcaag ctttgataaa   1080

aagctttcct ggttccgcga aattttggaa tttcagaatg agtcgagcga tgccgaagaa   1140

tttatggaat ctcttaaaat cgatttgttt tcggacatgg tattcgtttt tacgccgaaa   1200

ggggacgtca tcgaattgcc gtcaggatcc gtgccgatcg acttttcgta ccgaatccat   1260

tcagaaatag gcaataaaac gatcggggcc aaagtaaacg gcaaaatggt cacccttgat   1320

tacaagctgc gcacagggga tatcgtagaa attctgacgt ccaagcattc gtacggtccg   1380

agtcaggact ggatcaacct tgcgcagaca tctcaagcga agcataaaat ccgtcagttc   1440

tttaaaaagc agcgcagaga ggaaaatgtc gaaaaaggca gagaactggt tgaaaaagaa   1500

attaaaaacc tggactttga agtgaaggac gtcttaacag ccgagaatct gcagaaggtc   1560

gccgacaaat tcaactttgc caatgaagaa gacatgtatg ccgctgtcgg ctataacggc   1620

attacagccg ctcaagttgc aaaccgcctt acggaaaaag aacggaagat cagagatcag   1680
```

-continued

```
gaagaacagg tgaaaagcgt tcaggacgta acgcctgaag tgaaacctta ccaagggaag   1740

aaacgcgaag cgggtgttcg cgtcaaaggc gttgacaacc ttttgatcag gctgtcaaaa   1800

tgctgcaacc ctgttccggg agatccgatc gtcggattca ttacaaaagg caggggcgta   1860

tccgtccatc gcgaggactg cccgaatgtt ttaacaaatg aagcgctcga ccggctcatt   1920

caagtagaat gggagcatga accgcagacc cagcggagaa aagaatataa cgtcgaaatt   1980

gagattctcg gctatgaccg ccgcggtctt cttaatgaag ttctacaggc agttaatgag   2040

acaaaaacaa atatttcatc tgtttcaggt aaatcggacc gcaataaagt ggcgacgatc   2100

catatggcga tcttcattca aaatattaac catttgcata aagtagttga acggattaag   2160

cagatcaaag atatttactc cgtgcgcagg gtgatgaatt ag                      2202
```

<210> SEQ ID NO 46
<211> LENGTH: 733
<212> TYPE: PRT
<213> ORGANISM: Bacillus licheniformis

<400> SEQUENCE: 46

```
Met Ala Asn Glu Gln Val Leu Thr Ala Glu Gln Val Ile Glu Lys Ala
1               5                   10                  15

Lys Ser Tyr Leu Ser Asp Glu His Val Ala Phe Ile Lys Lys Ala Tyr
            20                  25                  30

Gln Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ala Thr Ile Ala Gly Gly Phe Leu His Asp Val Val
65                  70                  75                  80

Glu Asp Thr Ser Val Thr Leu Glu Asp Leu Lys Glu Ala Phe Asn Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Glu Glu Val Val Asn Glu
    210                 215                 220

Val Lys Ser Arg Val Glu Glu Val Asn Ile Lys Ala Asp Phe Ser Gly
225                 230                 235                 240

Arg Pro Lys His Ile Tyr Ser Ile Tyr Arg Lys Met Ala Met Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285
```

-continued

```
Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Gly
305                 310                 315                 320

Asp Pro Leu Glu Val Gln Ile Arg Thr Phe Glu Met His Glu Ile Ala
                325                 330                 335

Glu Tyr Gly Ile Ala Ala His Trp Ala Tyr Lys Glu Gly Lys Asn Ala
            340                 345                 350

Asn Glu Asp Ser Ser Phe Asp Lys Lys Leu Ser Trp Phe Arg Glu Ile
        355                 360                 365

Leu Glu Phe Gln Asn Glu Ser Ser Asp Ala Glu Glu Phe Met Glu Ser
    370                 375                 380

Leu Lys Ile Asp Leu Phe Ser Asp Met Val Phe Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp Tyr Lys Leu Arg Thr Gly Asp Ile
        435                 440                 445

Val Glu Ile Leu Thr Ser Lys His Ser Tyr Gly Pro Ser Gln Asp Trp
    450                 455                 460

Ile Asn Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Val Lys Asp Val Leu
            500                 505                 510

Thr Ala Glu Asn Leu Gln Lys Val Ala Asp Lys Phe Asn Phe Ala Asn
        515                 520                 525

Glu Glu Asp Met Tyr Ala Ala Val Gly Tyr Asn Gly Ile Thr Ala Ala
    530                 535                 540

Gln Val Ala Asn Arg Leu Thr Glu Lys Glu Arg Lys Ile Arg Asp Gln
545                 550                 555                 560

Glu Glu Gln Val Lys Ser Val Gln Asp Val Thr Pro Glu Val Lys Pro
                565                 570                 575

Tyr Gln Gly Lys Lys Arg Glu Ala Gly Val Arg Val Lys Gly Val Asp
            580                 585                 590

Asn Leu Leu Ile Arg Leu Ser Lys Cys Cys Asn Pro Val Pro Gly Asp
        595                 600                 605

Pro Ile Val Gly Phe Ile Thr Lys Gly Arg Gly Val Ser Val His Arg
    610                 615                 620

Glu Asp Cys Pro Asn Val Leu Thr Asn Glu Ala Leu Asp Arg Leu Ile
625                 630                 635                 640

Gln Val Glu Trp Glu His Glu Pro Gln Thr Gln Arg Arg Lys Glu Tyr
                645                 650                 655

Asn Val Glu Ile Glu Ile Leu Gly Tyr Asp Arg Arg Gly Leu Leu Asn
            660                 665                 670

Glu Val Leu Gln Ala Val Asn Glu Thr Lys Thr Asn Ile Ser Ser Val
        675                 680                 685

Ser Gly Lys Ser Asp Arg Asn Lys Val Ala Thr Ile His Met Ala Ile
    690                 695                 700

Phe Ile Gln Asn Ile Asn His Leu His Lys Val Val Glu Arg Ile Lys
705                 710                 715                 720
```

Gln Ile Lys Asp Ile Tyr Ser Val Arg Arg Val Met Asn
725 730

<210> SEQ ID NO 47
<211> LENGTH: 2205
<212> TYPE: DNA
<213> ORGANISM: Bacillus subtilis

<400> SEQUENCE: 47
atggcgaacg aacaagtatt gactgccgag caagttatag ataaagcacg cagctatcta 60
tctgatgagc atatcgcatt tgtcgaaaaa gcatatctgt acgctgaaga tgctcatcgc 120
gagcaatacc gcaaatcggg cgagccatat attattcatc cgattcaggt tgcggggata 180
ctcgttgatc ttgaaatgga cccttccaca atcgcgggcg gatttttgca cgatgtcgtg 240
gaagatacag atgtgacgct cgatgacctg aaagaagcat tttccgaaga agtggcaatg 300
cttgtagacg gcgtaacgaa actcggcaaa attaaatata aatctcaaga ggaacagcag 360
gcggaaaatc atcgcaaaat gtttgtcgct atggctcaag atatcagggt catattgatc 420
aagctggcgg atcgtcttca caatatgcgg acactgaaac atctgcctca ggaaaaacag 480
cggagaatct ccaatgaaac gctggaaatt tttgctcctt tggcgcatcg tctcgggatt 540
tcaaaaatta agtgggaatt ggaagatacg gcgctccgtt atttgaaccc tcagcaatat 600
tacagaattg tcaacctcat gaagaagaaa cgtgcagaac gagagcttta tgtcgatgag 660
gttgtcaatg aagtgaagaa acgtgtcgaa gaagtaaata tcaaggctga cttctcggga 720
cgcccgaaac atatttacag catttatcga aaaatggtgc tgcaaaataa gcaattcaat 780
gaaatttacg atttgttggc tgtccgtatt cttgtgaata gcataaagga ctgctacgcg 840
gtgcttggca tcattcacac atgctggaaa ccgatgccag gcagattcaa agattatatc 900
gcaatgccga agccgaatat gtatcaatcg cttcatacaa cggttattgg gcctaaagcg 960
gatccgcttg aagtgcagat ccgcaccttt gaaatgcatg aaatagcgga atacggggtt 1020
gcggctcact gggcttataa agaagggaaa gcagccaatg aaggtgcaac ctttgagaaa 1080
aagctttctt ggttccgtga aattttagaa tttcaaaatg aatcgacaga tgcagaagaa 1140
tttatggaat cgctcaaaat tgatttgttc tctgacatgg tgtatgtctt tacgccaaaa 1200
ggagatgtaa tcgagcttcc gtccggttct gttccgattg acttttctta ccggattcac 1260
tctgaaatcg gcaataaaac aatcggtgcc aaagtaaacg gaaaaatggt tacgcttgac 1320
cataagcttc ggacaggtga tatcgttgaa attctcacct ctaagcattc ctacggtccg 1380
agccaggatt gggtgaagct tgcccaaaca tcccaagcga agcataaaat ccgtcaattc 1440
tttaagaaac agcggcgtga agaaaatgtc gaaaaaggcc gtgagctggt cgaaaaagaa 1500
attaaaaact tggattttga attgaaggat gttttaacgc cggagaatat tcaaaaggtt 1560
gctgacaaat ttaatttctc aaatgaagag gatatgtacg cggcggtcgg ttacaacggc 1620
atcacagctc tgcaggtggc gaaccgccta acagaaaaag agagaaagca gcgcgaccag 1680
gaagaacagg aaaagatcgt tcaggaagtc actggggaac ctaagccata cccgcaagga 1740
agaaaacggg aagctggcgt tcgtgtcaag ggcattgaca acctccttgt ccgtttatca 1800
aaatgctgca atcctgtgcc aggtgatgat attgtcggct ttatcacaaa aggcagaggg 1860
gtttcggtcc atcgcgaaga ctgtccgaat gtcaaaacga atgaagccca agagcggctg 1920
atcccggtag agtgggaaca tgagtcacaa gttcaaaagc gcaaggaata caatgttgag 1980
atagagattc ttgggtatga ccgccgcgga ttgctgaacg aggtactcca ggcagtgaat 2040

-continued

```
gaaacgaaaa ccaatatttc atctgtctct ggcaaatcgg atcgcaataa agtggcaacc   2100

atccatatgg cgatttttat ccagaatatc aatcacttgc ataaagtcgt cgagcgtatt   2160

aaacagatta gagatatcta ttctgtgcgc cgcgtcatga actaa                   2205


<210> SEQ ID NO 48
<211> LENGTH: 734
<212> TYPE: PRT
<213> ORGANISM: Bacillus subtilis

<400> SEQUENCE: 48

Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
                325                 330                 335

Glu Tyr Gly Val Ala Ala His Trp Ala Tyr Lys Glu Gly Lys Ala Ala
            340                 345                 350
```

-continued

```
Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
    610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
        675                 680                 685

Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 49
<211> LENGTH: 2241
<212> TYPE: DNA
<213> ORGANISM: Pseudomonas putida

<400> SEQUENCE: 49

-continued

```
atggtacagg tgagagtgca ccagccggtc aacactgacg gcagtatcaa tctcgaagca      60
tggttggacc atgtggtaag cgtcgattcg gcactggatc gcgcagcgct gaaagaagcc     120
tgcgagtttg ctcttgaggt agagaaaaag ggcaacccgg ccaagcattc ctgggcggat     180
ggtacgtcca gcttccaggc aggcctggaa atcgccgaaa ttctggctga cctcaagctc     240
gaccaggact ccctggtggc tgcggtcatc taccgctcgg tgcgcgaggg caaggtcacc     300
ctcgccgagg tcagccagcg gtttggcccg gtggtgtcca agctgatcga cggtgtgctg     360
cgcatggccg ccatcagtgc cagcctcagc ccacgacagt cgctggtgct gggctcgcag     420
gcgcaggtag agaacctgcg caagatgctg gtggccatgg tcgacgacgt gcgcgtggcg     480
ctgatcaagc tggccgaacg cacgtgcgca atccgggcgg tcaagtccgc cgatgacgag     540
aaacgcctgc gtgtcgcgcg tgaagtgttc gacatctacg cgccgctcgc gcaccgcctg     600
ggtatcggtc acatcaagtg ggagctggaa gacctgtcct tccgctacct ggagcccgac     660
cagtacaagc agatcgccaa gctgttgcat gagcggcggc tggaccgcga gcgcttcatc     720
agcgacgtga tgaaccagct gcagaacgag ttgctcgcca ctggcgtgaa ggccgacatc     780
agcggccggg cgaaacatat ctattcgatc tggcgcaaga tgcagcgcaa aggcctggag     840
ttcagccaga tctacgacgt gcgtgcggtg cgcgtgctgg tgccggaaat ccgcgactgc     900
tacaccgcgc tgggcatcgt gcacaccttg tggcggcata ttcccaagga gttcgacgac     960
tacatcgcca accccaagga gaacggctac cgctcgttgc acactgcggt aatcggcccc    1020
gagggcaagg tgctggaggt gcagatccgt acccacggca tgcacgaaga ggccgaactt    1080
ggcgtatgcg cccactggcg ctacaagggc accgacgtca agcccagctc caaccactac    1140
gaagaaaaga tttcctggtt gcgtcaggtg ctggagtggc acgaagagct gggcgacatc    1200
ggtggcctgg ccgagcagtt gcgggtcgac atcgagcctg accgggttta tgtgttcacc    1260
cccgacggcc acgccatcga cctgcccaaa ggcgccacgc cattggactt cgcctaccgc    1320
gtgcacaccg agatcggcca caactgccgc ggcgcgaaga tcaacggccg tatcgtgccg    1380
ctgaactaca gcctgcagac tggcgagcag gtggagatca tcaccagcaa gcacggcaac    1440
cccagccgtg actggttgaa ctccaacctg ggctacgtca ccacctcgcg ggcgcgggcc    1500
aagatcgtcc actggttcaa attgcaggcc cgcgaccaga acgttgctgc cggcaagacc    1560
ttgcttgagc gcgagctcag tcgtctgggc ctgccgcagg ttgatttcga gcgcctggcc    1620
gagaagacca acgtcaagac cgccgaggac atgtttgcct cgctcggtgc tggcgacctg    1680
cgcctggctc atctggtcaa cgctgcccag cagttgctgg agcctgagcg tatcgagcag    1740
atcgagctgg tgccgcgcaa gcctaccggg ccgcgtaccg gcaagcgtgg cgacattcag    1800
atccagggtg tcggcaacct gctgacacag atggccggct gctgccagcc gctaccgggc    1860
gatgccattg tcggttacat cacccagggc cggggcgtga gcattcatcg ccaggactgc    1920
gcctcggtac tgcagctggc gggcaaagag ccagagcgca tgatccaggt gagctggggg    1980
ccgatcccgg tgcagaccta cccggtcgac atcgtcatcc gcgcctacga ccgcccgggc    2040
ctgctgcgcg atgtgtcgca ggtgctgctg aacgagaaga tcaacgtgct ggcggtgaac    2100
acccgttcga acaaggaaga caacaccgcg ctgatgtcgc tgaccatcga gattccaggc    2160
ctggacgcgc tggggcgcct gctggggcgg atctcgcagt tgccgaacat catcgagacg    2220
cggcgtaatc gtaccccttg a                                               2241
```

<210> SEQ ID NO 50
<211> LENGTH: 746
<212> TYPE: PRT

<213> ORGANISM: Pseudomonas putida

<400> SEQUENCE: 50

Met Val Gln Val Arg Val His Gln Pro Val Asn Thr Asp Gly Ser Ile
1               5                   10                  15

Asn Leu Glu Ala Trp Leu Asp His Val Val Ser Val Asp Ser Ala Leu
            20                  25                  30

Asp Arg Ala Ala Leu Lys Glu Ala Cys Glu Phe Ala Leu Glu Val Glu
        35                  40                  45

Lys Lys Gly Asn Pro Ala Lys His Ser Trp Ala Asp Gly Thr Ser Ser
    50                  55                  60

Phe Gln Ala Gly Leu Glu Ile Ala Glu Ile Leu Ala Asp Leu Lys Leu
65                  70                  75                  80

Asp Gln Asp Ser Leu Val Ala Ala Val Ile Tyr Arg Ser Val Arg Glu
                85                  90                  95

Gly Lys Val Thr Leu Ala Glu Val Ser Gln Arg Phe Gly Pro Val Val
            100                 105                 110

Ser Lys Leu Ile Asp Gly Val Leu Arg Met Ala Ala Ile Ser Ala Ser
        115                 120                 125

Leu Ser Pro Arg Gln Ser Leu Val Leu Gly Ser Gln Ala Gln Val Glu
    130                 135                 140

Asn Leu Arg Lys Met Leu Val Ala Met Val Asp Asp Val Arg Val Ala
145                 150                 155                 160

Leu Ile Lys Leu Ala Glu Arg Thr Cys Ala Ile Arg Ala Val Lys Ser
                165                 170                 175

Ala Asp Asp Glu Lys Arg Leu Arg Val Ala Arg Glu Val Phe Asp Ile
            180                 185                 190

Tyr Ala Pro Leu Ala His Arg Leu Gly Ile Gly His Ile Lys Trp Glu
        195                 200                 205

Leu Glu Asp Leu Ser Phe Arg Tyr Leu Glu Pro Asp Gln Tyr Lys Gln
    210                 215                 220

Ile Ala Lys Leu Leu His Glu Arg Arg Leu Asp Arg Glu Arg Phe Ile
225                 230                 235                 240

Ser Asp Val Met Asn Gln Leu Gln Asn Glu Leu Leu Ala Thr Gly Val
                245                 250                 255

Lys Ala Asp Ile Ser Gly Arg Ala Lys His Ile Tyr Ser Ile Trp Arg
            260                 265                 270

Lys Met Gln Arg Lys Gly Leu Glu Phe Ser Gln Ile Tyr Asp Val Arg
        275                 280                 285

Ala Val Arg Val Leu Val Pro Glu Ile Arg Asp Cys Tyr Thr Ala Leu
    290                 295                 300

Gly Ile Val His Thr Leu Trp Arg His Ile Pro Lys Glu Phe Asp Asp
305                 310                 315                 320

Tyr Ile Ala Asn Pro Lys Glu Asn Gly Tyr Arg Ser Leu His Thr Ala
                325                 330                 335

Val Ile Gly Pro Glu Gly Lys Val Leu Glu Val Gln Ile Arg Thr His
            340                 345                 350

Gly Met His Glu Glu Ala Glu Leu Gly Val Cys Ala His Trp Arg Tyr
        355                 360                 365

Lys Gly Thr Asp Val Lys Pro Ser Ser Asn His Tyr Glu Glu Lys Ile
    370                 375                 380

Ser Trp Leu Arg Gln Val Leu Glu Trp His Glu Glu Leu Gly Asp Ile
385                 390                 395                 400

Gly Gly Leu Ala Glu Gln Leu Arg Val Asp Ile Glu Pro Asp Arg Val

-continued

```
                405                 410                 415

Tyr Val Phe Thr Pro Asp Gly His Ala Ile Asp Leu Pro Lys Gly Ala
            420                 425                 430

Thr Pro Leu Asp Phe Ala Tyr Arg Val His Thr Glu Ile Gly His Asn
        435                 440                 445

Cys Arg Gly Ala Lys Ile Asn Gly Arg Ile Val Pro Leu Asn Tyr Ser
    450                 455                 460

Leu Gln Thr Gly Glu Gln Val Glu Ile Ile Thr Ser Lys His Gly Asn
465                 470                 475                 480

Pro Ser Arg Asp Trp Leu Asn Ser Asn Leu Gly Tyr Val Thr Thr Ser
                485                 490                 495

Arg Ala Arg Ala Lys Ile Val His Trp Phe Lys Leu Gln Ala Arg Asp
            500                 505                 510

Gln Asn Val Ala Ala Gly Lys Thr Leu Leu Glu Arg Glu Leu Ser Arg
        515                 520                 525

Leu Gly Leu Pro Gln Val Asp Phe Glu Arg Leu Ala Glu Lys Thr Asn
    530                 535                 540

Val Lys Thr Ala Glu Asp Met Phe Ala Ser Leu Gly Ala Gly Asp Leu
545                 550                 555                 560

Arg Leu Ala His Leu Val Asn Ala Ala Gln Gln Leu Leu Glu Pro Glu
                565                 570                 575

Arg Ile Glu Gln Ile Glu Leu Val Pro Arg Lys Pro Thr Gly Pro Arg
            580                 585                 590

Thr Gly Lys Arg Gly Asp Ile Gln Ile Gln Gly Val Gly Asn Leu Leu
        595                 600                 605

Thr Gln Met Ala Gly Cys Cys Gln Pro Leu Pro Gly Asp Ala Ile Val
    610                 615                 620

Gly Tyr Ile Thr Gln Gly Arg Gly Val Ser Ile His Arg Gln Asp Cys
625                 630                 635                 640

Ala Ser Val Leu Gln Leu Ala Gly Lys Glu Pro Glu Arg Met Ile Gln
                645                 650                 655

Val Ser Trp Gly Pro Ile Pro Val Gln Thr Tyr Pro Val Asp Ile Val
            660                 665                 670

Ile Arg Ala Tyr Asp Arg Pro Gly Leu Leu Arg Asp Val Ser Gln Val
        675                 680                 685

Leu Leu Asn Glu Lys Ile Asn Val Leu Ala Val Asn Thr Arg Ser Asn
    690                 695                 700

Lys Glu Asp Asn Thr Ala Leu Met Ser Leu Thr Ile Glu Ile Pro Gly
705                 710                 715                 720

Leu Asp Ala Leu Gly Arg Leu Leu Gly Arg Ile Ser Gln Leu Pro Asn
                725                 730                 735

Ile Ile Glu Thr Arg Arg Asn Arg Thr Pro
            740                 745
```

<210> SEQ ID NO 51
<211> LENGTH: 2109
<212> TYPE: DNA
<213> ORGANISM: Pseudomonas putida

<400> SEQUENCE: 51

```
atgccgggta tagaagcctt ggccgaacgg ctttcgacct atcttggccc cgaacaggtc      60

aacctggttc ggcgtgccta tttctacgcc gaacaggccc acgatgggca acgccgccgc     120

agtggcgagc cctacgtgac ccacccgctg gccgtggcca gcatcctcgc cgacatgcac     180

atggaccatc agagcctgat ggcggccatg ctgcacgatg tgatcgaaga caccggcatc     240
```

```
gccaaggaag ccctcagcca gcagtttggc gagaccgtgg ccgaattggt cgatggggtc    300

agcaagctga cccagatgaa tttcgagacc aaggccgagg cgcaggcgga aaacttccag    360

aagatggcca tggccatggc ccgcgatatc cgcgtgatcc tggtcaagct ggccgaccgc    420

ctgcacaaca tgcgcaccct ggaagtgctg tctggcgaaa agcgccggcg cattgccaag    480

gaaaccctcg agatctacgc ccccatcgca aaccgcctgg ggatgcacac cgtgcgcgta    540

gagttcgaag accttggctt caaggccatg cacccgatgc gctcgtcgct gattcatcgt    600

gcagtgaaga gcgcgcgcgg caaccgcaaa gagatcgtcg ccaagatcga gcactcgctg    660

gccaactgcc tggccgccga cggcatcgag ggcgaagtca gcggtcggca gaaacacctc    720

tatggcatct acaagaagat gcgcggcaag cgccgtgcct tcaacgagat catggacgtg    780

tatgccttcc gcatcatcgt cgacaaggtt gacacctgtt accgcgtgct cggcgccgta    840

cacaacctgt acaagccgct gcccggacgc ttcaaggatt acatcgcgat ccccaaggcc    900

aacggctacc agtcgttgca caccaccctg ttcggcatgc acggcgtgcc catcgaaatc    960

cagattcgca cccgcgaaat ggaagagatg gccaacaacg gcatcgccgc gcactggctg   1020

tacaagtcaa acgacgacga gcagcccaag ggcagccacg cgcgcgcccg ccagtgggtc   1080

aagggtatcc ttgaactgca gcaacgtgcc ggcaactccc tggaattcat cgagagcgtg   1140

aagatcgacc tgttcccgga cgaggtctac gtgttcacgc ccaaaggccg gatcatggag   1200

ttgcccaaag gctccacggc cgtcgacttc gcctacgcgg tccacaccga cgtcggcaac   1260

agttgcatcg cttgccgcat caaccgccgc ctggcgccgc tgtccgaacc gctacaaagc   1320

ggctcgacag tggaaatcgt cagcgccccg ggcgctcggc caaacccggc atggctcaac   1380

tttgtggtct cgggcaaggc acgcacgaat atccgccacg cgctcaagca acagcgccgc   1440

tcggagtcca tcagcctggg cgagcgcctg ctgaacaagg tactcactgg cttcgacagc   1500

agcctggaga aaatccccca ggaacgcatc cagtctattc tcgccgagta ccgcctggag   1560

ctcatagaag acctgctcga agacatcggc ctgggcaacc gcatggccta cgtggtcgcg   1620

cgccgcctgc tgtcggccga aggcgaacag ctgccggcgc cagaaggccc actggcgatc   1680

cgcggcaccg aaggcctggt gctcagctac gccaagtgct gcacgccgat cccgggtgac   1740

ccgattgtcg gccacctgtc ggccggcaag ggcatggtcg tgcacctgga gaactgccgc   1800

aacatcagtg aaatccgcca caaccccgaa aagtgcgtgc aactctcctg ggccaaggac   1860

atcactggcg agttcaatgt cgaactgcgt gtcgaactgg aacaccagcg cgggctgatc   1920

gccctgctgg ccagcagcgt caacgccgcc gacggcaaca ttgagaagat cagcatggac   1980

gaacgcgacg gccgtatcag cgtggtccaa ctggtggtca gcgtgcacga ccgcgtgcac   2040

ctggcgcgtg tgatcaagaa gctgcgtacc ctgaccggtg tggtccgcat cacccgcatg   2100

cgtacgtag                                                           2109
```

<210> SEQ ID NO 52
<211> LENGTH: 702
<212> TYPE: PRT
<213> ORGANISM: Pseudomonas putida

<400> SEQUENCE: 52

```
Met Pro Gly Ile Glu Ala Leu Ala Glu Arg Leu Ser Thr Tyr Leu Gly
1               5                   10                  15

Pro Glu Gln Val Asn Leu Val Arg Arg Ala Tyr Phe Tyr Ala Glu Gln
            20                  25                  30

Ala His Asp Gly Gln Arg Arg Arg Ser Gly Glu Pro Tyr Val Thr His
```

```
        35                  40                  45

Pro Leu Ala Val Ala Ser Ile Leu Ala Asp Met His Met Asp His Gln
    50                  55                  60

Ser Leu Met Ala Ala Met Leu His Asp Val Ile Glu Asp Thr Gly Ile
65                  70                  75                  80

Ala Lys Glu Ala Leu Ser Gln Gln Phe Gly Glu Thr Val Ala Glu Leu
                85                  90                  95

Val Asp Gly Val Ser Lys Leu Thr Gln Met Asn Phe Glu Thr Lys Ala
            100                 105                 110

Glu Ala Gln Ala Glu Asn Phe Gln Lys Met Ala Met Ala Met Ala Arg
        115                 120                 125

Asp Ile Arg Val Ile Leu Val Lys Leu Ala Asp Arg Leu His Asn Met
    130                 135                 140

Arg Thr Leu Glu Val Leu Ser Gly Glu Lys Arg Arg Arg Ile Ala Lys
145                 150                 155                 160

Glu Thr Leu Glu Ile Tyr Ala Pro Ile Ala Asn Arg Leu Gly Met His
                165                 170                 175

Thr Val Arg Val Glu Phe Glu Asp Leu Gly Phe Lys Ala Met His Pro
            180                 185                 190

Met Arg Ser Ser Leu Ile His Arg Ala Val Lys Ser Ala Arg Gly Asn
        195                 200                 205

Arg Lys Glu Ile Val Ala Lys Ile Glu His Ser Leu Ala Asn Cys Leu
    210                 215                 220

Ala Ala Asp Gly Ile Glu Gly Glu Val Ser Gly Arg Gln Lys His Leu
225                 230                 235                 240

Tyr Gly Ile Tyr Lys Lys Met Arg Gly Lys Arg Arg Ala Phe Asn Glu
                245                 250                 255

Ile Met Asp Val Tyr Ala Phe Arg Ile Ile Val Asp Lys Val Asp Thr
            260                 265                 270

Cys Tyr Arg Val Leu Gly Ala Val His Asn Leu Tyr Lys Pro Leu Pro
        275                 280                 285

Gly Arg Phe Lys Asp Tyr Ile Ala Ile Pro Lys Ala Asn Gly Tyr Gln
    290                 295                 300

Ser Leu His Thr Thr Leu Phe Gly Met His Gly Val Pro Ile Glu Ile
305                 310                 315                 320

Gln Ile Arg Thr Arg Glu Met Glu Glu Met Ala Asn Asn Gly Ile Ala
                325                 330                 335

Ala His Trp Leu Tyr Lys Ser Asn Asp Asp Glu Gln Pro Lys Gly Ser
            340                 345                 350

His Ala Arg Ala Arg Gln Trp Val Lys Gly Ile Leu Glu Leu Gln Gln
        355                 360                 365

Arg Ala Gly Asn Ser Leu Glu Phe Ile Glu Ser Val Lys Ile Asp Leu
    370                 375                 380

Phe Pro Asp Glu Val Tyr Val Phe Thr Pro Lys Gly Arg Ile Met Glu
385                 390                 395                 400

Leu Pro Lys Gly Ser Thr Ala Val Asp Phe Ala Tyr Ala Val His Thr
                405                 410                 415

Asp Val Gly Asn Ser Cys Ile Ala Cys Arg Ile Asn Arg Arg Leu Ala
            420                 425                 430

Pro Leu Ser Glu Pro Leu Gln Ser Gly Ser Thr Val Glu Ile Val Ser
        435                 440                 445

Ala Pro Gly Ala Arg Pro Asn Pro Ala Trp Leu Asn Phe Val Val Ser
    450                 455                 460
```

```
Gly Lys Ala Arg Thr Asn Ile Arg His Ala Leu Lys Gln Gln Arg Arg
465                 470                 475                 480

Ser Glu Ser Ile Ser Leu Gly Glu Arg Leu Leu Asn Lys Val Leu Thr
                485                 490                 495

Gly Phe Asp Ser Ser Leu Glu Lys Ile Pro Gln Glu Arg Ile Gln Ser
            500                 505                 510

Ile Leu Ala Glu Tyr Arg Leu Glu Leu Ile Glu Asp Leu Leu Glu Asp
        515                 520                 525

Ile Gly Leu Gly Asn Arg Met Ala Tyr Val Val Ala Arg Arg Leu Leu
    530                 535                 540

Ser Ala Glu Gly Glu Gln Leu Pro Ala Pro Glu Gly Pro Leu Ala Ile
545                 550                 555                 560

Arg Gly Thr Glu Gly Leu Val Leu Ser Tyr Ala Lys Cys Cys Thr Pro
                565                 570                 575

Ile Pro Gly Asp Pro Ile Val Gly His Leu Ser Ala Gly Lys Gly Met
            580                 585                 590

Val Val His Leu Glu Asn Cys Arg Asn Ile Ser Glu Ile Arg His Asn
        595                 600                 605

Pro Glu Lys Cys Val Gln Leu Ser Trp Ala Lys Asp Ile Thr Gly Glu
    610                 615                 620

Phe Asn Val Glu Leu Arg Val Glu Leu Glu His Gln Arg Gly Leu Ile
625                 630                 635                 640

Ala Leu Leu Ala Ser Ser Val Asn Ala Ala Asp Gly Asn Ile Glu Lys
                645                 650                 655

Ile Ser Met Asp Glu Arg Asp Gly Arg Ile Ser Val Val Gln Leu Val
            660                 665                 670

Val Ser Val His Asp Arg Val His Leu Ala Arg Val Ile Lys Lys Leu
        675                 680                 685

Arg Thr Leu Thr Gly Val Val Arg Ile Thr Arg Met Arg Thr
    690                 695                 700
```

<210> SEQ ID NO 53
<211> LENGTH: 2223
<212> TYPE: DNA
<213> ORGANISM: CLostridium acetobutylicum

<400> SEQUENCE: 53

```
atggctgaat tatcagattt attagaaaag atagatgaaa attgtaataa tgtagataaa      60

gatattgtca ttaaagctta caattttgca tatgaggctc ataaacatca aatgagggag     120

tccggagaac cttacataag tcatcctctc gatgtagcgt gtattttagc agagatgggt     180

atggatatga gtactatagt tgcaggaata ctccatgatg ttatagagga cacaagttat     240

agctatgatg atattacaga aatgtttagc aaagaagttg ctgatttagt atcaggggta     300

acaaagctag ataaaataac ttataagacg aaggaagagc agcaagctga taatgtaaga     360

aagatgcttc ttgcaatggc taaggatata agagttattt taataaaact tgcagataga     420

cttcataata tgcgtactct taaatttaaa cgtgagcaaa aacaaaaaga gaaggcaaag     480

gagactctgg atatatatgc tccacttgca catagacttg gtatgtctaa gataaaatgg     540

gaacttgaag atttgtcctt cagatatttg aaaccaaagg aatactatga gcttgtggat     600

ctaatagctg aaaaaagagt tgaaagagaa gaatacataa gcaagatagt agaagaactt     660

aaacttaatt tggaagcatc agggataact ccagatattg atggaaggcc aaaacatttt     720

tatagtatat atagaaagat gttaaataag agtaaaagct tagatcagat tttgatttta     780

acagctgtta gaatactagt aaataacata aaagagtgtt atgctgccct tggaatagtg     840
```

```
catacaatgt ataaacctat accaggcaga tttaaagatt atatagctat gccaaaacct    900

aatatgtatc aatcacttca ttctacggta ataggacctg agggaaagcc ttttgagatt    960

cagattagaa cttatgacat gcataagaca gctgaatatg gaatagctgc tcattggaaa   1020

tataaggaag gaacaataga aagtactcaa aatgttcctc aaaataagaa tgcaaataaa   1080

gatgatacta agcttacatg gataagagag atgcttgaat ggcaaagaga aacgccaagt   1140

gctcaagagt tcatggaaaa ctttaagata gatttatttt cagatgaaat ttttgttttt   1200

acacctaaag gtaaggtaat aaatttgccg tataatgcaa caccagtaga ctttgcttat   1260

aaaatacata cagatatagg aaataggtgt gtgggtgcaa aggttaatgg taaaatagtt   1320

ccacttgatt ataagcttaa aacaggagaa atagttgata tactaacaac atctttagtt   1380

aaaggtccga atattaattg gcttaattct gttactagca atcaggctaa aagcaaaata   1440

aggtcttggt ttaaaaaggc taaaagagat gaaaacataa gcaagggcaa agaactctta   1500

gaaaaagaat cgaaaaagca ggaatttaat tttggagaga tagctaaggg tgaaaattta   1560

gagttagtat taaaacgata taatatgaac tcaatagacg atttatatgc ttctgttgga   1620

ataggtgcag taggggcatc agtgatatta agtagattta aagatattta tgaaaagaat   1680

aaggataatg gttctcttac aaatgaagaa gtacttgaaa atgtaaataa gaacattcat   1740

aaagaacact cctctaaaaa gatttctaag agtgagcagc ctggagtaac ggttaagggc   1800

gtttctgatg tcctagtaag atttgcgaaa tgctgtacac cagttcctgg tgatcctata   1860

ataggttata ttacaaaagg cagaggagtt tcagttcata ggactgattg cacaaatgta   1920

aataatttaa tcaaagagga tagttcaaga atcatagaag taaaatgggg aaaaagtaaa   1980

aacgaaagtt atatggctga agttgaaatt aaagcggaag ataggcaagc tcttcttgcg   2040

gatgtggtag aagttataag ttacatggaa atagcaatag aatcggttaa tgcaaaaact   2100

tcaaagggat cagcatatct caatttgaag ttaaagatac aggatgttga gcatttagcg   2160

ctgcttatga aaaagcttag aaggcttcca ggcattattg atatatatag aactaatagc   2220

tag                                                                 2223
```

<210> SEQ ID NO 54
<211> LENGTH: 740
<212> TYPE: PRT
<213> ORGANISM: Clostridium acetobutylicum

<400> SEQUENCE: 54

```
Met Ala Glu Leu Ser Asp Leu Leu Glu Lys Ile Asp Glu Asn Cys Asn
1               5                   10                  15

Asn Val Asp Lys Asp Ile Val Ile Lys Ala Tyr Asn Phe Ala Tyr Glu
            20                  25                  30

Ala His Lys His Gln Met Arg Glu Ser Gly Glu Pro Tyr Ile Ser His
        35                  40                  45

Pro Leu Asp Val Ala Cys Ile Leu Ala Glu Met Gly Met Asp Met Ser
    50                  55                  60

Thr Ile Val Ala Gly Ile Leu His Asp Val Ile Glu Asp Thr Ser Tyr
65                  70                  75                  80

Ser Tyr Asp Asp Ile Thr Glu Met Phe Ser Lys Glu Val Ala Asp Leu
                85                  90                  95

Val Ser Gly Val Thr Lys Leu Asp Lys Ile Thr Tyr Lys Thr Lys Glu
            100                 105                 110

Glu Gln Gln Ala Asp Asn Val Arg Lys Met Leu Leu Ala Met Ala Lys
        115                 120                 125
```

-continued

```
Asp Ile Arg Val Ile Leu Ile Lys Leu Ala Asp Arg Leu His Asn Met
    130                 135                 140

Arg Thr Leu Lys Phe Lys Arg Glu Gln Lys Gln Lys Glu Lys Ala Lys
145                 150                 155                 160

Glu Thr Leu Asp Ile Tyr Ala Pro Leu Ala His Arg Leu Gly Met Ser
                165                 170                 175

Lys Ile Lys Trp Glu Leu Glu Asp Leu Ser Phe Arg Tyr Leu Lys Pro
            180                 185                 190

Lys Glu Tyr Tyr Glu Leu Val Asp Leu Ile Ala Glu Lys Arg Val Glu
        195                 200                 205

Arg Glu Glu Tyr Ile Ser Lys Ile Val Glu Glu Leu Lys Leu Asn Leu
    210                 215                 220

Glu Ala Ser Gly Ile Thr Pro Asp Ile Asp Gly Arg Pro Lys His Phe
225                 230                 235                 240

Tyr Ser Ile Tyr Arg Lys Met Leu Asn Lys Ser Lys Ser Leu Asp Gln
                245                 250                 255

Ile Phe Asp Leu Thr Ala Val Arg Ile Leu Val Asn Asn Ile Lys Glu
            260                 265                 270

Cys Tyr Ala Ala Leu Gly Ile Val His Thr Met Tyr Lys Pro Ile Pro
        275                 280                 285

Gly Arg Phe Lys Asp Tyr Ile Ala Met Pro Lys Pro Asn Met Tyr Gln
    290                 295                 300

Ser Leu His Ser Thr Val Ile Gly Pro Glu Gly Lys Pro Phe Glu Ile
305                 310                 315                 320

Gln Ile Arg Thr Tyr Asp Met His Lys Thr Ala Glu Tyr Gly Ile Ala
                325                 330                 335

Ala His Trp Lys Tyr Lys Glu Gly Thr Ile Glu Ser Thr Gln Asn Val
            340                 345                 350

Pro Gln Asn Lys Asn Ala Asn Lys Asp Asp Thr Lys Leu Thr Trp Ile
        355                 360                 365

Arg Glu Met Leu Glu Trp Gln Arg Glu Thr Pro Ser Ala Gln Glu Phe
    370                 375                 380

Met Glu Asn Phe Lys Ile Asp Leu Phe Ser Asp Glu Ile Phe Val Phe
385                 390                 395                 400

Thr Pro Lys Gly Lys Val Ile Asn Leu Pro Tyr Asn Ala Thr Pro Val
                405                 410                 415

Asp Phe Ala Tyr Lys Ile His Thr Asp Ile Gly Asn Arg Cys Val Gly
            420                 425                 430

Ala Lys Val Asn Gly Lys Ile Val Pro Leu Asp Tyr Lys Leu Lys Thr
        435                 440                 445

Gly Glu Ile Val Asp Ile Leu Thr Thr Ser Leu Val Lys Gly Pro Asn
    450                 455                 460

Ile Asn Trp Leu Asn Ser Val Thr Ser Asn Gln Ala Lys Ser Lys Ile
465                 470                 475                 480

Arg Ser Trp Phe Lys Lys Ala Lys Arg Asp Glu Asn Ile Ser Lys Gly
                485                 490                 495

Lys Glu Leu Leu Glu Lys Glu Ser Lys Lys Gln Glu Phe Asn Phe Gly
            500                 505                 510

Glu Ile Ala Lys Gly Glu Asn Leu Glu Leu Val Leu Lys Arg Tyr Asn
        515                 520                 525

Met Asn Ser Ile Asp Asp Leu Tyr Ala Ser Val Gly Ile Gly Ala Val
    530                 535                 540

Gly Ala Ser Val Ile Leu Ser Arg Phe Lys Asp Ile Tyr Glu Lys Asn
```

```
545                 550                 555                 560

Lys Asp Asn Gly Ser Leu Thr Asn Glu Glu Val Leu Glu Asn Val Asn
                565                 570                 575

Lys Asn Ile His Lys Glu His Ser Ser Lys Lys Ile Ser Lys Ser Glu
            580                 585                 590

Gln Pro Gly Val Thr Val Lys Gly Val Ser Asp Val Leu Val Arg Phe
        595                 600                 605

Ala Lys Cys Cys Thr Pro Val Pro Gly Asp Pro Ile Ile Gly Tyr Ile
    610                 615                 620

Thr Lys Gly Arg Gly Val Ser Val His Arg Thr Asp Cys Thr Asn Val
625                 630                 635                 640

Asn Asn Leu Ile Lys Glu Asp Ser Ser Arg Ile Ile Glu Val Lys Trp
                645                 650                 655

Gly Lys Ser Lys Asn Glu Ser Tyr Met Ala Glu Val Glu Ile Lys Ala
            660                 665                 670

Glu Asp Arg Gln Ala Leu Leu Ala Asp Val Val Glu Val Ile Ser Tyr
        675                 680                 685

Met Glu Ile Ala Ile Glu Ser Val Asn Ala Lys Thr Ser Lys Gly Ser
    690                 695                 700

Ala Tyr Leu Asn Leu Lys Leu Lys Ile Gln Asp Val Glu His Leu Ala
705                 710                 715                 720

Leu Leu Met Lys Lys Leu Arg Arg Leu Pro Gly Ile Ile Asp Ile Tyr
                725                 730                 735

Arg Thr Asn Ser
            740


<210> SEQ ID NO 55
<211> LENGTH: 2157
<212> TYPE: DNA
<213> ORGANISM: Enterococcus faecium

<400> SEQUENCE: 55

atgggtcccg aacatgtagc atttgttgag aaagcatgcg aatacgcgac tgctgcacat     60

gacggacagt ttagaaaatc aggcgaaccc tacattattc atcctatcca agtcgcaggt    120

atattagcag atttaaaaat ggatccccat acagtggcta caggcttctt acatgatgtt    180

gttgaagata cagaaatcac tttagaagat ctgagagaag aatttggcga tgacgttgct    240

atgttagtgg acggcgtaac caaattaggg aaaataaaat ataaatccca cgaagagcag    300

ctagcagaaa accaccgaaa gatgctgcta gcaatggctc aagatttacg agttatcatg    360

gtcaaattag ctgatagact acataacatg cgtacgttga agcacctgcg agaagataag    420

caaagaagga tcgctcagga aactttagaa atctatgcgc ctcttgcaca tcgtctaggg    480

atcagccgga tcaaatggga attagaagat acagcacttc gttatctaaa tccaaaacag    540

tattaccgta tcgtccactt gatgcagacg aagagagaag aacgtgaaaa atacgtaagt    600

ggtactgttg aagatattcg aatagcgaca gaagagctgg ggatttttgc agaaatctat    660

ggacggccaa aacacattta ttcaatctat cgtaaaatga aagatcagaa aaagcagttc    720

aacgaaattt atgacttgct agctattcga gtgatcgtag attcaatcaa ggattgttat    780

gctgtattag gagcaatcca cacaaaatgg aaaccaatgc ccggcagatt taaggattat    840

attgccatgc caaaagctaa tatgtaccaa tctttgcata ctaccgtgat cggtccggca    900

ggaaatccgg tagaaattca aatccgaaca caggaaatgc atgaaatcgc tgaattcggg    960

gttgctgcac actgggccta taaagaagga aaaaatgaaa aagtagaacc agatggtatg   1020
```

-continued

```
acgaaacaat taagctggtt ccatgagata ctcgaacttc aagacgaaag ctatgatgct   1080

tctgaattta tggaaggcgt aaaaggagat atctttagtg ataaagtcta cgtcttcaca   1140

ccaaaaggag acgttactga gttaccaaaa ggatccggac cattggactt tgcatacagt   1200

atccatacag atatcggtaa caaaaccact ggtgcaaaag taaatggcaa aatggtgcag   1260

cttgattaca aattgaaaaa cggagatatc attgagatca tgacttctcc aaattcattt   1320

ggcccaagtc gcgactggtt gaaattagtt gctactagca aagcaagaaa taagatcaaa   1380

cgtttcttca aagcccaaga tcgagaagaa aatgtgatca aaggccacga atccgtggtc   1440

aaatgtatta cagatctagg atttacgcct aaagatattt tgacgaagaa caaactgcaa   1500

gaagcactcg atcgttttaa ttatcaaaca gaagatgatc tctatgcagc tgtagggtat   1560

ggagaagtta gccccttgac gatggccaat cgtctgactg aaaaagaacg taaagaacaa   1620

aaaatcgagc agcaaaagca agaagcagaa gaaatcatga atcagccgaa aaaagaacct   1680

gacaaaatga aagtacgtca tgaaggtggc gttgtcattc aaggggtaga aaacttacta   1740

attcgtatca gtcgctgctg taatccgatt cctggtgatg atatcgttgg ttatatcact   1800

aaaggcagag ggatatccat tcatcgtcga gattgtccga atgttcagcc tgacaaacca   1860

aatgtagcag aacgtttgat tgaagtcgaa tgggaagata catcgaatac acgaaaagag   1920

tatgatgcag atttggaaat ttacggctat aatcgttcag gcttattgaa tgatgtactt   1980

caaacagtca atgcgctaac gaaaaatctc aacagcgttg aagcacggac gaataaagat   2040

aaaatggcga cgatccattt gacggttggt atccagaatt tatcccacct aaagagtatc   2100

gtggataaaa tcaaagcagt acctgatgtc tacagtgtac gccggacgaa tggatag      2157
```

```
<210> SEQ ID NO 56
<211> LENGTH: 718
<212> TYPE: PRT
<213> ORGANISM: Enterococcus faecium

<400> SEQUENCE: 56

Met Gly Pro Glu His Val Ala Phe Val Glu Lys Ala Cys Glu Tyr Ala
1               5                   10                  15

Thr Ala Ala His Asp Gly Gln Phe Arg Lys Ser Gly Glu Pro Tyr Ile
            20                  25                  30

Ile His Pro Ile Gln Val Ala Gly Ile Leu Ala Asp Leu Lys Met Asp
        35                  40                  45

Pro His Thr Val Ala Thr Gly Phe Leu His Asp Val Val Glu Asp Thr
    50                  55                  60

Glu Ile Thr Leu Glu Asp Leu Arg Glu Glu Phe Gly Asp Asp Val Ala
65                  70                  75                  80

Met Leu Val Asp Gly Val Thr Lys Leu Gly Lys Ile Lys Tyr Lys Ser
                85                  90                  95

His Glu Glu Gln Leu Ala Glu Asn His Arg Lys Met Leu Leu Ala Met
            100                 105                 110

Ala Gln Asp Leu Arg Val Ile Met Val Lys Leu Ala Asp Arg Leu His
        115                 120                 125

Asn Met Arg Thr Leu Lys His Leu Arg Glu Asp Lys Gln Arg Arg Ile
    130                 135                 140

Ala Gln Glu Thr Leu Glu Ile Tyr Ala Pro Leu Ala His Arg Leu Gly
145                 150                 155                 160

Ile Ser Arg Ile Lys Trp Glu Leu Glu Asp Thr Ala Leu Arg Tyr Leu
                165                 170                 175

Asn Pro Lys Gln Tyr Tyr Arg Ile Val His Leu Met Gln Thr Lys Arg
```

-continued

```
            180                 185                 190

Glu Glu Arg Glu Lys Tyr Val Ser Gly Thr Val Glu Asp Ile Arg Ile
        195                 200                 205

Ala Thr Glu Glu Leu Gly Ile Phe Ala Glu Ile Tyr Gly Arg Pro Lys
    210                 215                 220

His Ile Tyr Ser Ile Tyr Arg Lys Met Lys Asp Gln Lys Lys Gln Phe
225                 230                 235                 240

Asn Glu Ile Tyr Asp Leu Leu Ala Ile Arg Val Ile Val Asp Ser Ile
                245                 250                 255

Lys Asp Cys Tyr Ala Val Leu Gly Ala Ile His Thr Lys Trp Lys Pro
            260                 265                 270

Met Pro Gly Arg Phe Lys Asp Tyr Ile Ala Met Pro Lys Ala Asn Met
        275                 280                 285

Tyr Gln Ser Leu His Thr Thr Val Ile Gly Pro Ala Gly Asn Pro Val
    290                 295                 300

Glu Ile Gln Ile Arg Thr Gln Glu Met His Glu Ile Ala Glu Phe Gly
305                 310                 315                 320

Val Ala Ala His Trp Ala Tyr Lys Glu Gly Lys Asn Glu Lys Val Glu
                325                 330                 335

Pro Asp Gly Met Thr Lys Gln Leu Ser Trp Phe His Glu Ile Leu Glu
            340                 345                 350

Leu Gln Asp Glu Ser Tyr Asp Ala Ser Glu Phe Met Glu Gly Val Lys
        355                 360                 365

Gly Asp Ile Phe Ser Asp Lys Val Tyr Val Phe Thr Pro Lys Gly Asp
    370                 375                 380

Val Thr Glu Leu Pro Lys Gly Ser Gly Pro Leu Asp Phe Ala Tyr Ser
385                 390                 395                 400

Ile His Thr Asp Ile Gly Asn Lys Thr Thr Gly Ala Lys Val Asn Gly
                405                 410                 415

Lys Met Val Gln Leu Asp Tyr Lys Leu Lys Asn Gly Asp Ile Ile Glu
            420                 425                 430

Ile Met Thr Ser Pro Asn Ser Phe Gly Pro Ser Arg Asp Trp Leu Lys
        435                 440                 445

Leu Val Ala Thr Ser Lys Ala Arg Asn Lys Ile Lys Arg Phe Phe Lys
    450                 455                 460

Ala Gln Asp Arg Glu Glu Asn Val Ile Lys Gly His Glu Ser Val Val
465                 470                 475                 480

Lys Cys Ile Thr Asp Leu Gly Phe Thr Pro Lys Asp Ile Leu Thr Lys
                485                 490                 495

Asn Lys Leu Gln Glu Ala Leu Asp Arg Phe Asn Tyr Gln Thr Glu Asp
            500                 505                 510

Asp Leu Tyr Ala Ala Val Gly Tyr Gly Glu Val Ser Pro Leu Thr Met
        515                 520                 525

Ala Asn Arg Leu Thr Glu Lys Glu Arg Lys Glu Gln Lys Ile Glu Gln
    530                 535                 540

Gln Lys Gln Glu Ala Glu Glu Ile Met Asn Gln Pro Lys Lys Glu Pro
545                 550                 555                 560

Asp Lys Met Lys Val Arg His Glu Gly Gly Val Val Ile Gln Gly Val
                565                 570                 575

Glu Asn Leu Leu Ile Arg Ile Ser Arg Cys Cys Asn Pro Ile Pro Gly
            580                 585                 590

Asp Asp Ile Val Gly Tyr Ile Thr Lys Gly Arg Gly Ile Ser Ile His
        595                 600                 605
```

Arg Arg Asp Cys Pro Asn Val Gln Pro Asp Lys Pro Asn Val Ala Glu
    610                 615                 620

Arg Leu Ile Glu Val Glu Trp Glu Asp Thr Ser Asn Thr Arg Lys Glu
625                 630                 635                 640

Tyr Asp Ala Asp Leu Glu Ile Tyr Gly Tyr Asn Arg Ser Gly Leu Leu
                645                 650                 655

Asn Asp Val Leu Gln Thr Val Asn Ala Leu Thr Lys Asn Leu Asn Ser
            660                 665                 670

Val Glu Ala Arg Thr Asn Lys Asp Lys Met Ala Thr Ile His Leu Thr
        675                 680                 685

Val Gly Ile Gln Asn Leu Ser His Leu Lys Ser Ile Val Asp Lys Ile
    690                 695                 700

Lys Ala Val Pro Asp Val Tyr Ser Val Arg Arg Thr Asn Gly
705                 710                 715

<210> SEQ ID NO 57
<211> LENGTH: 2205
<212> TYPE: DNA
<213> ORGANISM: Enterococcus faecium

<400> SEQUENCE: 57
atggcgaacg aacaagtatt gactgccgag caagttatag ataaagcacg cagctatcta 60
tctgatgagc atatcgcatt tgtcgaaaaa gcatatctgt acgctgaaga tgctcatcgc 120
gagcaatacc gcaaatcggg cgagccatat attattcatc cgattcaggt tgcggggata 180
ctcgttgatc ttgaaatgga cccttccaca atcgcgggcg gatttttgca cgatgtcgtg 240
gaagatacag atgtgacgct cgatgacctg aaagaagcat tttccgaaga agtggcaatg 300
cttgtagacg gcgtaacgaa actcggcaaa attaaatata aatctcaaga ggaacagcag 360
gcggaaaatc atcgcaaaat gtttgtcgct atggctcaag atatcagggt catattgatc 420
aagctggcgg atcgtcttca caatatgcgg acactgaaac atctgcctca ggaaaaacag 480
cggagaatct ccaatgaaac gctggaaatt tttgctcctt tggcgcatcg tctcgggatt 540
tcaaaaatta agtgggaatt ggaagatacg gcgctccgtt atttgaaccc tcagcaatat 600
tacagaattg tcaacctcat gaagaagaaa cgtgcagaac gagagcttta tgtcgatgag 660
gttgtcaatg aagtgaagaa acgtgtcgaa gaagtaaata tcaaggctga cttctcggga 720
cgcccgaaac atatttacag catttatcga aaaatggtgc tgcaaaataa gcaattcaat 780
gaaatttacg atttgttggc tgtccgtatt cttgtgaata gcataaagga ctgctacgcg 840
gtgcttggca tcattcacac atgctggaaa ccgatgccag gcagattcaa agattatatc 900
gcaatgccga agccgaatat gtatcaatcg cttcatacaa cggttattgg gcctaaagcg 960
gatccgcttg aagtgcagat ccgcaccttt gaaatgcatg aaatagcgga atacggggtt 1020
gcggctcact gggcttataa agaagggaaa gcagccaatg aaggtgcaac ctttgagaaa 1080
aagctttctt ggttccgtga aattttagaa tttcaaaatg aatcgacaga tgcagaagaa 1140
tttatggaat cgctcaaaat tgatttgttc tctgacatgg tgtatgtctt tacgccaaaa 1200
ggagatgtaa tcgagcttcc gtccggttct gttccgattg acttttctta ccggattcac 1260
tctgaaatcg gcaataaaac aatcggtgcc aaagtaaacg gaaaaatggt tacgcttgac 1320
cataagcttc ggacaggtga tatcgttgaa attctcacct ctaagcattc ctacggtccg 1380
agccaggatt gggtgaagct tgcccaaaca tcccaagcga agcataaaat ccgtcaattc 1440
tttaagaaac agcggcgtga agaaaatgtc gaaaaaggcc gtgagctggt cgaaaaagaa 1500
attaaaaact tggattttga attgaaggat gttttaacgc cggagaatat tcaaaaggtt 1560
gctgacaaat ttaatttctc aaatgaagag gatatgtacg cggcggtcgg ttacaacggc 1620
atcacagctc tgcaggtggc gaaccgccta acagaaaaag agagaaagca gcgcgaccag 1680
gaagaacagg aaaagatcgt tcaggaagtc actggggaac ctaagccata cccgcaagga 1740
agaaaacggg aagctggcgt tcgtgtcaag ggcattgaca acctccttgt ccgtttatca 1800
aaatgctgca atcctgtgcc aggtgatgat attgtcggct ttatcacaaa aggcagaggg 1860
gtttcggtcc atcgcgaaga ctgtccgaat gtcaaaacga atgaagccca agagcggctg 1920
atcccggtag agtgggaaca tgagtcacaa gttcaaaagc gcaaggaata caatgttgag 1980
atagagattc ttgggtatga ccgccgcgga ttgctgaacg aggtactcca ggcagtgaat 2040
gaaacgaaaa ccaatatttc atctgtctct ggcaaatcgg atcgcaataa agtggcaacc 2100
atccatatgg cgatttttat ccagaatatc aatcacttgc ataaagtcgt cgagcgtatt 2160
aaacagatta gagatatcta ttctgtgcgc cgcgtcatga actaa 2205

<210> SEQ ID NO 58
<211> LENGTH: 734
<212> TYPE: PRT
<213> ORGANISM: Enterococcus faecium

<400> SEQUENCE: 58

Met Ala Asn Glu Gln Val Leu Thr Ala Glu Gln Val Ile Asp Lys Ala
1 5 10 15

Arg Ser Tyr Leu Ser Asp Glu His Ile Ala Phe Val Glu Lys Ala Tyr
20 25 30

Leu Tyr Ala Glu Asp Ala His Arg Glu Gln Tyr Arg Lys Ser Gly Glu
35 40 45

Pro Tyr Ile Ile His Pro Ile Gln Val Ala Gly Ile Leu Val Asp Leu
50 55 60

Glu Met Asp Pro Ser Thr Ile Ala Gly Gly Phe Leu His Asp Val Val
65 70 75 80

Glu Asp Thr Asp Val Thr Leu Asp Asp Leu Lys Glu Ala Phe Ser Glu
85 90 95

Glu Val Ala Met Leu Val Asp Gly Val Thr Lys Leu Gly Lys Ile Lys
100 105 110

Tyr Lys Ser Gln Glu Glu Gln Gln Ala Glu Asn His Arg Lys Met Phe
115 120 125

Val Ala Met Ala Gln Asp Ile Arg Val Ile Leu Ile Lys Leu Ala Asp
130 135 140

Arg Leu His Asn Met Arg Thr Leu Lys His Leu Pro Gln Glu Lys Gln
145 150 155 160

Arg Arg Ile Ser Asn Glu Thr Leu Glu Ile Phe Ala Pro Leu Ala His
165 170 175

Arg Leu Gly Ile Ser Lys Ile Lys Trp Glu Leu Glu Asp Thr Ala Leu
180 185 190

Arg Tyr Leu Asn Pro Gln Gln Tyr Tyr Arg Ile Val Asn Leu Met Lys
195 200 205

Lys Lys Arg Ala Glu Arg Glu Leu Tyr Val Asp Glu Val Val Asn Glu
210 215 220

Val Lys Lys Arg Val Glu Glu Val Asn Ile Lys Ala Asp Phe Ser Gly
225 230 235 240

Arg Pro Lys His Ile Tyr Ser Ile Tyr Arg Lys Met Val Leu Gln Asn
245 250 255

Lys Gln Phe Asn Glu Ile Tyr Asp Leu Leu Ala Val Arg Ile Leu Val

-continued

```
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
                325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
    610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
        675                 680                 685
```

```
Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730


<210> SEQ ID NO 59
<211> LENGTH: 2205
<212> TYPE: DNA
<213> ORGANISM: Enterococcus faecalis

<400> SEQUENCE: 59

atggcgaacg aacaagtatt gactgccgag caagttatag ataaagcacg cagctatcta     60

tctgatgagc atatcgcatt tgtcgaaaaa gcatatctgt acgctgaaga tgctcatcgc    120

gagcaatacc gcaaatcggg cgagccatat attattcatc cgattcaggt tgcggggata    180

ctcgttgatc ttgaaatgga cccttccaca atcgcgggcg gatttttgca cgatgtcgtg    240

gaagatacag atgtgacgct cgatgacctg aaagaagcat tttccgaaga agtggcaatg    300

cttgtagacg gcgtaacgaa actcggcaaa attaaatata aatctcaaga ggaacagcag    360

gcggaaaatc atcgcaaaat gtttgtcgct atggctcaag atatcagggt catattgatc    420

aagctggcgg atcgtcttca caatatgcgg acactgaaac atctgcctca ggaaaaacag    480

cggagaatct ccaatgaaac gctggaaatt tttgctcctt tggcgcatcg tctcgggatt    540

tcaaaaatta agtgggaatt ggaagatacg gcgctccgtt atttgaaccc tcagcaatat    600

tacagaattg tcaacctcat gaagaagaaa cgtgcagaac gagagcttta tgtcgatgag    660

gttgtcaatg aagtgaagaa acgtgtcgaa gaagtaaata tcaaggctga cttctcggga    720

cgcccgaaac atatttacag catttatcga aaaatggtgc tgcaaaataa gcaattcaat    780

gaaatttacg atttgttggc tgtccgtatt cttgtgaata gcataaagga ctgctacgcg    840

gtgcttggca tcattcacac atgctggaaa ccgatgccag gcagattcaa agattatatc    900

gcaatgccga agccgaatat gtatcaatcg cttcatacaa cggttattgg gcctaaagcg    960

gatccgcttg aagtgcagat ccgcaccttt gaaatgcatg aaatagcgga atacggggtt   1020

gcggctcact gggcttataa agaagggaaa gcagccaatg aaggtgcaac ctttgagaaa   1080

aagctttctt ggttccgtga aattttagaa tttcaaaatg aatcgacaga tgcagaagaa   1140

tttatggaat cgctcaaaat tgatttgttc tctgacatgg tgtatgtctt tacgccaaaa   1200

ggagatgtaa tcgagcttcc gtccggttct gttccgattg acttttctta ccggattcac   1260

tctgaaatcg gcaataaaac aatcggtgcc aaagtaaacg gaaaaatggt tacgcttgac   1320

cataagcttc ggacaggtga tatcgttgaa attctcacct ctaagcattc ctacggtccg   1380

agccaggatt gggtgaagct tgcccaaaca tcccaagcga agcataaaat ccgtcaattc   1440

tttaagaaac agcggcgtga agaaaatgtc gaaaaaggcc gtgagctggt cgaaaaagaa   1500

attaaaaact tggattttga attgaaggat gttttaacgc cggagaatat tcaaaaggtt   1560

gctgacaaat ttaatttctc aaatgaagag gatatgtacg cggcggtcgg ttacaacggc   1620

atcacagctc tgcaggtggc gaaccgccta acagaaaaag agagaaagca gcgcgaccag   1680

gaagaacagg aaaagatcgt tcaggaagtc actggggaac ctaagccata cccgcaagga   1740

agaaaacggg aagctggcgt tcgtgtcaag ggcattgaca acctccttgt ccgtttatca   1800

aaatgctgca atcctgtgcc aggtgatgat attgtcggct ttatcacaaa aggcagaggg   1860

gtttcggtcc atcgcgaaga ctgtccgaat gtcaaaacga atgaagccca agagcggctg   1920
```

```
atcccggtag agtgggaaca tgagtcacaa gttcaaaagc gcaaggaata caatgttgag   1980

atagagattc ttgggtatga ccgccgcgga ttgctgaacg aggtactcca ggcagtgaat   2040

gaaacgaaaa ccaatatttc atctgtctct ggcaaatcgg atcgcaataa agtggcaacc   2100

atccatatgg cgatttttat ccagaatatc aatcacttgc ataaagtcgt cgagcgtatt   2160

aaacagatta gagatatcta ttctgtgcgc cgcgtcatga actaa                    2205


<210> SEQ ID NO 60
<211> LENGTH: 734
<212> TYPE: PRT
<213> ORGANISM: Enterococcus faecalis

<400> SEQUENCE: 60

Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
```

```
                325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380

Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
    610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
        675                 680                 685

Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 61
<211> LENGTH: 2205

<212> TYPE: DNA
<213> ORGANISM: Rhodococcus erythropolis

<400> SEQUENCE: 61
atggcgaacg aacaagtatt gactgccgag caagttatag ataaagcacg cagctatcta 60
tctgatgagc atatcgcatt tgtcgaaaaa gcatatctgt acgctgaaga tgctcatcgc 120
gagcaatacc gcaaatcggg cgagccatat attattcatc cgattcaggt tgcggggata 180
ctcgttgatc ttgaaatgga cccttccaca atcgcgggcg gatttttgca cgatgtcgtg 240
gaagatacag atgtgacgct cgatgacctg aaagaagcat tttccgaaga agtggcaatg 300
cttgtagacg gcgtaacgaa actcggcaaa attaaatata aatctcaaga ggaacagcag 360
gcggaaaatc atcgcaaaat gtttgtcgct atggctcaag atatcagggt catattgatc 420
aagctggcgg atcgtcttca caatatgcgg acactgaaac atctgcctca ggaaaaacag 480
cggagaatct ccaatgaaac gctggaaatt tttgctcctt tggcgcatcg tctcgggatt 540
tcaaaaatta agtgggaatt ggaagatacg gcgctccgtt atttgaaccc tcagcaatat 600
tacagaattg tcaacctcat gaagaagaaa cgtgcagaac gagagcttta tgtcgatgag 660
gttgtcaatg aagtgaagaa acgtgtcgaa gaagtaaata tcaaggctga cttctcggga 720
cgcccgaaac atatttacag catttatcga aaaatggtgc tgcaaaataa gcaattcaat 780
gaaatttacg atttgttggc tgtccgtatt cttgtgaata gcataaagga ctgctacgcg 840
gtgcttggca tcattcacac atgctggaaa ccgatgccag gcagattcaa agattatatc 900
gcaatgccga agccgaatat gtatcaatcg cttcatacaa cggttattgg gcctaaagcg 960
gatccgcttg aagtgcagat ccgcaccttt gaaatgcatg aaatagcgga atacggggtt 1020
gcggctcact gggcttataa agaagggaaa gcagccaatg aaggtgcaac ctttgagaaa 1080
aagctttctt ggttccgtga aattttagaa tttcaaaatg aatcgacaga tgcagaagaa 1140
tttatggaat cgctcaaaat tgatttgttc tctgacatgg tgtatgtctt tacgccaaaa 1200
ggagatgtaa tcgagcttcc gtccggttct gttccgattg acttttctta ccggattcac 1260
tctgaaatcg gcaataaaac aatcggtgcc aaagtaaacg gaaaaatggt tacgcttgac 1320
cataagcttc ggacaggtga tatcgttgaa attctcacct ctaagcattc ctacggtccg 1380
agccaggatt gggtgaagct tgcccaaaca tcccaagcga agcataaaat ccgtcaattc 1440
tttaagaaac agcggcgtga agaaaatgtc gaaaaaggcc gtgagctggt cgaaaaagaa 1500
attaaaaact tggattttga attgaaggat gttttaacgc cggagaatat tcaaaaggtt 1560
gctgacaaat ttaatttctc aaatgaagag gatatgtacg cggcggtcgg ttacaacggc 1620
atcacagctc tgcaggtggc gaaccgccta acagaaaaag agagaaagca gcgcgaccag 1680
gaagaacagg aaaagatcgt tcaggaagtc actggggaac ctaagccata cccgcaagga 1740
agaaaacggg aagctggcgt tcgtgtcaag ggcattgaca acctccttgt ccgtttatca 1800
aaatgctgca atcctgtgcc aggtgatgat attgtcggct ttatcacaaa aggcagaggg 1860
gtttcggtcc atcgcgaaga ctgtccgaat gtcaaaacga atgaagccca agagcggctg 1920
atcccggtag agtgggaaca tgagtcacaa gttcaaaagc gcaaggaata caatgttgag 1980
atagagattc ttgggtatga ccgccgcgga ttgctgaacg aggtactcca ggcagtgaat 2040
gaaacgaaaa ccaatatttc atctgtctct ggcaaatcgg atcgcaataa agtggcaacc 2100
atccatatgg cgatttttat ccagaatatc aatcacttgc ataaagtcgt cgagcgtatt 2160
aaacagatta gagatatcta ttctgtgcgc cgcgtcatga actaa 2205

<210> SEQ ID NO 62
<211> LENGTH: 734
<212> TYPE: PRT
<213> ORGANISM: Rhodococcus erythropolis

<400> SEQUENCE: 62

```
Met Ala Asn Glu Gln Val Leu Thr Ala Glu Gln Val Ile Asp Lys Ala
1               5                   10                  15

Arg Ser Tyr Leu Ser Asp Glu His Ile Ala Phe Val Glu Lys Ala Tyr
            20                  25                  30

Leu Tyr Ala Glu Asp Ala His Arg Glu Gln Tyr Arg Lys Ser Gly Glu
        35                  40                  45

Pro Tyr Ile Ile His Pro Ile Gln Val Ala Gly Ile Leu Val Asp Leu
    50                  55                  60

Glu Met Asp Pro Ser Thr Ile Ala Gly Gly Phe Leu His Asp Val Val
65                  70                  75                  80

Glu Asp Thr Asp Val Thr Leu Asp Asp Leu Lys Glu Ala Phe Ser Glu
                85                  90                  95

Glu Val Ala Met Leu Val Asp Gly Val Thr Lys Leu Gly Lys Ile Lys
            100                 105                 110

Tyr Lys Ser Gln Glu Glu Gln Gln Ala Glu Asn His Arg Lys Met Phe
        115                 120                 125

Val Ala Met Ala Gln Asp Ile Arg Val Ile Leu Ile Lys Leu Ala Asp
    130                 135                 140

Arg Leu His Asn Met Arg Thr Leu Lys His Leu Pro Gln Glu Lys Gln
145                 150                 155                 160

Arg Arg Ile Ser Asn Glu Thr Leu Glu Ile Phe Ala Pro Leu Ala His
                165                 170                 175

Arg Leu Gly Ile Ser Lys Ile Lys Trp Glu Leu Glu Asp Thr Ala Leu
            180                 185                 190

Arg Tyr Leu Asn Pro Gln Gln Tyr Tyr Arg Ile Val Asn Leu Met Lys
        195                 200                 205

Lys Lys Arg Ala Glu Arg Glu Leu Tyr Val Asp Glu Val Val Asn Glu
    210                 215                 220

Val Lys Lys Arg Val Glu Glu Val Asn Ile Lys Ala Asp Phe Ser Gly
225                 230                 235                 240

Arg Pro Lys His Ile Tyr Ser Ile Tyr Arg Lys Met Val Leu Gln Asn
                245                 250                 255

Lys Gln Phe Asn Glu Ile Tyr Asp Leu Leu Ala Val Arg Ile Leu Val
            260                 265                 270

Asn Ser Ile Lys Asp Cys Tyr Ala Val Leu Gly Ile Ile His Thr Cys
        275                 280                 285

Trp Lys Pro Met Pro Gly Arg Phe Lys Asp Tyr Ile Ala Met Pro Lys
    290                 295                 300

Pro Asn Met Tyr Gln Ser Leu His Thr Thr Val Ile Gly Pro Lys Ala
305                 310                 315                 320

Asp Pro Leu Glu Val Gln Ile Arg Thr Phe Glu Met His Glu Ile Ala
                325                 330                 335

Glu Tyr Gly Val Ala Ala His Trp Ala Tyr Lys Glu Gly Lys Ala Ala
            340                 345                 350

Asn Glu Gly Ala Thr Phe Glu Lys Lys Leu Ser Trp Phe Arg Glu Ile
        355                 360                 365

Leu Glu Phe Gln Asn Glu Ser Thr Asp Ala Glu Glu Phe Met Glu Ser
    370                 375                 380
```

```
Leu Lys Ile Asp Leu Phe Ser Asp Met Val Tyr Val Phe Thr Pro Lys
385                 390                 395                 400

Gly Asp Val Ile Glu Leu Pro Ser Gly Ser Val Pro Ile Asp Phe Ser
                405                 410                 415

Tyr Arg Ile His Ser Glu Ile Gly Asn Lys Thr Ile Gly Ala Lys Val
            420                 425                 430

Asn Gly Lys Met Val Thr Leu Asp His Lys Leu Arg Thr Gly Asp Ile
        435                 440                 445

Val Glu Ile Leu Thr Ser Lys His Ser Tyr Gly Pro Ser Gln Asp Trp
    450                 455                 460

Val Lys Leu Ala Gln Thr Ser Gln Ala Lys His Lys Ile Arg Gln Phe
465                 470                 475                 480

Phe Lys Lys Gln Arg Arg Glu Glu Asn Val Glu Lys Gly Arg Glu Leu
                485                 490                 495

Val Glu Lys Glu Ile Lys Asn Leu Asp Phe Glu Leu Lys Asp Val Leu
            500                 505                 510

Thr Pro Glu Asn Ile Gln Lys Val Ala Asp Lys Phe Asn Phe Ser Asn
        515                 520                 525

Glu Glu Asp Met Tyr Ala Ala Val Gly Tyr Asn Gly Ile Thr Ala Leu
    530                 535                 540

Gln Val Ala Asn Arg Leu Thr Glu Lys Glu Arg Lys Gln Arg Asp Gln
545                 550                 555                 560

Glu Glu Gln Glu Lys Ile Val Gln Glu Val Thr Gly Glu Pro Lys Pro
                565                 570                 575

Tyr Pro Gln Gly Arg Lys Arg Glu Ala Gly Val Arg Val Lys Gly Ile
            580                 585                 590

Asp Asn Leu Leu Val Arg Leu Ser Lys Cys Cys Asn Pro Val Pro Gly
        595                 600                 605

Asp Asp Ile Val Gly Phe Ile Thr Lys Gly Arg Gly Val Ser Val His
    610                 615                 620

Arg Glu Asp Cys Pro Asn Val Lys Thr Asn Glu Ala Gln Glu Arg Leu
625                 630                 635                 640

Ile Pro Val Glu Trp Glu His Glu Ser Gln Val Gln Lys Arg Lys Glu
                645                 650                 655

Tyr Asn Val Glu Ile Glu Ile Leu Gly Tyr Asp Arg Arg Gly Leu Leu
            660                 665                 670

Asn Glu Val Leu Gln Ala Val Asn Glu Thr Lys Thr Asn Ile Ser Ser
        675                 680                 685

Val Ser Gly Lys Ser Asp Arg Asn Lys Val Ala Thr Ile His Met Ala
    690                 695                 700

Ile Phe Ile Gln Asn Ile Asn His Leu His Lys Val Val Glu Arg Ile
705                 710                 715                 720

Lys Gln Ile Arg Asp Ile Tyr Ser Val Arg Arg Val Met Asn
                725                 730
```

<210> SEQ ID NO 63
<211> LENGTH: 28
<212> TYPE: DNA
<213> ORGANISM: artificial sequence
<220> FEATURE:
<223> OTHER INFORMATION: primer

<400> SEQUENCE: 63
ctggtccacc tacaacaaag ctctcatc 28

-continued

<210> SEQ ID NO 64
<211> LENGTH: 34
<212> TYPE: DNA
<213> ORGANISM: artificial sequence
<220> FEATURE:
<223> OTHER INFORMATION: primer

<400> SEQUENCE: 64
cttgtgcaat gtaacatcag agattttgag acac 34

<210> SEQ ID NO 65
<211> LENGTH: 25
<212> TYPE: DNA
<213> ORGANISM: artificial sequence
<220> FEATURE:
<223> OTHER INFORMATION: primer

<400> SEQUENCE: 65
gttgtggaag atactggtgt tactt 25

<210> SEQ ID NO 66
<211> LENGTH: 20
<212> TYPE: DNA
<213> ORGANISM: artificial sequence
<220> FEATURE:
<223> OTHER INFORMATION: primer

<400> SEQUENCE: 66
agtccttgat tgaatccacg 20

<210> SEQ ID NO 67
<211> LENGTH: 38
<212> TYPE: DNA
<213> ORGANISM: artificial sequence
<220> FEATURE:
<223> OTHER INFORMATION: primer

<400> SEQUENCE: 67
aaaaaagcgg ccgctcttta ttcttcaact aaagcacc 38

<210> SEQ ID NO 68
<211> LENGTH: 42
<212> TYPE: DNA
<213> ORGANISM: artificial sequence
<220> FEATURE:
<223> OTHER INFORMATION: primer

<400> SEQUENCE: 68
aaaaaagcgg ccgcaatgta tttagaaaaa taaacaaata gg 42

<210> SEQ ID NO 69
<211> LENGTH: 20
<212> TYPE: DNA
<213> ORGANISM: artificial sequence
<220> FEATURE:
<223> OTHER INFORMATION: primer

<400> SEQUENCE: 69
tgtaattttg cggtcggtgg 20

<210> SEQ ID NO 70
<211> LENGTH: 22
<212> TYPE: DNA
<213> ORGANISM: artificial sequence
<220> FEATURE:
<223> OTHER INFORMATION: primer -continued

<400> SEQUENCE: 70

```
gcggataaca atttcacaca gg                                              22
```

PRODUCTION OF FOUR CARBON ALCOHOLS USING IMPROVED STRAIN

This application claims the benefit of U.S. Provisional Application 61/015,689, and 61/015,694 both filed Dec. 21, 2007.

FIELD OF INVENTION

The invention relates to the fields of microbiology and genetic engineering. More specifically, a bacterial regulatory system involving (p)ppGpp was identified as playing a role in butanol response in bacteria.

BACKGROUND OF INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known. For example, 1-butanol may be produced using the Oxo process, the Reppe process, or the hydrogenation of crotonaldehyde (*Ullmann's Encyclopedia of Industrial Chemistry, 6$^{th}$* edition, 2003, Wiley-VCHVerlag GmbH and Co., Weinheim, Germany, Vol. 5, pp. 716-719). 2-Butanol may be produced using n-butene hydration (*Ullmann's Encyclopedia of Industrial Chemistry, 6$^{th}$* edition, 2003, Wiley-VCHVerlag GmbH and Co., Weinheim, Germany, Vol. 5, pp. 716-719). Additionally, isobutanol may be produced using Oxo synthesis, catalytic hydrogenation of carbon monoxide (*Ullmann's Encyclopedia of Industrial Chemistry, 6$^{th}$* edition, 2003, Wiley-VCHVerlag GmbH and Co., Weinheim, Germany, Vol. 5, pp. 716-719) or Guerbet condensation of methanol with n-propanol (Carlini et al., *J. Molec. Catal. A: Chem.* 220:215-220 (2004)). These processes use starting materials derived from petrochemicals, are generally expensive, and are not environmentally friendly.

Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (Donaldson et al., copending and commonly owned U.S. Patent Application Publication No. US20080182308A), a 2-butanol biosynthetic pathway (Donaldson et al., copending and commonly owned U.S. Patent Application Publication Nos. US20070259410A1 and US20070292927A1 US 20070292927A1), and an isobutanol biosynthetic pathway (Maggio-Hall et al., copending and commonly owned U.S. Patent Publication No. US 20070092957) have been described. However, biological production of butanols is believed to be limited by butanol toxicity to the host microorganism used in the fermentation.

In addition, 2-butanone is a valuable compound that can be produced by fermentation using microorganisms. 2-Butanone, also referred to as methyl ethyl ketone (MEK), is a widely used solvent and is the most important commercially produced ketone, after acetone. It is used as a solvent for paints, resins, and adhesives, as well as a selective extractant and activator of oxidative reactions. In addition, it has been shown that substantially pure 2-butanone can be converted to 2-butanol by reacting with hydrogen in the presence of a catalyst (Nystrom, R. F. and Brown, W. G. (J. Am. Chem. Soc. (1947) 69:1198). 2-butanone can be made by omitting the last step of the 2-butanol biosynthetic pathway (Donaldson et al., copending and commonly owned U.S. Patent Application Publication Nos. US20070259410A1 and US20070292927A1). US 20070292927A). Production of 2-butanone would be enhanced by using microbial host strains with improved tolerance as fermentation biocatalysts.

Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., Current Microbiology 14(5):295-299 (1987)). Desmond et al. (*Appl. Environ. Microbiol.* 70(10):5929-5936 (2004)) report that overexpression of GroESL, two stress responsive proteins, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) has been described. Additionally some *Lactobacillus* sp are known to be tolerant to ethanol (see for example, Couto, Pina and Hogg Biotechnology. Letter 19: 487-490) Ingram and Burke (1984) Adv. Micribial. Physiol 25: 253-300. However, for most bacteria described in the art, growth is highly inhibited at low concentrations of 1-butanol. Moreover butanol is much more toxic than ethanol and mechanisms that affect the ethanol tolerance of *E. coli* have not been found to affect the butanol response.

There is a need, therefore, for butanol or 2-butanone producing bacterial host strains that are more tolerant to these chemicals, as well as methods of producing butanols or 2-butanone using bacterial host strains that are more tolerant to these chemicals.

SUMMARY OF THE INVENTION

The invention provides a recombinant bacterial host which produces butanol or 2-butanone and comprises a genetic modification that results in reduced accumulation of (p)ppGppa and methods of using the same for the production of butanols and 2-butanone. Such cells have an increased tolerance to butanol or 2-butanone as compared with cells that lack the genetic modification. Reduction in the accumulation of (p)ppGpp may be accomplished via mutation of endogenous genes that impact (p)ppGpp synthesis. Host cells of the invention may produce butanol or 2-butanone naturally or may be engineered to do so via an engineered pathway.

Accordingly, the invention provides a recombinant bacterial cell producing butanol or 2-butanone said bacterial cell comprising at least one genetic modification which reduces accumulation of (p)ppGpp.

In another embodiment the invention provides a process for generating the bacterial host cell of claim 1 comprising:

a) providing a recombinant bacterial host cell producing butanol or 2-butanone; and
b) creating at least one genetic modification which reduces accumulation of (p)ppGpp In another embodiment the invention provides a process for production of butanol or 2-butanone from a recombinant bacterial cell comprising:

(a) providing a recombinant bacterial host cell which
 1) produces butanol or 2-butanone and
 2) comprises at least one genetic modification which reduces (p)ppGpp accumulation; and
(b) culturing the strain of (a) under conditions wherein butanol or 2-butanone is produced.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 9:
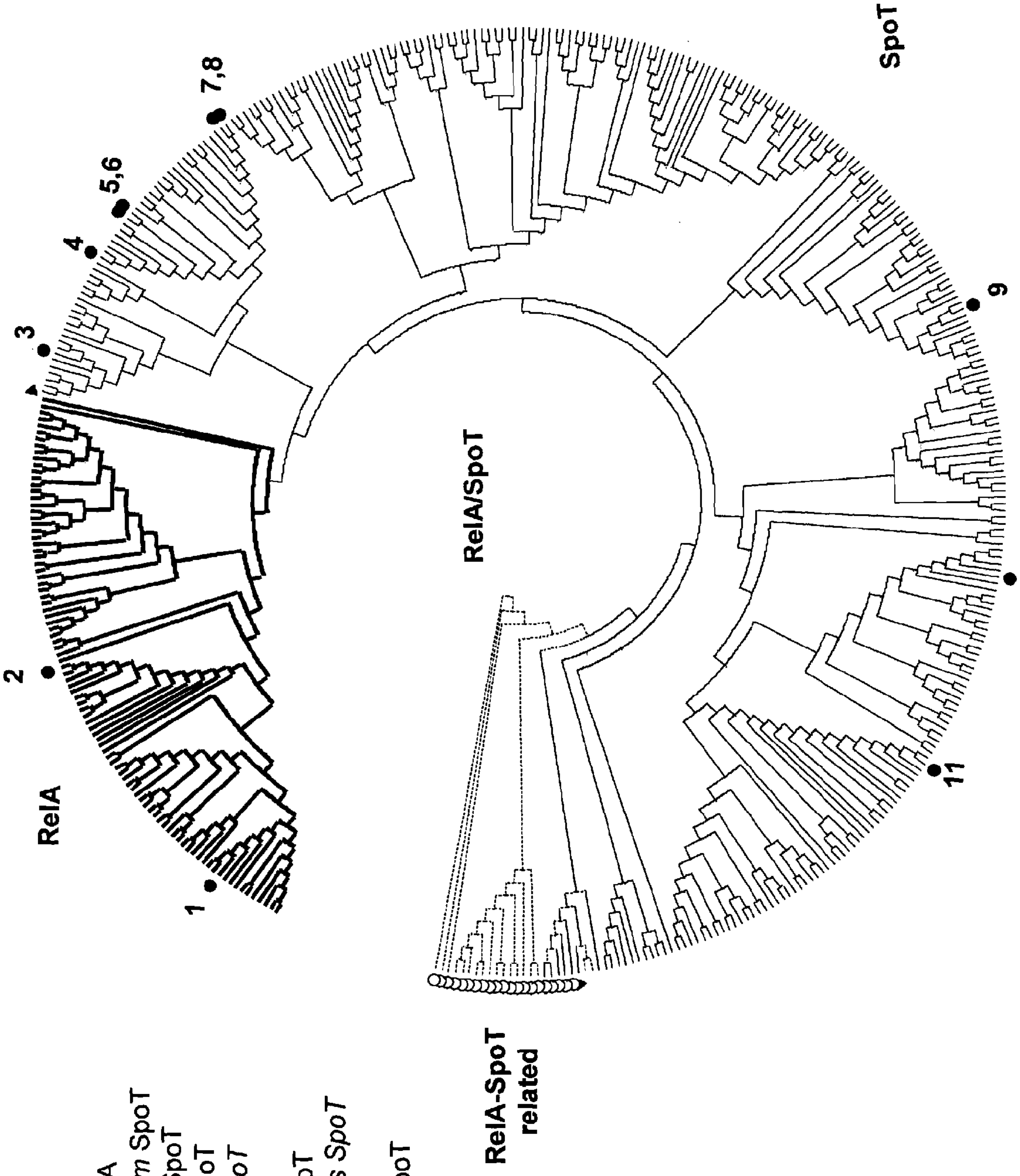

FIG. 9 is a diagram of a sequence relationship tree showing SpoT and RelA (bold) protein families, as well as related non SpoT/RelA proteins. Positions in the tree of some proteins of specific bacterial hosts are marked with numbers and given by number in a list. The arrowhead marks the division between RelA and SpoT protein families.

FIG. 10 shows growth yield improvement assays for a relA mutant strain grown in different concentrations of isobutanol (A) or 2-butanol (B).

Figure 11A:
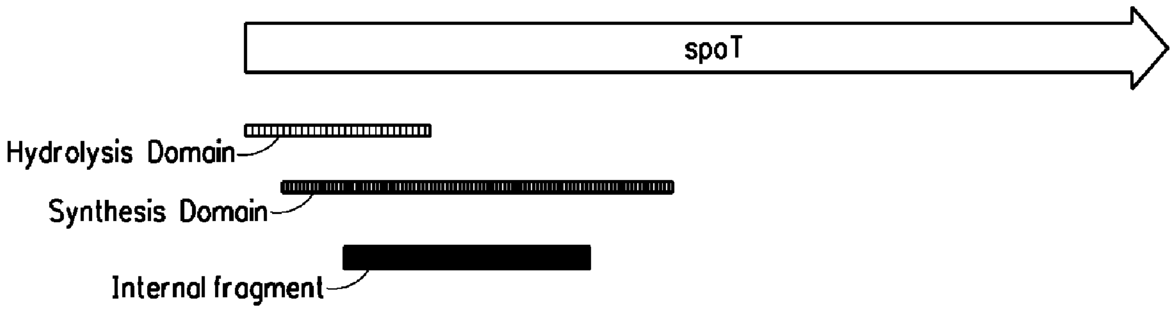
Figure 11B:
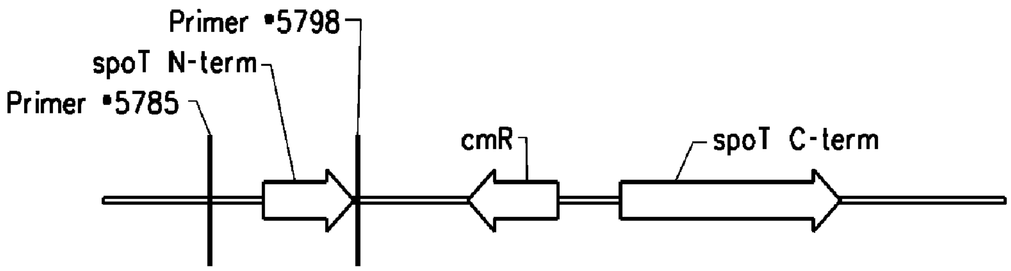

FIG. 11 shows a diagram of domains of the SpoT protein, and the internal fragment used in the insertional disruption plasmid pMPE69 (in A), and a diagram of the structure of the chromosomal spoT locus after insertion of plasmid pMPE69, with positions of the primers used for confirmation (in B).

Table 5 is a table of the Profile HMM for the RelA/SpoT domain. Table 5 is submitted herewith electronically and is incorporated herein by reference.

Table 6 is a table of the Profile HMM for the TGS domain. Table 6 is submitted herewith electronically and is incorporated herein by reference.

Table 7 is a table of the Profile HMM for the HD domain. Table 7 is submitted herewith electronically and is incorporated herein by reference.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| 3-Hydroxybutyryl-CoA dehydrogenase from *Clostridium acetobutylicum* ATCC 824 | 5 | 6 |
| Crotonase from *Clostridium acetobutylicum*ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum ATCC 824* | 15 | 16 |

TABLE 2

Summary of Gene and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus ruber* 219 | 29 | 30 |

TABLE 3

Summary of Gene and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *E. coli* ilvC (acetohydroxy acid reductoisomerase) | 31 | 32 |
| *E. coli* ilvD (acetohydroxy acid dehydratase) | 33 | 34 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Representative spoT and relA modification target genes and encoded proteins

| Organism | Gene name | SEQ ID NO: Nucleic acid | SEQ ID NO: Peptide |
|---|---|---|---|
| *E. coli* | spoT | 39 | 40 |
| *E. coli* | relA | 41 | 42 |
| *Lactobacillus plantarum* WCFS1 | spoT | 43 | 44 |
| *Bacillus licheniformis* ATCC 14580 | spoT | 45 | 46 |
| *Bacillus subtilis*subsp. *subtilis* str. 168 | spoT | 47 | 48 |
| *Pseudomonas putida* KT2440 | relA | 49 | 50 |
| *Pseudomonas putida* KT2440 | spoT | 51 | 52 |
| *Clostridium acetobutylicum* ATCC 824 | spoT | 53 | 54 |
| *Enterococcus faecium* | spoT-1 | 55 | 56 |
| *Enterococcus faecium* | spoT-2 | 57 | 58 |
| *Enterococcus faecalis* | spoT | 59 | 60 |
| *Rhodococcus erythropolis* | spoT | 61 | 62 |

SEQ ID NOs:63 and 64 are primers for sequencing of genomic DNA adjacent to transposon insertions.

SEQ ID NOs:65 and 66 are primers for PCR amplification of *L. plantarum* relA internal fragment SEQ ID NOs:67 and 68 are primers for PCR amplification of a portion of the pMK4 vector.

SEQ ID NOs:69 and 70 are primers for PCR confirmation of pMPE69 insertion in *L. plantarum* relA.

DETAILED DESCRIPTION OF THE INVENTION

The invention provides a recombinant bacterial host which produces butanol or 2-butanone and comprises a genetic modification that results in reduced accumulation of (p)ppGpp. Such cells have an increased tolerance to butanol or 2-butanone as compared with cells that lack the genetic modification. A tolerant bacterial strain of the invention has at least one genetic modification that causes reduced accumulation of (p)ppGpp. Reduction in the accumulation of (p)ppGpp may be accomplished via mutation of endogenous genes that impact (p)ppGpp synthesis. Host cells of the invention may produce butanol or 2-butanone naturally or may be engineered to do so via an engineered pathway.

Butanol produced using the present strains may be used as an alternative energy source to fossil fuels, and 2-butanone may be used as a solvent or may be chemically converted to 2-butanol. Fermentive production of butanol and 2-butanone results in less pollutants than typical petrochemical synthesis.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The terms "butanol tolerant bacterial strain" and "tolerant" when used to describe a modified bacterial strain of the invention, refers to a modified bacterium that shows better growth in the presence of butanol than the parent strain from which it is derived. 2-butanone tolerance is used similarly.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "2-butanone biosynthetic pathway" refers to an enzyme pathway to produce 2-butanone from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 *[Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from

*Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" or "genetic construct" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "(p)ppGpp" refers to either ppGpp or pppGpp, or a combination of both compounds.

The term "relA" refers to a gene that encodes a RelA protein which is a mono-functional enzyme with GTP pyrophosphokinase activity (EC 2.7.6.5), for synthesis of (p)ppGpp. Although in the literature some genes encoding enzymes with (p)ppGpp synthesis and degradation activities are called relA, herein these will be referred to as spoT instead of relA.

The term "spoT" refers to a gene that encodes a SpoT protein, which is a bi-functional enzyme with both GTP pyrophosphokinase, (EC 2.7.6.5) activity for synthesis of (p)ppGpp, and ppGpp pyrophosphohydrolase (EC3.1.7.2) activity for degradation of (p)ppGpp. The related RelA and SpoT proteins and their encoding genes are distinguished by both enzyme activities and domain architectures as described below.

The term "dksA" refers to a gene that encodes the DksA protein, which binds directly to RNA polymerase affecting transcript elongation and augmenting the effect of the alarmone ppGpp on transcription initiation.

The term "RelA/SpoT" domain will refer to a portion of the SpoT or RelA proteins that may be used to identity SpoT or RelA homologs.

As used herein "TGS domain" will refer to a portion of the SpoT or RelA protein that may be used to identity SpoT and RelA homologs. The TGS domain is named after ThrRS, GTPase, and SpoT and has been detected at the amino terminus of the uridine kinase from the spirochaete *Treponema pallidum*. TGS is a small domain that consists of ~50 amino acid residues and is predicted to possess a predominantly beta-sheet structure. Its presence in two types of regulatory proteins (the GTPases and guanosine polyphosphate phosphohydrolases/synthetases) suggests that it has a nucleotide binding regulatory role. The TGS domain is not unique to the SpoT or RelA protein, however, in combination with the presence of the HD domain and the SpoT/RelA domain it is diagnostic for a protein having SpoT function. In combination with the SpoT/RelA domain, the TGS domain is diagnostic for a protein having RelA function.

The term "HD domain" refers to an amino acid motif that is associated with a superfamily of metal-dependent phosphohydrolases that includes a variety of uncharacterized proteins and domains associated with nucleotidyltransferases and helicases from bacteria, archaea, and eukaryotes (Yakunin et al., *J. Biol. Chem.*, Vol. 279, Issue 35, 36819-36827, Aug. 27, 2004). The HD domain is not unique to the SpoT protein, however in combination with the SpoT/RelA domain and the TGS domain, it may be used to identify SpoT proteins according to the methods described herein.

Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Screening for Butanol Tolerance: Involvement of (p)ppGpp

The invention relates to the discovery that events that reduces the accumulation of (p)ppGpp in a bacterial cell have the unexpected effect of rendering the cell more tolerant to butanols. The discovery came out of screening studies for genetic mutations that affected butanol tolerance. In those studies, bacterial cells were subjected to random mutagenesis and then screened for altered tolerance to butanol. Those mutants showing higher butanol tolerance were analyzed and the affected genes identified. The modified gene leading to butanol tolerance in a mutant may be identified by methods as described herein in Example 2 for a transposon insertion strain, or by directed genome sequencing of candidate genes in the case of chemical mutagenesis. If the bacterial cell has a means of genetic exchange, then genetic crosses may be performed to verify that the effect is due to the observed alteration in the genome.

These studies indicated that disruptions in SpoT protein production correlated to an increase in butanol tolerance. Both SpoT and a related protein, RelA, are known to influence the accumulation of ppGpp (the nucleotide guanosine 3',5'-bis(diphosphate)) or pppGpp (the nucleotide guanosine 3',5'-bis(triphosphate), where ppGpp and/or pppGpp are referred to as (p)ppGpp. Because the (p)ppGpp regulatory system is known to mediate a bacterial stress response to nutritional limitation, where increased (p)ppGpp synthesis regulates factors that often improve the stress situation, it is surprising that reducing (p)ppGpp synthesis improves the bacterial response to the stress of having butanol in the medium.

ppGpp is known to mediate the pleiotropic stringent response to amino acid starvation, and levels of ppGpp rise following nutrient and environmental stresses (Cashel et al. (1996) The stringent response, p 1458-1496 In F. C. Neidhardt (ed.), *Escherichia coli* and *Salmonella*: Cellular and Molecular Biology. ASM Press, Washington, D.C.). The bacterial (p)ppGpp regulatory system is involved in a variety of regulatory functions (Mittenhuber J. Mol. Microbiol. Biotechnol. (2001) 3:585-600, Cashel et al. ibid). Some phenotypes associated with reduced (p)ppGpp synthesis include amino acid auxotrophies, reduced sporulation efficiency in *Bacillus subtilis*, slower aerobic growth rate and lower survival in extended anaerobic incubation in *Mycobacterium tuberculoses*, effects on antibiotic and pigment production as well as morphological differentiation in *Streptomuces* species, and inability to form fruiting bodies in *Myxococcus xanthus*. None of these or other known phenotypes points to a relationship between reduced (p)ppGpp accumulation and increased butanol tolerance in bacteria.

Creation of Mutants Having Reduced (p)ppGpp Accumulation

The present finding suggests that bacterial cells harboring mutations that reduce the accumulation of (p)ppGpp will have increased tolerance to butanols. Hence, the identification of (p)ppGpp mutants is a useful tool in engineering a butanol tolerant host.

Methods for creating genetic mutations are common and well known in the art and may be applied to the exercise of creating (p)ppGpp mutants. Commonly used random genetic modification methods (reviewed in Miller, J. H. (1992) A Short Course in Bacterial Genetics. Cold Spring Harbor Press, Plainview, N.Y.) include spontaneous mutagenesis, mutagenesis caused by mutator genes, chemical mutagenesis, irradiation with UV or X-rays, and transposon insertion. Transposons have been introduced into bacteria in a variety of ways including:

1. phage-mediated transduction: This has been used in both species specific and cross-species contexts.
2. conjugation: Again, this can be between members of the same or different species.
3. Transformation: Chemically aided and electric shock mediated uptake of DNA can be used.

In these methods the transposon expresses a transposase in the recipient that catalyzes gene hopping from the incoming DNA to the recipient genome. The transposon DNA can be naked, incorporated in a phage or plasmid nucleic acid or complexed with a transposase. Most often the replication and/or maintenance of the incoming DNA containing the transposon is prevented, such that genetic selection for a marker on the transposon (most often antibiotic resistance). insures that each recombinant is the result of movement of the transposon from the entering DNA molecule to the recipient genome. An alternative method is one in which transposition is carried out with chromosomal DNA, fragments thereof or a fragment thereof in vitro, and then the novel insertion allele that has been created is introduced into a recipient cell where it replaces the resident allele by homologous recombination. Transposon insertion may be performed as described in Kleckner and Botstein ((1977) J. Mol. Biol. 116:125-159), or as indicated above via any number of derivative methods, or as described in Example 1 using the Transposome™ system (Epicentre; Madison, Wis.).

Chemical mutagenesis may be performed as described in Miller (Unit 4 of Miller J H (1992) A Short Course in Bacterial Genetics, Cold Spring Harbor Laboratory Press, pp 81-211). Collections of modified cells produced from these processes may be screened either for butanol tolerance, as described in Example 1 herein, or for reduced accumulation of (p)ppGpp directly or indirectly. A number of indirect measures have been described including radioactive precursor incorporation during amino acid starvation (Martin (1968) J. Mol. Biol. 31:127-134), aminotriazole based screening (Toone et al. (1992) J. Bacteriol. 174:5479-81; Sarubbi et al. (1988) Mol. Gen. Genet. 213:214-22; Sarubbi et al. (1989) M. J Biol. Chem. 264:15074-82; Rudd et al. (1985) J. Bacteriol. 163:534-42), and SMG screens (Uzan and Danchin (1978) Mol. Gen. Genet. 165:21-30).

Once the mutations have been created the cells must be screened for altered (p)ppGpp accumulation. A number of methods may be used to analyze the level of (p)ppGpp including by thin layer chromotagraphy (TLC; described in Gallant and Cashel (1967) J. Mol. Biol. 25:545-553) or column chromatography (Little and Bremer (1982) Anal. Biochem. 126: 381-388). In addition, indirect screens based upon amino acid antagonists such as serine-methionine-glycine sensitivity (Uzan and Danchin (1978) Mol. Gen. Genet. 165:21-30), aminotriazole sensitivity (Rudd et al. (1985) J. Bacteriol. 163:534-542; Sarubbi et al. (1988) Mol. Gen. Genet. 213: 214-222) and sulfometuron methyl sensitivity (LaRossa and Smulski. (1984) J. Bacteriol. 160:391-394) may be used.

Modifications Affecting SpoT or RelA Production

As noted above, mutations that affect production of the SpoT protein of bacterial cells have been associated with reduced accumulation of (p)ppGpp and an increase in tolerance of the cell to butanol. Accordingly the invention provides a bacterial cell comprising at least one genetic modification which reduces accumulation of (p)ppGpp via a disruption in an endogenous gene selected from the group consisting of spoT and relA or in an operon comprising an open reading frame encoding SpoT or RelA.

Studies on the function of SpoT and RelA are well documented. The protein encoded by the spoT gene of *E. coli* (coding region SEQ ID NO:39; protein SEQ ID NO:40) is an enzyme having both guanosine 3'5'-bis(diphosphate) 3'-pyrophosphohydrolase (ppGppase) and 3',5'-bis(diphosphate synthetase (PSII) activities (Gentry and Cashel (Molec. Micro. 19:1373-1384 (1996)). In *E. coli* there is a closely related gene called relA (coding region SEQ ID NO:41; protein SEQ ID NO:42), which encodes an enzyme with 3',5'-bis(diphosphate synthetase (PSI) activity. In *E. coli*, the RelA protein is associated with ribosomes and is activated by binding of uncharged tRNAs to the ribosomes. RelA activation and synthesis of (p)ppGpp results in decreased production of ribosomes, and stimulation of amino acid synthesis. The spoT gene product is responsible for synthesis of (p)ppGpp (Hernandez and Bremer, J. Biol. Chem. (1991) 266:5991-9) during carbon source starvation (Chaloner-Larsson and Yamazaki Can. J. Biochem. (1978) 56:264-72; (Seyfzadeh and Keener, Proc. Natl. Acad. Sci. USA (1993) 90:11004-8) in *E. coli.*

Any bacterial gene identified as a spoT or relA gene is a target for modification in the corresponding organism to create a strain of the present invention with reduced (p)ppGpp accumulation and increased butanol tolerance. SpoT and/or relA genes and gene products from *E. coli, Lactobacillus plantarum, Bacillus licheniformis, Pseudomonas putida, Clostridium acetobutylicum, Enterococcus faecium, Rhodococcus erythropolis* are specifically described herein (see SEQ ID NO 39-62). Many other examples are identified in the literature and in bioinformatics databases well known the skilled person. Additionally, the sequences described herein or those recited in the art may be used to identify other homologs in nature. For example each of the SpoT/RelA nucleic acid fragments described herein may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the spoT and relA genes described herein could be isolated directly by using all or a portion of the instant nucleic acid fragments as DNA hybridization probes to screen libraries from any desired bacteria using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described spoT or relA sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Bioinformatic Approaches

Alternatively, because spoT and relA sequences are so well known and abundant, suitable spoT and relA targets may be identified on the basis of various identifying domains and via Profile Hidden Markov Models (HMM). SpoT and RelA proteins are associated with various identifying domains which can be utilized for the identification of homologs using bioinfomratic approaches. One such domain is the TGS domain associated with SpoT and RelA, which senses acylated-Acyl Carrier Protein thereby serving as the switch linking the SpoT-dependent stress response to fatty acid metabolism (Battesti and Bouveret (2006) Molecular Microbiology 62:1048-10630). The interplay of SpoT synthesis and degradation activities is complex and not well understood. Another domain is the HD domain which is associated with the SpoT protein and is also associated with a superfamily of metal-dependent phosphohydrolases. In addition to the TGS and HD domains, SpoT and RelA each have a RelA/SpoT domain that is common to both proteins.

It is relevant to note here that within the current art there is some inconsistency with respect to the differentiation between SpoT and RelA proteins. For example, although *E. coli* has both spoT and relA genes, many bacteria have a gene called spot, but no gene called relA, or vice versa. The genetic nomenclature is not consistent from one species to another with regard to encoded enzyme activity, since in some species the protein called RelA has both synthesis and degradation activities for (p)ppGpp. In *Lactobacillus plantarum* there is no gene called spoT, and there is a gene called relA (coding region SEQ ID NO:43) which encodes a protein (SEQ ID NO:44) with both ppGppase and PSII activities. In the nomenclature herein, the *Lactobacillus plantarum* gene called relA falls under the definition of a spoT gene, and is considered to be a spoT gene encoding a SpoT protein.

For the purposes of this invention it will be understood that a SpoT protein is one that structurally contains all of the RelA/SpoT, TGS and HD domains as described below, encodes a SpoT protein which is a bi-functional enzyme with both guanosine 3'5'-bis(diphosphate) 3'-pyrophosphohydrolase (ppGppase) and 3',5'-bis(diphosphate synthetase (PSII) activities, and whose disruption affects the levels of (p)ppGpp accumulation in the cell. Similarly a RelA protein is one that contains both the RelA/SpoT and TGS domains, encodes a RelA protein which is a mono-functional enzyme with 3',5'-bis(diphosphate synthetase (PSI) activity, and whose disruption affects the levels of (p)ppGpp accumulation in the cell.

Accordingly, proteins with RelA or SpoT activities have been characterized as containing the RelA/SpoT domain and the TGS domain. These domains were identified by Pfam (*Pfam: clans, web tools and services*: R. D. Finn, J. Mistry, B. Schuster-Böckler, S. Griffiths-Jones, V. Hollich, T. Lassmann, S. Moxon, M. Marshall, A. Khanna, R. Durbin, S. R. Eddy, E. L. L. Sonnhammer and A. Bateman, Nucleic Acids Research (2006) Database Issue 34:D247-D251), and each is characterized by a Profile Hidden Markov Model (HMM). The Profile HMM is prepared using the hmmsearch algorithm of the HMMER software package (Janelia Farm Research Campus, Ashburn, Va.). The theory behind Profile HMMs is described in Durbin et al. ((1998) *Biological sequence analysis: probabilistic models of proteins and nucleic acids*, Cambridge University Press) and Krogh et al. ((1994) J. Mol. Biol. 235:1501-1531), which characterizes a set of proteins based on the probability of each amino acid occurring at each position in the alignment of the proteins of the set. The Profile HMM for the RelA/SpoT domain is in Table 5 and the Profile HMM for the TGS domain is in Table 6. In addition to the RelA/SpoT and TGS domains common to RelA and SpoT proteins, SpoT proteins have an HD domain, also identified by Pfam as above. The Profile HMM for the HD domain is given in Table 7. Tables 5, 6 and 7 are submitted herewith electronically and are incorporated herein by reference. Any protein which has an E-value parameter of 0.01 or less when queried using the Profile HMM for the RelA/SpoT domain and Profile HMM for the TGS domain and that lacks an HD domain can be identified as a RelA protein. Any protein which has an E-value parameter of 0.01 or less when queried using the profiles for these two domains and the Profile HMM for the HD domain can be identified as a SpoT protein. A tree of all known sequences fitting these profiles is shown in FIG. 9. Also marked on the tree are a set of RelA-SpoT related proteins that do not fit the Profile HMMs for RelA and SpoT proteins.

Accordingly the invention provides recombinant bacterial cells wherein the genetic modification down regulates a genetic construct encoding, or causes reduced production of, a protein having a) an E-value parameter of 0.01 or less when queried using the Pfam Profile HMM for the RelA/SpoT domain; and b) an E-value parameter of 0.01 or less when queried using the Pfam Profile HMM for the TGS domain; and c) an E-value parameter of 0.01 or less when queried using the Pfam Profile HMM for the HD domain. In another embodiment the invention provides a recombinant bacterial cell wherein the genetic modification down regulates a genetic construct encoding, or causes reduced production of, a protein having; a) an E-value parameter of 0.01 or less when queried using the Pfam Profile HMM for the TGS domain; and an E-value parameter of 0.01 or less when queried using the Pfam Profile HMM for the RelA/SpoT domain.

Sequences encoding RelA and SpoT proteins identify relA and spoT genes that may be modified to create bacterial strains of the present invention. Some representative spoT and relA coding region sequences and the encoded protein sequences are listed in Table 4 and have SEQ ID NOs: 39-62.

In the present bacterial strains, a modification is engineered that results in reduced (p)ppGpp accumulation. This may be accomplished by reduction or elimination of expression of an endogenous spoT and/or relA gene in several ways. Synthesis of ppGpp can be blocked by insuring that the pools of charged tRNA are balanced. The genetic modification may down regulate a genetic construct encoding a SpoT or RelA protein. If the bacterial host has only a relA or a spoT gene, then reduced (p)ppGpp accumulation is obtained by modification of the endogenous relA or spoT gene, causing reduced expression to confer butanol tolerance. If the bacterial host has both genes, then both relA and spoT genes are modified, causing reduced expression of both genes, to confer butanol tolerance. The spoT gene may be modified so that there is no expression, if expression of the relA gene is reduced. Alternatively, with relA unmodified, the expression of spoT may be lowered to provide increased tolerance. In addition, when the bacterial host has both genes, then modification for reduced expression of relA is sufficient to confer butanol tolerance under conditions where an aminoacyl-tRNA species is low and RelA production of (p)ppGpp would be high. Thus effects of the relA mutation in limited aminoacyl-tRNA species conditions better exemplifies the impact on butanol tolerance of RelA-dependent (p)ppGpp synthesis. For example, *E. coli* has both relA and spoT genes, as shown on the tree in FIG. 9. Elimination of spoT expression in a strain where relA expression is reduced, as demonstrated in Example 3, confers butanol tolerance. Reduced expression of spoT in a strain where relA expression is unmodified, as demonstrated in Example 4, confers butanol tolerance.

*Pseudomonas putida* also has a relA (coding region of SEQ ID NO:49; encoded protein of SEQ ID NO:50) and a spoT gene (coding region of SEQ ID NO:51; encoded protein of SEQ ID NO:52) which can be modified as described for *E. coli* to confer butanol tolerance.

*Lactobacillus plantarum* has only a spoT gene (which is called relA in the literature), and this gene (coding region has SEQ ID NO:43; encoded protein of SEQ ID NO:44) may be modified to reduce expression and confer butanol tolerance. *Bacillus licheniformis Bacillus subtilis, Clostridium acetobutylicum, Enterococcus faecalis*, and *Rhodococcus erythropolis* each have a SpoT protein, as shown on the tree in FIG. 9 (SEQ ID NOs: 46, 48, 54, 60, and 62, respectively). In each bacterial host the encoding spoT gene (coding regions of SEQ ID NOs:45, 47, 53, 59, and 61, respectively) can be modified to reduce expression, reduce (p)ppGpp synthesis, and increase tolerance. *Enterococcus faecium* has two SpoT proteins (SEQ ID NOs: 56 and 58) encoded by genes with coding regions (SEQ ID NOs: 55 and 57) that may be modified to reduce expression, reduce (p)ppGpp synthesis, and increase tolerance.

Any genetic modification method known by one skilled in the art for reducing the presence of a functional enzyme may be used to alter spoT or relA gene expression to reduce (p)ppGpp accumulation. Methods include, but are not limited to, deletion of the entire gene or a portion of the gene encoding SpoT or RelA, inserting a DNA fragment into the spoT or relA gene (in either the promoter or coding region) so that the protein is not expressed or expressed at lower levels, introducing a mutation into the spoT or relA coding region which adds a stop codon or frame shift such that a functional protein is not expressed, and introducing one or more mutations into the spoT or relA coding region to alter amino acids so that a non-functional or a less enzymatically active protein is expressed. In addition, spoT or relA expression may be blocked by expression of an antisense RNA or an interfering RNA, and constructs may be introduced that result in cosuppression. Moreover, a spoT or relA gene may be synthesized whose expression is low because rare codons are substituted for plentiful ones, and this gene substituted for the endogenous corresponding spoT or relA gene. Such a gene will produce the same polypeptide but at a lower rate. In addition, the synthesis or stability of the transcript may be lessened by mutation. Similarly the efficiency by which a protein is translated from mRNA may be modulated by mutation. All of these methods may be readily practiced by one skilled in the art making use of the known sequences encoding SpoT or RelA enzymes. Hundreds of spoT and relA sequences are publicly available as indicated on the tree in FIG. 9, and representative sequences are listed in Table 4. One skilled in the art may choose specific modification strategies to eliminate or lower the expression of the relA or spoT gene as desired in the situations described above.

Alternatively, to reduce (p)ppGpp accumulation, a genetic modification may be made that increases the (p)ppGpp degradation activity present in a bacterial cell. The endogenous spoT gene may be modified to reduce the (p)ppGpp synthetic function of the encoded protein. Alternatively, a modified spoT gene encoding a protein with only degradative activity may be introduced. Regions of the SpoT protein that are responsible for the synthetic and degradative activities have been mapped (Gentry and Cashel Mol. Microbiol. (1996) 19:1373-1384). The RelA/SpoT and TGS domains (described above) function in ppGpp synthesis while the HD domain is responsible for ppGpp hydrolysis. Gentry and Cashel showed that destruction of the HD domain eliminated the hydrolytic activity without loss of biosynthetic capacity while elimination of either of the other 2 domains resulted in loss of the synthetic capacity without loss of the hydrolytic activity. Thus the sequences encoding the RelA/SpoT and/or TGS domains in the endogenous spoT gene may be mutated to reduce (p)ppGpp synthetic activity. For example, in frame deletions eliminating the various dolmans can be readily synthesized in vitro and recombined into the chromosome by standard methods of allelic replacement. Examples of such deletions are readily found in the literature for both RelA (Fujita et al. Biosci. Biotechnol. Biochem. (2002) 66:1515-1523; Mechold et al J. Bacteriol. (2002) 84:2878-88) and SpoT (Battesti and Bouveret (2006) Molecular Microbiology 62:1048-10630). Furthermore, residual degradative capacity can be enhanced by increasing expression of the modified endogenous gene via chromosomal promoter replacements using methods such as described by Yuan et al (Metab. Eng. (2006) 8:79-90), and White et al. (Can. J. Microbiol. (2007) 53:56-62). Alternatively, a mutation affecting the function of either the RelA/SpoT domain or the TGS domain may be made in a spoT gene, and this gene introduced into a bacterial cell to increase (p)ppGpp degradation activity with no increase in synthesis.

DNA sequences surrounding the spoT or relA coding sequence are also useful in some modification procedures and are available for numerous bacteria such as for *E. coli* in the complete genome sequence of the K12 strain: GenBank Accession #U00096.2; and the complete genome sequence of *Clostridium acetobutylicum*: GenBank Accession #AE001437.1. The genome sequences of *L. plantarum, L. salivarius, L sakei, L johnsonii, L. acidophilus* and *L. delbrueckii* are known (National Center for Biotechnology Information (NCBI) database), Genbank™ identification as follows:

*Lactobacillus plantarum* WCFS1, complete genome gi|28376974|ref|NC_004567.1|[28376974]

*Lactobacillus salivarius* subsp. *salivarius* UCC118, complete genome gi|90960990|ref|NC_007929.1|[90960990]

*Lactobacillus sakei* strain 23K complete genome gi|78609255|emb|CR936503.1|[78609255]

*Lactobacillus johnsonii* NCC 533, complete genome gi|42518084|ref|NC_005362.1|[42518084]

*Lactobacillus acidophilus* NCFM, complete genome gi|58336354|ref|NC_006814.1|[58336354]

*Lactobacillus delbrueckii* subsp. *bulgaricus* ATCC 11842, complete genomegi|104773257|ref|NC_008054.1|[104773257]

Additional bacterial genome sequences are available from the *E. coli* Genome Project (Madison, Wis.) and other genome sequencing projects. A listing of microbial genome sequences compiled by the National Library of Medicine includes 567 completed efforts (41 archael and the rest bacterial) with another 841 in progress. In all, 1408 genomes have been or are under investigation, and information on relA and spoT genes or surrounding DNA within these sequences may be used in making relA and/or spoT modifications.

In particular, DNA sequences surrounding the spoT or relA coding sequence are useful for modification methods using homologous recombination. An example of this method is using spoT gene flanking sequences bounding a selectable marker gene to mediate homologous recombination whereby the marker gene replaces the spoT gene. Also partial spoT gene sequences and spoT flanking sequences bounding a selectable marker gene may be used to mediate homologous recombination whereby the marker gene replaces a portion of the spoT gene. In addition, the selectable marker may be bounded by site-specific recombination sites, so that following expression of the corresponding site-specific recombinase, the resistance gene is excised from the spoT gene without reactivating the latter. The site-specific recombination leaves behind a recombination site which disrupts expression of the SpoT enzyme. The homologous recombination vector may be constructed to also leave a deletion in the spoT gene following excision of the selectable marker, as is well known to one skilled in the art. Moreover, promoter replacement methods may be used to exchange the endogenous transcriptional control elements allowing another means to modulate expression (Yuan et al. ibid).

The spoT gene of *E. coli* is within a demonstrated operon while the spoT gene of *Lactobacillus plantarum* is within a gene cluster whose structure is consistent with it being an operon. When part of an operon, expression of spoT or relA may also be reduced by genetic modification of a coding region that is upstream of the spoT or relA coding region in the operon. For example in the spoT-containing operon in *E. coli*, upstream of the spoT coding region are coding regions for gmk (guanosine monophosphate kinase) and rpoZ (DNA-directed RNA polymerase subunit omega). A modification of the gmk or rpoZ coding region which produces a polar effect will reduce or eliminate spoT expression. Polar mutations are typically nonsense, frameshift or insertion mutations. With these types of mutations, transcription may be truncated, translational coupling is prevented, and hence both interrupted and downstream genes are not expressed. This type of modification is described herein in Example 2, where a transposon insertion in rpoZ affects spoT expression and butanol tolerance. In addition, in Examples 3 and 4 herein, a polar modification in rpoZ was constructed resulting in butanol tolerance. In addition intergenic regions could be modified to prevent translational coupling when it is found.

In the same manner, the yrvE coding region that is upstream of the spoT coding region in an operon in the *Lactobacillus plantarum* genome (GenBank Accession #AL935263) may be modified to reduce spoT expression. Using gene organization information from genome sequencing of other bacterial strains allows targeted modification of coding regions in operons upstream of spoT or relA coding regions in those strains to reduce (p)ppGpp synthesis and confer butanol tolerance.

Butanol Tolerance of Reduced (p)ppGpp Strain

A bacterial strain of the present invention that is genetically modified for reduced accumulation of (p)ppGpp has improved tolerance to butanol. The tolerance of reduced (p)ppGpp strains may be assessed by assaying their growth in concentrations of butanol that are detrimental to growth of the parental (prior to genetic modification for reduced synthesis of (p)ppGpp) strains. Improved tolerance is to butanol compounds including 1-butanol, isobutanol, and 2-butanol. In addition, the present strains have improved tolerance to 2-butanone, which is also called methylethyl ketone (MEK). The amount of tolerance improvement will vary depending on the inhibiting chemical and its concentration, growth conditions and the specific genetically modified strain. For example, as shown in Example 7 Table 8 herein, a spoT modified strain of *E. coli* showed improved growth over the parental strain that was about 7% improved growth in 0.8% 2-butanol, about 13.5% improved growth in 0.8% isobutanol, about 16.5% improved growth in 0.4% 1-butanol, and about 3% improved growth in 3% 2-butanone.

Reduced Response to (p)ppGpp

The effect of reducing accumulation of (p)ppGpp may also be obtained in the present strains by reducing responsiveness to (p)ppGpp. Mutants with reduced response to (p)ppGpp were found in the RNA polymerase core subunit encoding genes and the RNA polymerase binding protein DksA (Potrykus and Cashel (2008) Ann. Rev. Microbiol. 62:35-51). Reduced expression of any of these proteins may be engineered to reduce the response to (p)ppGpp. In particular, reducing expression of DksA may be engineered in the present strains to confer increased tolerance to butanol and 2-butanone. Expression of the endogenous dksA gene in a target bacterial cell may be reduced using any genetic modification method such as described above for spoT or relA. The dksA gene of a target host cell may be readily recognized by one skilled in the art through bioinformatics analysis, or experimental methods as described for spoT.

Butanol or 2-Butanone Biosynthetic Pathway

The present genetically modified bacterial strains with improved tolerance to butanol and 2-butanone are additionally genetically modified by the introduction of a biosynthetic pathway for the synthesis of butanol or 2-butanone. Alternatively, a bacterial strain having a biosynthetic pathway for the synthesis of butanol or 2-butanone may be genetically modified for reduced synthesis of (p)ppGpp as described herein to confer butanol tolerance. The butanol biosynthetic pathway may be a 1-butanol, 2-butanol, or isobutanol biosynthetic pathway. Particularly suitable bacterial hosts for the production of butanol or 2-butanone and modification for increased butanol tolerance include, but are not limited to, members of the genera *Clostridium, Escherichia, Rhodococcus, Pseudomonas, Bacillus, Lactobacillus*, and *Enterococcus*. Preferred hosts include: *Clostridium acetobutylicum, Escherichia coli, Bacillus licheniformis, Rhodococcus erythropolis, Pseudomonas putida, Lactobacillus plantarum, Enterococcus faecium, Enterococcus faecalis*, and *Bacillus subtilis.*

1-Butanol Biosynthetic Pathway

A biosynthetic pathway for the production of 1-butanol is described by Donaldson et al. in co-pending and commonly owned U.S. patent application Ser. No. 11/527,995, published as US20080182308A1, which is incorporated herein by reference. This biosynthetic pathway comprises the following substrate to product conversions:

a) acetyl-CoA to acetoacetyl-CoA, as catalyzed for example by acetyl-CoA acetyltransferase encoded by the genes given as SEQ ID NO:1 or 3;
b) acetoacetyl-CoA to 3-hydroxybutyryl-CoA, as catalyzed for example by 3-hydroxybutyryl-CoA dehydrogenase encoded by the gene given as SEQ ID NO:5;
c) 3-hydroxybutyryl-CoA to crotonyl-CoA, as catalyzed for example by crotonase encoded by the gene given as SEQ ID NO:7;
d) crotonyl-CoA to butyryl-CoA, as catalyzed for example by butyryl-CoA dehydrogenase encoded by the gene given as SEQ ID NO:9;
e) butyryl-CoA to butyraldehyde, as catalyzed for example by butyraldehyde dehydrogenase encoded by the gene given as SEQ ID NO:11; and
f) butyraldehyde to 1-butanol, as catalyzed for example by 1-butanol dehydrogenase encoded by the genes given as SEQ ID NO:13 or 15.

The pathway requires no ATP and generates $NAD^+$ and/or $NADP^+$, thus, it balances with the central, metabolic routes that generate acetyl-CoA.

2-Butanol and 2-Butanone Biosynthetic Pathway

Biosynthetic pathways for the production of 2-butanol and 2-butanone are described by Donaldson et al. in co-pending and commonly owned U.S. Patent Application Publication Nos. US20070259410A1 and US2007US 2007-0292927A1, which are incorporated herein by reference. One 2-butanol biosynthetic pathway comprises the following substrate to product conversions:

a) pyruvate to alpha-acetolactate, as catalyzed for example by acetolactate synthase encoded by the gene given as SEQ ID NO:19;
b) alpha-acetolactate to acetoin, as catalyzed for example by acetolactate decarboxylase encoded by the gene given as SEQ ID NO:17;
c) acetoin to 2,3-butanediol, as catalyzed for example by butanediol dehydrogenase encoded by the gene given as SEQ ID NO:21;
d) 2,3-butanediol to 2-butanone, catalyzed for example by butanediol dehydratase encoded by genes given as SEQ ID NOs:23, 25, and 27; and
e) 2-butanone to 2-butanol, as catalyzed for example by 2-butanol dehydrogenase encoded by the gene given as SEQ ID NO:29.

Omitting the last step (e) of the above pathway provides a biosynthetic pathway for production of 2-butanone, also known as methyl ethyl ketone (MEK).

Isobutanol Biosynthetic Pathway

Biosynthetic pathways for the production of isobutanol are described by Maggio-Hall et al. in copending and commonly owned U.S. patent application Ser. No. 11/586,315, published as US20070092957 A1, which is incorporated herein by reference. One isobutanol biosynthetic pathway comprises the following substrate to product conversions:

a) pyruvate to acetolactate, as catalyzed for example by acetolactate synthase encoded by the gene given as SEQ ID NO:19;

b) acetolactate to 2,3-dihydroxyisovalerate, as catalyzed for example by acetohydroxy acid isomeroreductase encoded by the gene given as SEQ ID NO:31;

c) 2,3-dihydroxyisovalerate to α-ketoisovalerate, as catalyzed for example by acetohydroxy acid dehydratase encoded by the gene given as SEQ ID NO:33;

d) α-ketoisovalerate to isobutyraldehyde, as catalyzed for example by a branched-chain keto acid decarboxylase encoded by the gene given as SEQ ID NO:35; and e) isobutyraldehyde to isobutanol, as catalyzed for example by a branched-chain alcohol dehydrogenase encoded by the gene given as SEQ ID NO:37.

Construction of Bacterial Strains for Butanol or Butanone Production

Any bacterial strain that is genetically modified for butanol tolerance as described herein is additionally genetically modified (before or after modification to tolerance) to incorporate a butanol or 2-butanone biosynthetic pathway by methods well known to one skilled in the art. Genes encoding the enzyme activities described above, or homologs that may be identified and obtained by commonly used methods well known to one skilled in the art, are introduced into a bacterial host. Representative coding and amino acid sequences for pathway enzymes that may be used are given in Tables 1, 2, and 3, with SEQ ID NOs:1-38. Methods described in copending and commonly owned U.S. Patent Application Publication Nos. US20080182308A1, US2007025941 A1, US20070292927A1, and US20070092957A1 may be used.

Vectors or plasmids useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically, the vector or plasmid contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression Gram-positive bacteria, Eichenbaum et al. *Appl. Environ. Microbiol.* 64(8): 2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE® (Madison, Wis.).

Expression of a Butanol Biosynthetic Pathway in *E. coli*

Vectors useful for the transformation of *E. coli* are common and commercially available from the companies listed above. For example, the genes of an isobutanol, 1-butanol, or 2-butanol biosynthetic pathway may be isolated from various sources, as described above, cloned onto a modified pUC19 vector and transformed into *E. coli* host cells, as described in Examples herein. Alternatively, the genes encoding a butanol biosynthetic pathway may be divided into multiple operons, cloned onto expression vectors, and transformed into various *E. coli* strains. The 2-butanone biosynthesis pathway may be similarly expressed, omitting the butanol dehydrogenase.

Construction of *Lactobacillus* Strains for Butanol or Butanone Production

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. *Appl. Environ. Microbiol.* 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other Gram-positive organisms. A non-limiting example is the nisA promoter from *Lactococcus*. Termination control regions may also be derived from various genes native to the preferred hosts or related bacteria.

The various genes for a butanol or butanone biosynthetic pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224:1252-154 (1990)), Bringel and Hubert (*Appl. Microbiol. Biotechnol.* 33: 664-670 (1990)), and Teresa Alegre, Rodriguez and Mesas (*FEMS Microbiology letters* 241:73-77 (2004)). Plasmids can also be introduced to *Lactobacillus plantatrum* by conjugation (Shrago, Chassy and Dobrogosz *Appl. Environ. Micro.* 52: 574-576 (1986)). The butanol or butanone biosynthetic pathway genes can also be integrated into the chromosome of *Lactobacillus* using integration vectors (Hols et al. *Appl. Environ. Micro.* 60:1401-1403 (1990); Jang et al. *Micro. Lett.* 24:191-195 (2003)).

Fermentation of Butanol Tolerant Bacteria for Butanol or 2-Butanone Production

The present strains with reduced (p)ppGpp accumulation and having a butanol or 2-butanone biosynthesis pathway may be used for fermentation production of butanol or 2-butanone. Strains with reduced or no SpoT expression, or reduced SpoT expression in combination with reduced RelA expression, show butanol tolerance when grown in typical media. Enhanced butanol tolerance in strains with reduced or no RelA expression alone can be observed under conditions where the relA gene would be activated in a strain without relA modification. Activation of relA occurs in the presence of uncharged tRNAs, which results from inadequate presence of amino acids. Thus butanol tolerance is observed in strains with modification of relA alone when the medium is limiting for amino acids, or is otherwise inductive for relA expression.

Fermentation media for the production of butanol or butanone must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Sucrose may be obtained from feedstocks such as sugar cane, sugar beets, cassava, and sweet sorghum. Glucose and dextrose may be obtained through saccharification of starch based feedstocks including grains such as corn, wheat, rye, barley, and oats.

In addition, fermentable sugars may be obtained from cellulosic and lignocellulosic biomass through processes of pretreatment and saccharification, as described, for example, in commonly owned and co-pending US patent application publication US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol or butanone production.

Typically cells are grown at a temperature in the range of about 25° C. to about 40° C. in an appropriate medium. Suitable growth media are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Butanol or butanone may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Butanol or butanone may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol or butanone may be practiced using either batch, fed-batch or continuous processes and that any known mode of fermentation would be suitable. Additionally, it is contemplated that cells may be immobilized on a substrate as whole cell catalysts and subjected to fermentation conditions for butanol or butanone production.

Methods for Butanol and 2-Butanone Isolation from the Fermentation Medium

Bioproduced butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation. These same methods may be adapted to isolate bioproduced 2-butanone from the fermentation medium.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec' means second(s), "μl" means microliter(s), "ml" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "rpm" means revolutions per minute, "w/v" means weight/volume, "OD" means optical density, and "OD600" means optical density measured at a wavelength of 600 nm.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987. Additional methods used in the Examples are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992).

These references include descriptions of the media and buffers used including TE, M9, MacConkey and LB.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Freezing Medium

The following medium was used to store cells in microtitre plates.

Stock solutions (autoclaved each solution after making):

0.68 M Ammonium Sulfate $(NH_4)_2SO_4$: 44.95 g, brought to 500 mL with $dIH_2O$ 0.04 M Magnesium Sulfate $MgSO_4$: 2.4 g, brought g to 500 mL with $dIH_2O$ 0.17 M Sodium Citrate: 25 g, brought g to 500 mL with $dIH_2O$ 1.32 M $KH_2PO_4$: 17.99 g, brought to 100 mL with $dIH_2O$ 3.6 M $K_2HPO_4$: 62.7 g, brought to 100 mL with $dIH_2O$ To make 10× freezing medium, 138.6 g glycerol was weighed into a tared 250 mL plastic beaker. 25 mL of each of the above five stock solutions were added with stirring mediated with a magnetic stirrer and a stir plate until thoroughly mixed. Distilled water was added until a final volume of 250 mL was achieved. The solution was filtered through a 0.2 micron sterile filter.

To use, a 1 volume of 10× freezing medium was added to 9 volumes of LB. The final concentrations are: 36 mM $K_2HPO_4$, 13.2 mM $KH_2PO_4$, 1.7 mM Sodium Citrate, 0.4 mM $MgSO_4$, 6.8 mM $(NH_4)_2SO_4$, 4.4% v/v glycerol in LB. Sterile flat-bottomed clear polystyrene 96-well plates (Corning Costar #3370, pre-bar-coded) were used for storing libraries of mutants in freezing medium in a $^-80°$ C. freezer.

Agar Plates

LB agar media supplemented with butanol was prepared fresh one day before innoculating at an appropriate volume and cooled for 2 hours in a 50° C. water bath. LB agar plates supplemented with butanol were prepared by dispensing 67 mls of melted agar, using a peristaltic pump and sterile Nalgene tubing, into sterile Omni trays with lids (Nunc mfg no. 242811). The 1-butanol (Sigma Aldrich, Part No. B7906-500 ml) was added and mixed by vigorous swirling immediately before dispensing the agar to minimize evaporation of the butanol. The plates were allowed to cool and set for approximately an hour before they were stored overnight in closed anaerobic chambers at room temperature in the chemical/biological hood. The next morning, the chambers harboring the plates were opened and allowed to air dry for approximately 1 hour before using.

Methods for Determining Isobutanol, 1-butanol, 2-butanol, and 2-butanone Concentration in Culture Media The concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. 1-Butanol had a retention time of 52.8 min under the conditions used. Under the conditions used, 2-butanone and 2-butanol had retention times of 39.5 and 44.3 min, respectively.

Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min. The retention time of 1-butanol was 5.4 min. The retention times of 2-butanone and 2-butanol were 3.61 and 5.03 min, respectively.

Example 1

Generation of Knockout Library and Screening to Identify 1-Butanol Phenotypes

*E. coli* strain EC100 (Epicentre; Madison, Wis.], whose genotype is F-mcrA Δ (mrr-hsdRMS-mcrBC) φ80dlacZM15 ΔlacX74 recA1 relA1 endA1 araD139 Δ (ara, leu)7697 galU galK λ-rpsL nupG, was transposome mutagenized. This was performed according to the vendor's (Epicentre; Madison, Wis.) protocol, using purchased electro-competent cells as the recipient in the genetic cross with the EZ-Tn5™ <KAN-2> Tnp Transposome™. 1 μl of the EZ-Tn5 <KAN-2> Tnp Transposome was electroporated into EC100 cells. Immediately after electroporation, SOC medium was added to a final volume of 1 ml and the mixture was gently agitated before transfer to a tube that was incubated at 37° C. with shaking for 1 hr. The genetic cross yielded a titer ranging from 4 to $7\times10^4$ kanamycin-resistant colony-forming units per ml of electroporated cells.

100 μl aliquots of undiluted cells and dilutions were separately plated on LB medium containing 50 μg/ml kanamycin to yield about 500 colonies per plate, that could be picked and stored. This process utilized a robotic AutoGenesys Colony Picker to select individual colonies from 22 $cm^2$ LB kanamycin (50 μg/mL) agar plates. The colony picker used a CCD camera image with select parameters to discriminate colonies for picking based on size, roundness, and proximity to other colonies. For size, the parameters were 0.5 mm to 1.8 mm for small cells, 1.8 to 3.0 mm for large cells. Roundness determinations were made from 1.30 mm ellipticity with a 1.50 mm variance for small cells, and 1.50 mm ellipticity with a 1.50 mm variance for large cells. The cells also had to be 1.3 mm or 500 pixels apart from neighboring cells. The individual, well-separated colonies were imaged and picked to media-containing microtiter wells. The colonies were picked into 92 of the 96 wells of archive microtiter plates containing 150 μl per well of freezing medium supplemented with 50 μg/ml kanamycin (see General Methods). Four wells were left blank and served as negative controls. The archive plates were lidded and placed in a humidified static incubator at 37° C. for overnight incubation. The plates were then placed in ⁻80° C. storage for future use. The record of archive plate barcode IDS were transferred from the colony picker to the Blaze Systems Laboratory Information System (LIMS). A total of 11,886 colonies were picked to the microtiter wells. This library was expected to have a 90% probability of containing a mutation inactivating any non-essential gene, which would be a mutation in 3600 of a possible 4000 ORFs.

To determine inhibitory 1-butanol concentrations, strain EC100 was grown overnight in LB medium and aliquots of various dilutions were plated on solidified LB medium appended with concentrations of 1-butanol up to 1% at 0.1% integrals. Plates were incubated in a closed chamber at 37° C. for 1 day. The number of colonies arising and their sizes were scored. Colonies were progressively smaller starting at 0.2% 1-butanol, with only pinpoint colonies seen at 0.6%. No change in titer was seen in the range of 0 to 0.6%. No colony formation after overnight incubation was observed at concentrations ≧0.7% (w/v). Butanol concentrations of 0.4% and 0.6% were chosen to screen for tolerance.

For screening of the transposon library, archive plates were removed from ⁻80° C. storage and allowed to thaw at room temperature for an hour. Using a 96-pin HDRT (high density replication tool) on a Biomek 2000 robot, an archive plate was sampled multiple times with inocula printed on multiple agar plates. The final agar plate was an LB plate used as a quality control for verifying instrument and experimental conditions. The Biomek printing method employed a pin decontamination step at both the beginning and the end of each run. The pins were dipped first into 10% bleach solution (10 sec.), followed by water and 70% ethanol dips (10 sec. each). The pins were then dried over a room temperature fan (25 sec.). The archive plates were returned to the ⁻80° C. freezer.

The control printed agar plates were lidded, put into plastic bags, and placed in a 37° C. incubator. Printed plates containing 1-butanol were handled in a chemical fume hood where they were placed in sealed portable anaerobic chambers: 7.0 liter AnaeroPack Rectangular Jars (Remel Inc.; Lenexa, Kans.).

Incubation at 20° C. or 37° C. was performed for 2 days; scoring was done on both days. Scoring of 1-butanol-containing plates was performed in a chemical hood. A visual screen identified 23 variants which grew slightly better than their neighbors on the butanol containing plates.

Example 2

Mapping of Transposon Insertions in 1-Butanol Tolerant Strains

In order to link 1-butanol phenotypic alterations with a gene/protein/function, the transposon insertion positions were determined by sequencing. Genomic DNA was prepared from the identified 1-butanol tolerant lines using a GenomiPhi™ DNA Amplification kit (GE/Amersham Biosciences; Piscataway, N.J.) which utilizes Phi29 DNA polymerase and random hexamers to amplify the entire chromosome, following the manufacturer's protocol. A portion of a colony from a culture plate was diluted in 100 μl of water, and 1-2 μl of this sample was then added to the lysis reagent and heated for 3 minutes at 95° C. and cooled to 4° C. Next the polymerase was added and the amplification proceeded overnight at 30° C. The final step was enzyme inactivation for 10 minutes at 65° C. and cooling to 4° C.

The resulting genomic DNA was sequenced using the following primers that read outward from each end of the transposon:

```
SEQ ID NO: 63 Kan2cb-Fwd:
CTGGTCCACCTACAACAAAGCTC TCATC

SEQ ID NO: 64 Kan2cb-Rev:
CTTGTGCAATGTAACATCAGAGATTTTGAGACAC.
```

From each 20 μl GenomiPhi™ amplified sample, 8 μl was removed and added to 16 μl of BigDye v3.1 Sequencing reagent (PN #4337457; Applied Biosystems; Foster City, Calif.), 3 μl of 10 μM primer (SEQ ID NO:1 or 2), 1 μl Thermofidelase (Fidelity Systems; Gaithersburg, Md.) and 12 µl Molecular Biology Grade water (Mediatech, Inc.; Herndon, Va.). The sequencing reactions were then thermal cycled as follows; 3 minutes at 96° C. followed by 200 cycles of (95° C. 30 sec+55° C. 20 sec+60° C. 2 min), then stored at 4° C. The unincorporated ddNTPs were removed prior to sequencing using Edge Biosystems (Gaithersburg, Md.) clean-up plates. For each sequencing reaction the total 40 µl was pipetted into one well of a pre-spun 96-well clean up plate. The plate was then spun for 5 min at 5,000×g in a Sorvall RT-7 refrigerated centrifuge. The cleaned up reactions were then placed directly onto an Applied Biosystems 3700 DNA sequencer and sequenced with automatic base-calling.

The sequences that were obtained were aligned with the *E. coli* K12 genome using BLAST (2.2.9, Basic Local Alignment Search Tool). The output was a string of matched nucleotides within the *E. coli* genome designated by nucleotide number, which then was used to identify open reading frames into which each transposon was inserted, using the EcoCyc database (SRI International; Menlo Park, Calif.)

Figure 1:
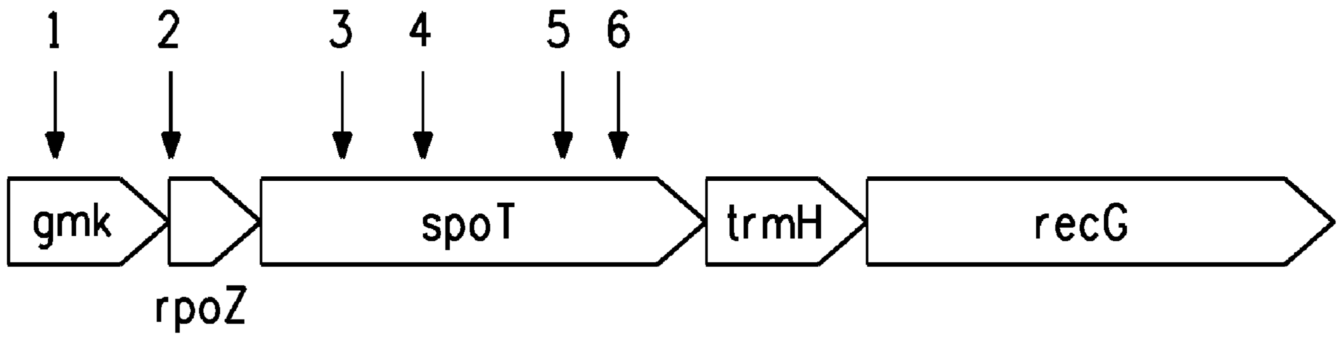
FIG. 1 shows a diagram of the operon that includes spoT with transposon insertion sites marked by arrows, and a table identifying the transposon insertion lines.

In four separate strains, the transposon insertion was in the spoT coding region. Two of these spoT mutant strains are designated DPD1850 and DPD1848. In another strain the insertion was in the gmk coding region, which is in the same operon as spoT. In another strain the insertion was in the rpoZ coding region, which is in the same operon as spoT. The sites of these insertions in the reported operon structure p gmk-rpoZ-spoT-trmH-recG are shown in FIG. 1 as vertical arrows. A knockout of spoT is viable in the EC100 strain due to the presence of the relA1 allele, which reduces expression of RelA.

Example 3

1-Butanol Tolerant Mutant Phenotypes in Liquid Cultures

Figure 2:
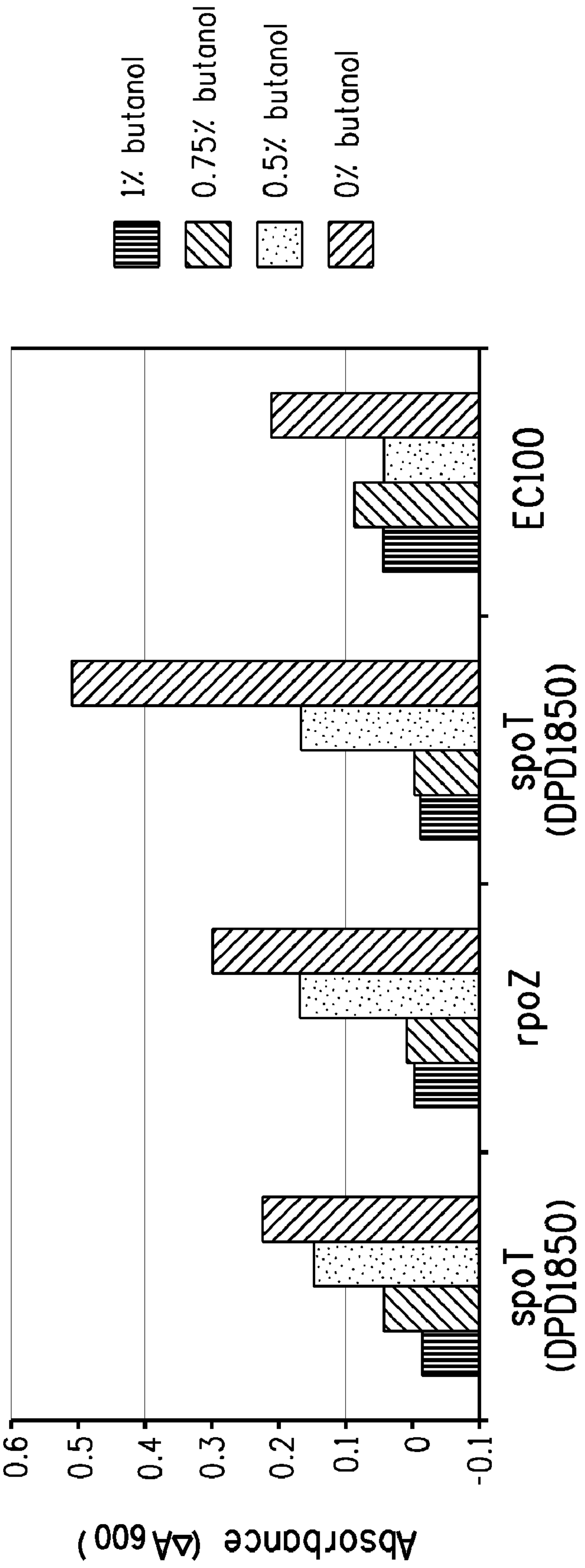
FIG. 2 shows a graph of the difference between 4 hour and 2 hour growth time points for different insertion mutants and EC100 parental strain in different concentrations of 1-butanol.

Transposition mutant strains DPD1850 (spoT), DPD1848 (spoT), and DPD1865 (rpoZ) isolated in the above examples, and the EC100 control, were cultured overnight with shaking at 37° C. in LB before 1:100 dilution in fresh LB. After a 1 hr incubation, the culture was split into 1 ml aliquots (microfuge tubes) and 1-butanol was added to 0, 0.5%, 0.75% or 1% (w/v). After a further 2 hr incubation at 37° C. with shaking, 200 µl samples were transferred to a microtiter plate and optical density at $A_{600}$ recorded. The microtiter plate was moved to a platform shaker that was located within a plastic box that is in a 37° C. incubator. Optical density was subsequently recorded at 4 hour and the results are shown in FIG. 2 as the difference between the 4 and 2 hr time points. In this experiment, the spoT and rpoZ lines showed improved growth in 0.5% 1-butanol.

Kinetic growth studies were performed for the DPD1848 and the control (EC100) using the Bioscreen C Automated Microbial Growth Curve Analyis System (Oy Growth Curves Ab Ltd., Helsinki, Finland), which is an automated 96 well plate system, that monitors growth of many cultures simultaneously, each in a volume of 150 µl. Overnight triplicate cultures of each strain were grown and diluted (1:10) into either LB or LB freshly supplemented with 0.2%, 0.3%. 0.4% or 0.6% 1-butanol (w/v). The growth of each culture was followed for approximately 18 hours. The triplicates were averaged and plotted in FIG. 3 as the final 18 hour time point, normalized to EC100, and given as the percent growth inhibition relative to the no butanol control for each strain.

Figure 4A:
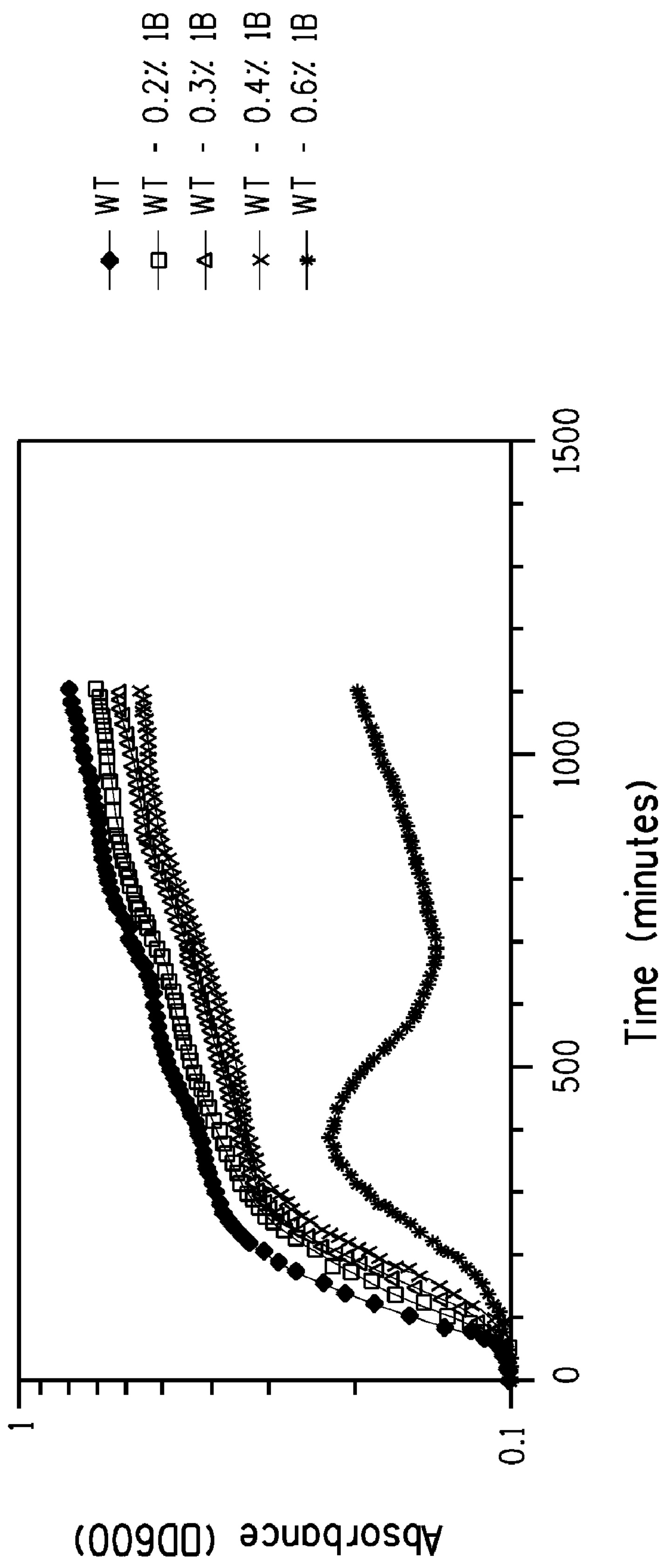
FIG. 4 shows a graph of growth of spoT transposon insertion mutant (A) and EC100 parental strain (wt: wild type) (B) in different concentrations of 1-butanol.
Figure 4B:
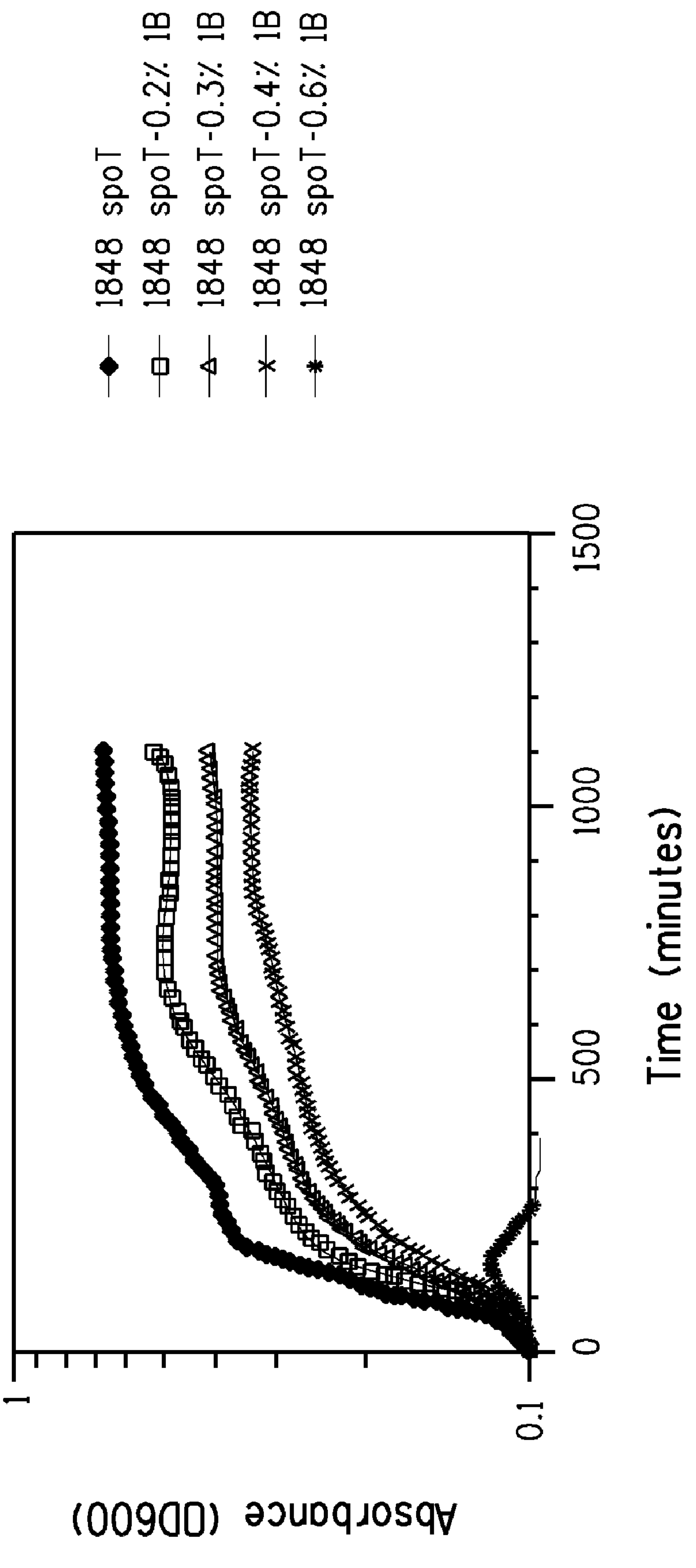

An additional kinetic growth study was performed as described above. The data is shown in FIG. 4 plotted as OD600 over time for the DPD1848 spoT mutant (A), and wild type (B, EC100). The spoT mutant was more tolerant to all of the concentrations of 1-butanol tested than the wild type strain in terms of growth rate.

Example 4

1-Butanol Tolerance of rpoZ Insertion in Additional Host Strain

Figure 5:
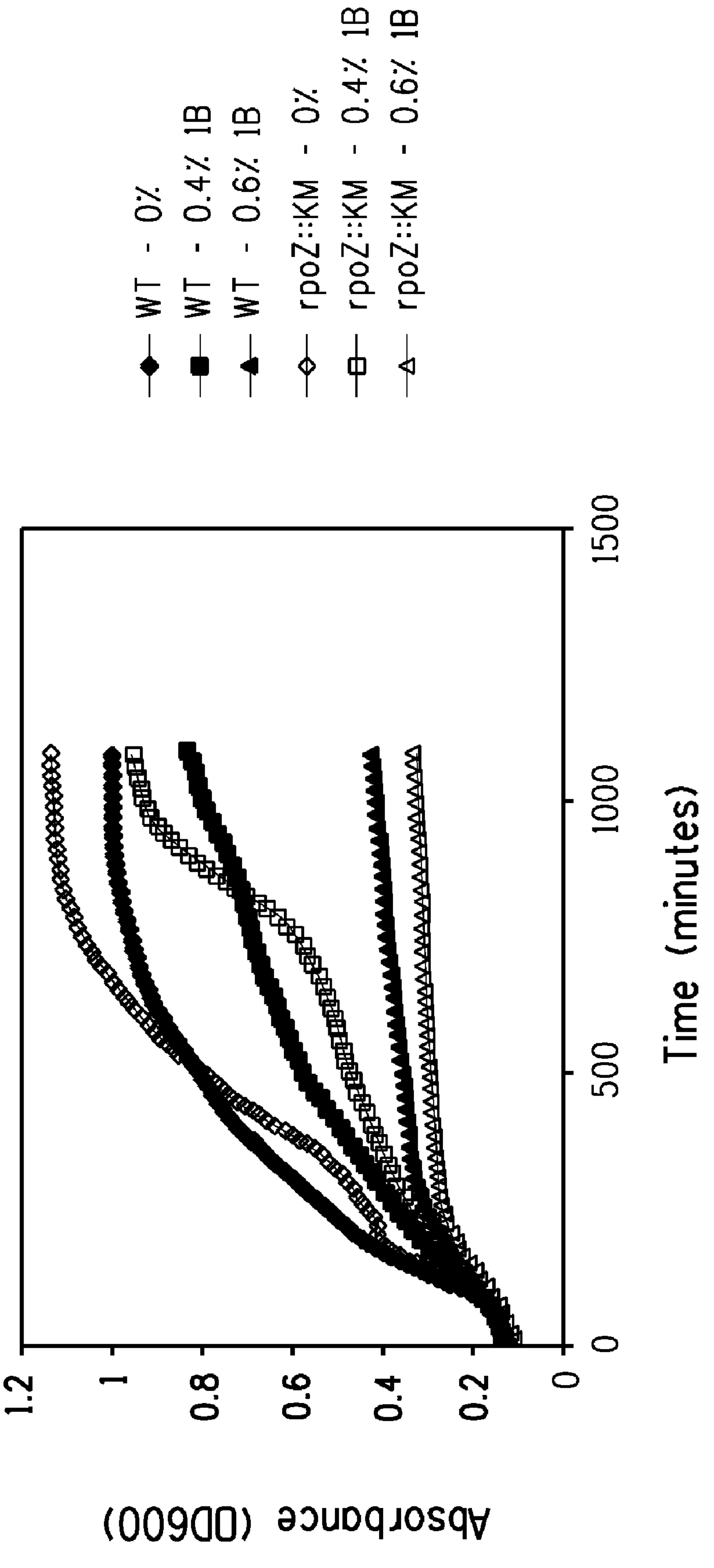
FIG. 5 shows a graph of growth of the Keio rpoZ transposon insertion line and BW25113 parental strain (WT: wild type) in different concentrations of 1-butanol.

A strain of *E. coli* K12 having an insertion in the rpoZ coding region is available in the Keio knockout collection (Baba et al. (2006) Mol. Syst. Biol. 2:2006.0008). This is a collection of lines, each with a kanamycin marker insertion in an identified location, made in the BW25113 strain (Coli Genetic Stock Center #: 7636; Datsenko and Wanner (2000) Proc. Natl. Acad. Sci. USA 97:6640-6645). The rpoZ insertion line (JW3624) was assayed for 1-butanol tolerance. Kinetic growth studies were performed for a the rpoZ and wild type strains using Bioscreen, as described in Example 3, with 0%, 0.4% and 0.6% 1-butanol. The growth points of triplicate cultures were averaged and plotted in FIG. 5 as absorbance at OD600. The butanol tolerant phenotype was seen at 0.4% 1-butanol.

Figure 6:
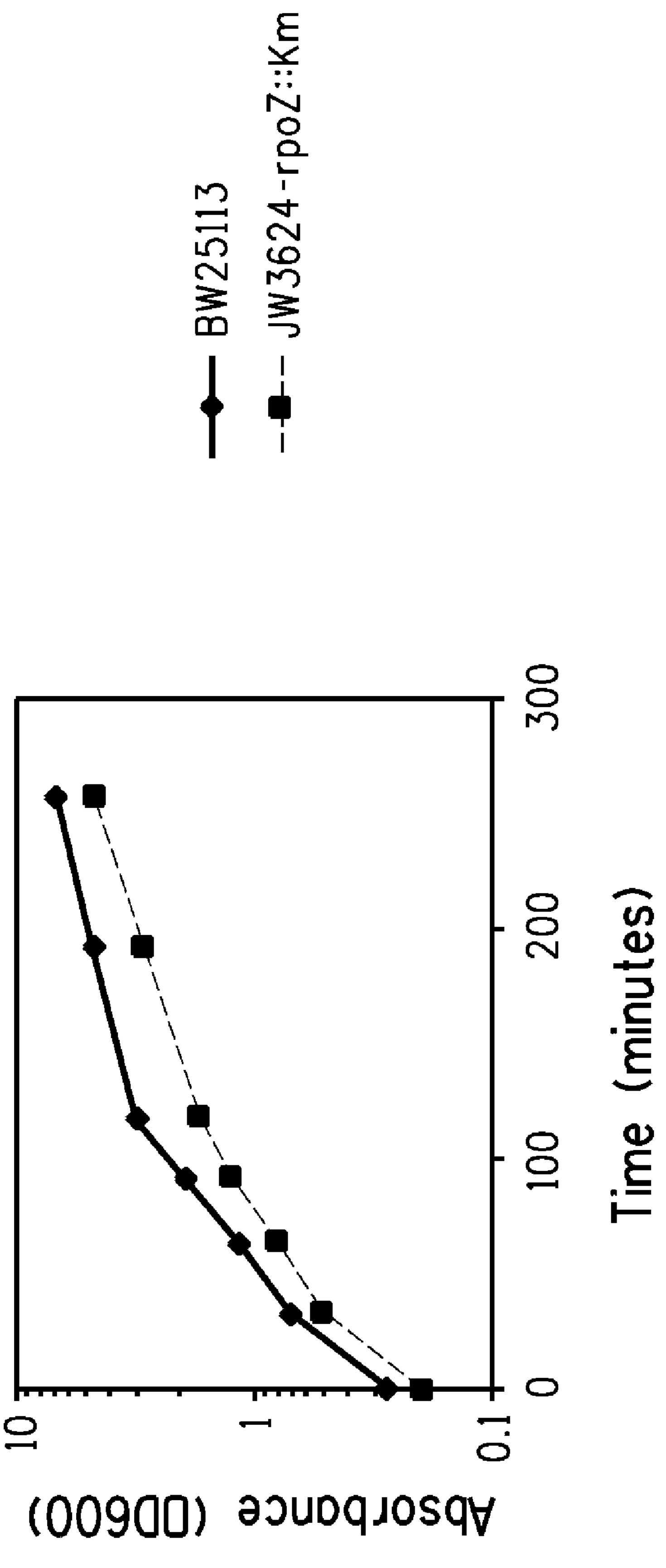
FIG. 6 shows a graph of growth of the rpoZ marker insertion line and the BW25113 parental strain in the absence of 1-butanol.
Figure 7B:
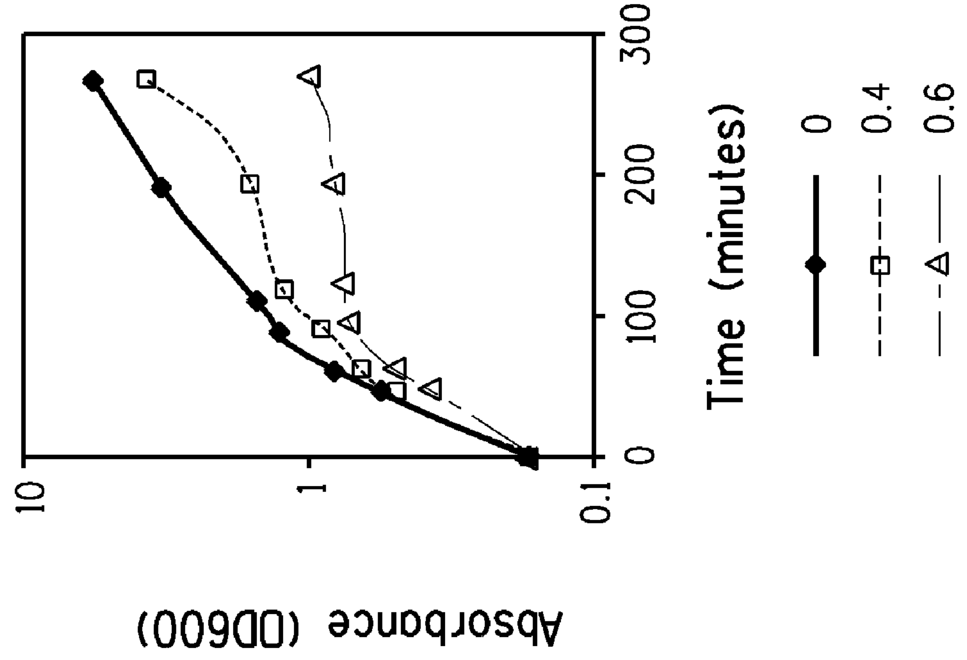
FIG. 7 shows graphs of growth in 0, 0.4% or 0.6% 1-butanol of the BW25113 parental strain (A) and constructed rpoZ marker insertion line (B).
Figure 7A:
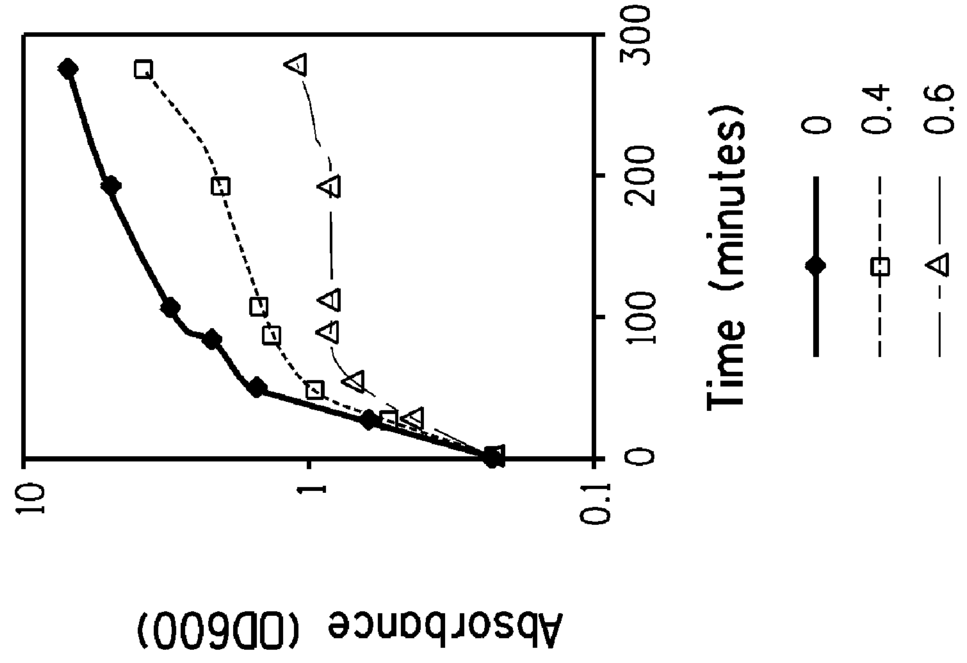

Shake flask experiments were performed on the rpoZ::kan line JW3624 and the wild type control BW25113 line. Cultures were grown in LB medium containing 0%, 0.4% or 0.6% 1-butanol in shake flasks. The experiments were performed by inoculating 100 ml of medium in a 250 ml plastic flask with 2 ml of an overnight culture grown from a single colony grown at 37° C. and incubating with shaking for approximately two doubling times (1 hour), to an OD600 between 0.2 and 0.3. Each culture was split into five 25 ml cultures in plastic screw top 125 ml flasks and the cultures were maintained at 37° C. in a shaking water bath at 200 rpm. The OD600 was monitored at 0, 30, 90, 120 190, and 260 minutes. The growth data in the absence of 1-butanol is shown in FIG. 6. The growth data in the presence of 0.4% or 0.6% 1-butanol for BW25113 and JW3624 are shown in FIGS. 7 A and B, respectively.

Figure 8:
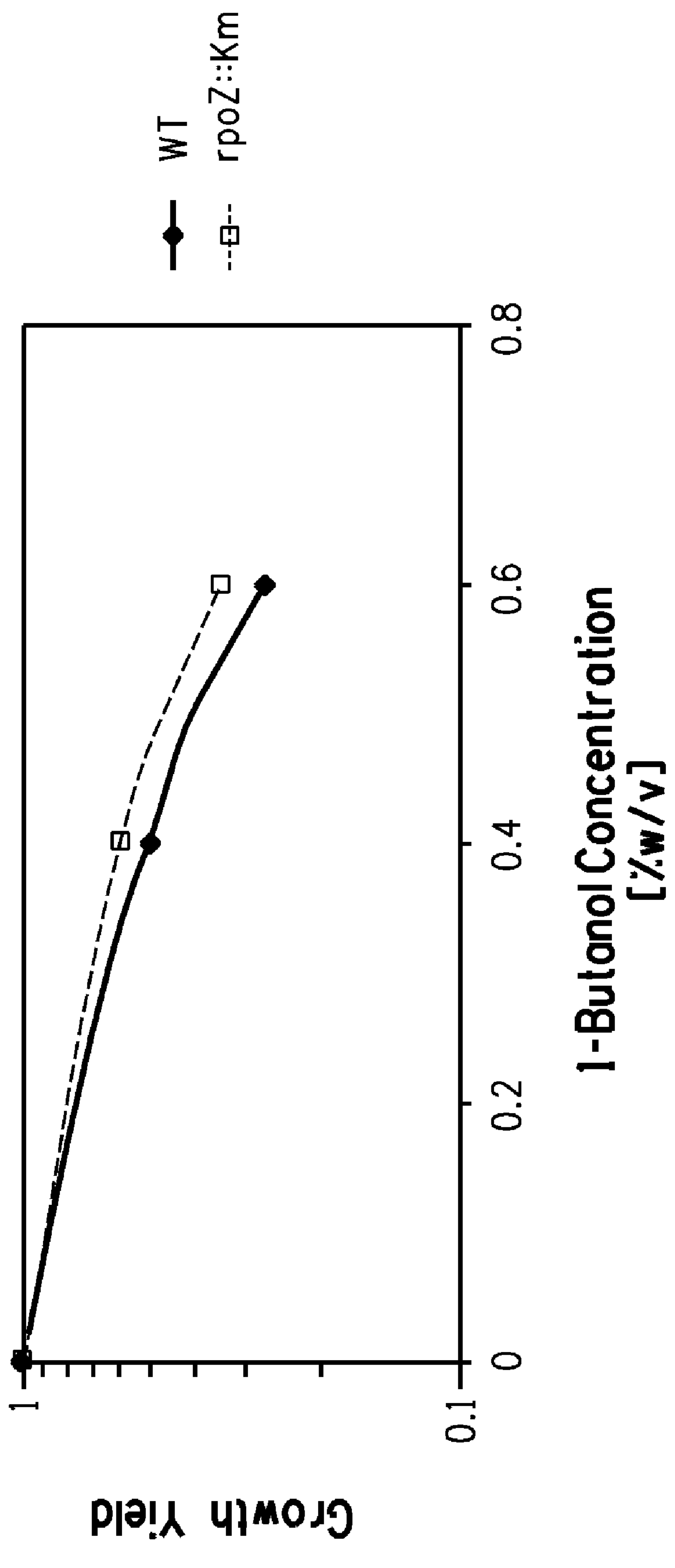
FIG. 8 shows a graph of the fractional growth of the rpoZ marker insertion line and the parental line (WT) in different concentrations of 1-butanol.

In the cultures above, a final time point was taken at 18 hr and used to calculate growth yield as a function of 1-butanol challenge. For each line grown in 0, 0.4% or 0.6% 1-butanol, the final 18 hour time point was divided by the no 1-butanol 18 hr time point. The results given in FIG. 8 show that the wild type cells were the most sensitive to growth inhibition in the presence of 0.4 and 0.6% 1-butanol. The rpoZ mutant had higher growth yields than wild type.

Example 5

Growth Analysis of spoT Mutant Line in Other Chemicals

A Bioscreen experiment, as described in Example 3, was used to compare growth of the mutant spoT DPD1848 line as compared to wild type EC100 in the following chemicals:

1-butanol at 0, 0.2%, 0.3%. 0.4% and 0/6% (w/v)

methyl ethyl ketone (MEK; also called 2-butanone) at 0, 2.5%, 3%. 3.5% and 4% (w/v) 2-butanol at 0, 0.8%, 1.2%. 1.4% and 1.6% (w/v)

isobutanol at 0, 0.8%, 1.2%. 1.4% and 1.6% (w/v)

The growth of each culture was followed for approximately 18 hours. Triplicate samples were averaged, and expressed as the percent growth relative to the no chemical control for each strain. The data given in Table 8 is represented as percent growth improvement of the spoT mutant relative to wild type, which is the spoT mutant percent growth minus the wild type percent growth for each challenge. The spoT mutant strain showed tolerance to other butanols and to MEK.

TABLE 8

Growth of spoT mutant in different chemicals.

| | % improved spoT growth over wt |
|---|---|
| MEK conc | |
| 2.50% | 0 |
| 3% | 3.1 |
| 3.50% | 4.3 |
| 4% | 33.5 |
| 2-BuOH conc | |
| 0.80% | 7.2 |
| 1.20% | 0 |
| 1.40% | 0 |
| 1.60% | 0 |
| IsoBuOH conc | |
| 0.80% | 13.5 |
| 1.20% | 12.1 |
| 1.40% | 11.4 |
| 1.60% | 10.7 |
| 1-BuOH conc | |
| 0.2% | 11.4 |
| 0.3% | 13.8 |
| 0.4% | 16.5 |
| 0.6% | 9.7 |

Example 6

Producing Isobutanol Using Strain with Reduced SpoT Expression

*E. coli* strains engineered to express an isobutanol biosynthetic pathway are described in commonly owned and co-pending US patent application publication #US20070092957A1, Examples 9-15, which are herein incorporated by reference. Strain BL21 (DE) 1.5GI yqhD/pTrc99a::budB-ilvC-ilvD-kivD was derived from BL21 (DE3) (Invitrogen) and was engineered to contain an operon expressed from the trc promoter that includes the *Klebsiella pneumoniae* budB coding region for acetolactate synthase, the *E. coli* ilvC coding region for acetohydroxy acid reductoisomerase, the *E. coli* ilvD coding region for acetohydroxy acid dehydratase and the *Lactococcus lactis* kivD coding region for branched chain α-keto acid decarboxylase. In addition, in this strain the native promoter of the yqhD gene (encoding 1,3-propanediol dehydrogenase) was replaced with the 1.5GI promoter (WO 2003/089621). The same promoter replacement was made in *E. coli* strain MG1655 to create MG1655 1.5GI-yqhD::Cm, and the same plasmid was introduced resulting in strain MG655 1.5/GI yqhD/pTrc99A::budB-ilvC-ilvD-kivD.

These isobutanol pathway containing strains are engineered for butanol tolerance by introducing a modification in either the spoT gene or the rpoZ gene. The strains are transduced to Kanamycin resistance with 2 distinct phage P1 lysates (either $P1_{vir}$ or P1clr100Cam can be used). To make one lysate, for inactivating the spoT gene, phage are grown on one of the spoT::Tn strains isolated by transposon mutagenesis of strain EC100 described above in Example 2 (DPD1850 or DPD1848). For the second lysate, phage are grown on strain JW3624 of the Keio collection to pick up DNA for introducing the other mutation to be introduced: the rpoZ::kan allele that is polar on spoT. Kanamycin resistance is selected on agar solidified LB medium using 50 μg/ml of the antibiotic. The resultant transductants have reduced (rpoZ::kan) or no (spoT::Tn) SpoT activity.

Separately, an isobutanol biosynthetic pathway and butanol tolerance are engineered in the same strain by adding the isobutanol pathway to spoT or rpoZ modified strains. EC100 spoT::Tn (DPD1850 or DPD1848) and BW25113 rpoZ::kan (JW3624), along with EC100 and BW25113 controls, are transduced to chloramphenicol resistance with a phage P1 lysate of *E. coli* MG1655 1.5GI yqhD::Cm to replace the yqhD promoter with the 1.5GI promoter. The resulting strains are transformed with pTrc99A::budB-ilvC-ilvD-kivD yielding pTrc99A::budB-ilvC-ilvD-kivD/EC100 1.5GI yqhD::Cm, pTrc99A::budB-ilvC-ilvD-kivD/EC100 spoT::Tn 1.5GI yqhD::Cm, pTrc99A::budB-ilvC-ilvD-kivD/BW25113 1.5GI yqhD::Cm and pTrc99A::budB-ilvC-ilvD-kivD/BW25113 rpoZ::kan 1.5GI yqhD::Cm. These strains in the MG1655, EC100 and BW25113 backgrounds are analyzed for butanol production.

The cells from cultures or each strain are used to inoculate shake flasks (approximately 175 mL total volume) containing 50 or 170 mL of TM3a/glucose medium (with appropriate antibiotics) to represent high and low oxygen conditions, respectively. TM3a/glucose medium contains (per liter): glucose (10 g), $KH_2PO_4$ (13.6 g), citric acid monohydrate (2.0 g), $(NH_4)_2SO_4$ (3.0 g), $MgSO_4.7H_2O$ (2.0 g), $CaCl_2.2H_2O$ (0.2 g), ferric ammonium citrate (0.33 g), thiamine HCl (1.0 mg), yeast extract (0.50 g), and 10 mL of trace elements solution. The pH was adjusted to 6.8 with $NH_4OH$. The trace elements solution contains: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L).

The flasks are inoculated at a starting $OD_{600}$ of ≦0.01 units and incubated at 34° C. with shaking at 300 rpm. The flasks containing 50 mL of medium are closed with 0.2 μm filter caps; the flasks containing 150 mL of medium are closed with sealed caps. IPTG is added to a final concentration of 0.04 mM when the cells reach an $OD_{600}$ of ≧0.4 units. Approximately 18 h after induction, an aliquot of the broth is analyzed by HPLC (Shodex Sugar SH1011 column (Showa Denko America, Inc. NY) with refractive index (RI) detection) and GC (Varian CP-WAX 58(FFAP) CB, 0.25 mm×0.2 μm×25 m (Varian, Inc., Palo Alto, Calif.) with flame ionization detection (FID)) for isobutanol content, as described in the General Methods section. No isobutanol is detected in control strains. Molar selectivities and titers of isobutanol produced by strains carrying pTrc99A::budB-ilvC-ilvD-kivD are obtained. Significantly higher titers of isobutanol are obtained in the spoT and rpoZ cultures than in the parental strains.

Example 7

Producing 2-Butanol Using Strain with Reduced SpoT Expression

The engineering of *E. coli* for expression of a 2-butanol biosynthetic pathway is described in commonly owned and co-pending US Patent Application Publication US20070259410A1, Examples 6 and 7, which are herein incorporated by reference. Construction is described of two plasmids for upper and lower pathway expression. In pBen-budABC, an NPR promoter (*Bacillus amyloliquefaciens* neutral protease promoter) directs expression of *Klebsiella pneu-*

*moniae* budABC coding regions for acetolactate decarboxylase, acetolactate synthase, and butanediol dehydrogenase. In pBen-pdd-sadh an NPR promoter directs expression of *Klebsiella oxytoca* pddABC coding regions for butanediol dehydratase alpha subunit, butanediol dehydratase beta subunit, and butanediol dehydratase gamma subunit, and the *Rhodococcus ruber* sadh coding region for butanol dehydrogenase. Plasmid p2BOH is described containing both operons, and strain NM522/p2BOH containing this plasmid for 2-butanol pathway expression is described.

The NM522/p2BOH strain is engineered for butanol tolerance by introducing a modification in either the spoT gene or the rpoZ gene to lower or eliminated spoT expression as described next. The strain is transduced to kanamycin resistance with 2 distinct P1 lysates (either $P1_{vir}$ or P1clr100Cam can be used). To make one lysate, for inactivating the spoT gene, phage are grown on one of the spoT::Tn strains isolated by transposon mutagenesis of strain EC100 described above in Example 2 (DPD1850 or DPD1848). For the second lysate, phage are grown on strain JW3624 of the Keio collection to pick up DNA for introducing the other mutation to be introduced: the rpoZ::kan allele that is polar on spoT. Kanamycin resistance is selected on agar solidified LB medium using 50 μg/ml of the antibiotic. The resultant transductants have reduced (rpoZ::kan) or no (spoT::Tn) SpoT activity and are called NM522 rpoZ::Kan/p2BOH and NM522 spoT::Tn/p2BOH.

*E. coli* NM522/p2BOH, NM522 rpoZ::Kan/p2BOH and NM522 spoT::Tn/p2BOH are inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 μM; $CoCl_2$, 253 μM; and $Na_2MoO_4$, 242 μM. After 18 h, 2-butanol is detected by HPLC or GC analysis using methods that are well known in the art, for example, as described in the General Methods section above. Higher titers are obtained from the rpoZ and spoT derivatives.

Example 8

Producing 1-Butanol Using Strain with Reduced SpoT Expression

*E. coli* strains engineered to express a 1-butanol biosynthetic pathway are described in commonly owned and co-pending US Patent Application Publication US20080182308A1, Example 13, which is herein incorporated by reference. Two plasmids were constructed that carry genes encoding the 1-butanol pathway. Plasmid pBHR T7-ald contains a gene for expression of butyraldehyde dehydrogenase (ald). Plasmid pTrc99a-E-C-H-T contains a four gene operon comprising the upper pathway, for expression of acetyl-CoA acetyltransferase (thlA), 3-hydroxybutyryl-CoA dehydrogenase (hbd), crotonase (crt), and butyryl-CoA dehydrogenase (trans-2-enoyl-CoA reductase, EgTER(opt)) (EgTER(opt), crt, hbd and thlA). In addition, in this strain the native promoter of the yqhD gene (encoding 1,3-propanediol dehydrogenase) was replaced with the 1.5GI promoter (WO 2003/089621).

All genes of this 1-butanol pathway are combined with reduced (p)ppGpp accumulation in strains with reduced SpoT activity for increased butanol tolerance as follows. EC100 spoT::Tn (DPD1850 or DPD1848) and BW25113 rpoZ::kan (JW3624), along with EC100 and BW25113 controls, are transduced to chloramphenicol resistance with a phage P1 lysate of *E. coli* MG1655 1.5GI yqhD::Cm to replace the yqhD promoter with the 1.5GI promoter. The resulting strains are transformed with pBHR T7-ald and pTrc99a-E-C-H-T producing engineered strains with the 1-butanol biosynthetic pathway.

Strains containing the 1-butanol pathway and butanol tolerance are also constructed by introducing a modified spoT gene or rpoZ gene into 1-butanol pathway containing strains. Construction of *E. coli* strain MG1655 (DE3) 1.5GI-yqhD::Cm/pTrc99a-E-C-H-T/pBHR T7-ald was also described in US Patent Application Publication US20080182308A1 Example 13. This strain was then modified to introduce rpoZ and spoT alleles by generalized transduction with phage P1. The transformants were transduced to Kanamycin resistance with 2 distinct phage P1 lysates (either P1 vir or P1clr100Cam can be used). To make one lysate, for inactivating the spoT gene, phage are grown on one of the spoT::Tn strains isolated by transposon mutagenesis of strain EC100 described above in Example 2 (DPD1850 or DPD1848). For the second lysate, phage are grown on strain JW3624 of the Keio collection to pickup DNA for introducing the other mutation to be introduced: the rpoZ::kan allele that is polar on spoT. Kanamycin resistance is selected on agar solidified LB medium using 50 μg/ml of the antibiotic. The resultant transductants have reduced (rpoZ::kan) or no (spoT::Tn) SpoT activity in the MG1655 background.

The transductants from the MG1655 background and the transformants from the EC100 and BW25113 backgrounds are used to inoculate shake flasks (approximately 175 mL total volume) containing 15, 50 and 150 mL of TM3a/glucose medium (with appropriate antibiotics) to represent high, medium and low oxygen conditions, respectively. TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine HCl, 0.50 g yeast extract, and 10 mL trace elements solution, adjusted to pH 6.8 with $NH_4OH$. The solution of trace elements contains: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks are inoculated at a starting $OD_{600}$ of ≦0.01 units and incubated at 34° C. with shaking at 300 rpm. The flasks containing 15 and 50 mL of medium are capped with vented caps; the flasks containing 150 mL, are capped with non-vented caps to minimize air exchange. IPTG is added to a final concentration of 0.04 mM; the $OD_{600}$ of the flasks at the time of addition is ≧0.4 units. Approximately 15 h after induction, an aliquot of the broth is analyzed by HPLC (Shodex Sugar SH1011 column) with refractive index (RI) detection and GC (Varian CP-WAX 58(FFAP) CB column, 25 m×0.25 mm id×0.2 μm film thickness) with flame ionization detection (FID) for 1-butanol content, as described in the General Methods section. Titers of 1-butanol are found to be higher in strains harboring either the rpoZ::kan or spoT::Tn alleles.

Example 9

Effect of relA Mutation in Rich Medium

Figure 10A:
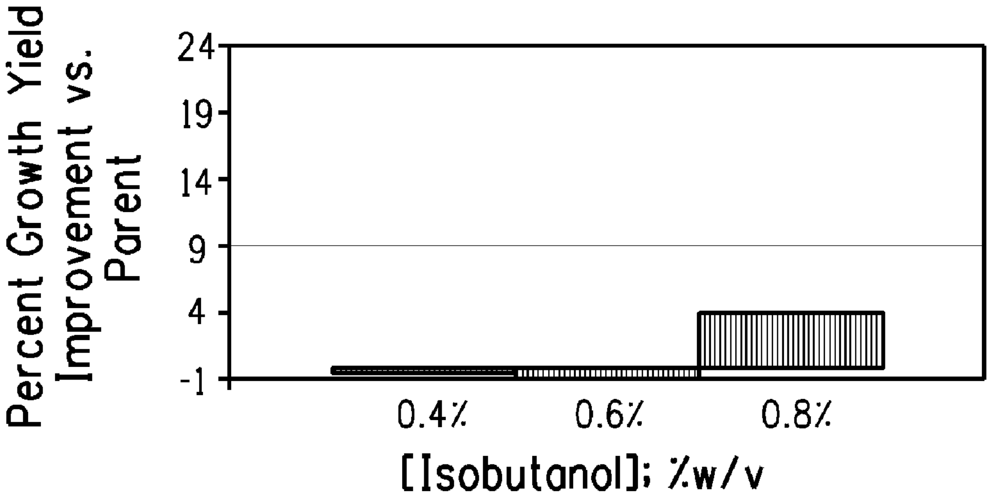
Figure 10B:
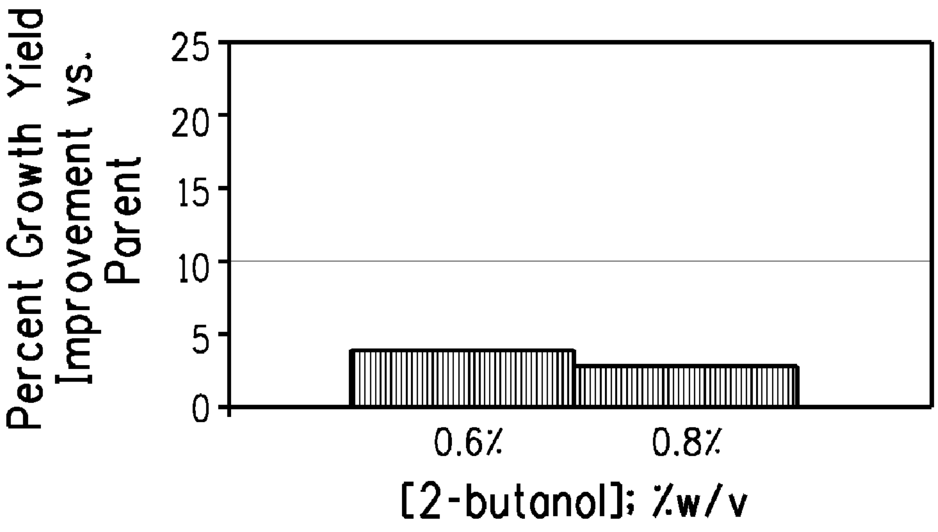

A strain of *E. coli* K12 having a kanamycin marker insertion in the relA coding region (relA::kan) is available in the Keio knockout collection that is described in Example 4. Overnight cultures of the relA::kan line (strain JW2755) and the parent BW25113 were inoculated with fresh colonies and grown in LB at 37° C. with shaking. The next day the cultures were diluted 1:100 into 100 ml of fresh LB in a 1 liter flask and grown for approximately 2 hours. The culture was split into 20 ml aliquots in 125 ml plastic screw top flasks. One culture remained unaltered serving as the no add control, and various concentrations of either 2-butanol or isobutanol were added to the remaining flasks. Absorbance (OD600) was monitored over time. Using a 3 hr time point for growth in isobutanol and a 2.5 hr time point for growth in 2-butanol, fractional growth yields were determined and percent improvement was calculated by subtracting the mutant fractional growth from that of the wild type and multiplying by 100. Averages of replicate experiments performed on different days are shown in FIG. 10. A small improvement relative to the parent was observed in 0.8% isobutanol (FIG. 10A), and in 0.6% and 0.8% 2-butanol (FIG. 10B).

Example 10

Effect of relA Mutation Under Conditions of (p)ppGpp Induction

In the rich medium conditions used in Example 9 the tRNA pools would be fully charged and so little (p)ppGpp would be produced by RelA, Under conditions where an aminoacyl-tRNA species is low, RelA production of (p)ppGpp would be high. Thus effects of a relA mutation in limited aminoacyl-tRNA species conditions better exemplifies the impact on butanol tolerance of RelA-dependent (p)ppGpp synthesis. Seryl-tRNA can be reduced by including serine hydroxymate, a competitive inhibitor of serine for seryl-tRNA synthetase (Belrhali et al. (1994) Science 263:1432-1436).

Cultures (50 ml) of the parental strain (BW25113) and the relA::kan derivative strain JW2755 are grown in L broth supplemented with L-serine at 37° C. to mid-log phase. Samples (5 ml) are untreated or treated for 30 minutes with serine hydroxymate at the sub-inhibitory culture concentration of 2 mM (as described in Shand et al. (1989) J. Bacteriol. 171:737-743). Butanols are then added to a pair of strain JW2755 and BW25113 cultures as follows: isobutanol at 0.4%, 0.6% and 0.8%; 2-butanol at 0.6% and 0.8%. Growth of the cultures is assayed using the Bioscreen device as described in Example 3. Growth of the serine-hydroxymate challenged relA mutant is significantly less impeded by butanols at butanol concentrations where the serine hydroxymate treated parental strain is inhibited.

Example 11

Construction of Insertional Mutants in *Lactobacillus* spoT

An internal fragment amplified from the *L. plantarum* (ATCC #BAA-793; also called NCIMB 8826 and WCFS1) spoT gene (SEQ ID NO:43) was chosen to disrupt both the ppGpp synthase and hydrolase domains. The 601 bp internal fragment, from nucleotide position 235 to 835, counting from the A of the initiator ATG, was chosen as it is predicted to disrupt the function of both domains, removing the first 234 bp of the hydrolase domain, and the last 191 bp of the synthesis domain as shown in FIG. 11, A.

The internal fragment was PCR amplified using the primers #5807 and #5808 (SEQ ID NOs:65 and 66):

```
#5807: 5'-GTTGTGGAAGATACTGGTGTTACTT-3'

#5808: 5'-AGTCCTTGATTGAATCCACG-3'
```

These primers bound a portion of the spoT gene at nucleotide positions 235-259 and 816-835, respectively.

*Lactobacillus plantarum* BAA-793 genomic DNA was used as the template in a PCR reaction using HI-FI Taq polymerase. An annealing temperature of 60° C. and an elongation time of 1 minute were used for 30 rounds of amplification. The amplified PCR product was inserted into the TOPO cloning vector pCR2.1-TOPO as per the manufacturer's (Invitrogen) instructions. The insertion of the PCR product was confirmed by restriction digestion. This construct was designated pTOPO-relAint.

A plasmid pMPE3 was constructed by amplifying a 2.45 kb fragment of the *Bacillus* shuttle vector pMK4 (purchased from *Bacillus* Genetics Stock center) using the primers pUCCMNotIR (AAAAAAGCGGCCGCTCTTTATTCTTCAACTAAAGCACC; SEQ ID NO:67) and pUCCMNotIF (AAAAAAGCGGCCGCAATGTATTTAGAAAAATAAACAAATAGG; SEQ ID NO:68). The amplified fragment contained the multiple cloning site, lacZ-alpha, pMB1 origin of replication and chloramphenicol resistance gene from pMK4. The amplified fragment was digested with NotI and then circularized by ligation, generating pMPE3 which can replicate in *E. coli* but not in *Lactobacillus plantarum.*

The spot fragment was excised from the pTOPO-relAint plasmid using BamHI and PstI sites that flank the inserted PCR product. The resulting ~650 bp band was gel purified and ligated into similarly digested plasmid pMPE3. The resulting plasmid was again confirmed by restriction digestion and designated pMPE69.

pMPE69 was transformed into *L. plantarum* PNO512 (ATCC #PTA-7727), using 5 μg of DNA and 60 μl of competent cells prepared using standard procedures. Aliquots of the transformation were plated on MRS with 10 ug/ml chloramphenicol and incubated at 30° C. overnight. 10 putative single crossover integrants were transferred into MRS with 10 ug/ml of chloramphenicol and again grown up overnight at 30° C. Aliquots of the 10 integrant cultures were used for Instagene [Bio-Rad Laboratories, Hercules, Calif.] preparations of genomic DNA. PCR confirmation of pMPE69 insertion into the spoT gene was performed using primers #5785 and #5798 (SEQ ID NOs:69 and 70):

```
#5785: 5'-TGTAATTTTGCGGTCGGTGG-3'

#5798: 5'-GCGGATAACAATTTCACACAGG-3'
```

Figure 3:
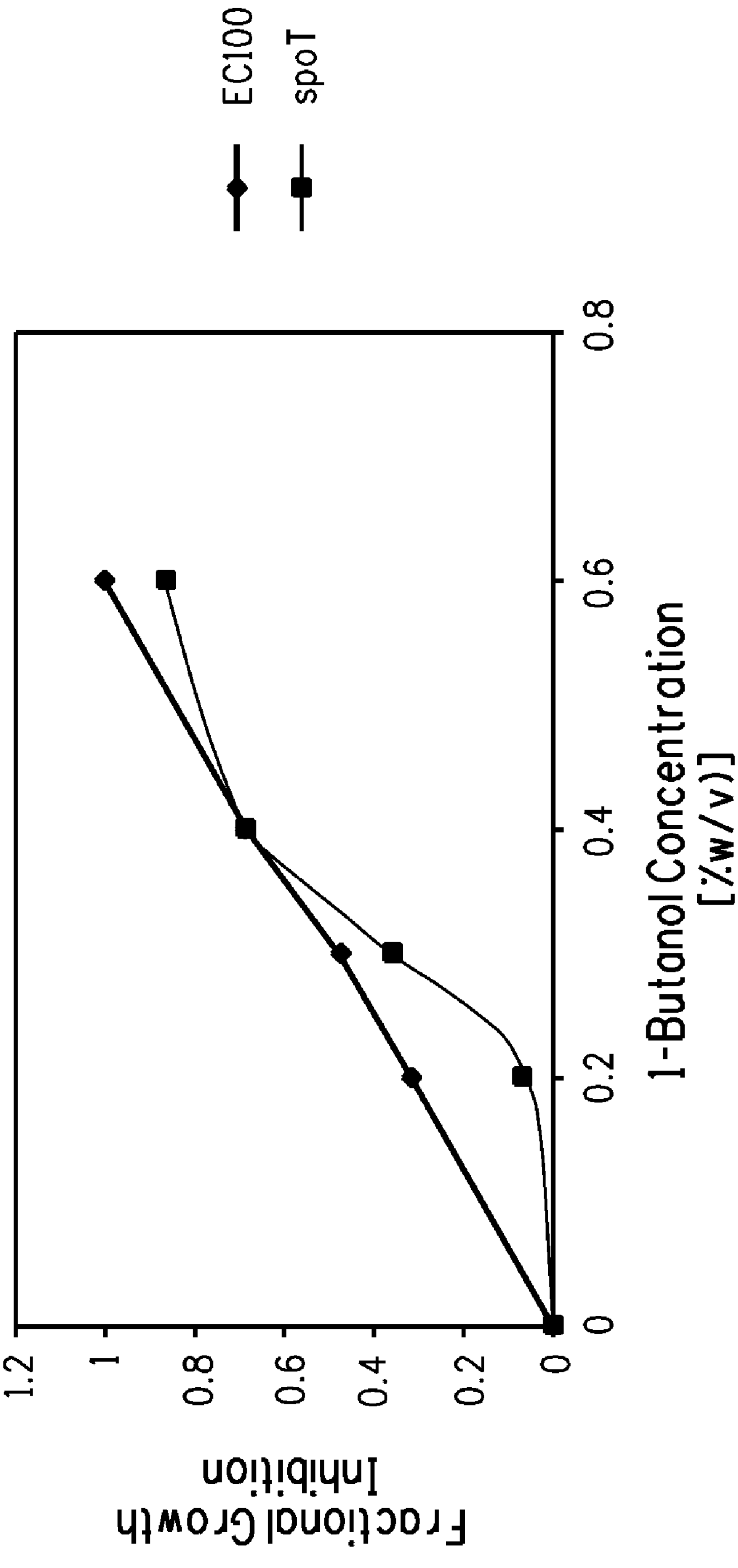
FIG. 3 shows a graph of percent growth inhibition by different concentrations of 1-butanol in the DPD1848 spoT insertion mutant and CE100 parental strains.

Primer #5785 binds upstream of the spoT gene, while #5798 binds within the pMPE3 backbone (see FIG. 3). The PCR reactions were predicted to produce a ~1400 bp product. This product was observed in 8 of the 10 putative integrants. The first two integrants were saved and designated MS0280 and MS0281. The structure of the chromosomal spoT locus after insertion of plasmid pMPE69, and positions of the primers used for confirmation, are shown in FIG. 11, B

Example 12

Increased Tolerance of spoT Mutants to Low Concentrations of Isobutanol

Strains MS0280 and MS0281, and *Lactobacillus plantarum* PN0512 (ATCC #PTA-7727), were tested for tolerance to isobutanol. The strains were streaked on semi-synthetic medium plates, pH 6 (medium composition: 10 mM ammonium sulfate, 5 mM potassium phosphate buffer, pH 6.0, 50 mM MES, pH 6.0, 2 mM $MgCl_2$, 0.7 mM $CaCl_2$, 50 μM $MnCl_2$, 1 μM $FeCl_3$, 1 μM $ZnCl_2$, 1.72 μM $CuCl_2$, 2.53 μM $CoCl_2$, 2.42 μM $Na_2MoO_4$, 2 μM thiamine hydrochloride, 10 mM glucose, 0.01% casamino acids, 0.2% yeast extract and 1.5% agar), from frozen stock cultures. The plates that the two mutants (MS0280 and MS0281) were streaked onto also included chloramphenicol at 10 μg/ml. The plates were incubated overnight at 30° C. under anaerobic conditions. The next day, overnight cultures were started by inoculating Lacto Synthetic Medium (LSM; medium composition: 10 mM ammonium sulfate, 5 mM potassium phosphate buffer, pH 6.0, 50 mM MES, pH 6.0, 2 mM $MgCl_2$, 0.7 mM $CaCl_2$, 50 μM $MnCl_2$, 1 μM $FeCl_3$, 1 μM $ZnCl_2$, 1.72 μM $CuCl_2$, 2.53 μM $CoCl_2$, 2.42 μM $Na_2MoO_4$, 2 μM thiamine hydrochloride, 10 mM glucose, 0.01% casamino acids and 0.2% yeast extract) with a diluted (1:6) culture with an initial OD600 of 0.02. These overnight cultures were allowed to incubate at 30° C. in a gently shaking water bath. The next morning, the overnight cultures were diluted to have an initial OD600 of 0.1, in a volume of 220 ml of LSM. These starter cultures were allowed to incubate at 30° C. in a gently shaking water bath for 1.25 hours, to ensure the cultures were not in a lag phase. At this time, 20 ml aliquots were dispensed to duplicate flasks containing different volumes of isobutanol, to give final concentrations of 0, 0.5, 1, 1.5 and 2%. The growth of each flask was followed by taking OD600 readings every hour. The natural log of the OD600 values were plotted on a linear scale vs time. The slopes of the linear portions from the above plots provide the growth rates (μ/hour) which are given in Table 9.

TABLE 9

Growth rates of *L. plantarum* spoT mutants and parental control in different concentrations of isobutanol.

| | Isobutanol Concentration (%) | | | | |
|---|---|---|---|---|---|
| | 0 | 0.5 | 1 | 1.5 | 2 |
| PN0512 | 0.462 | 0.424 | 0.385 | 0.364 | 0.349 |
| MS0280 | 0.475 | 0.464 | 0.426 | 0.382 | 0.359 |
| MS0281 | 0.487 | 0.467 | 0.426 | 0.397 | 0.359 |

Growth rate inhibition calculations made by comparing the growth rates in the presence and absence of isobutanol show that the mutants are inhibited only by 5% at 0.5% isobutanol concentration compared to the parent which is inhibited 9%.

TABLE 5

| | |
|---|---|
| HMMER2.0 [2.3.2] | Program name and version |
| NAME RelA__SpoT | Name of input sequence alighment file |
| DESC Region found in RelA/SpoT proteins | Domain description |
| LENG 131 | Length of alignment |
| ALPH Amino | Type of residues |
| MAP yes | Map of the match states to the columns of the alignment |
| COM hmmbuild -F --wme HMM__ls.ann SEED.ann | Commands used to generate the file: this one means that hmmbuild (default parameters) was applied to the alignment file |
| COM hmmcalibrate --seed 0 HMM__ls.ann | Commands used to generate the file: this one means that hmmcalibrate (default parametrs) was applied to the hmm profile |
| NSEQ 105 | Number of sequences in the alignment file |
| DATE Sun Apr 29 16:27:35 2007 | When file was generated |
| XT -8455 -4 -1000 -1000 -8455 -4 -8455 -4 | |
| NULT -4 -8455 | The transition probability distribution for the null model (single G state). |
| NULE 595 -1558 85 338 -294 453 -1158 197 249 902 -1085 -142 -21 -313 45 531 201 384 -1998 -644 | The symbol emission probability distribution for the null model (G state) |
| EVD -69.960602 0.225039 | The extreme value distribution parameters μ and lambda respectively |
| The highest probability is highlighted for each position | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m→m | m→i | m→d | i→m | i→i | d→m | d→d | b→m | m→e | | | | | | | | | | | | |
| | -36 | * | -5356 | | | | | | | | | | | | | | | | | | |
| 1(S) | -269 | -3394 | -3033 | -1314 | -3476 | 1305 | 1299 | 179 | -2367 | -3304 | -21 | -2699 | -3943 | -2287 | -134 | 2447 | 587 | -2807 | -600 | -3142 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | -36 | * | | | | | | | | | | | | |
| | | | | | | | | | | | | | | | | | | | | | |
| 2(R) | -8636 | -7266 | -8174 | -8366 | -8675 | -7221 | -7550 | -9684 | -7568 | -9015 | -8918 | -8342 | -7640 | -8024 | 4273 | -9078 | -8724 | -9380 | -7386 | -8557 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 3(I) | 346 | -2709 | -5178 | -1171 | -2663 | -4419 | -3247 | 2104 | -4149 | 475 | -1911 | -2635 | 754 | -2873 | -3589 | -3342 | 180 | 1910 | -3166 | 782 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 4(K) | 379 | -5857 | -6629 | -4816 | -6997 | -5784 | -3655 | -6203 | 3759 | -5791 | -5155 | -4564 | -5740 | -3239 | 546 | -5247 | -5012 | -5975 | -5575 | -5575 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 5(S) | -2636 | -4111 | 545 | 897 | -4431 | -1109 | 2025 | -4183 | 95 | -4127 | -3200 | 1523 | -1245 | -1807 | -966 | 2270 | -291 | -3733 | -4294 | -3610 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 6(P) | 24 | -2715 | -5120 | -2766 | 701 | -4410 | -1823 | 1032 | -4108 | 586 | -470 | -1629 | 2144 | 1120 | 218 | -2515 | -2814 | 607 | 1680 | -1014 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 7(Y) | -523 | -3971 | 1548 | -166 | -774 | 99 | -921 | -2261 | -7 | -3964 | 807 | -1289 | -3233 | -1852 | -1705 | 475 | -824 | -54 | -29 | 2960 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 8(S) | -2932 | -4786 | -3950 | -3310 | -5645 | -1484 | 2163 | -5264 | 832 | -5129 | -4299 | -3445 | -4731 | -2796 | -515 | 3051 | 689 | -4806 | -5167 | -4744 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 9(L) | -836 | -3136 | -5739 | 568 | -3139 | -5005 | -3930 | 1925 | -4759 | 2017 | 453 | -4650 | -5023 | -4394 | -4581 | -4110 | 748 | 760 | -3763 | -3421 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 10(H) | -743 | -2709 | -5175 | -4542 | -975 | -3798 | 2757 | 1631 | 1480 | 567 | 1236 | -4049 | -4469 | -3336 | -1344 | -3501 | -239 | -1729 | 1427 | 1587 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 11(E) | 812 | -2296 | 359 | 2322 | -4413 | -120 | -2251 | -4164 | 1065 | -2680 | -1059 | 753 | -3686 | -234 | 851 | -1728 | -2361 | -3714 | -4275 | -1555 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 12(K) | -6000 | -6172 | -6992 | -6261 | -7382 | -6247 | -5316 | -6761 | 3952 | -6949 | -6478 | -5972 | -6585 | -5040 | -4055 | -6134 | -6056 | 28 | -6575 | -6738 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -152 | -10485 | -3328 | -894 | -1115 | -701 | -1378 | * | * | | | | | | | | | | | | |
| | | | | | | | | | | | | | | | | | | | | | |
| 13(M) | 137 | 813 | -5304 | -4679 | -2722 | -4525 | -3418 | 1984 | -4284 | 1963 | 2332 | -4173 | -4564 | -3911 | -4091 | -6 | -2738 | -53 | -3271 | -2929 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 14(R) | -239 | -3927 | -2354 | 695 | -4232 | -3472 | -543 | 1665 | 63 | -1374 | -3020 | 56 | -3565 | 931 | 2320 | -532 | -715 | -1005 | -4120 | -1420 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 15(R) | -2550 | -4002 | -1611 | -873 | -4325 | -3228 | -2166 | -3858 | 1929 | -2335 | -3093 | -1941 | -3612 | -592 | 3410 | -1607 | -1881 | -1789 | -4177 | -796 | 15 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 16(K) | -2592 | -4054 | 441 | -1541 | -2782 | -1228 | 1146 | -4128 | 2757 | -4065 | -3145 | 345 | -3645 | 62 | 2325 | -2471 | -2528 | -3682 | -4223 | -2987 | 16 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -10 | -10334 | -7388 | -894 | -1115 | -2589 | -262 | * | * | | | | | | | | | | | | |
| | | | | | | | | | | | | | | | | | | | | | |
| 17(G) | -439 | -3947 | -910 | -411 | -4264 | 2055 | 412 | -1602 | -540 | -932 | -3037 | 1223 | 1400 | 456 | -2125 | -1475 | 285 | -1173 | -4132 | -1559 | 17 |
| - | -148 | -503 | 230 | 43 | -384 | 397 | 103 | -624 | 210 | -463 | -723 | 279 | 395 | 42 | 93 | 356 | 120 | -372 | -297 | -225 | |
| - | -2030 | -764 | -2589 | -9 | -7320 | -2351 | -315 | * | * | | | | | | | | | | | | |
| | | | | | | | | | | | | | | | | | | | | | |
| 18(R) | -2270 | -3720 | 1435 | 161 | -4031 | -3248 | -1632 | -709 | 1079 | 1110 | -2811 | -1818 | 486 | -137 | 1515 | -1074 | -1407 | -113 | -3909 | -3232 | 19 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -933 | -10074 | -1073 | -894 | -1115 | -2322 | -322 | * | * | | | | | | | | | | | | |
| | | | | | | | | | | | | | | | | | | | | | |
| 19(Y) | -1704 | -2350 | -2063 | 357 | -2425 | 330 | -1574 | 766 | -1385 | 638 | -1511 | 847 | -1019 | 176 | 354 | -1814 | -1643 | -225 | -2702 | 2577 | 20 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -59 | -9265 | -4693 | -894 | -1115 | -4748 | -55 | * | * | | | | | | | | | | | | |
| | | | | | | | | | | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 20(A) | 1291 | -3051 | -1441 | -892 | -3368 | -1078 | 1251 | -3115 | 1274 | -1686 | -2141 | -1202 | 1189 | 807 | 949 | -657 | 1066 | -2671 | -3236 | -2557 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9209 | -10252 | -894 | -1115 | -4786 | -53 | * | * | | | | | | | | | | | | |
| | | | | | | | | | | | | | | | | | | | | | |
| 21(E) | 1183 | -1955 | -1696 | 2066 | -496 | -3023 | -1792 | -1306 | -1882 | 442 | 1796 | -2114 | -2398 | -1737 | -929 | -1208 | 532 | -69 | -2366 | -1289 | 22 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -142 | -9209 | -3439 | -894 | -1115 | -4786 | -53 | * | * | | | | | | | | | | | | |
| | | | | | | | | | | | | | | | | | | | | | |
| 22(K) | -1206 | -2955 | 636 | 1415 | -3275 | -2459 | -187 | -1129 | 2085 | 592 | -2044 | 110 | -2552 | 332 | 491 | -1366 | -1424 | -2047 | -3139 | -2457 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -243 | -9071 | -2706 | -894 | -1115 | -4871 | -50 | * | * | | | | | | | | | | | | |
| | | | | | | | | | | | | | | | | | | | | | |
| 23(Y) | -190 | -2753 | -1190 | 199 | -3056 | -2310 | -976 | -2792 | -566 | -2763 | -1852 | 2167 | 1110 | -524 | 188 | 740 | -377 | -2366 | -2952 | 2331 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -220 | -8833 | -2844 | -894 | -1115 | -317 | -2340 | * | * | | | | | | | | | | | | |
| | | | | | | | | | | | | | | | | | | | | | |
| 24(Y) | 589 | -3857 | -323 | 1165 | -4178 | -774 | 528 | -82 | 564 | -1707 | -2947 | 655 | 624 | 1450 | -1620 | -304 | -2324 | -2385 | -4041 | 1578 | 25 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -25 | -10213 | -5947 | -894 | -1115 | -3206 | -165 | * | * | | | | | | | | | | | | |
| | | | | | | | | | | | | | | | | | | | | | |
| 25(L) | -2433 | -2599 | 287 | -592 | 1393 | -3986 | -2798 | 632 | -992 | 1726 | -491 | -3290 | 1216 | -2592 | -1706 | -963 | -2509 | -1387 | -3035 | 1676 | 26 |
| - | -160 | -511 | 238 | 56 | -357 | 388 | 95 | -626 | 218 | -467 | -713 | 280 | 390 | 34 | 89 | 357 | 110 | -373 | -305 | -198 | |
| - | -570 | -1618 | -11232 | -2833 | -218 | -644 | -1475 | * | * | | | | | | | | | | | | |
| | | | | | | | | | | | | | | | | | | | | | |
| 26(E) | -1873 | -4007 | 501 | 1640 | -4329 | -1258 | -627 | -4079 | 1047 | -3289 | -3097 | 1574 | -3601 | -1555 | 1328 | 578 | 837 | -3630 | -4191 | -406 | 37 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10387 | -11429 | -894 | -1115 | -214 | -2856 | * | * | | | | | | | | | | | | |
| | | | | | | | | | | | | | | | | | | | | | |
| 27(E) | -2620 | -4093 | 1181 | 2198 | -4414 | -2323 | 35 | -832 | 14 | -4109 | -3182 | 1504 | -3686 | -362 | 1046 | -370 | 824 | -3715 | -4276 | -2893 | 38 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -152 | -10485 | -3328 | -894 | -1115 | -701 | -1378 | * | * | | | | | | | | | | | | |
| | | | | | | | | | | | | | | | | | | | | | |
| 28(I) | -4696 | -4224 | -7270 | -6828 | -3963 | 34 | -6270 | 2763 | -6665 | 1361 | 2414 | -6604 | -6610 | -6204 | -6563 | -6223 | -4653 | 1300 | -5515 | -5324 | 39 |
| - | -149 | -500 | 233 | 43 | -381 | 399 | 106 | -626 | 210 | -466 | -720 | 280 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 29(H) | 11 | -3932 | -2351 | -1019 | -808 | -3470 | 2074 | -3981 | -380 | -1097 | -1102 | 464 | -3563 | 1970 | -775 | 724 | 1837 | -3547 | -4124 | 1088 | 40 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 30(D) | -8244 | -7150 | 4231 | -7134 | -8528 | -6919 | -7294 | -9565 | -8093 | -8923 | -8858 | -7383 | -7382 | -7716 | -7899 | -8437 | -8388 | -9207 | -7288 | -8394 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 31(I) | -1871 | -3171 | -5759 | -5138 | 836 | -5012 | -3897 | 2342 | -4756 | 2340 | 1079 | -4661 | -4994 | -4328 | -4547 | -1960 | -3024 | -515 | -3655 | -3362 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 32(I) | 1206 | -1286 | -5086 | -4450 | 899 | 7 | -1562 | 2311 | -4045 | 495 | -485 | -3935 | -4339 | -3668 | -3090 | -466 | -2682 | 431 | -3026 | 909 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 33(G) | 1730 | -4170 | -6390 | -6633 | -6820 | 3263 | -5895 | -6670 | -6002 | -6872 | -5939 | -5150 | -5219 | -5907 | 507 | -3823 | -4041 | -5382 | -6876 | -6914 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 34(V) | -4715 | 495 | -7356 | -6983 | 48 | -7148 | -6799 | 2376 | -6900 | 1439 | -3040 | -6807 | -6806 | -6588 | -6917 | -6494 | -4688 | 2503 | -5991 | -5708 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 35(R) | -6891 | -6578 | -7555 | -6772 | -6828 | -6642 | -5674 | -7049 | -4555 | -322 | -6244 | -6542 | -6904 | -5501 | 4149 | -7034 | -6798 | -7202 | -6476 | -6615 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 36(I) | -808 | -2626 | -7283 | -6968 | -4807 | -7135 | -7181 | 3148 | -6942 | -2135 | -927 | -6787 | -6871 | -6918 | -7124 | -6513 | -4581 | 2629 | -6565 | -6024 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 37(I) | -2877 | -2705 | 842 | 558 | -2684 | -4440 | -3321 | 2114 | -4135 | 1302 | 724 | -4051 | -4484 | -3782 | -3978 | -3035 | 756 | 1139 | -3212 | -2865 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 38(C) | 463 | 3678 | -5102 | -4467 | -678 | -4306 | 1997 | -2059 | -4063 | 1068 | -1474 | -3953 | -4356 | -3686 | -3864 | -3392 | 779 | 1688 | -3045 | -2703 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 39(Y) | -1716 | -3961 | 1444 | 370 | -4281 | -1092 | -467 | -529 | -137 | 594 | -2157 | 189 | -2473 | 1437 | 1009 | -1138 | -593 | -3582 | -4144 | 1770 | 50 |
| - | -150 | -493 | 237 | 46 | -385 | 397 | 101 | -624 | 207 | -466 | -713 | 272 | 399 | 41 | 94 | 362 | 114 | -366 | -286 | -254 | |
| - | -157 | -3284 | -11376 | -3067 | -183 | -2589 | -262 | * | * | | | | | | | | | | | | |
| | | | | | | | | | | | | | | | | | | | | | |
| 40(F) | -2498 | -3888 | -170 | 776 | 2736 | -236 | 2134 | -3902 | -1588 | 495 | -2986 | -85 | -3577 | -1699 | -941 | -445 | -818 | -3492 | -4092 | 1033 | 62 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 41(K) | -1410 | -3932 | 462 | 917 | -4239 | -3470 | -2130 | 895 | 1496 | 403 | -2749 | -2111 | -532 | 616 | -1216 | 406 | -125 | 345 | -4123 | -3449 | 63 |
| - | -149 | -500 | 234 | 43 | -381 | 398 | 105 | -627 | 210 | -459 | -721 | 275 | 393 | 45 | 95 | 359 | 117 | -370 | -295 | -250 | |
| - | -188 | -3034 | -11376 | -42 | -5124 | -2589 | -262 | * | * | | | | | | | | | | | | |
| | | | | | | | | | | | | | | | | | | | | | |
| 42(D) | 339 | -3961 | 2081 | 1022 | -1210 | 477 | -609 | -1360 | 72 | -2393 | -1457 | -76 | 123 | -844 | -562 | -674 | -120 | -3582 | -4144 | 744 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -158 | -3266 | * | * | | | | | | | | | | | | |
| | | | | | | | | | | | | | | | | | | | | | |
| 43(D) | -101 | -4094 | 2856 | 1495 | -4414 | -3181 | -1173 | 648 | -1257 | -1565 | -3184 | -450 | -3691 | 1371 | -1233 | -2505 | -2017 | -3716 | -4278 | -3596 | 66 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 44(C) | -909 | 4411 | -5205 | 415 | 203 | -4444 | -3315 | 1011 | -4178 | -2572 | -1931 | -4077 | -4493 | 1120 | -3992 | -3528 | -2838 | 1245 | 2022 | -2847 | 67 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 45(Y) | -281 | -4059 | -1394 | 965 | -1715 | -3602 | 150 | -434 | -384 | -4069 | -3152 | 216 | -260 | -63 | -2353 | -2510 | 722 | -3673 | 1528 | 3505 | 68 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 46(H) | 891 | -4091 | -206 | -506 | -4411 | -3440 | 2694 | -2567 | 467 | -641 | -1587 | 1059 | -605 | 216 | 1753 | -1642 | -892 | -362 | -4274 | -3592 | 69 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 47(I) | 1027 | -3968 | -6946 | -6495 | -4336 | -6512 | -5844 | 2389 | -6289 | 916 | -10 | -6163 | -6380 | -6047 | -6253 | -5739 | -525 | 2177 | -5501 | -5107 | 70 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 48(H) | 333 | 1113 | -760 | -2481 | 81 | -4388 | 2787 | -1134 | -2869 | 1860 | -1935 | -3954 | -4441 | -3668 | -809 | -722 | -2809 | 118 | -3187 | 1374 | 71 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 49(G) | 372 | -4099 | 266 | 1262 | -4420 | 1836 | 293 | -4171 | 1088 | -4115 | -3188 | 697 | -3691 | -1797 | 1238 | -793 | -2564 | -2805 | -4282 | -3599 | 72 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -134 | -10485 | -3508 | -894 | -1115 | -701 | -1378 | * | * | | | | | | | | | | | | |
| | | | | | | | | | | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 50(E) | -721 | -2620 | -4816 | 1550 | 1391 | -4263 | -3119 | 1195 | -177 | 1133 | 68 | -3815 | -4316 | -1938 | -2286 | -522 | -1502 | 258 | -3073 | 934 | 73 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10353 | -11395 | -894 | -1115 | -2459 | -290 | * | * | | | | | | | | | | | | |
| | | | | | | | | | | | | | | | | | | | | | |
| 51(I) | -4963 | -4419 | -7610 | -7245 | -4166 | -7488 | -7164 | 2857 | -7197 | 1545 | -951 | -7156 | -6997 | -6719 | -7162 | -6890 | -4927 | 2143 | -6022 | -5889 | 74 |
| - | -152 | -503 | 238 | 40 | -384 | 395 | 102 | -617 | 211 | -462 | -724 | 278 | 390 | 42 | 99 | 356 | 119 | -369 | -249 | -253 | |
| - | -5517 | -3374 | -182 | -2761 | -230 | -883 | -1127 | * | * | | | | | | | | | | | | |
| | | | | | | | | | | | | | | | | | | | | | |
| 52(E) | -3896 | -4207 | -2040 | 3880 | -5087 | -3451 | -3239 | -5508 | -3501 | -5270 | -4921 | -2730 | -3971 | -3131 | -3885 | -3752 | -4038 | -5087 | -4437 | -4574 | 82 |
| - | -149 | -500 | 232 | 42 | -373 | 398 | 105 | -623 | 212 | -467 | -721 | 275 | 393 | 45 | 95 | 359 | 119 | -370 | -295 | -250 | |
| - | -2941 | -205 | -8819 | -35 | -5382 | -5289 | -37 | * | * | | | | | | | | | | | | |
| | | | | | | | | | | | | | | | | | | | | | |
| 53(C) | -883 | 3248 | -2990 | -2490 | -1202 | -2158 | -1617 | -655 | -2161 | 1453 | -406 | -2017 | 1405 | -1885 | -2120 | -1338 | 1496 | -540 | -1720 | -1379 | 84 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -309 | -7777 | -2410 | -894 | -1115 | -2972 | -197 | * | * | | | | | | | | | | | | |
| | | | | | | | | | | | | | | | | | | | | | |
| 54(K) | -2617 | -3525 | -2979 | -1922 | -4255 | -3281 | -1323 | -3669 | 2824 | -3376 | -2649 | -1937 | -3250 | 1605 | 1993 | -2492 | 1260 | -3386 | -3274 | -3067 | 85 |
| - | -156 | -488 | 238 | 40 | -372 | 395 | 120 | -619 | 218 | -474 | -728 | 289 | 386 | 42 | 97 | 351 | 121 | -374 | -277 | -243 | |
| - | -3429 | -143 | -9307 | -2786 | -226 | -5185 | -40 | * | * | | | | | | | | | | | | |
| | | | | | | | | | | | | | | | | | | | | | |
| 55(Y) | -1491 | -2411 | -1434 | 1638 | -2300 | -2442 | -1017 | -2203 | 1581 | 848 | -1536 | -1170 | -2539 | -682 | -778 | -1473 | -1410 | -1966 | -2445 | 2677 | 93 |
| - | -150 | -501 | 240 | 42 | -381 | 398 | 105 | -627 | 210 | -467 | -721 | 277 | 393 | 44 | 95 | 358 | 116 | -365 | -295 | -250 | |
| - | -3429 | -409 | -2697 | -29 | -5653 | -4128 | -85 | * | * | | | | | | | | | | | | |
| | | | | | | | | | | | | | | | | | | | | | |
| 56(G) | -2187 | -3222 | -986 | 2351 | -3705 | 2526 | -1945 | -3430 | -1890 | 353 | -2862 | -1468 | -3052 | -1643 | -2389 | -2104 | -2290 | -3086 | -3841 | -3203 | 95 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -203 | -8207 | -2965 | -894 | -1115 | -2841 | -217 | * | * | | | | | | | | | | | | |
| | | | | | | | | | | | | | | | | | | | | | |
| 57(Y) | 2024 | -1844 | -3412 | -2976 | 1771 | 284 | -2011 | -1674 | -2755 | -1961 | -1326 | -2601 | 1523 | -2465 | -2791 | -2091 | -1787 | -1525 | -1974 | 2354 | 96 |
| - | -152 | -479 | 239 | 40 | -383 | 396 | 125 | -629 | 211 | -469 | -723 | 273 | 395 | 42 | 93 | 359 | 114 | -372 | -297 | -223 | |
| - | -3779 | -111 | -9656 | -998 | -1002 | -27 | -5755 | * | * | | | | | | | | | | | | |
| | | | | | | | | | | | | | | | | | | | | | |
| 58(H) | 578 | -4067 | -2480 | -738 | 1104 | -3600 | 3545 | -4119 | 887 | -1353 | -3159 | 217 | -3693 | 84 | -590 | 660 | -582 | -622 | -4257 | -3582 | 99 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 59(S) | -556 | -4088 | -468 | 837 | -4407 | 461 | -1081 | -1740 | 905 | 154 | -1263 | 339 | -3687 | 398 | -1962 | 1191 | 588 | -1311 | -4272 | 383 | 100 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 60(Q) | 362 | 1839 | -1029 | -2484 | -244 | -4092 | 718 | 1745 | -2940 | 89 | 855 | 132 | -4162 | 1893 | 587 | -1372 | -78 | -1629 | -3446 | -3034 | 101 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 61(W) | -2409 | -4076 | 1458 | 6 | 614 | -3598 | -1974 | -4135 | 176 | -3634 | 1345 | 985 | 1026 | -1544 | -560 | -1556 | -2560 | -3694 | 4075 | 1228 | 102 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 62(K) | -1621 | -4092 | 1605 | 1195 | -4414 | -1552 | -2069 | -4164 | 1733 | -3177 | -3181 | 292 | -141 | 1444 | -183 | -454 | 633 | -3714 | -4276 | -568 | 103 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 63(P) | -2065 | -954 | -4981 | -273 | 1718 | -1238 | 653 | -756 | -4006 | -1387 | -168 | 1092 | 2910 | -3672 | -2681 | -2968 | -854 | -531 | 1505 | -263 | 104 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 64(I) | 311 | -4053 | 864 | 14 | -4356 | -3604 | -825 | 2348 | 694 | -1463 | -307 | -273 | -3696 | -481 | -495 | -844 | -867 | 644 | -4247 | -3575 | 105 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 65(P) | -2751 | 372 | -713 | -3859 | 63 | -4294 | -3120 | 1670 | 455 | -2163 | -2015 | -454 | 2400 | -3019 | -3649 | 353 | -2784 | 1484 | -3261 | -2896 | 106 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 66(H) | -557 | -4087 | 605 | -193 | -4406 | -6 | 2487 | -947 | -871 | 315 | -1927 | 190 | -3687 | 751 | 1403 | 644 | -2559 | -1098 | -4272 | -836 | 107 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 67(D) | -2027 | -4091 | 1587 | 1501 | -4412 | -3593 | -2189 | -1142 | 1262 | -2253 | -3180 | -1100 | -3686 | -1105 | 1509 | 289 | 1031 | -2573 | -4275 | -32 | 108 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 68(F) | -2821 | -1798 | -5155 | 77 | 2369 | -4416 | -3283 | -75 | -4133 | 1275 | -574 | -781 | -4466 | -2448 | -2434 | 918 | -170 | 1306 | -3168 | -2803 | 109 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 69(K) | -3209 | 551 | -141 | -2811 | 1280 | -4232 | -2803 | -3863 | 2906 | -3993 | -3223 | -3007 | -4306 | -2443 | 2119 | -3227 | -153 | -555 | -4300 | -3826 | 110 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 70(D) | -4918 | -6975 | 3727 | 529 | -7088 | -432 | -4115 | -7070 | -360 | -6902 | 33 | 594 | -5267 | -3802 | -5471 | -4528 | -5011 | -6513 | -7104 | -5985 | 111 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 71(Y) | -584 | -3368 | -3100 | -212 | 1352 | -3890 | 2686 | -3039 | 579 | -3272 | -2529 | -501 | -3971 | -2336 | -2820 | -2845 | -435 | -1020 | 1448 | 3474 | 112 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 72(I) | -611 | -3580 | -873 | -289 | -3712 | -3773 | -2465 | 2846 | -501 | -15 | -2724 | -2538 | 797 | 1139 | -2628 | -704 | -2625 | -178 | -3890 | -3347 | 113 |
| - | -149 | -500 | 233 | 43 | -381 | 398 | 105 | -626 | 214 | -466 | -721 | 275 | 394 | 45 | 96 | 359 | 117 | -369 | -295 | -250 | |
| - | -453 | -4367 | -2179 | -90 | -4041 | -701 | -1376 | * | * | | | | | | | | | | | | |
| | | | | | | | | | | | | | | | | | | | | | |
| 73(A) | 1788 | 147 | 422 | 37 | -4104 | -834 | -1444 | -3855 | 420 | -748 | -2873 | 134 | 1049 | -461 | -429 | 498 | -272 | -3405 | -3967 | -875 | 115 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10125 | -11167 | -894 | -1115 | -3509 | -133 | * | * | | | | | | | | | | | | |
| | | | | | | | | | | | | | | | | | | | | | |
| 74(N) | -743 | -3484 | -2342 | 149 | -3684 | -3375 | 619 | 1364 | -1438 | -577 | -2606 | 1367 | -3465 | 725 | 868 | -706 | 1250 | 365 | -3745 | 482 | 116 |
| - | -148 | -502 | 230 | 50 | -383 | 396 | 103 | -618 | 208 | -469 | -723 | 277 | 391 | 48 | 98 | 357 | 123 | -369 | -297 | -252 | |
| - | -319 | -2335 | -11167 | -1571 | -592 | -780 | -1260 | * | * | | | | | | | | | | | | |
| | | | | | | | | | | | | | | | | | | | | | |
| 75(P) | -1131 | -3355 | -2856 | -2299 | -3456 | -3718 | -1331 | -3068 | 115 | -821 | -2163 | -2526 | 3269 | 689 | -2218 | 150 | -1574 | 1034 | -3687 | -3176 | 120 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| | | | | | | | | | | | | | | | | | | | | | |
| 76(K) | -3329 | -4732 | 530 | -348 | -5126 | -535 | 705 | -4822 | 3267 | -4704 | -3839 | -2744 | -4250 | 1304 | 514 | -3185 | -3247 | -4401 | -4800 | -4211 | 121 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -166 | -3202 | * | * | | | | | | | | | | | | |
| | | | | | | | | | | | | | | | | | | | | | |
| 77(H) | -288 | -4090 | -2172 | 1044 | 709 | -671 | 1942 | -2762 | 1192 | -2271 | -3180 | -926 | 1802 | 434 | 580 | -33 | -2558 | -2113 | -671 | -3592 | 122 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 78(N) | 381 | -4094 | -5118 | -5061 | 2133 | -2547 | 229 | -5663 | -5171 | -5890 | -5049 | 3573 | -5038 | -4885 | -5347 | 622 | -1690 | -4867 | -6147 | -5793 | 123 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -9 | -10485 | -7539 | -894 | -1115 | -701 | -1378 | * | * | | | | | | | | | | | | |
| | | | | | | | | | | | | | | | | | | | | | |
| 79(G) | -3141 | 1351 | -3469 | -4628 | -2952 | 3386 | 968 | -2874 | -4181 | 306 | -2569 | -3106 | -4705 | -4107 | -4335 | -3625 | -3192 | -1881 | -3769 | -3387 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10477 | -11520 | -894 | -1115 | -596 | -1563 | * | * | | | | | | | | | | | | |
| | | | | | | | | | | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 80(Y) | -7124 | -6061 | -7507 | -7869 | 1269 | -7364 | -3601 | -6055 | -7436 | -5357 | -5454 | -6019 | -171 | -6163 | -6799 | -6643 | -6989 | -6208 | -2848 | 4723 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 81(Q) | -3629 | -4894 | -3611 | 793 | -5374 | -678 | -2881 | -4996 | 667 | -4836 | 37 | -3129 | -4534 | 3181 | 2436 | -3505 | -300 | -4611 | -4874 | -4407 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 82(S) | 614 | -3589 | -5585 | -5196 | -4321 | -1350 | -4438 | -157 | -4853 | -1079 | -3526 | -4524 | -4882 | -4605 | -223 | 3232 | -1918 | -3607 | -4752 | -4430 | 127 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 83(L) | -4083 | -3821 | -6195 | -5712 | 426 | -5522 | 1811 | -107 | -5307 | 2301 | -2844 | -4974 | -5518 | -4767 | -5041 | -4633 | -4015 | 1438 | 1385 | 1880 | 128 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 84(H) | -5529 | -6097 | -5071 | -4692 | -6225 | -5755 | 5216 | -6683 | -2887 | -6282 | -5697 | -8 | -5949 | -3804 | 889 | -5418 | -5367 | -6386 | -5724 | -5336 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| 85(T) | -2884 | -2710 | -5229 | -2438 | -4 | -4432 | -3304 | 961 | -4188 | 541 | 1053 | -1020 | -4482 | -3811 | -3989 | -3517 | 2237 | 1405 | -3169 | 2193 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -138 | -10485 | -3468 | -894 | -1115 | -701 | -1378 | * | * | | | | | | | | | | | | |
| 86(W) | 799 | -2601 | -5102 | -656 | -2558 | -4322 | -3195 | 1547 | -4068 | 171 | -1804 | -3962 | -4371 | -3695 | -3876 | -2350 | 2103 | 1266 | 2902 | -2722 | 131 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -168 | -10349 | -3192 | -894 | -1115 | -2488 | -283 | * | * | | | | | | | | | | | | |
| 87(V) | -4376 | -2356 | -6906 | -6422 | -3681 | -6476 | -5665 | 1833 | -6203 | 1429 | 1919 | -6134 | -6222 | -5750 | -6070 | -5707 | -4329 | 2685 | -5062 | -1119 | 132 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -246 | -10182 | -2683 | -894 | -1115 | -3322 | -152 | * | * | | | | | | | | | | | | |
| 88(R) | 541 | -3631 | 569 | 1591 | -3952 | -709 | -1791 | -3702 | -986 | -1505 | -2720 | -1767 | -3225 | 84 | 2620 | 59 | -815 | -3253 | -3814 | -3132 | 133 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9939 | -10981 | -894 | -1115 | -1244 | -791 | * | * | | | | | | | | | | | | |
| 89(V) | -493 | -2433 | -4949 | -4313 | 76 | -4153 | -3024 | 798 | -3908 | 1075 | 1324 | -3798 | 668 | -3532 | 552 | -733 | -480 | 1737 | -2891 | 1016 | 134 |
| - | -149 | -502 | 237 | 42 | -379 | 396 | 105 | -622 | 208 | -464 | -723 | 273 | 397 | 47 | 94 | 360 | 118 | -371 | -297 | -250 | |
| - | -3109 | -3075 | -386 | -1969 | -425 | -3322 | -152 | * | * | | | | | | | | | | | | |
| 90(P) | -1522 | -2968 | -714 | 570 | -3327 | -2199 | -993 | -3060 | 1810 | -2978 | -2121 | 798 | 2922 | -570 | -942 | -1364 | -916 | -2626 | -3120 | -2459 | 139 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8093 | -9135 | -894 | -1115 | -3809 | -107 | * | * | | | | | | | | | | | | |
| 91(Q) | -1021 | -2350 | 932 | 858 | -2615 | -2015 | -681 | 150 | 1342 | -427 | -1455 | -675 | -2108 | 1923 | -780 | -929 | -960 | 797 | -2568 | -1922 | 140 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8354 | -9396 | -894 | -1115 | -2844 | -216 | * | * | | | | | | | | | | | | |
| 92(D) | -1408 | 1541 | 2699 | -284 | 1533 | -666 | -1311 | 1066 | -1167 | -1874 | -1142 | -1220 | -2666 | -357 | -1553 | -1088 | -1348 | -1451 | -2341 | -1213 | 141 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8833 | -9875 | -894 | -1115 | -3458 | -138 | * | * | | | | | | | | | | | | |
| 93(M) | 15 | -2122 | 1765 | -1428 | -2178 | 1522 | 731 | -1784 | -1318 | 400 | 2311 | -1615 | -2810 | -1222 | -1704 | -1692 | 539 | -1607 | -2498 | -2024 | 142 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9015 | -10057 | -894 | -1115 | -4902 | -49 | * | * | | | | | | | | | | | | |
| 94(F) | 434 | -1932 | -2214 | 782 | 2754 | -51 | -1539 | -254 | 915 | -302 | -1109 | -1779 | -2868 | -1387 | -1833 | -488 | -1233 | -678 | -2324 | -1887 | 143 |
| - | -144 | -502 | 234 | 45 | -383 | 396 | 103 | -623 | 208 | -461 | -723 | 277 | 391 | 43 | 93 | 357 | 122 | -372 | -297 | -242 | |
| - | -1576 | -591 | -10057 | -998 | -1002 | -4902 | -49 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 95(D) | -1461 | -2878 | 1725 | 1319 | -333 | -2438 | -696 | 726 | -695 | -2884 | -1974 | 1469 | -2533 | 817 | -1199 | -241 | -1329 | -2487 | -3075 | 1698 | 146 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9914 | -10057 | -894 | -1115 | -1013 | -987 | * | * | | | | | | | | | | | | |
| | | | | | | | | | | | | | | | | | | | | | |
| 96(G) | 754 | -3611 | 878 | 1003 | -3932 | 2097 | -1758 | -3683 | -891 | -1399 | -2700 | 91 | -3037 | -320 | -881 | 689 | -1098 | -3233 | -3794 | -3112 | 147 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1277 | -9914 | -770 | -894 | -1115 | -2715 | -238 | * | * | | | | | | | | | | | | |
| | | | | | | | | | | | | | | | | | | | | | |
| 97(E) | -1416 | -1618 | -1727 | 1935 | 970 | -2744 | 1535 | 592 | -1651 | 514 | -803 | -1867 | -2812 | 1175 | -1895 | -1749 | -1356 | 875 | -2033 | -1629 | 148 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8803 | -9845 | -894 | -1115 | -3428 | -141 | * | * | | | | | | | | | | | | |
| | | | | | | | | | | | | | | | | | | | | | |
| 98(T) | 302 | -2867 | -1385 | -829 | -3162 | -2476 | -1124 | -2881 | 1103 | -66 | -1968 | -1127 | 1085 | 1473 | 655 | -1144 | 1941 | -2476 | -3062 | -2414 | 149 |
| - | -147 | -502 | 238 | 41 | -382 | 400 | 114 | -622 | 211 | -468 | -722 | 273 | 392 | 47 | 94 | 357 | 118 | -371 | -296 | -251 | |
| - | -4160 | -84 | -10038 | -14 | -6680 | -670 | -1428 | * | * | | | | | | | | | | | | |
| | | | | | | | | | | | | | | | | | | | | | |
| 99(E) | -1276 | -3754 | 216 | 2239 | -1832 | -2976 | 630 | -3824 | 623 | -1468 | -2552 | -1352 | 1581 | -180 | -193 | -1987 | -485 | -2182 | -3938 | 1629 | 151 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10091 | -11133 | -894 | -1115 | -765 | -1281 | * | * | | | | | | | | | | | | |
| | | | | | | | | | | | | | | | | | | | | | |
| 100(D) | -609 | -3961 | 1121 | 583 | -2379 | -309 | -136 | -3270 | 616 | -1599 | 81 | 43 | 921 | 132 | 638 | 872 | -593 | -445 | -4144 | -691 | 152 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -10334 | -9944 | -894 | -1115 | -2589 | -262 | * | * | | | | | | | | | | | | |
| | | | | | | | | | | | | | | | | | | | | | |
| 101(D) | 474 | -1087 | 1676 | -1803 | -1820 | 1628 | -1200 | -1690 | 1435 | -3899 | -2959 | 307 | -3557 | -1691 | 387 | -1741 | 28 | -580 | -4097 | -1180 | 153 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -10333 | -8824 | -894 | -1115 | -2559 | -268 | * | * | | | | | | | | | | | | |
| | | | | | | | | | | | | | | | | | | | | | |
| 102(F) | -2707 | -33 | -4343 | -1698 | 1250 | 493 | 687 | 38 | -1868 | 623 | -593 | -2876 | 200 | 961 | -187 | -1810 | 1158 | 727 | -3117 | 359 | 154 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10331 | -11373 | -894 | -1115 | -2505 | -280 | * | * | | | | | | | | | | | | |
| | | | | | | | | | | | | | | | | | | | | | |
| 103(W) | -2739 | 1251 | -5025 | -3597 | -583 | -4280 | -3149 | 1173 | -1928 | 525 | -1777 | 1247 | 708 | -3636 | 1450 | -1131 | -793 | 1408 | 1631 | -1440 | 155 |
| - | -149 | -500 | 240 | 42 | -381 | 398 | 105 | -627 | 210 | -467 | -721 | 275 | 393 | 45 | 95 | 359 | 121 | -370 | -295 | -250 | |
| - | -74 | -4333 | -11376 | -1540 | -608 | -2589 | -262 | * | * | | | | | | | | | | | | |
| | | | | | | | | | | | | | | | | | | | | | |
| 104(V) | 438 | 2329 | -5197 | -4566 | 2047 | -4409 | -3288 | 456 | -4166 | -942 | 1371 | -4055 | -4453 | -3790 | -3968 | -3497 | -2786 | 2467 | -3147 | 773 | 159 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 105(E) | -8291 | -7147 | -6862 | 3979 | -8533 | -6942 | -7335 | -9573 | -8101 | -8925 | -8867 | -7489 | -7401 | -7786 | -7871 | -8517 | -8434 | -9223 | -7285 | -8412 | 160 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 106(I) | -4994 | -4450 | -7620 | -7234 | -829 | -7477 | -7024 | 3212 | -7166 | 748 | -1833 | -7148 | -6959 | -6609 | -7080 | -6867 | -4950 | 2064 | -5866 | -5777 | 161 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -2589 | -262 | * | * | | | | | | | | | | | | |
| | | | | | | | | | | | | | | | | | | | | | |
| 107(Q) | -6886 | -6510 | -6906 | -7042 | -5962 | -6671 | -6416 | -6343 | -6317 | -302 | -5628 | -6950 | -7071 | 4507 | -6207 | -7179 | -7041 | -6814 | -6361 | -6170 | 162 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10334 | -11376 | -894 | -1115 | -158 | -3266 | * | * | | | | | | | | | | | | |
| | | | | | | | | | | | | | | | | | | | | | |
| 108(I) | -2795 | -4275 | -7484 | -7164 | -781 | -7345 | -7344 | 3562 | -7137 | -974 | -3511 | -6999 | -7043 | -7038 | -7288 | -6730 | -4783 | 1828 | -6609 | -6149 | 163 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 109(R) | -5786 | -6172 | -6929 | -5121 | -7234 | -6077 | -3950 | -6516 | 737 | -6082 | -5466 | -4887 | -6018 | -3544 | 4095 | -5670 | -5392 | -6324 | -5792 | -5852 | 164 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 110(T) | -3873 | -4640 | -1889 | -4266 | -6955 | -4496 | -5137 | -6843 | -5651 | -6971 | -6127 | -1319 | -5246 | -4951 | -6113 | 1214 | 3761 | -5675 | -7120 | -6627 | 165 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 111(I) | -1052 | -2860 | -4257 | 914 | -1869 | -4250 | 1817 | 2158 | -419 | 810 | 920 | -3557 | -3817 | -1892 | 526 | -1069 | -1857 | 282 | -3034 | -1253 | 166 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 112(F) | 536 | -4010 | 209 | 1431 | 1527 | -2480 | -2279 | -4020 | -876 | 981 | 600 | -1359 | -3708 | 885 | -212 | -1276 | -2567 | 364 | -4216 | -3556 | 167 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 113(M) | -4643 | -6360 | -2587 | 1113 | -6714 | -4642 | -3955 | -6594 | -4007 | -6463 | 4367 | 1023 | -5159 | 2379 | -4662 | -643 | -4711 | -6073 | -6627 | -5707 | 168 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 114(H) | -4743 | -6697 | 2419 | 1515 | -6849 | -4633 | 3499 | -242 | -4274 | -6645 | -5988 | 1402 | -5175 | -3668 | -5164 | 382 | -4813 | -6252 | -6842 | -5796 | 169 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 115(F) | 747 | -3929 | -1018 | -780 | 1668 | 543 | -612 | 250 | 930 | 1056 | -957 | -1686 | -3732 | 2 | -797 | -1003 | -2576 | -3513 | -4156 | 227 | 170 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 116(W) | -2877 | -2705 | -4202 | -3546 | -225 | -3381 | -3295 | 1434 | -4176 | -1157 | -790 | -428 | -4474 | -2237 | -3870 | -2288 | -1345 | 592 | 5179 | 1395 | 171 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10485 | -11527 | -894 | -1115 | -701 | -1378 | * | * | | | | | | | | | | | | |
| | | | | | | | | | | | | | | | | | | | | | |
| 117(A) | 3188 | -4152 | -6000 | -6359 | -6833 | 1270 | 972 | -6670 | -6580 | -6914 | -5952 | -3398 | -5204 | -6011 | -6351 | 240 | -4003 | -5355 | -7046 | -6966 | 172 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1206 | -10485 | -822 | -894 | -1115 | -701 | -1378 | * | * | | | | | | | | | | | | |
| | | | | | | | | | | | | | | | | | | | | | |
| 118(E) | -107 | -4101 | -1399 | 3347 | -4390 | -3132 | -2087 | -4161 | -1100 | -4111 | -3264 | 1172 | -3425 | -1224 | -2415 | -2394 | -2556 | -347 | -4300 | -3551 | 173 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9282 | -10324 | -894 | -1115 | -4736 | -55 | * | * | | | | | | | | | | | | |
| | | | | | | | | | | | | | | | | | | | | | |
| 119(R) | 1014 | -2925 | -1588 | -175 | 1466 | 556 | -1330 | -2865 | -105 | -794 | -1165 | -437 | -2753 | -411 | 2180 | -832 | -1593 | -2504 | -3157 | 478 | 174 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9282 | -10324 | -894 | -1115 | -283 | -2487 | * | * | | | | | | | | | | | | |
| | | | | | | | | | | | | | | | | | | | | | |
| 120(G) | -3803 | -4611 | -3535 | 2686 | -6829 | 2723 | -4860 | -6715 | -5328 | -6816 | -5994 | -3974 | -5107 | -4649 | -5860 | -218 | -48 | -5591 | -6972 | -6414 | 175 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| | | | | | | | | | | | | | | | | | | | | | |
| 121(I) | -2762 | -2590 | -2282 | -1294 | 929 | -4310 | -3181 | 2665 | -4054 | 513 | -1620 | -2444 | -4359 | -3681 | -3862 | -1349 | -532 | 2026 | -3052 | -2709 | 176 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| | | | | | | | | | | | | | | | | | | | | | |
| 122(E) | 2282 | -3689 | 1469 | 2373 | -5606 | -4253 | -3712 | -4203 | -3698 | -5393 | -4622 | -3233 | -4724 | -3377 | -4276 | -2893 | -3823 | 776 | -5719 | -5046 | 177 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| | | | | | | | | | | | | | | | | | | | | | |
| 123(H) | 1750 | -3963 | -6384 | -6675 | -6408 | -4257 | 4524 | -6183 | -6431 | -6516 | -5608 | -5019 | -5061 | -5949 | -6125 | 498 | -3833 | 756 | -6683 | -6541 | 178 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10343 | -11386 | -894 | -1115 | -2524 | -275 | * | * | | | | | | | | | | | | |
| | | | | | | | | | | | | | | | | | | | | | |
| 124(H) | -1628 | -3951 | 1518 | -1647 | -4263 | -3477 | 3429 | -1015 | 1109 | -451 | -3042 | -2115 | -3570 | 788 | -438 | 142 | -1534 | -3568 | -4139 | 1603 | 179 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -110 | -10343 | -3781 | -894 | -1115 | -2524 | -275 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 125(W) | -761 | -2492 | -5011 | -4375 | -1936 | -4214 | -3085 | 1010 | -3971 | 1570 | 1433 | -3860 | -4263 | -3592 | -3770 | 45 | -2606 | 393 | 3828 | 1786 | 180 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10235 | -11277 | -894 | -1115 | -755 | -1295 | * | * | | | | | | | | | | | | |
| | | | | | | | | | | | | | | | | | | | | | |
| 126(N) | -1247 | -3072 | -3373 | -2806 | -2817 | -1310 | -2682 | 1261 | 797 | -15 | -1145 | 2612 | -4014 | -2532 | 2219 | -2923 | -2062 | -2529 | -3462 | -1900 | 181 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10387 | -11429 | -894 | -1115 | -2179 | -360 | * | * | | | | | | | | | | | | |
| | | | | | | | | | | | | | | | | | | | | | |
| 127(Y) | -6975 | -5957 | -7400 | -7762 | 1411 | 621 | -3521 | -5974 | -7341 | -5279 | -5374 | -5928 | -7131 | -6076 | -6708 | -6522 | -6864 | -6119 | -2769 | 4593 | 182 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10387 | -11429 | -894 | -1115 | -2179 | -360 | * | * | | | | | | | | | | | | |
| | | | | | | | | | | | | | | | | | | | | | |
| 128(K) | -4600 | -5225 | -5076 | -4581 | -5453 | -5168 | -3874 | -6204 | 3604 | -5897 | -5269 | -4398 | 1148 | -3590 | -2693 | -957 | -4658 | -5728 | -5293 | 1623 | 183 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -53 | -10387 | -4835 | -894 | -1115 | -2179 | -360 | * | * | | | | | | | | | | | | |
| | | | | | | | | | | | | | | | | | | | | | |
| 129(N) | -2151 | 1342 | -1005 | 1531 | -4024 | -215 | 1376 | -4033 | -1437 | -2124 | -3051 | 1878 | -3557 | -257 | 10 | 1397 | -1140 | -2713 | -4146 | 1288 | 184 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10336 | -11378 | -894 | -1115 | -1699 | -531 | * | * | | | | | | | | | | | | |
| | | | | | | | | | | | | | | | | | | | | | |
| 130(N) | -1259 | -3989 | 801 | -622 | -4310 | 679 | -757 | -4061 | 137 | 995 | -3078 | 1476 | -97 | 890 | -553 | 515 | -1592 | -3611 | -4172 | 357 | 185 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10301 | -11343 | -894 | -1115 | -188 | -3035 | * | * | | | | | | | | | | | | |
| | | | | | | | | | | | | | | | | | | | | | |
| 131(W) | -2442 | -3920 | -1325 | 934 | -4187 | 1231 | -686 | -39 | -522 | 301 | 821 | 1033 | -3200 | -108 | -2341 | 604 | -183 | 69 | 1481 | -3486 | 186 |
| - | * | * | * | * | * | * | * | * | * | * | * | * | * | * | * | * | * | * | * | * | |
| - | * | * | * | * | * | * | * | * | 0 | | | | | | | | | | | | |

TABLE 6

| | |
|---|---|
| HMMER2.0 [2.3.2] | Program name and version |
| NAME TGS | Name of input sequence alighment file |
| DESC TGS domain | Domain description |
| LENG 75 | Length of alignment |
| ALPH Amino | Type of residues |
| MAP yes | Map of the match states to the columns of the alignment |
| COM hmmbuild -F HMM_ls.ann SEED.ann | Commands used to generate the file: this one means that hmmbuild (default parameters) was applied to the alignment file |
| COM hmmcalibrate --seed 0 HMM_ls.ann | Commands used to generate the file: this one means that hmmcalibrate (default parameters) was applied to the hmm profile |
| NSEQ 62 | Number of sequences in the alignment file |
| DATE Fri Apr 27 19:07:53 2007 | When file was generated |
| XT -8455 -4 -1000 -1000 -8455 -4 -8455 -4 | |
| NULT -4 -8455 | The transition probability distribution for the null model (single G state). |
| NULE 595 -1558 85 338 -294 453 -1158 197 249 902 -1085 -142 -21 -313 -45 531 201 384 -1998 -644 | The symbol emission probability distribution for the null model (G state) |
| EVD -50.809875 0.221806 | The extreme value distribution parameters μ and lambda respectively |
| The highest probability is highlighted for each position | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->l | m->d | i->m | i->i | d->m | d->d | b->m | m->e | | | | | | | | | | | | |
| | -41 | * | -5168 | | | | | | | | | | | | | | | | | | |
| 1(I) | -2697 | -2550 | -4876 | -1956 | -1064 | -4226 | -3089 | 2627 | -854 | -1421 | 1812 | -1442 | -568 | -578 | -3742 | -1595 | -788 | 2091 | -3005 | -717 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 2(R) | -2518 | -402 | -1171 | -2139 | 1158 | 282 | 864 | 58 | 991 | -3310 | -2527 | -733 | -3699 | -690 | 2216 | -2551 | -365 | -628 | 191 | 1875 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 3(V) | -1740 | 55 | -4917 | -4289 | -2561 | -4268 | -9 | 2381 | -3865 | -2445 | -1802 | 634 | -4321 | -799 | -1609 | -3350 | -2684 | 2818 | -3061 | -2715 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 4(Y) | -2706 | -2538 | -5008 | -4375 | 2592 | -4248 | -3116 | -1084 | -1374 | -1493 | -1741 | -3880 | -4299 | -842 | -3794 | -1456 | 1353 | 1106 | -2992 | 3188 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 5(T) | -3121 | -2956 | -5433 | -4809 | 163 | -4649 | -3559 | -2267 | -4377 | 1935 | -9 | -4316 | -4691 | -4003 | -1351 | -998 | 2997 | -2314 | -3376 | -3054 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1646 | -10291 | -557 | -894 | -1115 | -701 | -1378 | * | * | | | | | | | | | | | | |
| 6(K) | -3330 | -4170 | 143 | -2361 | -4986 | -3733 | -1863 | -4361 | 3565 | -4013 | -3341 | -2393 | -3790 | -1450 | 1494 | -3165 | -3068 | -4098 | -3862 | -3698 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -33 | -5480 | * | * | | | | | | | | | | | | |
| 7(P) | -4636 | 1330 | -5058 | -4057 | -6367 | -5214 | -3346 | -5730 | 861 | -5415 | -4723 | -944 | 3908 | -1087 | -877 | -2109 | -4428 | -5432 | -5285 | -5145 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 8(D) | -1627 | -3947 | 2648 | -467 | -4269 | -3441 | 662 | -4020 | 2108 | -3963 | -3037 | -30 | 708 | 535 | 71 | -2353 | -1314 | -3570 | -4130 | -3447 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 9(G) | 447 | -3988 | -5373 | -5656 | -6525 | 3468 | -5550 | -6332 | -5983 | -6564 | -5633 | -1523 | -4996 | 594 | -5917 | -1966 | -3812 | -1128 | -6730 | -6576 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 10(K) | 193 | -3921 | 1189 | 741 | -659 | -365 | -2085 | -374 | 1704 | -1416 | 215 | -231 | -3520 | 1440 | -13 | -217 | -2391 | -1600 | -4105 | -3424 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 11(V) | -371 | -3806 | -1114 | 276 | -4075 | -1625 | -2124 | 783 | -124 | 450 | -473 | -131 | -586 | 1346 | -437 | -2370 | -335 | 1841 | -4022 | -3372 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -137 | -10291 | -3475 | -894 | -1115 | -701 | -1378 | * | * | | | | | | | | | | | | |
| 12(P) | -1500 | -2480 | -4414 | -3808 | -501 | -4051 | -211 | 634 | 1008 | -75 | -1679 | -3523 | 2182 | -46 | 371 | -3112 | -2504 | 1656 | -2928 | 568 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10156 | -11198 | -894 | -1115 | -2348 | -316 | * | * | | | | | | | | | | | | |
| 13(D) | -528 | -3817 | 2558 | 2089 | -4138 | -1482 | 576 | -3889 | -697 | -3833 | -2906 | -316 | -3409 | 312 | -2064 | -375 | -24 | -898 | -4000 | -3317 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1576 | -10156 | -591 | -894 | -1115 | -2348 | -316 | * | * | | | | | | | | | | | | |
| 14(F) | -4824 | -3963 | -5533 | -5724 | 3604 | -5356 | -1737 | -3748 | -5200 | -747 | -3198 | -4073 | -5231 | -4149 | 205 | -4582 | -4697 | -3893 | -999 | 3427 | 14 |
| - | -149 | -500 | 233 | 43 | -381 | 399 | 106 | -626 | 210 | -466 | -720 | 275 | 395 | 45 | 96 | 359 | 117 | -369 | -294 | -249 | |
| - | -149 | -4305 | -4391 | -976 | -1024 | -4198 | -81 | * | * | | | | | | | | | | | | |
| 15(D) | -1299 | -2788 | 2047 | 903 | -3104 | -2204 | -912 | -2860 | 297 | -2802 | -1884 | 232 | -2331 | 941 | -1041 | 1453 | 985 | -2408 | -2970 | -2275 | 17 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -6 | -8585 | -9627 | -894 | -1115 | -4198 | -81 | * | * | | | | | | | | | | | | |
| 16(D) | -1813 | -3374 | 2529 | 2243 | -3667 | -2480 | -1355 | -3448 | 437 | -3378 | -2493 | -1097 | -231 | 431 | -1646 | 215 | -1779 | -2985 | -3550 | -2802 | 18 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 17(P) | 539 | -2421 | -4342 | -4676 | -5052 | 467 | -4229 | -4886 | -4786 | -5130 | -4188 | -3352 | 3894 | -4270 | -4553 | -2056 | -2281 | -3610 | -5224 | -5180 | 19 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 18(L) | -3461 | -3003 | -5904 | -5350 | 127 | -5473 | -4387 | 1691 | -5100 | 2175 | 1175 | -5148 | -4991 | -4302 | -4791 | -4710 | -3369 | 1996 | -3447 | -3447 | 20 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4089 | -87 | * | * | | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 19(I) | 229 | -2576 | -5746 | -5431 | -3299 | -5463 | -5513 | 3129 | -5379 | -2095 | -2004 | -5191 | -5289 | -5326 | -5526 | -4825 | -3059 | 2438 | -4975 | -4452 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8723 | -9765 | -894 | -1115 | -33 | -5446 | * | * | | | | | | | | | | | | |
| 20(L) | -198 | -2604 | -5128 | -4493 | 585 | -444 | -3205 | -397 | -4090 | 2435 | 442 | -3981 | -4377 | -3706 | -3888 | -3420 | -2722 | 1114 | -3059 | 877 | 22 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 21(P) | -254 | -3925 | 144 | -1093 | -4247 | -3426 | 330 | -3997 | 1039 | -1905 | -3015 | -1007 | 2633 | -398 | 1765 | -612 | 213 | -3547 | -4109 | -3426 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 22(R) | 107 | -3925 | -972 | 729 | -347 | -1852 | -164 | -3996 | 1688 | -3941 | -673 | -273 | -1178 | -357 | 1860 | 654 | -219 | -1006 | -4108 | -385 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 23(G) | -1601 | -4537 | 157 | -705 | -4839 | 3160 | -2581 | -4609 | -1248 | -4546 | -3648 | 248 | -1400 | -743 | -2809 | -1763 | -2966 | -4152 | 2813 | -3992 | 25 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 24(S) | 1616 | -3800 | -2376 | 536 | -4066 | -3466 | -100 | 53 | -543 | -3792 | -2905 | -2126 | -3558 | -1691 | 1048 | 1860 | 465 | -478 | -4018 | -3372 | 26 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 25(T) | -2556 | -217 | -2821 | -2266 | -3440 | -805 | -2389 | -1163 | -1227 | -3256 | -2490 | -944 | -3764 | -746 | -1299 | 671 | 3424 | -1065 | -3668 | -3155 | 27 |
| - | -149 | -490 | 233 | 43 | -381 | 400 | 105 | -626 | 210 | -466 | -721 | 275 | 394 | 45 | 96 | 359 | 117 | -369 | -295 | -250 | |
| - | -2283 | -5310 | -378 | -984 | -1016 | -701 | -1378 | * | * | | | | | | | | | | | | |
| 26(T) | -1308 | -1921 | -3835 | -4072 | -4376 | -2182 | -3609 | -4171 | -4005 | -4450 | -3548 | -2822 | -2972 | -3622 | -3843 | 1755 | 3504 | -3023 | -4598 | -4452 | 30 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8178 | -9220 | -894 | -1115 | -59 | -4632 | * | * | | | | | | | | | | | | |
| 27(P) | 1187 | 243 | -5824 | -5395 | -3614 | -4409 | -4202 | 841 | -5014 | -3400 | -2805 | -4563 | 2828 | -4623 | -4802 | -1660 | -1104 | 2066 | -4160 | -3832 | 31 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10267 | -11309 | -894 | -1115 | -466 | -1857 | * | * | | | | | | | | | | | | |
| 28(M) | -579 | -2747 | -1398 | 1451 | -28 | -1034 | -2815 | 846 | 691 | 208 | 1870 | -3238 | -4084 | -2882 | 838 | -3041 | -2583 | 1018 | -3175 | -242 | 32 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 29(D) | -4832 | -6961 | 3746 | 1464 | -7043 | -4527 | 869 | -7059 | -4458 | -6875 | -6344 | -3104 | -5129 | -370 | -5514 | -1809 | -4940 | -6485 | -7083 | -5908 | 33 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 30(F) | 110 | -106 | -5395 | -4776 | 2935 | -4631 | -3528 | 1512 | -4387 | 937 | -1975 | -4277 | -4659 | -4012 | -4196 | -3727 | -2970 | 1534 | -3367 | -752 | 34 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 31(C) | 3159 | 3870 | -6715 | -7056 | -6591 | -4197 | -5976 | -6255 | -6660 | -6645 | -5699 | -5044 | -5013 | -6085 | -6250 | -1955 | -3780 | -650 | -6834 | -6815 | 35 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 32(Y) | -270 | -495 | -2342 | -149 | -613 | -1473 | 1320 | -1844 | 776 | -2137 | -774 | 1573 | -3540 | 471 | 443 | -2357 | -1347 | -3448 | -4050 | 3178 | 36 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 33(K) | 1595 | -3924 | -399 | -767 | -4245 | -179 | 1508 | -1607 | 1774 | -1396 | -149 | -768 | -3519 | 571 | 1104 | -122 | -2391 | -3546 | -4108 | -3425 | 37 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 34(I) | -4958 | -4437 | -7532 | -7093 | -3800 | -7295 | -6594 | 3471 | -6960 | 805 | 89 | -6968 | -6790 | -1108 | -6792 | -6630 | -4900 | 1148 | -5532 | -5480 | 38 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 35(H) | -4087 | -5292 | -2951 | -3009 | -5657 | 729 | 4722 | -5740 | -250 | -5608 | -4865 | -838 | -4875 | -3152 | -3209 | 1141 | -4118 | -5273 | -5515 | -729 | 39 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 36(T) | -1378 | -3899 | -2274 | -775 | -4220 | -802 | -2058 | -3970 | 1487 | -3915 | -121 | -582 | 186 | 441 | 1571 | 966 | 2014 | -3521 | -4082 | -3400 | 40 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -1296 | -755 | * | * | | | | | | | | | | | | |
| 37(D) | -2974 | -4506 | 2224 | 1617 | -4809 | 1101 | -2547 | -4580 | -2227 | -4515 | -3615 | -1156 | -3933 | -837 | -350 | 1601 | 124 | -4121 | -4685 | -3959 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -1296 | -755 | * | * | | | | | | | | | | | | |
| 38(L) | -2822 | -2641 | -1487 | -4533 | 635 | -4377 | 935 | 1674 | -4130 | 2209 | 753 | -4023 | -4413 | -3739 | -3926 | -3464 | -2761 | 1162 | 693 | -2750 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10260 | -11302 | -894 | -1115 | -424 | -1973 | * | * | | | | | | | | | | | | |
| 39(G) | 1745 | 296 | -1147 | -1011 | -3419 | 2149 | -2349 | -53 | 124 | -2081 | -2466 | -2446 | -3731 | 563 | -2532 | -2590 | -2470 | 687 | -3644 | -3126 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 40(K) | -1012 | -3928 | 1593 | 1007 | -32 | -3428 | 2070 | -4000 | 2071 | -3944 | -3018 | 1281 | -3521 | -399 | 345 | -812 | -2394 | -3550 | -4112 | -3429 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -67 | -10291 | -4492 | -894 | -1115 | -701 | -1378 | * | * | | | | | | | | | | | | |
| 41(K) | 520 | -3870 | 527 | -598 | -4191 | -1082 | 1272 | -3942 | 1772 | -3886 | -2959 | 660 | -3464 | 1433 | 1467 | 155 | -191 | -3492 | -4053 | -3370 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10226 | -11268 | -894 | -1115 | -1735 | -515 | * | * | | | | | | | | | | | | |
| 42(F) | 1552 | 2563 | -4990 | -4354 | 2952 | -4194 | -3065 | -1965 | -3949 | -517 | 1339 | -3839 | -4244 | -3573 | -3750 | -1391 | 847 | -521 | -2931 | -905 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10226 | -11268 | -894 | -1115 | -300 | -2412 | * | * | | | | | | | | | | | | |
| 43(I) | -292 | 242 | -4934 | -4306 | -2509 | -4243 | -3108 | 2033 | 1510 | 600 | -1755 | -3849 | -4294 | -3572 | 1179 | -1964 | -381 | 1226 | -3010 | -2666 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 44(Y) | 339 | -173 | -1340 | -4224 | -780 | 2159 | 1092 | 560 | -3862 | -2406 | -1758 | -1461 | -4275 | -3521 | -3731 | -3299 | -2639 | -339 | -3009 | 3122 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 45(A) | 3337 | 47 | -6711 | -7050 | -6592 | 232 | -5967 | -6387 | -6655 | -6669 | -5704 | -5038 | -5007 | -6077 | -6245 | -386 | -3775 | 117 | -6825 | -6808 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 46(K) | -1434 | -2999 | -3271 | -1147 | -3029 | -3851 | -2590 | 971 | 2046 | 1085 | -2175 | -2833 | -3925 | -57 | 1665 | -2833 | -525 | -143 | -3388 | 290 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 47(V) | -1559 | -3260 | 127 | -5233 | -3460 | -5213 | -4288 | 1561 | -4982 | -1561 | -2558 | -697 | -5247 | -4666 | -4882 | -2241 | -3472 | 3302 | -4163 | -3793 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 48(W) | 37 | -3847 | 57 | -1124 | -4103 | -1905 | -2220 | -3809 | -1845 | -3840 | -2965 | 3319 | -3634 | -1789 | -2343 | -1184 | -1126 | -1772 | 4072 | -1019 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -137 | -10291 | -3475 | -894 | -1115 | -701 | -1378 | * | * | | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 49(G) | -4588 | -6618 | 27 | -885 | -6758 | 3574 | -454 | -6734 | -4157 | -6568 | -5979 | -1229 | -4945 | -3479 | -1668 | -1436 | -4681 | -6177 | -6767 | -5659 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1511 | -10156 | -625 | -894 | -1115 | -2348 | -316 | * | * | | | | | | | | | | | | |
| 50(K) | -313 | -2214 | -1363 | -812 | -2394 | -2309 | -1017 | -522 | 2024 | -988 | -1378 | -1069 | -14 | -646 | -1154 | 1381 | 1577 | -1764 | -2534 | -1975 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 51(S) | -1853 | -2504 | -3099 | -3260 | -4321 | -2675 | -3378 | -4270 | -3456 | -4467 | 685 | 630 | -3394 | -3261 | -3581 | 3458 | -2254 | -3380 | -4582 | -4145 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 52(V) | 2066 | -1956 | -3760 | -3341 | -2659 | -2763 | -2703 | -1843 | -2900 | -2472 | -1826 | -2807 | -3247 | -2788 | 345 | -2007 | 1475 | 2359 | -3110 | -2775 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -4803 | -53 | * | * | | | | | | | | | | | | |
| 53(K) | -3429 | -4109 | -4119 | -2717 | -5012 | -3935 | -1792 | -4286 | 3425 | -3910 | -3244 | -2596 | 1211 | 738 | 1057 | -3296 | -3089 | -4062 | -3736 | -3656 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8650 | -9693 | -894 | -1115 | -2644 | -251 | * | * | | | | | | | | | | | | |
| 54(H) | -2743 | -2902 | -3619 | -2956 | 1756 | -3870 | 3947 | -39 | 858 | -2676 | -2104 | -2832 | -3890 | -2277 | 1101 | -2947 | -2644 | -2450 | -1985 | 2132 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -4612 | -60 | * | * | | | | | | | | | | | | |
| 55(P) | -1438 | -2910 | 962 | -736 | -3231 | -447 | -1070 | -2982 | 975 | -2926 | -1999 | 963 | 1212 | 872 | -68 | 1142 | 746 | -2532 | -3094 | -236 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -4612 | -60 | * | * | | | | | | | | | | | | |
| 56(P) | -3076 | -4867 | 308 | 192 | -5104 | 1841 | -2406 | -4978 | 1515 | -4858 | -4121 | -1758 | 2926 | -2052 | -3197 | -2778 | -3115 | -4470 | -5037 | -4110 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -4 | -9006 | -10048 | -894 | -1115 | -37 | -5289 | * | * | | | | | | | | | | | | |
| 57(Q) | -1419 | -3917 | -2305 | 1207 | -4234 | -3430 | 84 | -1890 | 1496 | -2165 | 1330 | -858 | -3523 | 2924 | 1094 | -1395 | -2393 | -1044 | -4102 | -3423 | 61 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -25 | -5885 | -11333 | -246 | -2675 | -701 | -1378 | * | * | | | | | | | | | | | | |
| 58(R) | -2654 | -2705 | -4009 | -504 | -170 | -4059 | -689 | 796 | 372 | 1198 | 359 | -1565 | 346 | -901 | 2253 | -3090 | -2594 | 29 | 214 | -842 | 63 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 59(W) | -663 | 1284 | -4998 | -4365 | -2490 | -4244 | -3113 | -781 | -480 | -1587 | -1738 | -3874 | -4294 | -3603 | -412 | -442 | -1067 | 2923 | 3099 | 588 | 64 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 60(D) | -382 | -4141 | 2495 | -4417 | -6327 | 2416 | -4862 | -6130 | -5070 | -2073 | -5398 | -4179 | 1894 | -4652 | -5380 | -865 | -1802 | -5093 | -6478 | -6094 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 61(L) | -465 | -2655 | -1752 | -534 | -1084 | -4109 | -2931 | 914 | -1022 | 2498 | 731 | -3469 | -206 | -3140 | -629 | -1595 | -2607 | -1192 | -3096 | -2729 | 66 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 62(D) | -1602 | 848 | 2184 | 705 | -4244 | -1863 | -326 | -3995 | -679 | -1987 | -208 | 1111 | -3519 | -1625 | -322 | 1608 | 664 | -3545 | -4107 | -3425 | 67 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 63(H) | -1539 | -3911 | -1064 | -1771 | -987 | -3440 | 3665 | -3965 | 89 | -3922 | -3003 | -2079 | -3533 | 414 | 1231 | -980 | 1434 | -3528 | -4099 | 2266 | 66 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |

TABLE 6-continued

| | | | | | | | | | | | | | | | | | | | | | |
|---|---|---|---|---|---|---|---|---|---|---|---|---|---|---|---|---|---|---|---|---|---|
| 64(P) | -1562 | -3849 | -2347 | 984 | -4135 | -3452 | 625 | -1059 | 923 | -2137 | -2948 | -2102 | 1978 | 275 | 621 | -2362 | 58 | 1752 | -4053 | -3394 | 69 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 65(L) | -5917 | -5267 | -8304 | -7710 | -63 | -8160 | -6754 | 1091 | -7532 | 2986 | 881 | -7898 | -7049 | -6185 | -6958 | -7579 | -5742 | -426 | -5154 | -5423 | 70 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 66(E) | -1601 | -3925 | -159 | 2553 | -4246 | -3426 | -2084 | -1908 | 1231 | -2098 | -140 | 654 | -1178 | 1570 | 384 | -1182 | -1332 | -3547 | -4108 | -3425 | 71 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 67(D) | -1385 | -3930 | 2537 | 650 | -1544 | -112 | 885 | -4001 | -1671 | -3946 | -643 | 2111 | -3524 | 169 | -2179 | 326 | -357 | -3552 | -4113 | -3431 | 72 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 68(G) | -2002 | -6836 | 1569 | 2060 | -6992 | 2666 | -3980 | -6995 | -4423 | -6821 | -6267 | 986 | -5111 | -3675 | -5457 | -1804 | -4888 | -6416 | -7028 | -5876 | 73 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 69(D) | 807 | 2570 | 3588 | -859 | -6772 | -1507 | -3941 | -6718 | -4285 | -6595 | -5957 | -3121 | -5040 | 237 | -5198 | -4231 | -4665 | -6110 | -6796 | -5756 | 74 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 70(V) | -2546 | -3222 | -2878 | 27 | -3303 | -3694 | -2405 | 1532 | 420 | -2296 | -396 | -882 | -3776 | -137 | -1587 | -1301 | 1582 | 2337 | -3570 | -3074 | 75 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 71(V) | -4634 | -4116 | -7310 | -1746 | -4535 | -7163 | -7086 | 1617 | -6943 | 1384 | -3239 | -6818 | -6846 | -6787 | -7061 | -6542 | -4619 | 3066 | -6314 | -5911 | 76 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 72(E) | -2453 | -3926 | -1058 | 2334 | -4247 | -3427 | -2085 | -3998 | 937 | -1905 | -3015 | -996 | -3520 | 1808 | 865 | 122 | 979 | -1417 | -4109 | -3426 | 77 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 73(I) | -5032 | -4481 | -7644 | -7246 | 140 | -7505 | -6959 | 3445 | -7172 | 999 | -2645 | -7178 | -6937 | -6532 | -7041 | -6899 | -4980 | 1004 | -5737 | -5682 | 78 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 74(V) | -2707 | 144 | -5051 | -4415 | 1002 | -4254 | 321 | 1953 | -714 | 1197 | -1735 | -3900 | -4304 | -3633 | -1785 | -3339 | -2647 | 2263 | -2990 | -854 | 79 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10291 | -11333 | -894 | -1115 | -701 | -1378 | * | * | | | | | | | | | | | | |
| 75(T) | 135 | 109 | -1468 | -3349 | -2712 | -4040 | -2842 | -623 | 1838 | -1521 | -33 | -3288 | -4104 | -2937 | -3291 | 119 | 2847 | -764 | -3160 | -2777 | 80 |
| - | * | * | * | * | * | * | * | * | * | * | * | * | * | * | * | * | * | * | * | * | |
| - | * | * | * | * | * | * | * | * | 0 | | | | | | | | | | | | |

TABLE 7

| | |
|---|---|
| HMMER2.0 [2.3.2] | Program name and version |
| NAME HD | Name of input sequence alighment file |
| DESC HD domain | Domain description |
| LENG 154 | Length of alignment |
| ALPH Amino | Type of residues |
| MAP yes | Map of the match states to the columns of the alignment |
| COM hmmbuild -F HMM_ls.ann SEED.ann | Commands used to generate the file: this one means that hmmbuild (default parameters) was applied to the alignment file |
| COM hmmcalibrate --seed 0 HMM_ls.ann | Commands used to generate the file: this one means that hmmcalibrate (default parameters) was applied to the hmm profile |
| NSEQ 160 | Number of sequences in the alignment file |
| DATE Sun Apr 29 14:25:51 2007 | When file was generated |
| XT -8455 -4 -1000 -1000 -8455 -4 -8455 -4 | |
| NULT -4 -8455 | The transition probability distribution for the null model (single G state). |
| NULE 595 -1558 85 338 -294 453 -1158 197 249 902 -1085 -142 -21 -313 45 531 201 384 -1998 -644 | The symbol emission probability distribution for the null model (G state) |
| EVD -43.966183 0.276183 | The extreme value distribution parameters μ and lambda respectively |
| The highest probability is highlighted for each position | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->l | m->d | i->m | i->i | d->m | d->d | b->m | m->e | | | | | | | | | | | | |
| | -10 | * | -7160 | | | | | | | | | | | | | | | | | | |
| 1(R) | -2416 | -4435 | -683 | -6310 | -327 | -400 | -5025 | 136 | -5907 | -100 | -519 | -1035 | -6205 | -5531 | 1904 | -2161 | 1210 | 1787 | -729 | 1644 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | -10 | * | | | | | | | | | | | | |
| 2(F) | 532 | -4556 | 252 | -1153 | 1895 | -146 | -1075 | 1016 | -2256 | 744 | -1710 | -5362 | -6064 | -2250 | -1047 | -635 | -2746 | -183 | 613 | 1850 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -11359 | -894 | -1115 | -701 | -1378 | * | * | | | | | | | | | | | | |
| 3(E) | -527 | -1390 | 691 | 1854 | -2832 | -231 | -155 | 372 | -548 | -3070 | -2239 | 762 | -5380 | 326 | -420 | 256 | 753 | -1860 | -5966 | 444 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -35 | -12317 | -5392 | -894 | -1115 | -701 | -1378 | * | * | | | | | | | | | | | | |
| 4(H) | -3183 | -6629 | -6277 | -6376 | -8583 | -6562 | 5396 | -8426 | -5521 | -8325 | -7574 | -1447 | -2678 | -6100 | -1632 | -6048 | -6240 | -7528 | -8205 | -7923 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -21 | -12282 | -6125 | -894 | -1115 | -2423 | -298 | * | * | | | | | | | | | | | | |
| 5(S) | -612 | 1679 | -6898 | -6262 | -1366 | -6102 | -4973 | -692 | -5857 | -505 | 834 | -5747 | 1116 | -2235 | -2476 | 2429 | 1404 | -10 | -4839 | -4497 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12262 | -13304 | -894 | -1115 | -2917 | -205 | * | * | | | | | | | | | | | | |
| 6(L) | -1733 | 7 | -3085 | -894 | 439 | -2985 | -4966 | 930 | -571 | 2172 | 520 | -5732 | -6147 | -2530 | 270 | -3052 | -4494 | 612 | 1224 | 329 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12262 | -13304 | -894 | -1115 | -1176 | -843 | * | * | | | | | | | | | | | | |
| 7(R) | 308 | -5752 | -1620 | 1313 | -2660 | 1137 | -1344 | -2220 | -820 | -1011 | 449 | 478 | -5348 | 101 | 2251 | -664 | -1116 | -5373 | -1053 | -1846 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12284 | -13326 | -894 | -1115 | -1284 | -763 | * | * | | | | | | | | | | | | |
| 8(V) | -536 | -160 | -6955 | -6321 | -2167 | -2340 | -5033 | -2309 | -5917 | -1649 | 1176 | -5805 | -6208 | -5540 | -5717 | -1330 | 1399 | 1263 | -4898 | -4555 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |
| 9(A) | 2327 | -4455 | -6573 | -493 | -102 | 86 | -4930 | -860 | -2705 | 369 | 1206 | -2785 | -6131 | -681 | -3038 | -468 | 35 | -556 | 850 | -50 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |
| 10(K) | 106 | 143 | -540 | 565 | 685 | -1207 | 519 | -254 | 759 | 301 | -153 | -86 | -5386 | 680 | 325 | -947 | -74 | -957 | -1277 | 752 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -2025 | -407 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 11(A) | -1672 | -4431 | -1705 | -6136 | 563 | -2139 | 579 | 2041 | -1029 | 1666 | -61 | -643 | -6160 | -996 | -1360 | -3179 | -672 | 229 | 120 | 931 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12294 | -13336 | -894 | -1115 | -873 | -1139 | * | * | | | | | | | | | | | | |
| 12(A) | 2331 | 708 | -6943 | -6307 | -942 | 70 | -1636 | -90 | -5901 | 969 | -53 | -5791 | -2589 | -5524 | -5701 | 529 | 266 | -557 | -4881 | -4539 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -38 | -12306 | -5292 | -894 | -1115 | -1510 | -624 | * | * | | | | | | | | | | | | |
| 13(R) | 1024 | -294 | -2416 | 793 | -1452 | 217 | 143 | -1928 | 44 | -225 | 380 | -921 | -5348 | 62 | 1539 | -450 | -606 | 101 | -5884 | -139 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12268 | -13311 | -894 | -1115 | -1705 | -528 | * | * | | | | | | | | | | | | |
| 14(E) | -61 | -460 | -736 | 1184 | -2769 | -906 | -428 | 232 | 796 | 76 | 823 | -980 | -2857 | 322 | 1100 | -471 | -263 | -1162 | 173 | 171 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12279 | -13321 | -894 | -1115 | -825 | -1199 | * | * | | | | | | | | | | | | |
| 15(I) | -802 | -1524 | -6937 | -2206 | 7 | -6139 | -522 | 2283 | -2763 | 2037 | 1603 | -5785 | -6189 | -1341 | -5695 | -3146 | -4532 | -870 | 995 | 545 | 15 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12300 | -13342 | -894 | -1115 | -1806 | -486 | * | * | | | | | | | | | | | | |
| 16(A) | 2333 | 1375 | -1364 | -1583 | -868 | 1228 | -980 | -1889 | -783 | -1301 | -1420 | -97 | -5429 | -497 | -1394 | -148 | -451 | -1153 | -901 | -2014 | 16 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -15 | -12300 | -6586 | -894 | -1115 | -1085 | -920 | * | * | | | | | | | | | | | | |
| 17(E) | -508 | -1353 | 1150 | 1704 | -6074 | -715 | -1372 | -581 | -54 | 185 | 626 | -191 | -131 | -580 | 1156 | -1161 | -2738 | -522 | 139 | -5259 | 17 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -41 | -12291 | -5172 | -894 | -1115 | -2155 | -367 | * | * | | | | | | | | | | | | |
| 18(D) | -229 | -5721 | 1297 | 1157 | -2426 | -361 | 1053 | -249 | 920 | -1935 | -197 | -289 | -2682 | -150 | 1188 | 61 | -816 | -1579 | -5904 | -517 | 18 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -30 | -12250 | -5594 | -894 | -1115 | -1947 | -433 | * | * | | | | | | | | | | | | |
| 19(L) | -683 | -5040 | -1357 | 560 | -260 | -2605 | 306 | 884 | -1771 | 1549 | 883 | -640 | 113 | -2005 | -1223 | -1317 | -466 | 286 | 168 | 551 | 19 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -13 | -12233 | -6827 | -894 | -1115 | -3401 | -143 | * | * | | | | | | | | | | | | |
| 20(G) | -33 | -5693 | 618 | 205 | -400 | 2100 | -1605 | -5764 | 598 | -789 | -4782 | 945 | 61 | -455 | -244 | -1169 | -745 | -5315 | -747 | -2247 | 20 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1376 | -12220 | -702 | -894 | -1115 | -3568 | -127 | * | * | | | | | | | | | | | | |
| 21(L) | -967 | -330 | -404 | 1355 | 819 | -3938 | 883 | -4321 | 715 | 1566 | 1186 | -1136 | -4030 | -2156 | 11 | -1333 | -546 | -3918 | -4527 | 330 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10845 | -11887 | -894 | -1115 | -6678 | -14 | * | * | | | | | | | | | | | | |
| 22(S) | -2938 | -4411 | 833 | 1016 | -4732 | 1037 | 1037 | -558 | -1768 | 17 | -4427 | -3500 | -2547 | 438 | 554 | 813 | 1452 | -469 | -639 | -4594 | 22 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2135 | -10845 | -374 | -894 | -1115 | -5759 | -27 | * | * | | | | | | | | | | | | |
| 23(K) | 653 | -2755 | -1181 | 1147 | -3063 | -2297 | -952 | 316 | 1700 | 199 | -1848 | 579 | -2389 | 1127 | 344 | -1206 | -1257 | -2370 | -2943 | -2273 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8811 | -9853 | -894 | -1115 | -7183 | -10 | * | * | | | | | | | | | | | | |
| 24(H) | -1361 | -2811 | 694 | -648 | -3121 | -2319 | 3483 | -2868 | -566 | -2822 | -1905 | -957 | 493 | 1015 | 711 | 302 | -1300 | -2430 | -2995 | 1919 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -121 | -8811 | -3679 | -894 | -1115 | -4003 | -93 | * | * | | | | | | | | | | | | |
| 25(P) | 561 | 1575 | -2251 | 763 | 315 | -2987 | -1765 | -2207 | -1584 | -2440 | -1695 | 429 | 2670 | -1496 | -1983 | 593 | -1800 | -76 | -2886 | -2401 | 25 |
| - | -142 | -502 | -230 | 45 | -378 | 396 | 103 | -623 | 212 | -460 | -723 | 273 | 391 | 43 | 98 | 357 | 115 | -369 | -297 | -252 | |
| - | -4564 | -63 | -10442 | -11 | -7098 | -7112 | -10 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 26(W) | 662 | 1121 | -3977 | -3360 | 201 | 1100 | -2296 | -1303 | -3018 | 361 | 1280 | 219 | -3495 | 1823 | -2923 | -2513 | -384 | -1220 | 2650 | 871 | 27 |
| - | -148 | -493 | 231 | 43 | -378 | 396 | 108 | -624 | 213 | -464 | -723 | 275 | 394 | 46 | 94 | 363 | 115 | -372 | -297 | -252 | |
| - | -4564 | -147 | -4190 | -11 | -7015 | -7112 | -10 | * | * | | | | | | | | | | | | |
| 27(E) | -124 | -3120 | -1534 | 1849 | 332 | -2653 | -1311 | -3173 | 1563 | -3131 | 474 | 464 | -2746 | -855 | 869 | -1561 | 1470 | -2737 | -3309 | -2635 | 29 |
| - | -149 | -500 | 233 | 43 | -381 | 398 | 105 | -627 | 210 | -464 | -721 | 278 | 393 | 45 | 96 | 359 | 119 | -370 | -295 | -250 | |
| - | -4484 | -2472 | -368 | -57 | -4701 | -7124 | -10 | * | * | | | | | | | | | | | | |
| 28(F) | -665 | -1391 | -929 | -444 | 1996 | -1685 | -451 | -1255 | 1745 | -1418 | -695 | -613 | -1850 | -202 | -447 | 1413 | -646 | -1024 | -1580 | -911 | 31 |
| - | -149 | -500 | 233 | 43 | -376 | 398 | 105 | -626 | 210 | -464 | -721 | 275 | 394 | 45 | 96 | 359 | 117 | -370 | -295 | -250 | |
| - | -2336 | -899 | -1912 | -82 | -4179 | -6161 | -20 | * | * | | | | | | | | | | | | |
| 29(F) | -2165 | -1761 | -4457 | -3893 | 2442 | -3991 | -2646 | 2145 | -3596 | 1858 | 559 | -3601 | -3602 | -2842 | -3298 | -3183 | -2068 | -224 | -1854 | -1590 | 33 |
| - | -150 | -501 | 234 | 44 | -382 | 398 | 105 | -623 | 212 | -465 | -721 | 274 | 393 | 48 | 98 | 358 | 116 | -370 | -295 | -250 | |
| - | -2334 | -325 | -8212 | -1212 | -815 | -5655 | -29 | * | * | | | | | | | | | | | | |
| 30(H) | 921 | -2125 | -640 | -137 | -2481 | 816 | 2372 | -2198 | 17 | -2183 | -1295 | 1292 | -1861 | 2 | 1445 | -699 | -744 | -1787 | -2375 | -1739 | 37 |
| - | -149 | -500 | 232 | 43 | -381 | 400 | 105 | -627 | 212 | -466 | -721 | 275 | 393 | 48 | 95 | 359 | 117 | -370 | -295 | -244 | |
| - | -1869 | -466 | -8764 | -43 | -5082 | -5244 | -39 | * | * | | | | | | | | | | | | |
| 31(V) | -1106 | -1168 | -2422 | -1835 | -1153 | 445 | -1301 | 700 | 774 | 1026 | -357 | -1761 | -2564 | 1168 | -1704 | -1535 | -1045 | 1667 | -1608 | -1229 | 39 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -7 | -8272 | -9314 | -894 | -1115 | -3590 | -125 | * | * | | | | | | | | | | | | |
| 32(L) | -2525 | -2329 | -4759 | -4141 | 1398 | -4064 | -2752 | 809 | -3685 | 2288 | -1194 | -3648 | -4062 | 372 | 1504 | -3158 | -2458 | -1664 | -2487 | 502 | 40 |
| - | -147 | -502 | 233 | 41 | -379 | 398 | 110 | -628 | 211 | -466 | -709 | 276 | 396 | 43 | 94 | 358 | 115 | -368 | -286 | -251 | |
| - | -1940 | -437 | -10450 | -14 | -6738 | -4999 | -46 | * | * | | | | | | | | | | | | |
| 33(Q) | -1949 | -2946 | -17 | 1465 | 877 | -3010 | -1696 | 1014 | -1381 | -75 | -2081 | -241 | 1422 | 1926 | -1844 | -1941 | -1889 | -2478 | -3235 | 432 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9620 | -10662 | -894 | -1115 | -3911 | -99 | * | * | | | | | | | | | | | | |
| 34(W) | -2450 | -2411 | -4111 | 22 | -25 | 2176 | -2734 | 1018 | 662 | 51 | -1608 | -3306 | -3964 | -2979 | 171 | -2958 | -2390 | -613 | 5120 | -2491 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -188 | -10029 | -3047 | -894 | -1115 | -5179 | -40 | * | * | | | | | | | | | | | | |
| 35(Y) | -660 | -3617 | 1283 | -234 | -3923 | 89 | 382 | -3662 | 1266 | -349 | -2710 | -1802 | -407 | -1366 | -1912 | -29 | 757 | 606 | -3810 | 1513 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9966 | -11008 | -894 | -1115 | -1630 | -563 | * | * | | | | | | | | | | | | |
| 36(E) | -1718 | -4708 | 1063 | 1951 | 101 | -1877 | -452 | -325 | -533 | -830 | -3797 | 183 | 866 | 828 | -280 | 229 | -1678 | -1022 | -4891 | -1535 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11173 | -12216 | -894 | -1115 | -644 | -1474 | * | * | | | | | | | | | | | | |
| 37(E) | 500 | 125 | -65 | 1207 | 81 | -342 | -1412 | 55 | -227 | 865 | 276 | -2309 | -155 | -1226 | -938 | -1391 | -658 | 626 | -5547 | -4911 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -12001 | -13043 | -894 | -1115 | -2448 | -292 | * | * | | | | | | | | | | | | |
| 38(D) | -452 | -5536 | 2804 | 412 | 378 | -5037 | -652 | -5608 | 322 | -3511 | -510 | 1811 | -1670 | -1101 | -147 | -239 | -2517 | -3012 | -5719 | -5037 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -12056 | -13099 | -894 | -1115 | -4789 | -53 | * | * | | | | | | | | | | | | |
| 39(P) | -55 | -5488 | -681 | 428 | -5786 | -1574 | -3712 | -49 | 758 | 154 | -202 | -3695 | 1630 | -1018 | 1236 | -2 | -4008 | 980 | -5684 | -5016 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -12056 | -13099 | -894 | -1115 | -4789 | -53 | * | * | | | | | | | | | | | | |
| 40(E) | -269 | -870 | 1503 | 2205 | -1301 | -1321 | -516 | -294 | -323 | -422 | -4622 | 404 | -5131 | -770 | -65 | -159 | -944 | -1046 | -5717 | -5035 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -12056 | -13099 | -894 | -1115 | -4789 | -53 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 41(L) | -764 | 664 | -606 | -965 | -5070 | -5259 | -1163 | 370 | 1275 | 1778 | -4109 | -2284 | -5343 | -997 | 645 | -4199 | 86 | 600 | -474 | -380 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -12056 | -13099 | -894 | -1115 | -33 | -5466 | * | * | | | | | | | | | | | | |
| 42(L) | 1140 | 1390 | -6954 | -1564 | -2054 | -6156 | -5027 | 1258 | -5913 | 1579 | -1826 | -5802 | -6206 | -5535 | -5712 | -1218 | 556 | 1302 | 1563 | -1075 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -43 | -12317 | -5098 | -894 | -1115 | -701 | -1378 | * | * | | | | | | | | | | | | |
| 43(R) | 31 | -4876 | -3076 | 154 | -520 | -2185 | -1420 | 163 | 292 | 929 | -270 | -4587 | -5719 | 397 | 1713 | -2015 | -1806 | 376 | 728 | 1566 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12274 | -13316 | -894 | -1115 | -153 | -3312 | * | * | | | | | | | | | | | | |
| 44(W) | 573 | 677 | -6914 | -1803 | 201 | -6150 | -5019 | 803 | 555 | 1139 | 921 | -2881 | -6200 | -2416 | 133 | -3346 | 678 | 1111 | 1796 | -4553 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 45(A) | 2913 | 326 | -6953 | -6317 | -4389 | 975 | -1402 | 188 | -5913 | -851 | 278 | -5802 | -6206 | -5536 | -5713 | -627 | -679 | -2661 | -4893 | -658 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 46(A) | 2785 | 1854 | -7201 | -6621 | -4736 | 1960 | -5343 | -1888 | -6218 | -3077 | -3983 | -6003 | -2518 | -5833 | -6010 | -1199 | -667 | -1348 | -5236 | -1073 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 47(L) | -1113 | -4435 | -6954 | -3337 | -45 | -6156 | -1733 | 1240 | -5913 | 2747 | -619 | -5802 | -895 | -5535 | -1997 | -5240 | -1821 | -1446 | -4892 | 579 | 56 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 48(L) | -810 | 364 | -7041 | -6405 | 941 | -6247 | -5117 | -619 | -6002 | 2713 | 733 | -5893 | -6289 | -5618 | -5800 | -2221 | -4634 | -216 | -4971 | 1438 | 57 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 49(H) | -10904 | -9193 | -10099 | -10486 | -10487 | -9143 | 5479 | -11804 | -10682 | -11065 | -11093 | -10541 | -9573 | -10579 | -10094 | -11509 | -11021 | -11538 | -9266 | -10430 | 58 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 50(D) | -6916 | -8991 | 4191 | -1873 | -9117 | -6590 | -6077 | -9156 | -6563 | -8965 | -8450 | -2365 | -7196 | -5780 | -7634 | -6502 | -7029 | -8579 | -9124 | -7992 | 59 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 51(I) | -869 | 410 | -7191 | -6566 | -1443 | -6415 | -5307 | 2973 | -6172 | 1082 | -79 | -6061 | -6453 | -5800 | -5980 | -5507 | 69 | 1364 | -5159 | -1099 | 60 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 52(G) | 810 | -1204 | -1331 | -6312 | -2257 | 3101 | -1437 | -246 | -5908 | -1368 | -1385 | -5799 | -1547 | -5532 | -5710 | -1667 | -2487 | 386 | -4893 | -4551 | 61 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 53(K) | -4313 | -5786 | -1770 | 1872 | -6107 | -2886 | 2495 | -5858 | 2750 | -2037 | -663 | -496 | -5380 | -1206 | 216 | -2114 | -1256 | -5408 | -5969 | -591 | 62 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 54(D) | 520 | 295 | 1427 | -1551 | -145 | 896 | -4933 | 776 | -5587 | -1516 | -355 | -5587 | 1181 | -1085 | -2646 | 130 | -507 | 602 | -4938 | 14 | 63 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 55(P) | -600 | -5636 | -1245 | -1015 | -630 | -398 | 235 | -40 | -177 | 545 | -1847 | -1526 | 1440 | -370 | 792 | -1748 | 883 | 481 | -1142 | 529 | 64 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -341 | -12317 | -2251 | -894 | -1115 | -701 | -1378 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 56(F) | -2461 | -5343 | -2308 | -195 | 1966 | -359 | 871 | 925 | -1423 | -1913 | -4446 | -836 | 1131 | -111 | -973 | -285 | 1184 | 631 | -399 | -1383 | 65 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11977 | -13019 | -894 | -1115 | -3241 | -161 | * | * | | | | | | | | | | | | |
| 57(P) | -4017 | -5489 | -1601 | -369 | -738 | 1622 | 56 | -5560 | -669 | -2674 | -406 | 174 | 1938 | -256 | 456 | 953 | -162 | -2251 | -5672 | 635 | 66 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -111 | -12007 | -3765 | -894 | -1115 | -1895 | -452 | * | * | | | | | | | | | | | | |
| 58(H) | -456 | -5470 | 2679 | 197 | -5790 | -707 | 3012 | -2004 | -2203 | -3345 | -356 | -1859 | -2388 | 6 | 244 | -468 | -690 | -1410 | -5653 | -827 | 67 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -711 | -11988 | -1362 | -894 | -1115 | -2047 | -400 | * | * | | | | | | | | | | | | |
| 59(W) | 186 | -4915 | -759 | 511 | 523 | 282 | 1063 | 206 | 485 | -2786 | -4005 | -1065 | -1111 | 109 | -852 | 509 | -200 | 235 | 1111 | 1045 | 68 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11406 | -12448 | -894 | -1115 | -6236 | -19 | * | * | | | | | | | | | | | | |
| 60(F) | -3516 | -4446 | 12 | -1005 | 2098 | 694 | -3285 | 1423 | -915 | -138 | 722 | -1439 | 233 | 412 | -1483 | -877 | 106 | -390 | -4749 | -1295 | 69 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11406 | -12448 | -894 | -1115 | -6236 | -19 | * | * | | | | | | | | | | | | |
| 61(E) | -1185 | -4871 | 302 | 2034 | -5168 | -4440 | -3101 | -1407 | -782 | 1593 | -3967 | -3085 | 98 | -430 | -798 | -388 | -506 | 64 | -5069 | -1222 | 70 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -143 | -11406 | -3411 | -894 | -1115 | -5306 | -37 | * | * | | | | | | | | | | | | |
| 62(E) | -95 | -4805 | -125 | 1652 | -5124 | -4310 | -2969 | -1517 | 1183 | -244 | -3894 | 1074 | -4403 | 734 | 1560 | -1202 | -3275 | -1052 | 250 | 248 | 71 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -40 | -11281 | -5212 | -894 | -1115 | -6363 | -18 | * | * | | | | | | | | | | | | |
| 63(K) | 611 | -3809 | 348 | -3620 | -3831 | -1134 | -3474 | 1558 | 1790 | -360 | 406 | 810 | -4796 | -3344 | -141 | -3708 | 251 | -179 | -4206 | 19 | 72 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11242 | -12284 | -894 | -1115 | -6399 | -17 | * | * | | | | | | | | | | | | |
| 64(Q) | 201 | -4524 | -1401 | -596 | 212 | -1050 | -3024 | 427 | -563 | 1134 | -3642 | -3038 | 1037 | 1176 | -340 | 164 | -412 | -1058 | -4773 | 616 | 73 |
| - | -150 | -501 | 232 | 42 | -382 | 397 | 104 | -628 | 209 | -465 | -722 | 277 | 397 | 44 | 97 | 358 | 118 | -367 | -265 | -251 | |
| - | -174 | -3704 | -4757 | -853 | -1164 | -5302 | -37 | * | * | | | | | | | | | | | | |
| 65(E) | 592 | -4743 | -969 | 1615 | -5065 | 988 | 890 | -2042 | 663 | -4759 | 1097 | 595 | -4337 | -952 | 501 | -329 | 753 | -4365 | -4927 | -4244 | 76 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -876 | -11211 | -1137 | -894 | -1115 | -4296 | -75 | * | * | | | | | | | | | | | | |
| 66(K) | -505 | 1389 | -998 | 1059 | -698 | 314 | -2233 | 565 | 2527 | -1590 | -3131 | 139 | -3666 | -1777 | 17 | -1183 | -2534 | -3654 | -4229 | -3554 | 77 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10453 | -11496 | -894 | -1115 | -4566 | -62 | * | * | | | | | | | | | | | | |
| 67(L) | -701 | 271 | 661 | -4531 | -543 | -150 | 1056 | 1380 | -4158 | 1637 | -2007 | 788 | -4539 | -638 | -4009 | -3566 | -2897 | -529 | -3281 | 1517 | 78 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -196 | -10578 | -2988 | -894 | -1115 | -6807 | -13 | * | * | | | | | | | | | | | | |
| 68(M) | 718 | -3961 | 340 | -1853 | 44 | 491 | 362 | 795 | 23 | -3969 | 2259 | 190 | 1143 | 494 | -2270 | 425 | -2475 | -3572 | -4156 | -3486 | 79 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -107 | -10384 | -3826 | -894 | -1115 | -4481 | -66 | * | * | | | | | | | | | | | | |
| 69(R) | -714 | -4046 | 448 | -791 | 709 | -658 | 448 | -4117 | 558 | 644 | -3135 | 1169 | -3640 | 1135 | 1755 | -1026 | -156 | -3667 | -4229 | -3546 | 80 |
| - | -144 | -505 | 228 | 47 | -370 | 396 | 105 | -632 | 217 | -467 | -726 | 273 | 398 | 46 | 96 | 358 | 112 | -371 | -300 | -249 | |
| - | -5596 | -31 | -11474 | -5 | -8151 | -4464 | -67 | * | * | | | | | | | | | | | | |
| 70(H) | -2694 | -4157 | -124 | 783 | -1390 | -195 | 2538 | -412 | 438 | -157 | -3247 | 30 | -852 | -354 | 1140 | -2576 | 361 | -1269 | -4343 | 1362 | 82 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10569 | -11612 | -894 | -1115 | -6811 | -13 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 71(H) | -2701 | -4173 | 1863 | 1171 | -4493 | 434 | 2194 | 635 | 476 | -4189 | -338 | -2308 | 432 | -317 | -2422 | 794 | -2640 | -3795 | -4356 | -3674 | 83 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -656 | -10569 | -1455 | -894 | -1115 | -5895 | -24 | * | * | | | | | | | | | | | | |
| 72(Q) | -2173 | -3634 | -574 | 1547 | -3949 | 1717 | -1808 | -578 | 821 | -3847 | 186 | -1786 | -509 | 1747 | -1897 | -95 | -2112 | 51 | -3820 | -3141 | 84 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1487 | -9958 | -639 | -894 | -1115 | -5197 | -40 | * | * | | | | | | | | | | | | |
| 73(L) | -1532 | -1473 | -3246 | 981 | -1395 | -3003 | -1831 | 1418 | -2332 | 1799 | 1683 | -2421 | -3050 | -2087 | 323 | -2059 | 566 | -849 | -1914 | -1563 | 85 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -5 | -8772 | -9814 | -894 | -1115 | -3661 | -119 | * | * | | | | | | | | | | | | |
| 74(P) | -3187 | -2946 | -5461 | -4875 | 1864 | -4784 | -3540 | 1543 | -4505 | 1882 | -1394 | 795 | 1970 | -3998 | -4274 | -3903 | -3120 | -2025 | -3149 | -2759 | 86 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9603 | -10645 | -894 | -1115 | -4951 | -47 | * | * | | | | | | | | | | | | |
| 75(T) | -591 | -3110 | 1410 | -1587 | -3278 | -3133 | -1816 | -127 | -319 | 794 | -2243 | -183 | -196 | -1432 | -1956 | 977 | 1815 | -2648 | -3394 | 62 | 87 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -9792 | -10835 | -894 | -1115 | -3098 | -179 | * | * | | | | | | | | | | | | |
| 76(P) | -2757 | -2940 | 410 | -3206 | -2941 | -4086 | 1890 | -976 | -3006 | -836 | -2130 | -3229 | 2783 | -2861 | -736 | -3102 | 2340 | -798 | -3361 | -2962 | 88 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -2 | -10402 | -11444 | -894 | -1115 | -3561 | -128 | * | * | | | | | | | | | | | | |
| 77(E) | 600 | -4259 | 289 | 1784 | -4577 | -3768 | 54 | -1398 | -238 | -650 | -3349 | -2405 | 530 | 547 | 374 | -854 | 4 | 22 | -4444 | 1095 | 89 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10682 | -11724 | -894 | -1115 | -3432 | -140 | * | * | | | | | | | | | | | | |
| 78(E) | -1711 | -4456 | -527 | 2330 | -1854 | -1549 | -2644 | -4510 | 57 | 390 | -3547 | -1128 | -4078 | -2188 | -1311 | 180 | 1487 | 552 | -4645 | -3969 | 90 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10919 | -11961 | -894 | -1115 | -2001 | -415 | * | * | | | | | | | | | | | | |
| 79(D) | -1425 | -566 | 2163 | 1620 | -5237 | -166 | -3081 | -4986 | -1343 | -287 | -104 | -1367 | -849 | 71 | -259 | -430 | -193 | -774 | -5102 | 1076 | 91 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11403 | -12445 | -894 | -1115 | -6240 | -19 | * | * | | | | | | | | | | | | |
| 80(F) | -36 | -414 | -1889 | -32 | 2385 | -438 | 769 | -4836 | 558 | -593 | -1232 | -537 | -1175 | -244 | 519 | -3358 | 73 | -289 | 1859 | 641 | 92 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11403 | -12445 | -894 | -1115 | -6240 | -19 | * | * | | | | | | | | | | | | |
| 81(E) | -1293 | -4920 | 143 | 1492 | -53 | 1150 | 276 | -2131 | -425 | -1715 | -4009 | 1198 | -317 | -1278 | 60 | -75 | -263 | 533 | -5103 | -4421 | 93 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -165 | -11403 | -3214 | -894 | -1115 | -3270 | -158 | * | * | | | | | | | | | | | | |
| 82(I) | -2079 | 653 | -1027 | 818 | -5117 | -1066 | -3066 | 1629 | 539 | -484 | -56 | -882 | 1048 | -605 | 102 | 448 | -503 | -149 | 716 | -4359 | 94 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11365 | -12407 | -894 | -1115 | -2529 | -274 | * | * | | | | | | | | | | | | |
| 83(M) | -2298 | -543 | -1544 | 1357 | 1983 | -267 | 705 | 754 | -258 | 274 | 2610 | -3731 | -4956 | -195 | -1656 | -1286 | -2027 | -1000 | -4707 | -4220 | 95 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11570 | -12613 | -894 | -1115 | -2225 | -347 | * | * | | | | | | | | | | | | |
| 84(H) | -688 | -5080 | -1979 | -160 | -1216 | -677 | 1920 | 450 | 1278 | 385 | 1004 | -1979 | -1090 | 90 | 1125 | -3721 | -2370 | 443 | -5310 | 649 | 96 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -42 | -11757 | -5146 | -894 | -1115 | -2091 | -386 | * | * | | | | | | | | | | | | |
| 85(S) | 542 | -5350 | 897 | -223 | -2003 | 941 | -322 | -348 | 81 | 371 | -4440 | -43 | -2010 | -923 | -622 | 1108 | -383 | -2981 | -452 | -731 | 97 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11865 | -12907 | -894 | -1115 | -719 | -1349 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 86(H) | -4276 | -5484 | -844 | -3668 | 535 | -5274 | 5023 | -2699 | -3580 | -5457 | -2130 | -19 | -831 | -1759 | -837 | -1604 | -2488 | -5054 | -5727 | -5111 | 98 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12156 | -13198 | -894 | -1115 | -417 | -1993 | * | * | | | | | | | | | | | | |
| 87(E) | 833 | -5727 | -447 | 982 | -943 | 110 | -450 | 437 | -522 | -819 | -462 | -370 | -61 | -1826 | -2362 | 784 | 284 | 641 | -5917 | -5241 | 99 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12280 | -13322 | -894 | -1115 | -171 | -3160 | * | * | | | | | | | | | | | | |
| 88(E) | -1407 | -5763 | 205 | 1018 | 93 | -3222 | -1465 | 988 | 982 | -1212 | -138 | -1574 | -854 | 181 | 400 | -940 | 249 | 985 | -5953 | 285 | 100 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 89(V) | 436 | -5272 | 839 | 450 | 330 | -5478 | -55 | 697 | -713 | 610 | -954 | -1425 | -458 | -910 | -1770 | -2199 | -889 | 1170 | 687 | 777 | 101 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 90(G) | 508 | -4444 | -6956 | -6321 | -339 | 2933 | -5037 | -1598 | -5918 | -2910 | -1739 | -5807 | -6211 | -5542 | -1761 | 1057 | 286 | -228 | -4905 | -4562 | 102 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 91(A) | 2127 | -362 | -1357 | 39 | -1134 | -1758 | -4787 | -774 | -1294 | -1394 | -1759 | -2472 | -6035 | -4941 | 1287 | -1488 | -3029 | 1353 | -753 | 1467 | 103 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -112 | -12317 | -3747 | -894 | -1115 | -701 | -1378 | * | * | | | | | | | | | | | | |
| 92(E) | -570 | -1209 | -47 | 2128 | -820 | -1232 | -1274 | -1185 | 886 | -1150 | -1569 | -474 | -2676 | -115 | 381 | -537 | 641 | -1255 | -5858 | 808 | 104 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12205 | -13247 | -894 | -1115 | -1639 | -559 | * | * | | | | | | | | | | | | |
| 93(I) | -2106 | -4474 | -211 | -93 | 136 | -5934 | -4758 | 2176 | 796 | 1062 | 1994 | -5302 | -2601 | -318 | -1115 | -4980 | -1873 | 139 | -4915 | -470 | 105 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12237 | -13280 | -894 | -1115 | -2468 | -288 | * | * | | | | | | | | | | | | |
| 94(L) | 1572 | -1591 | -6886 | -6250 | -1338 | -1408 | -4959 | 1159 | -5845 | 1676 | -3570 | -1557 | -2589 | -5467 | -5645 | -914 | -310 | 1496 | -4825 | -4483 | 106 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12245 | -13287 | -894 | -1115 | -3208 | -165 | * | * | | | | | | | | | | | | |
| 95(R) | 210 | 275 | -441 | 308 | -1383 | -1685 | 374 | -3081 | 1590 | -961 | -1548 | -3859 | -1641 | 115 | 1927 | 678 | -595 | -920 | -5891 | -663 | 107 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12245 | -13287 | -894 | -1115 | -2112 | -379 | * | * | | | | | | | | | | | | |
| 96(K) | -246 | -5727 | 1122 | 1400 | -6049 | -545 | 534 | -2023 | 1443 | -1689 | -4816 | -315 | -801 | 1384 | 995 | -815 | -1332 | -5349 | -5911 | -96 | 108 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12256 | -13298 | -894 | -1115 | -3019 | -190 | * | * | | | | | | | | | | | | |
| 97(F) | -424 | -1406 | -1791 | 877 | 1060 | -3307 | 377 | 355 | -769 | 641 | -193 | -441 | -5546 | -694 | 280 | 144 | -1229 | 694 | 567 | 904 | 109 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -49 | -12256 | -4905 | -894 | -1115 | -3019 | -190 | * | * | | | | | | | | | | | | |
| 98(F) | -33 | 1324 | -269 | 906 | 1374 | 774 | -696 | -1059 | 641 | 537 | -237 | 72 | -176 | -916 | -1791 | -1274 | -614 | -5291 | -5857 | -1406 | 110 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12207 | -13250 | -894 | -1115 | -2592 | -262 | * | * | | | | | | | | | | | | |
| 99(K) | -1012 | -5687 | -641 | 1017 | 633 | 322 | -56 | 414 | 1495 | 103 | -4776 | -63 | -3046 | -207 | -280 | -832 | -1329 | -493 | -5871 | 590 | 111 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12219 | -13261 | -894 | -1115 | -3580 | -126 | * | * | | | | | | | | | | | | |
| 100(R) | 120 | -985 | 491 | 130 | -73 | -2013 | -827 | -1509 | -581 | 238 | -2070 | -234 | 1573 | -1282 | 1646 | -572 | -2814 | 310 | 100 | -2091 | 112 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12219 | -13261 | -894 | -1115 | -3580 | -126 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 101(E) | -1479 | -798 | 617 | 1007 | 100 | -1433 | 740 | -88 | -569 | 604 | 212 | 598 | 329 | -432 | 353 | -194 | -557 | -2483 | -59 | 40 | 113 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -792 | -12219 | -1244 | -894 | -1115 | -2716 | -238 | * | * | | | | | | | | | | | | |
| 102(G) | 9 | -4952 | 691 | -45 | -53 | 1668 | -1223 | -233 | 912 | -1118 | 190 | -92 | -422 | 127 | 860 | -2158 | -3423 | -4572 | 909 | -1101 | 114 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11441 | -12484 | -894 | -1115 | -6196 | -20 | * | * | | | | | | | | | | | | |
| 103(W) | -2238 | -3702 | -915 | 1453 | 1039 | -5181 | -4008 | -590 | -448 | 1347 | -861 | -4565 | -440 | -4240 | -1163 | -93 | -522 | 683 | 1535 | 646 | 115 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1984 | -11441 | -421 | -894 | -1115 | -5297 | -37 | * | * | | | | | | | | | | | | |
| 104(N) | 422 | -3217 | 635 | -1157 | -3505 | -2813 | -1475 | 457 | 1974 | -3219 | -2315 | 2098 | -2905 | -1026 | 157 | -1723 | 32 | -2821 | 1417 | 209 | 116 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -3 | -9517 | -10559 | -894 | -1115 | -4757 | -54 | * | * | | | | | | | | | | | | |
| 105(Q) | -2007 | -3478 | -1855 | 657 | 333 | 703 | 976 | -3549 | 967 | -372 | -2567 | 701 | -3074 | 1391 | 452 | 1301 | -1946 | -3100 | -3661 | -2980 | 117 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -241 | -9754 | -2714 | -894 | -1115 | -5545 | -31 | * | * | | | | | | | | | | | | |
| 106(E) | -1911 | -3381 | 582 | 1799 | -3701 | 635 | -1543 | -3450 | 1113 | 335 | -2471 | -1519 | 561 | -1084 | 598 | -362 | -1850 | -3002 | -3565 | 286 | 118 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1784 | -9629 | -497 | -894 | -1115 | -7074 | -11 | * | * | | | | | | | | | | | | |
| 107(K) | -2457 | -3808 | 1635 | -910 | -4290 | -2543 | -1665 | -4144 | 3475 | -3974 | -3296 | -1242 | -2974 | -1319 | -1603 | -2208 | -2467 | -3700 | -3918 | -3329 | 119 |
| - | -150 | -501 | 232 | 42 | -378 | 399 | 105 | -627 | 209 | -467 | -721 | 274 | 395 | 47 | 97 | 360 | 118 | -368 | -295 | -250 | |
| - | -3019 | -1262 | -1121 | -1407 | -683 | -4773 | -54 | * | * | | | | | | | | | | | | |
| 108(Y) | -4177 | -3479 | -4751 | -4713 | 2821 | -4740 | 2600 | -3362 | -4026 | -2860 | -2810 | -3448 | -4641 | -3414 | 2053 | -3942 | -4051 | -3443 | -553 | 3186 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -8 | -8094 | -9136 | -894 | -1115 | -1593 | -581 | * | * | | | | | | | | | | | | |
| 109(D) | -260 | -4425 | 1518 | 244 | -1148 | 928 | -259 | -4496 | -601 | -626 | -3514 | 676 | 1492 | -724 | -2672 | 1054 | -606 | -4047 | -4608 | -3925 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10860 | -11902 | -894 | -1115 | -4294 | -75 | * | * | | | | | | | | | | | | |
| 110(P) | 450 | -422 | 92 | 1043 | -4837 | -44 | -282 | -4588 | 776 | -614 | -3605 | -1077 | 1766 | 1079 | -622 | -1724 | -1269 | -1096 | -4699 | 900 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10962 | -12004 | -894 | -1115 | -5125 | -42 | * | * | | | | | | | | | | | | |
| 111(E) | 244 | -4554 | 780 | 1683 | -1065 | 312 | -121 | -611 | 885 | -4570 | 455 | 800 | -165 | 751 | -14 | -1504 | -3020 | -4176 | -4737 | -4054 | 127 |
| - | -149 | -508 | 242 | 58 | -381 | 393 | 98 | -634 | 213 | -458 | -717 | 272 | 385 | 53 | 91 | 354 | 114 | -369 | -302 | -242 | |
| - | -6167 | -21 | -12045 | -3 | -8730 | -5734 | -27 | * | * | | | | | | | | | | | | |
| 112(I) | 753 | -3228 | -1508 | -1620 | -39 | -4880 | -3737 | 1659 | -792 | 366 | 1174 | -4441 | -4932 | -4154 | -156 | -1830 | 1468 | 1324 | -3682 | -3333 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11021 | -12063 | -894 | -1115 | -3670 | -118 | * | * | | | | | | | | | | | | |
| 113(E) | -677 | -4695 | 1529 | 2164 | -5015 | -4198 | -2856 | -225 | 497 | -729 | 1322 | -1416 | -1210 | 984 | -179 | -722 | -1351 | -4317 | 981 | -4196 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11160 | -12202 | -894 | -1115 | -472 | -1840 | * | * | | | | | | | | | | | | |
| 114(D) | 699 | -5480 | 1676 | 1262 | -2163 | -5080 | -3742 | 341 | -764 | -74 | -183 | -758 | -884 | -1899 | 497 | -580 | 345 | -151 | -5685 | -1838 | 131 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12077 | -13119 | -894 | -1115 | -428 | -1963 | * | * | | | | | | | | | | | | |
| 115(V) | 390 | -1260 | -1425 | -6246 | 364 | -2143 | -4969 | 1880 | -3164 | 311 | -1567 | -2699 | -6149 | -924 | -1444 | -3260 | -1069 | 2493 | -4840 | -1327 | 132 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12261 | -13303 | -894 | -1115 | -124 | -3603 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 116(C) | 1423 | 1712 | -1842 | -516 | -285 | -842 | -4557 | 612 | -127 | 1024 | -3956 | -4858 | -5865 | 313 | -603 | 257 | -1781 | -27 | -728 | -1020 | 133 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -10962 | -12004 | -894 | -1115 | -5125 | -42 | * | * | | | | | | | | | | | | |
| 117(H) | -249 | -5785 | 504 | 1156 | -2836 | -1623 | 1825 | -2077 | 1110 | -1422 | -4874 | 1283 | -829 | 479 | 495 | -224 | -630 | -1531 | 1265 | -930 | 134 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 118(I) | 1580 | -4439 | -6912 | -2094 | -2401 | -781 | -1712 | 1731 | -2202 | 1505 | 213 | -5783 | -6200 | -617 | -5697 | -866 | -172 | -460 | 1669 | -4553 | 135 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 119(I) | 859 | -1314 | -6951 | -2110 | -2383 | -6155 | -5026 | 2570 | -1556 | -1064 | -75 | -5801 | -6205 | -1809 | -2661 | -5240 | -899 | 2271 | -4892 | 121 | 136 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 120(R) | 999 | 312 | -1005 | 1277 | -1115 | -949 | -1769 | -871 | 245 | 687 | -1562 | -360 | -2037 | -1361 | 1554 | -587 | -1748 | -1881 | -1158 | -397 | 137 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 121(H) | 590 | -237 | -1178 | 1134 | -1253 | -690 | 2085 | -1410 | -281 | -768 | -1633 | 583 | -956 | -591 | 837 | 440 | -1943 | -3014 | 212 | 1219 | 138 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 122(H) | -4352 | -1143 | -2593 | -335 | -626 | -5385 | 4714 | -5363 | -448 | -567 | 899 | 222 | -5474 | -2303 | -1125 | -1879 | -4291 | -523 | -5753 | -2090 | 139 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 123(H) | -1398 | -1263 | -4501 | -1896 | 818 | -1726 | 3542 | -1112 | -2766 | 167 | -187 | 715 | -1059 | 337 | 517 | 86 | 1094 | -3153 | -5620 | -5067 | 140 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 124(E) | -1593 | -1311 | 1122 | 1374 | 887 | 827 | -28 | -791 | 425 | -390 | -4856 | 161 | -1647 | -3495 | 943 | -1292 | -521 | -1734 | -5954 | -274 | 141 |
| - | -154 | -520 | 239 | 42 | -377 | 393 | 107 | -637 | 216 | -461 | -669 | 265 | 401 | 39 | 112 | 365 | 103 | -376 | -290 | -259 | |
| - | -5929 | -24 | -13359 | -1 | -10036 | -701 | -1378 | * | * | | | | | | | | | | | | |
| 125(W) | -457 | -1303 | -1230 | 334 | 194 | 214 | 1284 | 401 | 563 | -466 | 558 | -1868 | -226 | -2353 | -626 | 309 | -914 | -1137 | 3031 | 378 | 143 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -107 | -12317 | -3808 | -894 | -1115 | -701 | -1378 | * | * | | | | | | | | | | | | |
| 126(M) | -1473 | -5660 | 1013 | 997 | -1403 | -915 | -454 | 230 | -506 | -489 | 1585 | 406 | 659 | -354 | 114 | -113 | -884 | 417 | -916 | -2004 | 144 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -590 | -12210 | -1575 | -894 | -1115 | -2171 | -362 | * | * | | | | | | | | | | | | |
| 127(G) | -136 | -5044 | -1271 | -1230 | -5318 | 1876 | -147 | 1143 | -998 | -625 | 734 | -948 | -664 | -1593 | 344 | -1585 | 1164 | -967 | 877 | -1604 | 145 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -54 | -11648 | -4792 | -894 | -1115 | -4037 | -91 | * | * | | | | | | | | | | | | |
| 128(A) | 1341 | -5135 | -546 | 843 | -1797 | -328 | -3297 | -1713 | 974 | -888 | 391 | -1249 | 372 | -386 | -478 | 10 | 886 | -4757 | -5319 | 394 | 146 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -439 | -11635 | -1931 | -894 | -1115 | -5931 | -24 | * | * | | | | | | | | | | | | |
| 129(G) | -1169 | -4730 | -137 | 634 | -1781 | 1868 | -2890 | -1311 | 1251 | -1143 | -3819 | -1326 | -1765 | 1230 | -646 | -538 | 276 | -4351 | -4913 | 988 | 147 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11196 | -12238 | -894 | -1115 | -5415 | -34 | * | * | | | | | | | | | | | | |
| 130(Y) | -14 | -4708 | -3146 | 735 | 158 | -2123 | -324 | -257 | 401 | -1122 | -3802 | -1351 | -661 | -353 | 1455 | -958 | -1478 | -4319 | 1092 | 2987 | 148 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -47 | -11217 | -4987 | -894 | -1115 | -6421 | -17 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 131(P) | 353 | -3950 | -3751 | 291 | -438 | -396 | 507 | -833 | -849 | -590 | -482 | -3390 | 2641 | -1102 | 535 | -2004 | -1438 | -194 | -4310 | 932 | 149 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1605 | -487 | -12213 | -3622 | -122 | -5037 | -45 | * | * | | | | | | | | | | | | |
| 132(W) | -673 | -4707 | 1234 | -162 | 1947 | -1172 | 947 | -2153 | -183 | -1123 | -3800 | -2888 | -489 | 1320 | 572 | -1129 | -799 | -540 | 2391 | 136 | 193 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11204 | -12247 | -894 | -1115 | -3149 | -173 | * | * | | | | | | | | | | | | |
| 133(G) | 291 | -4549 | -3486 | 327 | -655 | 1468 | 344 | -1997 | -372 | 6 | 603 | -1207 | 920 | -493 | 808 | -1145 | -3398 | -751 | 137 | 1061 | 194 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11368 | -12410 | -894 | -1115 | -4191 | -81 | * | * | | | | | | | | | | | | |
| 134(L) | -696 | -4583 | -3553 | 1392 | -762 | -1044 | -689 | -1234 | 371 | 1690 | -1136 | -1421 | 135 | -1269 | 185 | -583 | -1014 | -1051 | 710 | -499 | 195 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11424 | -12466 | -894 | -1115 | -2615 | -257 | * | * | | | | | | | | | | | | |
| 135(Y) | -296 | -5099 | 719 | -669 | -288 | 153 | -1088 | -2442 | 819 | -308 | -4189 | 331 | 378 | -172 | 801 | -1468 | -899 | -82 | 262 | 1890 | 196 |
| - | -140 | -499 | 228 | 58 | -393 | 409 | 93 | -619 | 208 | -465 | -708 | 267 | 391 | 39 | 94 | 348 | 118 | -366 | -307 | -243 | |
| - | -6766 | -14 | -12644 | -2 | -9333 | -2780 | -277 | * | * | | | | | | | | | | | | |
| 136(E) | 202 | -5216 | -329 | 1544 | -2025 | -727 | -963 | -1675 | 47 | -258 | 1363 | -435 | -448 | -290 | 1449 | -227 | 420 | -1591 | -5400 | -4717 | 198 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -1 | -11720 | -12762 | -894 | -1115 | -523 | -1717 | * | * | | | | | | | | | | | | |
| 137(P) | 392 | -59 | 530 | 1108 | -2297 | -878 | -1550 | -769 | -376 | -1289 | 1213 | -266 | 1589 | 1046 | -204 | -752 | -1285 | -542 | -934 | -1132 | 199 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12161 | -13203 | -894 | -1115 | -4149 | -84 | * | * | | | | | | | | | | | | |
| 138(I) | -745 | -1453 | -106 | -465 | -416 | -5244 | -3921 | 1662 | 107 | 531 | 1115 | -521 | 285 | 1193 | -26 | -479 | -203 | -793 | -5586 | -1049 | 200 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12161 | -13203 | -894 | -1115 | -906 | -1101 | * | * | | | | | | | | | | | | |
| 139(T) | -748 | 763 | 1156 | -732 | -2748 | -1127 | 9 | 75 | -819 | 35 | -4704 | -163 | 1040 | -3476 | -2236 | 1170 | 1492 | -1311 | -5816 | -1377 | 201 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12245 | -13287 | -894 | -1115 | -3213 | -165 | * | * | | | | | | | | | | | | |
| 140(L) | -832 | -1308 | -317 | 82 | -2724 | -5229 | -15 | 1022 | -201 | 1323 | -4772 | 12 | 1221 | -507 | 30 | -815 | 34 | 14 | -5872 | -5200 | 202 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12245 | -13287 | -894 | -1115 | -1419 | -676 | * | * | | | | | | | | | | | | |
| 141(E) | -1092 | -315 | -1199 | 2220 | -1396 | -629 | -1348 | -620 | -1607 | 515 | -4688 | -267 | -308 | -3523 | 1050 | -529 | -2466 | -120 | -5807 | 1019 | 203 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12269 | -13311 | -894 | -1115 | -139 | -3443 | * | * | | | | | | | | | | | | |
| 142(A) | 2031 | 290 | 443 | 217 | -6077 | -133 | -3952 | -765 | -420 | 301 | -4857 | -1446 | -2575 | -693 | -2326 | -323 | -1348 | 939 | -5954 | -5277 | 204 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 143(R) | -696 | 345 | -4871 | -868 | -1482 | -624 | -315 | 974 | 1002 | 55 | 304 | -1404 | -2714 | 1422 | 1873 | -2030 | -655 | 130 | -1180 | -1972 | 205 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 144(I) | -1176 | 1332 | 651 | -2001 | 59 | -2368 | -4902 | 2481 | -1474 | 946 | -3706 | -5518 | -2672 | -1515 | -1719 | -2054 | -877 | 909 | -4955 | 139 | 206 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 145(V) | 495 | -1326 | -6954 | -6318 | -229 | -6156 | -5027 | 1660 | -1955 | 1249 | 361 | -5802 | -6206 | -1434 | -2649 | -3143 | -1078 | 2352 | -4892 | -2253 | 207 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |

TABLE 7-continued

| | | | | | | | | | | | | | | | | | | | | | |
|---|---|---|---|---|---|---|---|---|---|---|---|---|---|---|---|---|---|---|---|---|---|
| 146(K) | 683 | 613 | 1226 | -2295 | 47 | -2915 | -72 | -2826 | 1887 | -5799 | 611 | -902 | -5380 | 800 | 251 | 546 | 217 | -2887 | -5967 | 312 | 208 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 147(I) | 49 | -4924 | 756 | -355 | -887 | -5679 | 253 | 1333 | -771 | 1272 | -4096 | -2538 | -5756 | -1111 | 903 | -4650 | -2576 | 1255 | -427 | -373 | 209 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 148(A) | 2971 | 187 | -6953 | -2933 | -481 | -3509 | -5027 | 515 | -5912 | -283 | 1273 | -5801 | -6206 | -2324 | -5712 | -816 | -1291 | -1528 | 114 | -990 | 210 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 149(D) | -6833 | -325 | 4153 | -2133 | -9067 | -6527 | -6012 | -9088 | -2921 | -8904 | -8381 | -2633 | -7135 | -5713 | -7558 | -3022 | -6950 | -8501 | -9112 | -7932 | 211 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 150(R) | 915 | -1446 | -1186 | -599 | -6094 | -2043 | 86 | -965 | 1293 | -2019 | -4867 | 486 | -5382 | -1891 | 1803 | 312 | -1938 | 220 | 229 | 1580 | 212 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12317 | -13359 | -894 | -1115 | -701 | -1378 | * | * | | | | | | | | | | | | |
| 151(L) | -2885 | 763 | -1829 | -1559 | 1009 | -6155 | -1446 | 645 | -2196 | 2171 | -1373 | -5798 | -6205 | -5532 | -1716 | -2128 | 246 | 727 | -759 | 1371 | 213 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12266 | -13308 | -894 | -1115 | -701 | -1378 | * | * | | | | | | | | | | | | |
| 152(H) | 688 | -1052 | 2063 | 1405 | -2415 | -2888 | 2292 | -1528 | -3618 | -1042 | -4614 | -4000 | -5405 | 227 | -2454 | 1018 | -315 | -1590 | -5745 | -1912 | 214 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12254 | -13296 | -894 | -1115 | -701 | -1378 | * | * | | | | | | | | | | | | |
| 153(A) | 2073 | -4641 | -5485 | -1843 | -940 | -1167 | -4575 | -2330 | -1825 | -1511 | 1417 | 1641 | -54 | -4567 | 1351 | -1062 | 229 | -1377 | -598 | -157 | 215 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | 0 | -12254 | -13296 | -894 | -1115 | -701 | -1378 | * | * | | | | | | | | | | | | |
| 154(M) | 596 | -1117 | 976 | -607 | -5529 | 291 | -4035 | 234 | -1252 | 783 | 2669 | 185 | -5442 | -1909 | -599 | -962 | -356 | -1614 | 516 | -385 | 216 |
| - | * | * | * | * | * | * | * | * | * | * | * | * | * | * | * | * | * | * | * | * | |
| - | * | * | * | * | * | * | * | * | 0 | | | | | | | | | | | | |

What is claimed is:

1. A recombinant bacterial cell producing butanol or 2-butanone said bacterial cell comprising at least one genetic modification which reduces accumulation of (p)ppGpp, wherein the at least one genetic modification is a disruption in an endogenous gene encoding SpoT or RelA or in an operon comprising an open reading frame encoding SpoT or RelA;
 a) the SpoT protein having:
  1) an E-value parameter of 0.01 or less when queried using the Pfam Profile HMM for the RelA/Spot domain; and
  2) an E-value parameter of 0.01 or less when queried using the Pfam Profile HMM for the TGS domain; and
  3) an E-value parameter of 0.01 or less when queried using the Pfam Profile HMM for the HD domain; and
 b) the RelA protein having:
  a) an E-value parameter of 0.01 or less when queried using the Pfam Profile HMM for the RelA/SpoT domain; and
  b) an E-value parameter of 0.01 or less when queried using the Pfam Profile HMM for the TGS domain.

2. The bacterial cell of claim 1 comprising a recombinant biosynthetic pathway selected from the group consisting of:
 a) a 1-butanol biosynthetic pathway;
 b) a 2-butanol biosynthetic pathway;
 c) an isobutanol biosynthetic pathway; and
 d) a 2-butanone biosynthetic pathway.

3. The recombinant bacterial cell of claim 1, wherein the cell is a member of a genus selected from the group consisting of *Clostridium, Escherichia, Rhodococcus, Pseudomonas, Bacillus, Lactobacillus*, and *Enterococcus.*

4. The recombinant bacterial cell of claim 2 wherein the 1-butanol biosynthetic pathway comprises:
 a) at least one genetic construct encoding an acetyl-CoA acetyltransferase;
 b) at least one genetic construct encoding 3-hydroxybutyryl-CoA dehydrogenase;
 c) at least one genetic construct encoding crotonase;
 d) at least one genetic construct encoding butyryl-CoA dehydrogenase;
 e) at least one genetic construct encoding butyraldehyde; dehydrogenase; and
 f) at least one genetic construct encoding 1-butanol dehydrogenase.

5. The recombinant bacterial cell of claim 2 wherein the 2-butanol biosynthetic pathway comprises:
 a) at least one genetic construct encoding an acetolactate synthase;
 b) at least one genetic construct encoding acetolactate decarboxylase;
 c) at least one genetic construct encoding butanediol dehydrogenase;
 d) at least one genetic construct encoding butanediol dehydratase; and
 e) at least one genetic construct encoding 2-butanol dehydrogenase.

6. The recombinant bacterial cell of claim 2 wherein the isobutanol biosynthetic pathway comprises:
 a) at least one genetic construct encoding an acetolactate synthase;
 b) at least one genetic construct encoding acetohydroxy acid isomeroreductase;
 c) at least one genetic construct encoding acetohydroxy acid dehydratase;
 d) at least one genetic construct encoding branched-chain keto acid decarboxylase; and
 e) at least one genetic construct encoding branched-chain alcohol dehydrogenase.

7. The recombinant bacterial cell of claim 2, wherein the 2-butanone biosynthetic pathway comprises:
 a) at least one genetic construct encoding an acetolactate synthase;
 b) at least one genetic construct encoding acetolactate decarboxylase;
 c) at least one genetic construct encoding butanediol dehydrogenase; and
 d) at least one genetic construct encoding butanediol dehydratase.

8. A process for production of butanol or 2-butanone from a recombinant bacterial cell comprising:
 (a) providing a recombinant bacterial host cell of claim 1; and
 (b) culturing the strain of (a) under conditions wherein butanol or 2-butanone is produced.

9. The process of claim 8 wherein the recombinant bacterial host comprises a recombinant biosynthetic pathway selected from the group consisting of:
 a) a 1-butanol biosynthetic pathway;
 b) a 2-butanol biosynthetic pathway;
 c) an isobutanol biosynthetic pathway; and
 d) a 2-butanone biosynthetic pathway.

10. The process of claim 9 wherein the 1-butanol biosynthetic pathway comprises:
 a) at least one genetic construct encoding an acetyl-CoA acetyltransferase;
 b) at least one genetic construct encoding 3-hydroxybutyryl-CoA dehydrogenase;
 c) at least one genetic construct encoding crotonase;
 d) at least one genetic construct encoding butyryl-CoA dehydrogenase;
 e) at least one genetic construct encoding butyraldehyde; dehydrogenase; and
 f) at least one genetic construct encoding 1-butanol dehydrogenase.

11. The process of claim 9 wherein the 2-butanol biosynthetic pathway comprises:
 a) at least one genetic construct encoding an acetolactate synthase;
 b) at least one genetic construct encoding acetolactate decarboxylase;
 c) at least one genetic construct encoding butanediol dehydrogenase;
 d) at least one genetic construct encoding butanediol dehydratase; and
 e) at least one genetic construct encoding 2-butanol dehydrogenase.

12. The process of claim 9 wherein the isobutanol biosynthetic pathway comprises:
 a) at least one genetic construct encoding an acetolactate synthase;

b) at least one genetic construct encoding acetohydroxy acid isomeroreductase;

c) at least one genetic construct encoding acetohydroxy acid dehydratase;

d) at least one genetic construct encoding branched-chain keto acid decarboxylase; and e) at least one genetic construct encoding branched-chain alcohol dehydrogenase.

13. The process of claim 9 wherein the 2-butanone biosynthetic pathway comprises:

a) at least one genetic construct encoding an acetolactate synthase;

b) at least one genetic construct encoding acetolactate decarboxylase;

c) at least one genetic construct encoding butanediol dehydrogenase; and d) at least one genetic construct encoding butanediol dehydratase.

* * * * *